(12) United States Patent
Soriani et al.

(10) Patent No.: US 8,377,446 B2
(45) Date of Patent: Feb. 19, 2013

(54) SERUM RESISTANCE FACTORS OF GRAM POSITIVE BACTERIA

(75) Inventors: Marco Soriani, Siena (IT); Isabella Santi, Siena (IT)

(73) Assignee: Novartis Vaccines and Diagnostics, Inc., Emeryville, CA (US)

(*) Notice: Subject to any disclaimer, the term of this patent is extended or adjusted under 35 U.S.C. 154(b) by 0 days.

(21) Appl. No.: 13/327,882

(22) Filed: Dec. 16, 2011

(65) Prior Publication Data

US 2012/0171211 A1    Jul. 5, 2012

Related U.S. Application Data

(62) Division of application No. 11/920,274, filed as application No. PCT/US2006/018411 on May 12, 2006, now Pat. No. 8,105,612.

(60) Provisional application No. 60/680,479, filed on May 13, 2005, provisional application No. 60/740,291, filed on Nov. 29, 2005.

(51) Int. Cl.
*A61K 39/40* (2006.01)

(52) U.S. Cl. ............... 424/165.1; 424/130.1; 424/150.1; 424/190.1; 530/387.1

(58) Field of Classification Search .................. None
See application file for complete search history.

(56) References Cited

U.S. PATENT DOCUMENTS 6,426,074 B1    7/2002    Michel et al.

FOREIGN PATENT DOCUMENTS

| WO | WO0234771 | 5/2002 |
|---|---|---|
| WO | WO02092818 | 11/2002 |
| WO | WO2004099242 | 11/2004 |

OTHER PUBLICATIONS

Chou and Fasman, "Prediction of the secondary structure of proteins from their amino acid sequence," Adv Enzymol Relat Areas Mol Biol. 1978;47:45-148.
Clothia et al., The EMBO Journal 5/4, 823-26, 1986.
Emini et al., "Induction of hepatitis A virus-neutralizing antibody by a virus-specific synthetic peptide," J Virol. Sep. 1985;55(3):836-9.
Greenspan et al., Nature Biotechnology 7, 936-37, 1999.
Karplus and Schulz, "Prediction of Chain Flexibility in Proteins—A tool for the Selection of Peptide Antigens," Naturwissenschafren 1985; 72:212-23.
Kolaskar et al., "A semi-empirical method for prediction of antigenic determinants on protein antigens." FEBS Lett. (1990) 276:172-4.
Mikayama et al., Proc. Natl. Acad. Sci. USA 90, 10056-60, 1993.
Parker et al., "New hydrophilicity scale derived from high-performance liquid chromatography peptide retention data: correlation of predicted surface residues with antigenicity and X-ray-derived accessible sites," Biochemistry. Sep. 23, 1986;25(19):5425-32.
Rudinger et al., Peptide Hormones, Bio Council, pp. 5-7, Jun. 1976.
Tettelin H et al., "Complete genome sequence and comparative genomic analysis of an emerging human pathogen, serotype V *Streptococcus agalactiae*" Proceeding of the National Academy of Sciences of USA, vol. 99, No. 19, Sep. 17, 2002, pp. 12391-12396.
Tettelin H et al., "Complete genome sequence of a virulent isolate of *Streptococcus pneumoniae*" Science, American Association for the Advancement of Science, vol. 293, No. 5529, 2001, pp. 498-506.

*Primary Examiner* — Jennifer Graser
(74) *Attorney, Agent, or Firm* — Banner & Witcoff, Ltd.

(57) ABSTRACT

A newly identified serum resistance factor of gram positive bacteria can be used to treat or prevent bacterial infection.

19 Claims, 56 Drawing Sheets

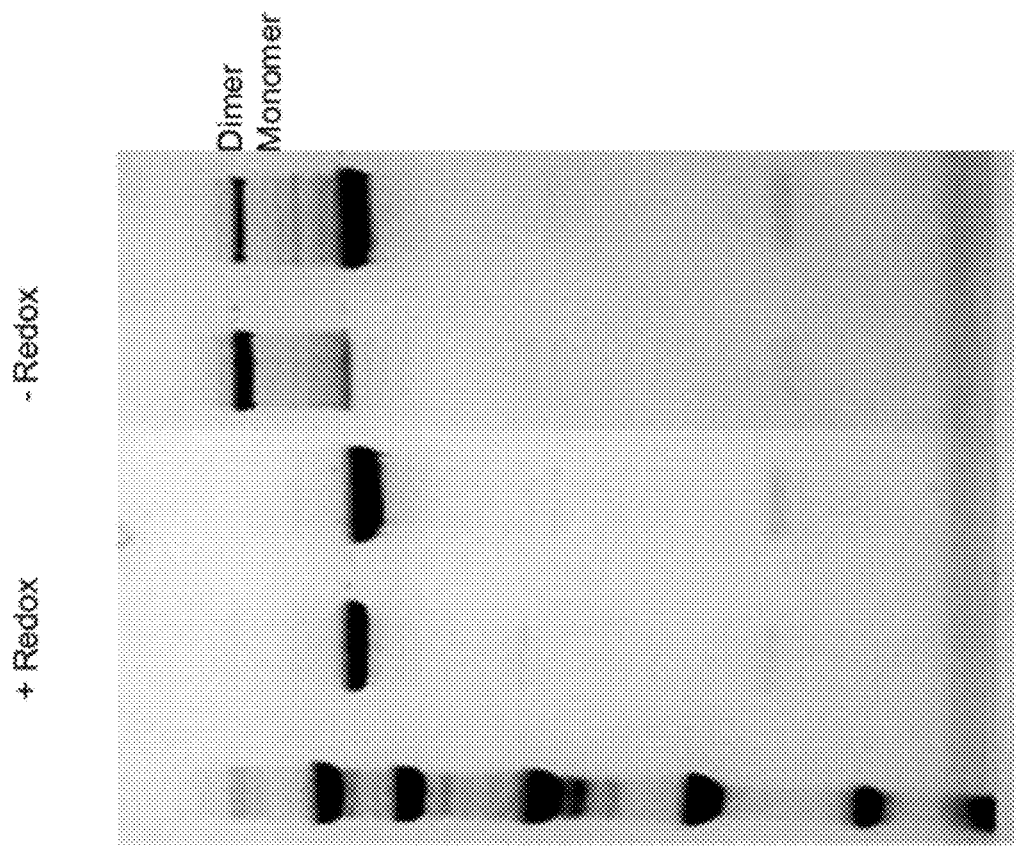

GBS3 gene (SAG2063) including its own promoter and terminator was cloned into the shuttle vector pAM401 vector and used to transform GBS strain 515.

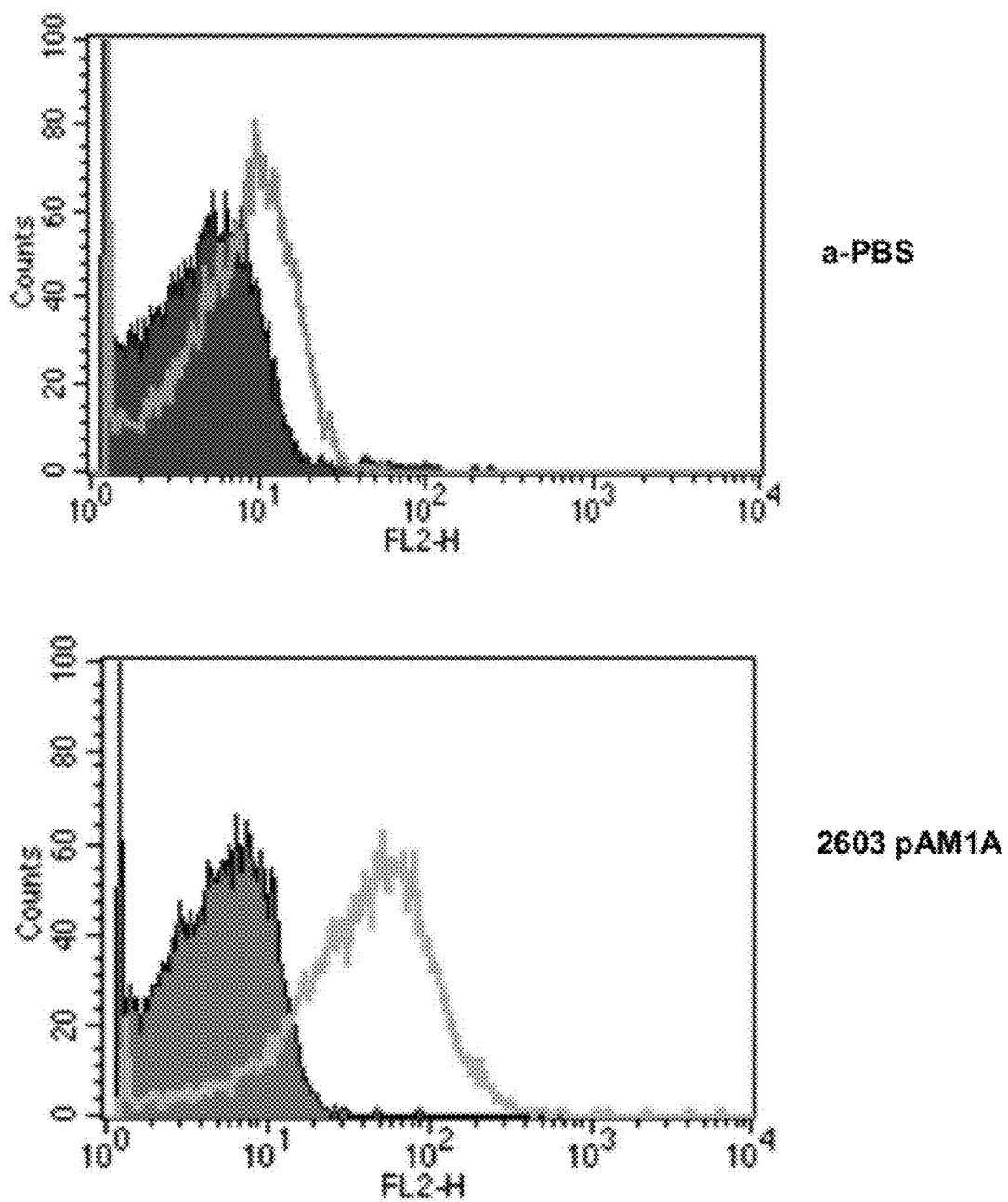
FIG. 8A, cont.

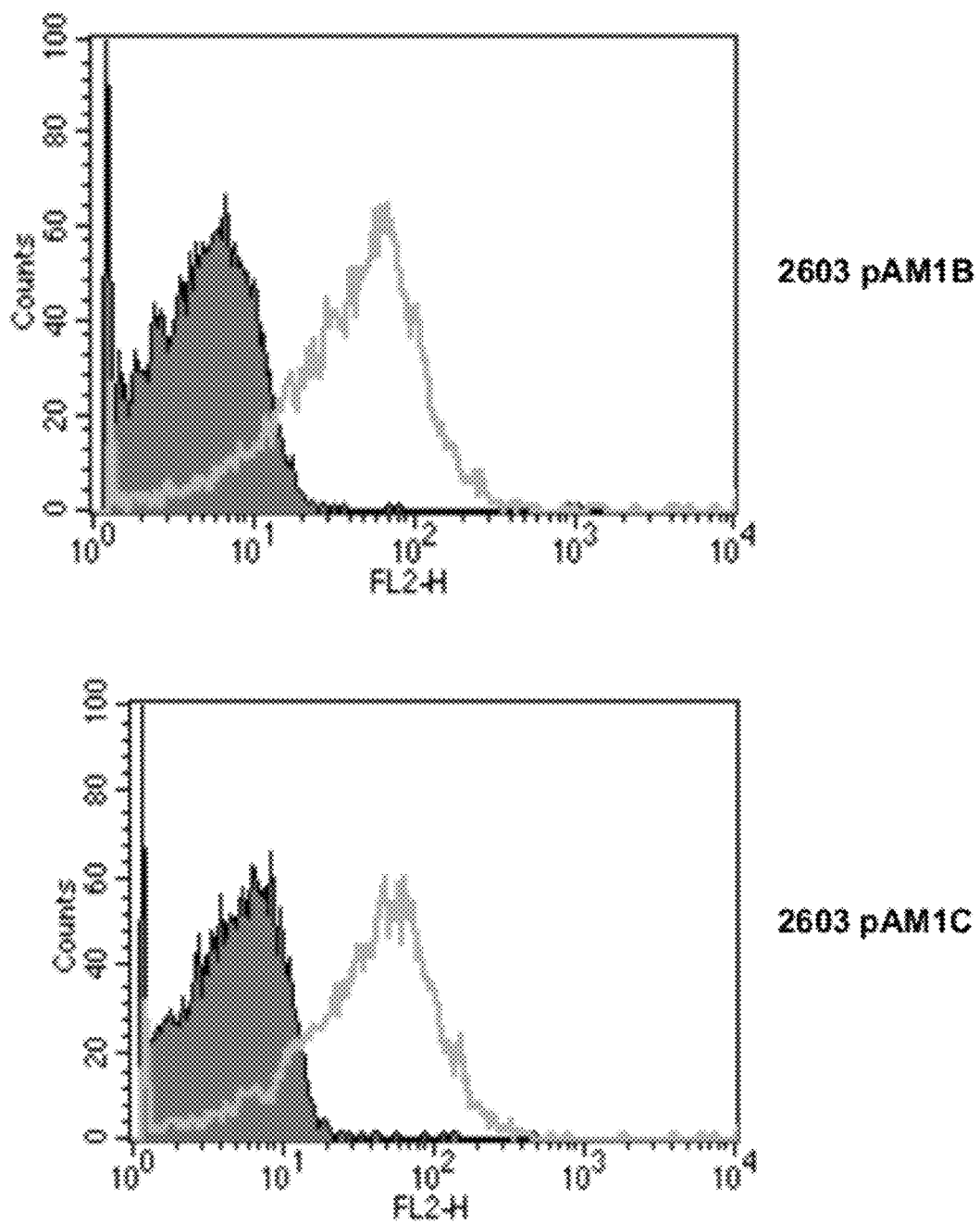
FIG. 8A, cont.

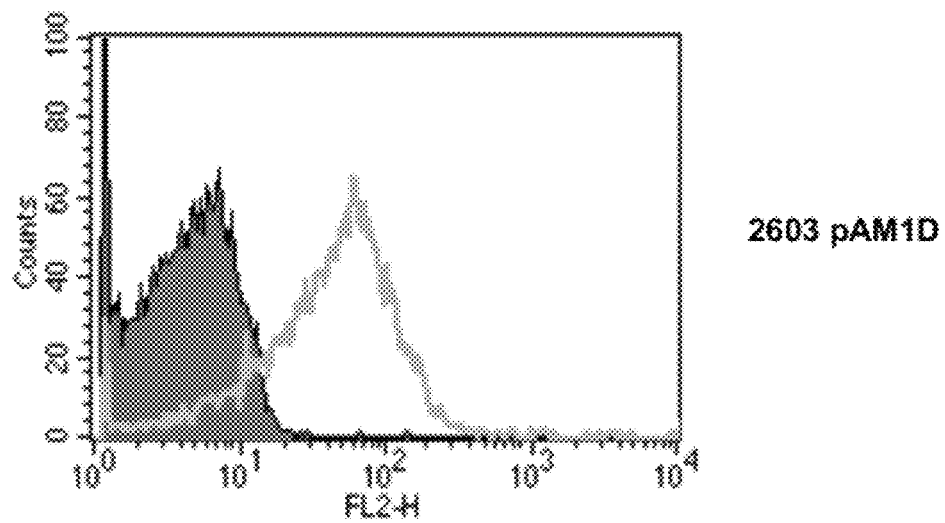
| GBS Strain | DMean GBS3 |
|---|---|
| 2603 pAMwt | 184 |
| 2603 pAM1A | 232 |
| 2603 pAM1B | 243 |
| 2603 pAM1C | 239 |
| 2603 pAM1D | 262 |
FIG. 8A, cont.

| GBS Strain | ΔMean GBS3 |
|---|---|
| 515 pAMwt | 28 |
| 515 pAM1A | 276 |
| 515 pAM1B | 291 |
| 515 pAM1C | 285 |

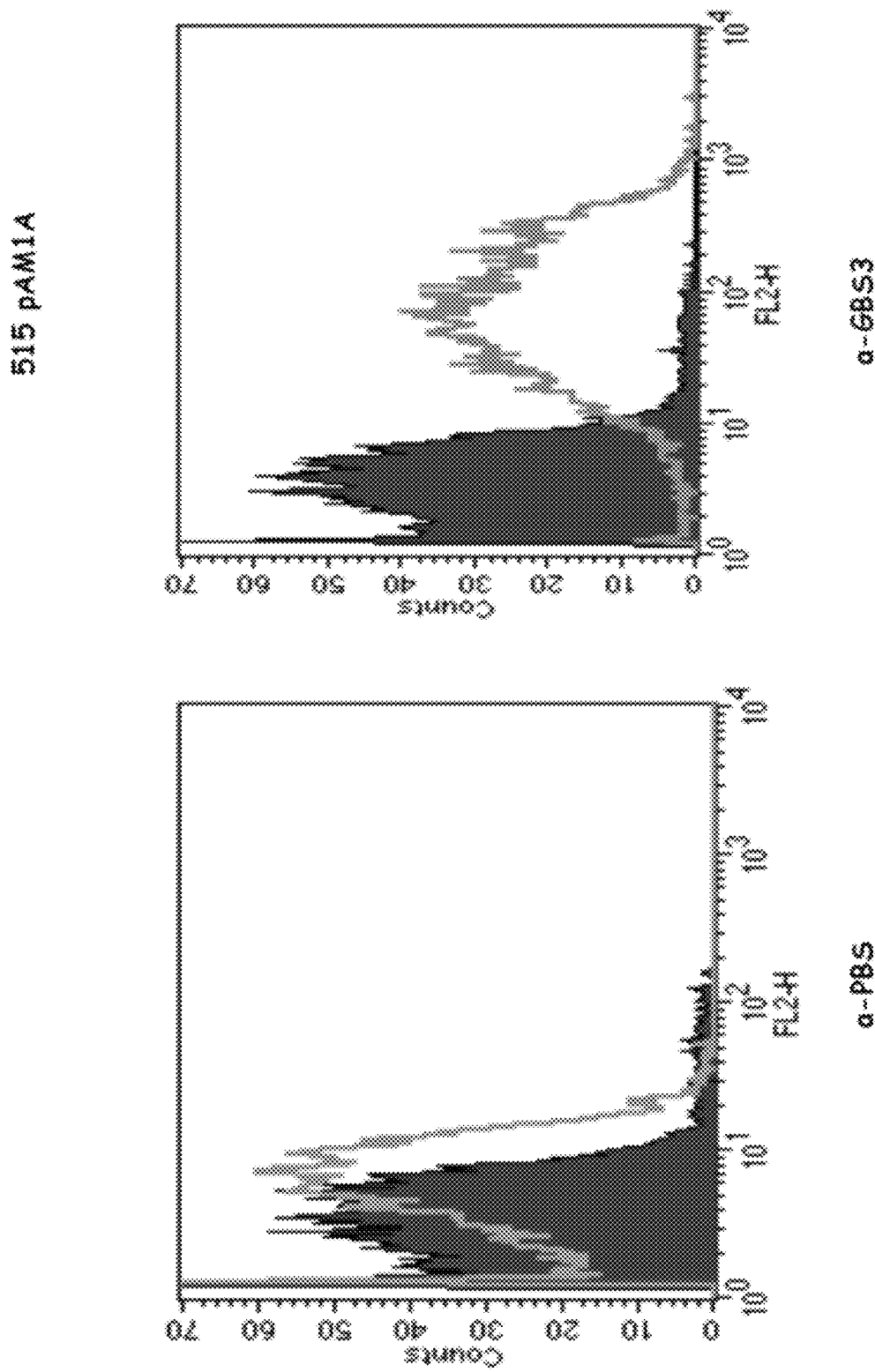
FIG. 8B, cont.

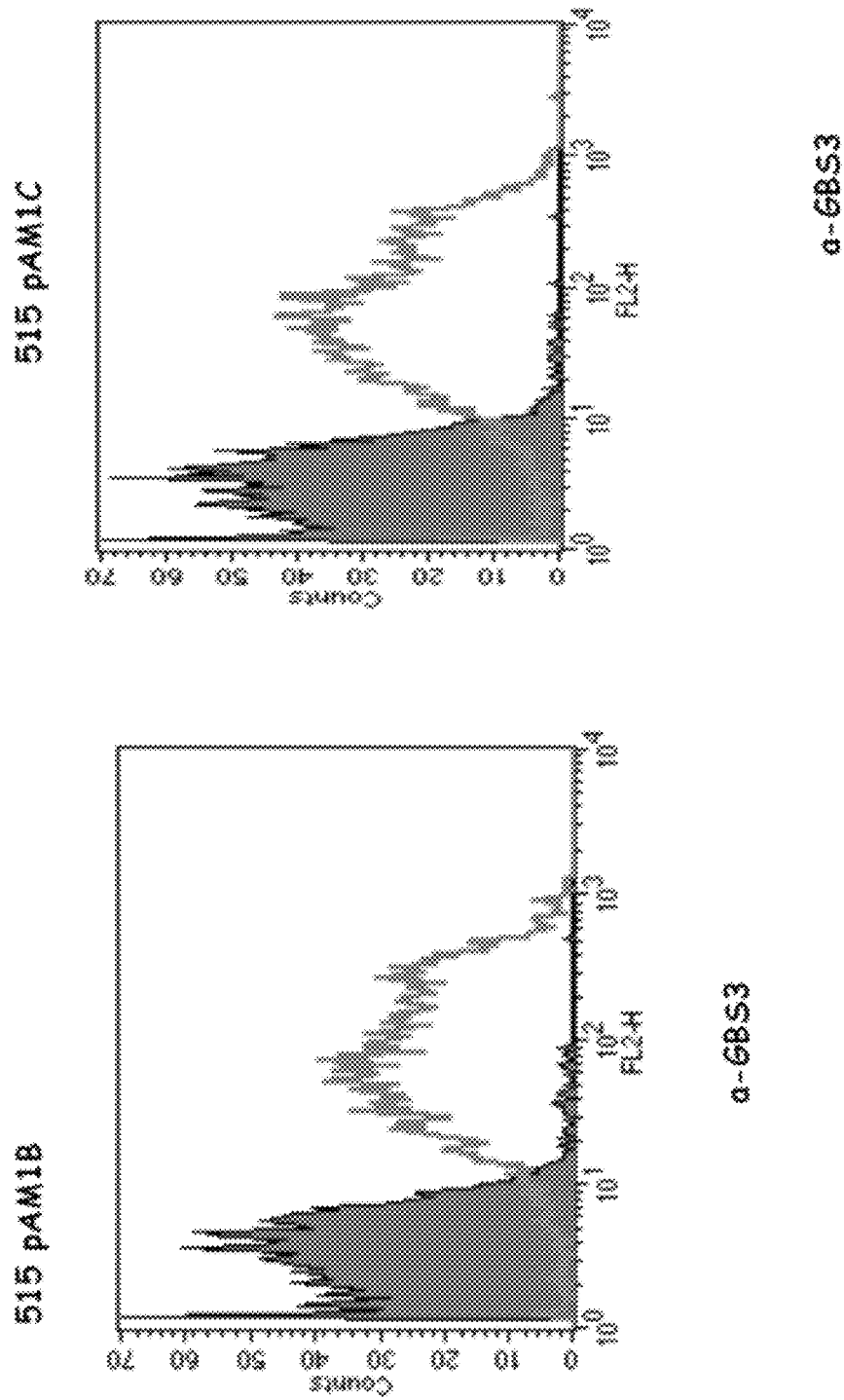
FIG. 8B, cont.

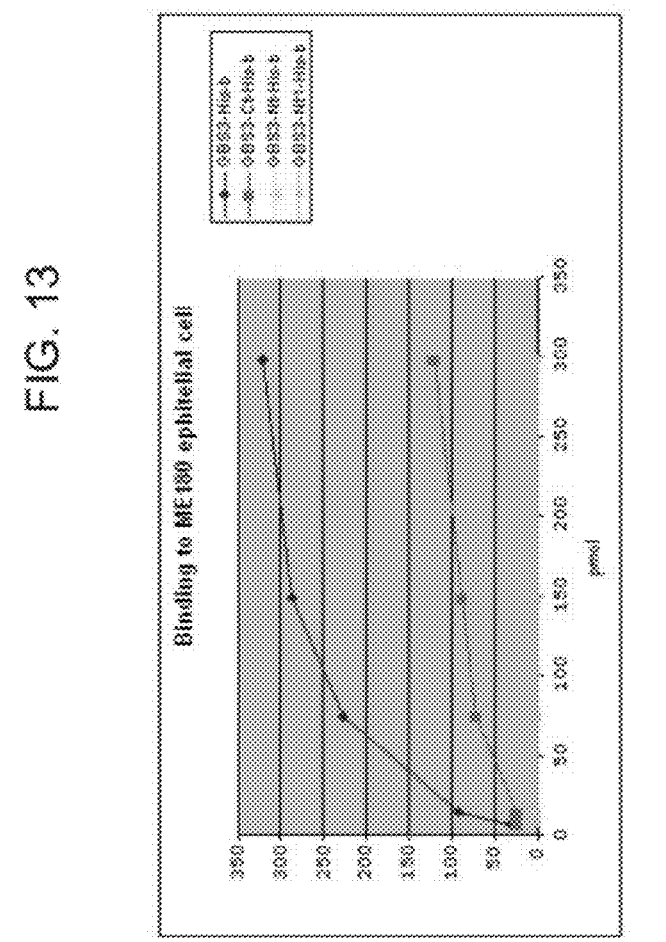
FIG. 13
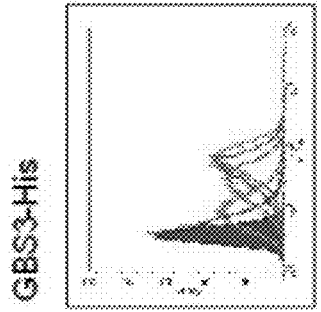
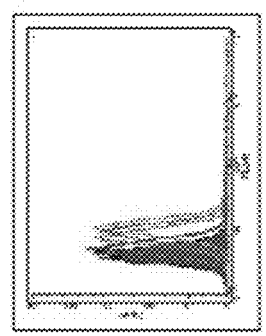
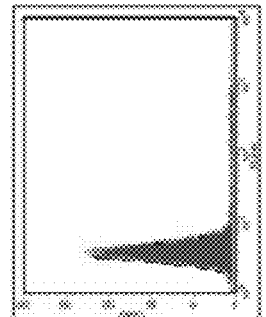

FIG. 14
FIG. 14B
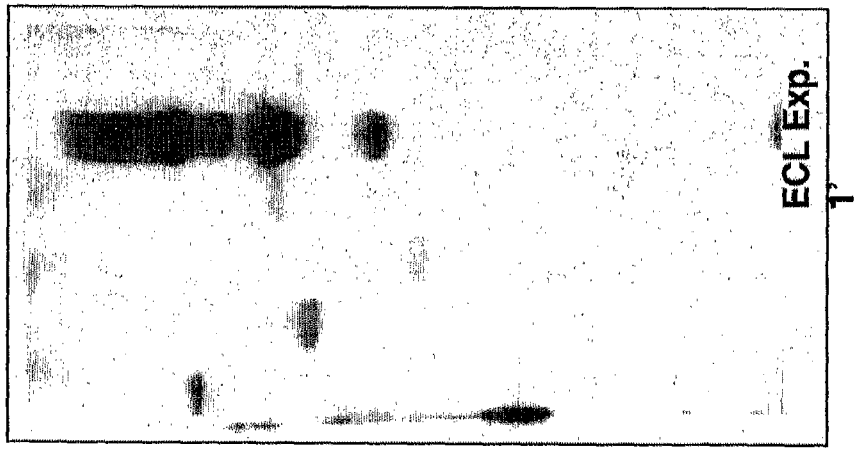
FIG. 14A

FIG. 17
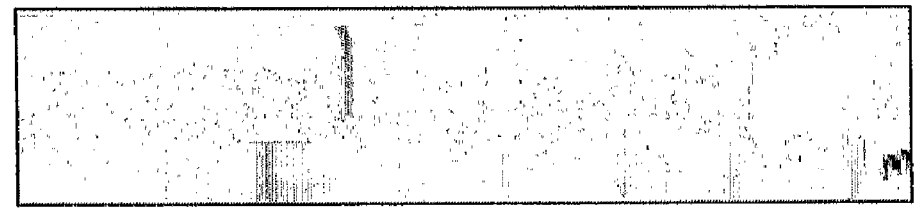
FIG. 17A
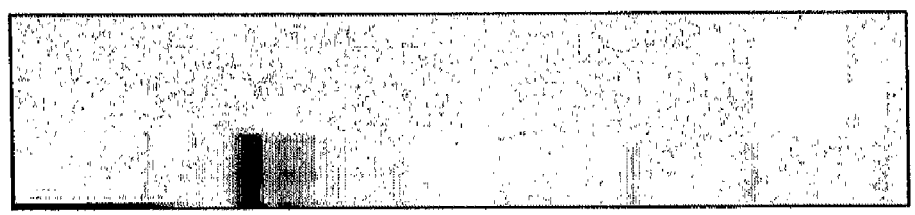
FIG. 17B
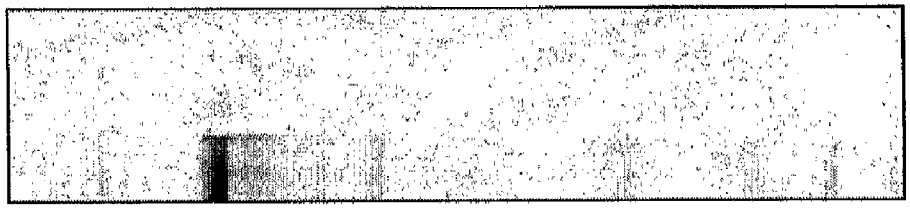
FIG. 17C

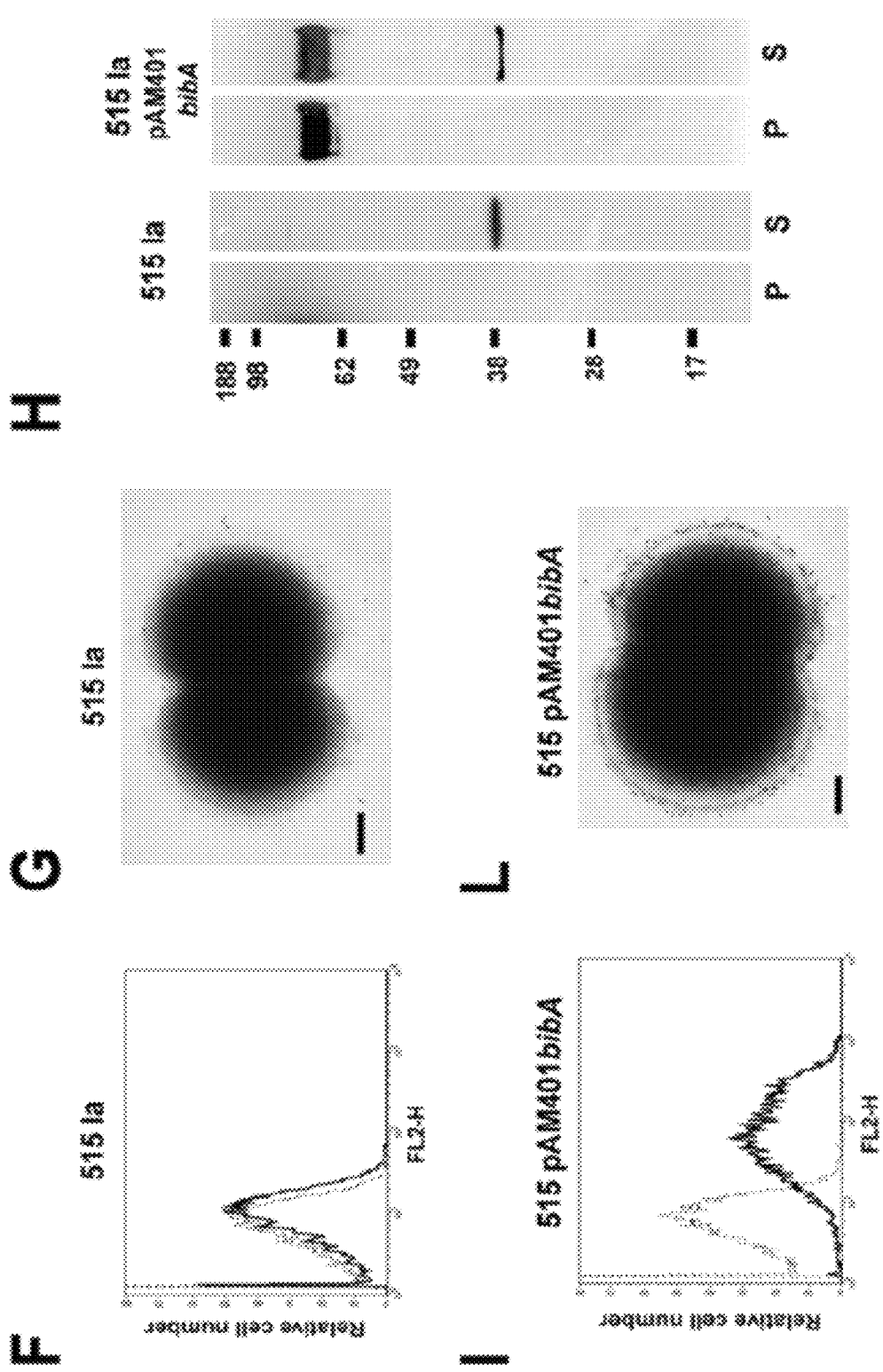
FIG. 19, cont.

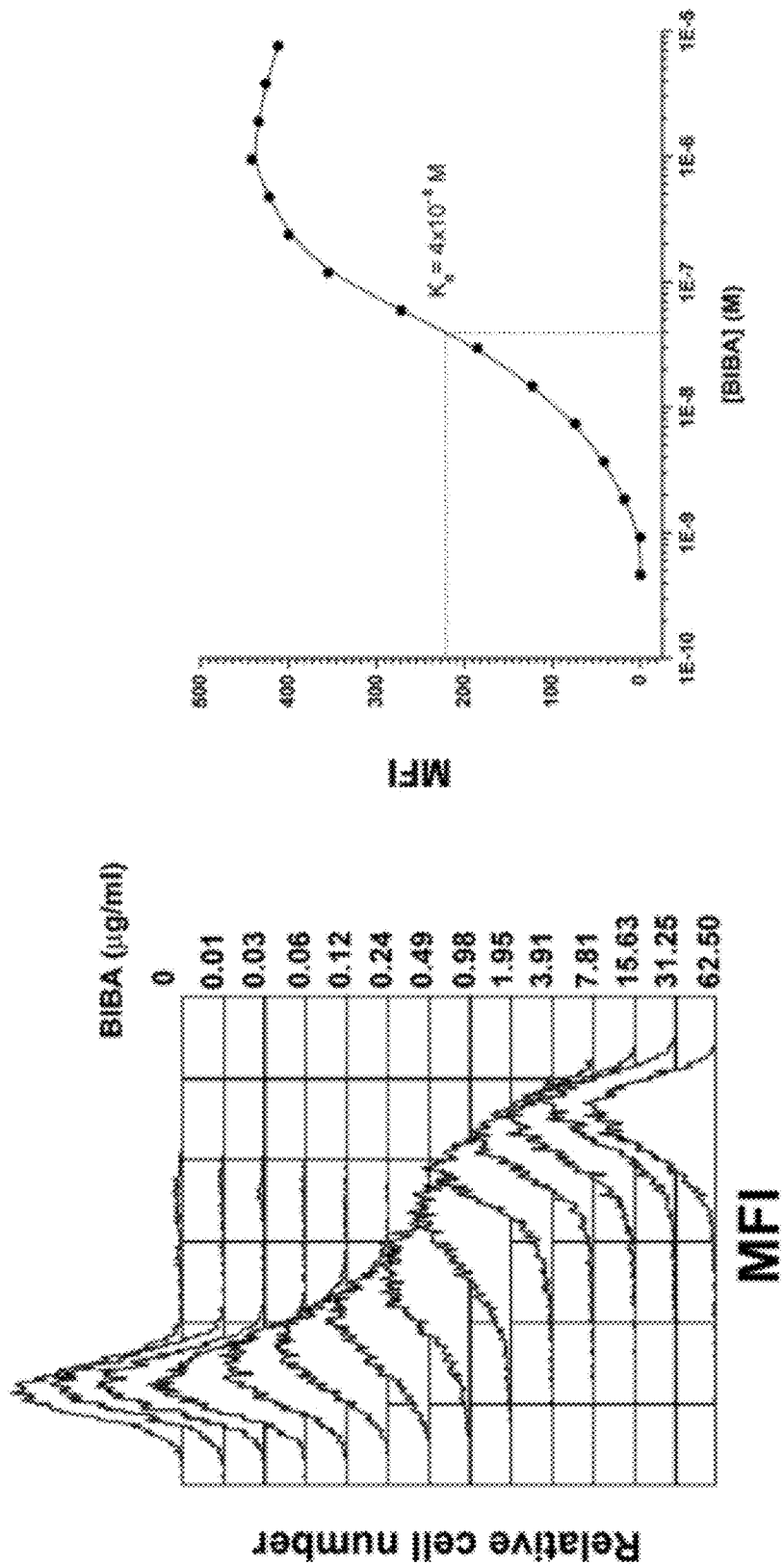

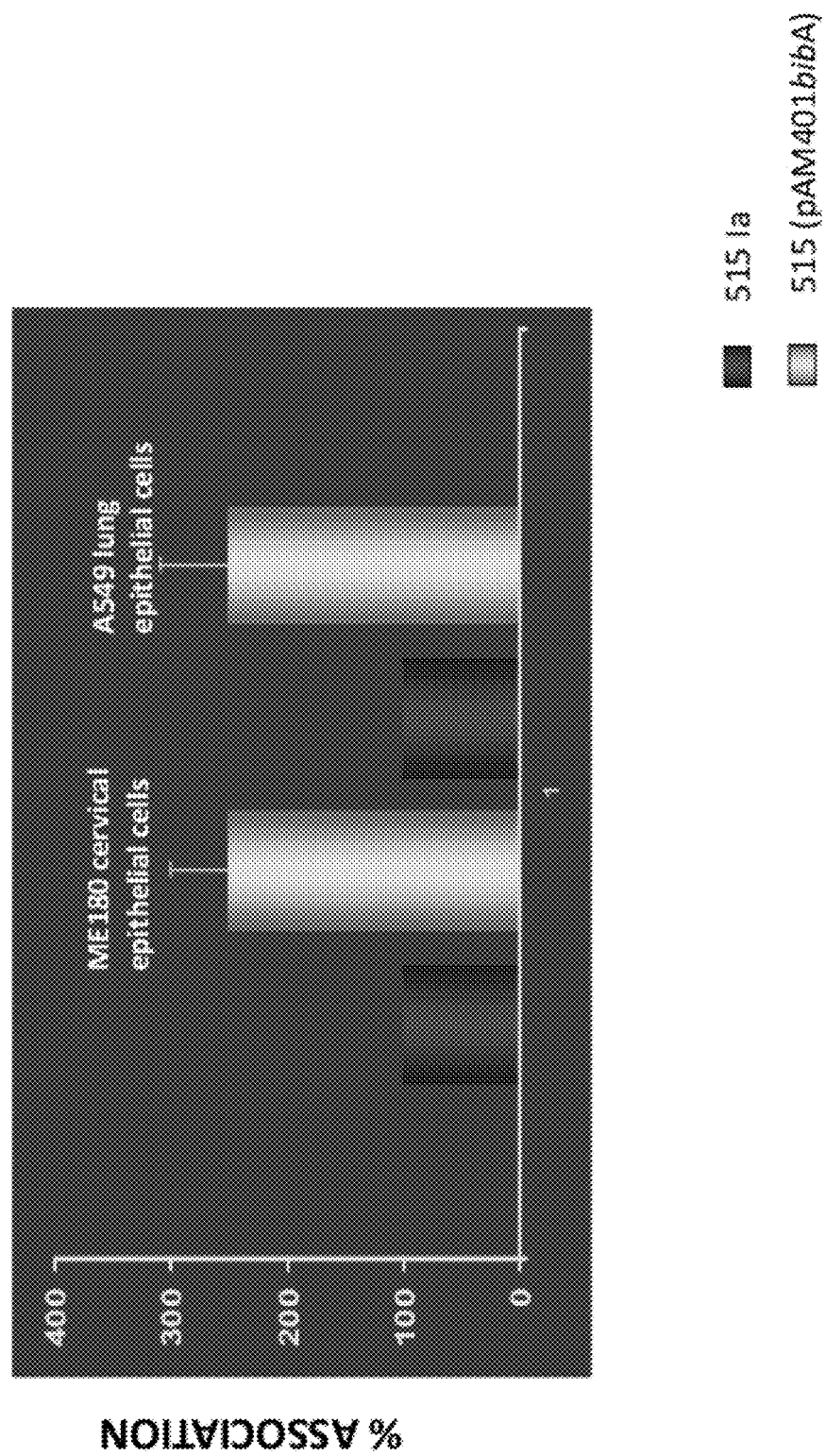

SEQUENCE LISTING

```
<160> NUMBER OF SEQ ID NOS: 67

<210> SEQ ID NO 1
<211> LENGTH: 630
<212> TYPE: PRT
<213> ORGANISM: Group B Streptococcus

<400> SEQUENCE: 1

Met Asn Asn Asn Glu Lys Lys Val Lys Tyr Phe Leu Arg Lys Thr Ala
1               5                   10                  15

Tyr Gly Leu Ala Ser Met Ser Ala Ala Phe Ala Val Cys Ser Gly Ile
            20                  25                  30

Val His Ala Asp Thr Ser Ser Gly Ile Ser Ala Ser Ile Pro His Lys
        35                  40                  45

Lys Gln Val Asn Leu Gly Ala Val Thr Leu Lys Asn Leu Ile Ser Lys
```

```
                50                  55                  60
Tyr Arg Gly Asn Asp Lys Ala Ile Ala Ile Leu Leu Ser Arg Val Asn
 65                  70                  75                  80

Asp Phe Asn Arg Ala Ser Gln Asp Thr Leu Pro Gln Leu Ile Asn Ser
                     85                  90                  95

Thr Glu Ala Glu Ile Arg Asn Ile Leu Tyr Gln Gly Gln Ile Gly Lys
                100                 105                 110

Gln Asn Lys Pro Ser Val Thr Thr His Ala Lys Val Ser Asp Gln Glu
                115                 120                 125

Leu Gly Lys Gln Ser Arg Arg Ser Gln Asp Ile Ile Lys Ser Leu Gly
130                 135                 140

Phe Leu Ser Ser Asp Gln Lys Asp Ile Leu Val Lys Ser Ile Ser Ser
145                 150                 155                 160

Ser Lys Asp Ser Gln Leu Ile Leu Lys Phe Val Thr Gln Ala Thr Gln
                165                 170                 175

Leu Asn Asn Ala Glu Ser Thr Lys Ala Lys Gln Met Ala Gln Asn Asp
                180                 185                 190

Val Ala Leu Ile Lys Asn Ile Ser Pro Glu Val Leu Glu Glu Tyr Lys
                195                 200                 205

Glu Lys Ile Gln Arg Ala Ser Thr Lys Ser Gln Val Asp Glu Phe Val
210                 215                 220

Ala Glu Ala Lys Lys Val Asn Ser Asn Lys Glu Thr Leu Val Asn
225                 230                 235                 240

Gln Ala Asn Gly Lys Lys Gln Glu Ile Ala Lys Leu Glu Asn Leu Ser
                245                 250                 255

Asn Asp Glu Met Leu Arg Tyr Asn Thr Ala Ile Asp Asn Val Val Lys
                260                 265                 270

Gln Tyr Asn Glu Gly Lys Leu Asn Ile Thr Ala Ala Met Asn Ala Leu
                275                 280                 285

Asn Ser Ile Lys Gln Ala Ala Gln Glu Val Ala Gln Lys Asn Leu Gln
                290                 295                 300

Lys Gln Tyr Ala Lys Lys Ile Glu Arg Ile Ser Ser Lys Gly Leu Ala
305                 310                 315                 320

Leu Ser Lys Lys Ala Lys Glu Ile Tyr Glu Lys His Lys Ser Ile Leu
                325                 330                 335

Pro Thr Pro Gly Tyr Tyr Ala Asp Ser Val Gly Thr Tyr Leu Asn Arg
                340                 345                 350

Phe Arg Asp Lys Gln Thr Phe Gly Asn Arg Ser Val Trp Thr Gly Gln
                355                 360                 365

Ser Gly Leu Asp Glu Ala Lys Lys Met Leu Asp Glu Val Lys Lys Leu
                370                 375                 380

Leu Lys Glu Leu Gln Asp Leu Thr Arg Gly Thr Lys Glu Asp Lys Lys
385                 390                 395                 400

Pro Asp Val Lys Pro Glu Ala Lys Pro Glu Ala Lys Pro Asp Val Lys
                    405                 410                 415

Pro Glu Ala Lys Pro Asp Val Lys Pro Glu Ala Lys Pro Asp Val Lys
                420                 425                 430

Pro Glu Ala Lys Pro Asp Val Lys Pro Glu Ala Lys Pro Asp Val Lys
                435                 440                 445

Pro Glu Ala Lys Pro Asp Val Lys Pro Lys Ala Lys Pro Asp Val Lys
                450                 455                 460

Pro Glu Ala Lys Pro Asp Val Lys Pro Asp Val Lys Pro Asp Val Lys
465                 470                 475                 480
```

```
Pro Glu Ala Lys Pro Glu Asp Lys Pro Asp Val Lys
            485                 490                 495

Pro Glu Ala Lys Pro Asp Val Lys Pro Glu Ala Lys
        500                 505                 510

Pro Glu Ala Lys Pro Glu Ala Lys Pro Glu Ala Lys
        515                 520                 525

Pro Asp Val Lys Pro Glu Ala Lys Pro Asp Val Lys
        530                 535                 540

Pro Glu Ala Lys Pro Glu Ala Lys Ser Glu Ala Lys Pro Glu Ala Lys
545                 550                 555                 560

Leu Glu Ala Lys Pro Glu Ala Lys Pro Ala Thr Lys Lys Ser Val Asn
            565                 570                 575

Thr Ser Gly Asn Leu Ala Ala Lys Lys Ala Ile Glu Asn Lys Lys Tyr
        580                 585                 590

Ser Lys Lys Leu Pro Ser Thr Gly Glu Ala Ala Ser Pro Leu Leu Ala
        595                 600                 605

Ile Val Ser Leu Ile Val Met Leu Ser Ala Gly Leu Ile Thr Ile Val
        610                 615                 620

Leu Lys His Lys Lys Asn
625                 630

<210> SEQ ID NO 2
<211> LENGTH: 594
<212> TYPE: PRT
<213> ORGANISM: Group B Streptococcus

<400> SEQUENCE: 2

Thr Ser Ser Gly Ile Ser Ala Ser Ile Pro His Lys Lys Gln Val Asn
  1               5                  10                  15

Leu Gly Ala Val Thr Leu Lys Asn Leu Ile Ser Lys Tyr Arg Gly Asn
            20                  25                  30

Asp Lys Ala Ile Ala Ile Leu Leu Ser Arg Val Asn Asp Phe Asn Arg
        35                  40                  45

Ala Ser Gln Asp Thr Leu Pro Gln Leu Ile Asn Ser Thr Glu Ala Glu
    50                  55                  60

Ile Arg Asn Ile Leu Tyr Gln Gly Gln Ile Gly Lys Gln Asn Lys Pro
65                  70                  75                  80

Ser Val Thr Thr His Ala Lys Val Ser Asp Gln Glu Leu Gly Lys Gln
                85                  90                  95

Ser Arg Arg Ser Gln Asp Ile Ile Lys Ser Leu Gly Phe Leu Ser Ser
            100                 105                 110

Asp Gln Lys Asp Ile Leu Val Lys Ser Ile Ser Ser Lys Asp Ser
        115                 120                 125

Gln Leu Ile Leu Lys Phe Val Thr Gln Ala Thr Gln Leu Asn Asn Ala
    130                 135                 140

Glu Ser Thr Lys Ala Lys Gln Met Ala Gln Asn Asp Val Ala Leu Ile
145                 150                 155                 160

Lys Asn Ile Ser Pro Glu Val Leu Glu Glu Tyr Lys Glu Lys Ile Gln
                165                 170                 175

Arg Ala Ser Thr Lys Ser Gln Val Asp Glu Phe Val Ala Glu Ala Lys
            180                 185                 190

Lys Val Val Asn Ser Asn Lys Glu Thr Leu Val Asn Gln Ala Asn Gly
        195                 200                 205

Lys Lys Gln Glu Ile Ala Lys Leu Glu Asn Leu Ser Asn Asp Glu Met
    210                 215                 220
```

```
Leu Arg Tyr Asn Thr Ala Ile Asp Asn Val Val Lys Gln Tyr Asn Glu
225                 230                 235                 240

Gly Lys Leu Asn Ile Thr Ala Met Asn Ala Leu Asn Ser Ile Lys
            245                 250                 255

Gln Ala Ala Gln Glu Val Ala Gln Lys Asn Leu Gln Lys Gln Tyr Ala
        260                 265                 270

Lys Lys Ile Glu Arg Ile Ser Ser Lys Gly Leu Ala Leu Ser Lys Lys
            275                 280                 285

Ala Lys Glu Ile Tyr Glu Lys His Lys Ser Ile Leu Pro Thr Pro Gly
        290                 295                 300

Tyr Tyr Ala Asp Ser Val Gly Thr Tyr Leu Asn Arg Phe Arg Asp Lys
305                 310                 315                 320

Gln Thr Phe Gly Asn Arg Ser Val Trp Thr Gly Gln Ser Gly Leu Asp
                325                 330                 335

Glu Ala Lys Lys Met Leu Asp Glu Val Lys Lys Leu Leu Lys Glu Leu
            340                 345                 350

Gln Asp Leu Thr Arg Gly Thr Lys Glu Asp Lys Lys Pro Asp Val Lys
        355                 360                 365

Pro Glu Ala Lys Pro Glu Ala Lys Pro Asp Val Lys Pro Glu Ala Lys
370                 375                 380

Pro Asp Val Lys Pro Glu Ala Lys Pro Asp Val Lys Pro Glu Ala Lys
385                 390                 395                 400

Pro Asp Val Lys Pro Glu Ala Lys Pro Asp Val Lys Pro Glu Ala Lys
                405                 410                 415

Pro Asp Val Lys Pro Lys Ala Lys Pro Asp Val Lys Pro Glu Ala Lys
            420                 425                 430

Pro Asp Val Lys Pro Asp Val Lys Pro Asp Val Lys Pro Glu Ala Lys
        435                 440                 445

Pro Glu Asp Lys Pro Asp Val Lys Pro Asp Val Lys Pro Glu Ala Lys
450                 455                 460

Pro Asp Val Lys Pro Glu Ala Lys Pro Glu Ala Lys Pro Glu Ala Lys
465                 470                 475                 480

Pro Glu Ala Lys Pro Glu Ala Lys Pro Glu Ala Lys Pro Asp Val Lys
                485                 490                 495

Pro Glu Ala Lys Pro Asp Val Lys Pro Glu Ala Lys Pro Glu Ala Lys
            500                 505                 510

Pro Glu Ala Lys Ser Glu Ala Lys Pro Glu Ala Lys Leu Glu Ala Lys
        515                 520                 525

Pro Glu Ala Lys Pro Ala Thr Lys Lys Ser Val Asn Thr Ser Gly Asn
530                 535                 540

Leu Ala Ala Lys Lys Ala Ile Glu Asn Lys Lys Tyr Ser Lys Lys Leu
545                 550                 555                 560

Pro Ser Thr Gly Glu Ala Ala Ser Pro Leu Leu Ala Ile Val Ser Leu
                565                 570                 575

Ile Val Met Leu Ser Ala Gly Leu Ile Thr Ile Val Leu Lys His Lys
            580                 585                 590

Lys Asn
```

<210> SEQ ID NO 3
<211> LENGTH: 5
<212> TYPE: PRT
<213> ORGANISM: Group B Streptococcus
<220> FEATURE:
<221> NAME/KEY: VARIANT
<222> LOCATION: 3
<223> OTHER INFORMATION: Xaa = Any Amino Acid

```
<220> FEATURE:
<221> NAME/KEY: VARIANT
<222> LOCATION: 3
<223> OTHER INFORMATION: Xaa = Any Amino Acid

<400> SEQUENCE: 3

Leu Pro Xaa Thr Gly
  1               5

<210> SEQ ID NO 4
<211> LENGTH: 559
<212> TYPE: PRT
<213> ORGANISM: Group B Streptococcus

<400> SEQUENCE: 4

Thr Ser Ser Gly Ile Ser Ala Ser Ile Pro His Lys Lys Gln Val Asn
  1               5                  10                  15

Leu Gly Ala Val Thr Leu Lys Asn Leu Ile Ser Lys Tyr Arg Gly Asn
                 20                  25                  30

Asp Lys Ala Ile Ala Ile Leu Leu Ser Arg Val Asn Asp Phe Asn Arg
             35                  40                  45

Ala Ser Gln Asp Thr Leu Pro Gln Leu Ile Asn Ser Thr Glu Ala Glu
         50                  55                  60

Ile Arg Asn Ile Leu Tyr Gln Gly Gln Ile Gly Lys Gln Asn Lys Pro
 65                  70                  75                  80

Ser Val Thr Thr His Ala Lys Val Ser Asp Gln Glu Leu Gly Lys Gln
                 85                  90                  95

Ser Arg Arg Ser Gln Asp Ile Ile Lys Ser Leu Gly Phe Leu Ser Ser
                100                 105                 110

Asp Gln Lys Asp Ile Leu Val Lys Ser Ile Ser Ser Ser Lys Asp Ser
            115                 120                 125

Gln Leu Ile Leu Lys Phe Val Thr Gln Ala Thr Gln Leu Asn Asn Ala
        130                 135                 140

Glu Ser Thr Lys Ala Lys Gln Met Ala Gln Asn Asp Val Ala Leu Ile
145                 150                 155                 160

Lys Asn Ile Ser Pro Glu Val Leu Glu Glu Tyr Lys Glu Lys Ile Gln
                165                 170                 175

Arg Ala Ser Thr Lys Ser Gln Val Asp Glu Phe Val Ala Glu Ala Lys
            180                 185                 190

Lys Val Val Asn Ser Asn Lys Glu Thr Leu Val Asn Gln Ala Asn Gly
        195                 200                 205

Lys Lys Gln Glu Ile Ala Lys Leu Glu Asn Leu Ser Asn Asp Glu Met
    210                 215                 220

Leu Arg Tyr Asn Thr Ala Ile Asp Asn Val Val Lys Gln Tyr Asn Glu
225                 230                 235                 240

Gly Lys Leu Asn Ile Thr Ala Ala Met Asn Ala Leu Asn Ser Ile Lys
                245                 250                 255

Gln Ala Ala Gln Glu Val Ala Gln Lys Asn Leu Gln Lys Gln Tyr Ala
            260                 265                 270

Lys Lys Ile Glu Arg Ile Ser Ser Lys Gly Leu Ala Leu Ser Lys Lys
        275                 280                 285

Ala Lys Glu Ile Tyr Glu Lys His Lys Ser Ile Leu Pro Thr Pro Gly
    290                 295                 300

Tyr Tyr Ala Asp Ser Val Gly Thr Tyr Leu Asn Arg Phe Arg Asp Lys
305                 310                 315                 320

Gln Thr Phe Gly Asn Arg Ser Val Trp Thr Gly Gln Ser Gly Leu Asp
                325                 330                 335
```

```
Glu Ala Lys Lys Met Leu Asp Glu Val Lys Lys Leu Leu Lys Glu Leu
                340                 345                 350
Gln Asp Leu Thr Arg Gly Thr Lys Glu Asp Lys Lys Pro Asp Val Lys
            355                 360                 365
Pro Glu Ala Lys Pro Glu Ala Lys Pro Asp Val Lys Pro Glu Ala Lys
        370                 375                 380
Pro Asp Val Lys Pro Glu Ala Lys Pro Asp Val Lys Pro Glu Ala Lys
385                 390                 395                 400
Pro Asp Val Lys Pro Glu Ala Lys Pro Asp Val Lys Pro Glu Ala Lys
                405                 410                 415
Pro Asp Val Lys Pro Lys Ala Lys Pro Asp Val Lys Pro Glu Ala Lys
            420                 425                 430
Pro Asp Val Lys Pro Asp Val Lys Pro Asp Val Lys Pro Glu Ala Lys
        435                 440                 445
Pro Glu Asp Lys Pro Asp Val Lys Pro Asp Val Lys Pro Glu Ala Lys
    450                 455                 460
Pro Asp Val Lys Pro Glu Ala Lys Pro Glu Ala Lys Pro Glu Ala Lys
465                 470                 475                 480
Pro Glu Ala Lys Pro Glu Ala Lys Pro Glu Ala Lys Pro Asp Val Lys
                485                 490                 495
Pro Glu Ala Lys Pro Asp Val Lys Pro Glu Ala Lys Pro Glu Ala Lys
            500                 505                 510
Pro Glu Ala Lys Ser Glu Ala Lys Pro Glu Ala Lys Leu Glu Ala Lys
        515                 520                 525
Pro Glu Ala Lys Pro Ala Thr Lys Lys Ser Val Asn Thr Ser Gly Asn
    530                 535                 540
Leu Ala Ala Lys Lys Ala Ile Glu Asn Lys Lys Tyr Ser Lys Lys
545                 550                 555

<210> SEQ ID NO 5
<211> LENGTH: 159
<212> TYPE: PRT
<213> ORGANISM: Group B Streptococcus

<400> SEQUENCE: 5

Pro Asp Val Lys Pro Glu Ala Lys Pro Asp Val Lys Pro Glu Ala Lys
1               5                   10                  15
Pro Asp Val Lys Pro Lys Ala Lys Pro Asp Val Lys Pro Glu Ala Lys
            20                  25                  30
Pro Asp Val Lys Pro Asp Val Lys Pro Asp Val Lys Pro Glu Ala Lys
        35                  40                  45
Pro Glu Asp Lys Pro Asp Val Lys Pro Asp Val Lys Pro Glu Ala Lys
    50                  55                  60
Pro Asp Val Lys Pro Glu Ala Lys Pro Glu Ala Lys Pro Glu Ala Lys
65              70                  75                  80
Pro Glu Ala Lys Pro Glu Ala Lys Pro Glu Ala Lys Pro Asp Val Lys
                85                  90                  95
Pro Glu Ala Lys Pro Asp Val Lys Pro Glu Ala Lys Pro Glu Ala Lys
            100                 105                 110
Pro Glu Ala Lys Ser Glu Ala Lys Pro Glu Ala Lys Leu Glu Ala Lys
        115                 120                 125
Pro Glu Ala Lys Pro Ala Thr Lys Lys Ser Val Asn Thr Ser Gly Asn
    130                 135                 140
Leu Ala Ala Lys Lys Ala Ile Glu Asn Lys Lys Tyr Ser Lys Lys
145                 150                 155
```

<210> SEQ ID NO 6
<211> LENGTH: 436
<212> TYPE: PRT
<213> ORGANISM: Group B Streptococcus

<400> SEQUENCE: 6

Met Asn Asn Asn Glu Lys Lys Val Lys Tyr Phe Leu Arg Lys Thr Ala
1               5                   10                  15

Tyr Gly Leu Ala Ser Met Ser Ala Ala Phe Ala Val Cys Ser Gly Ile
            20                  25                  30

Val His Ala Asp Thr Ser Ser Gly Ile Ser Ala Ser Ile Pro His Lys
        35                  40                  45

Lys Gln Val Asn Leu Gly Ala Val Thr Leu Lys Asn Leu Ile Ser Lys
    50                  55                  60

Tyr Arg Gly Asn Asp Lys Ala Ile Ala Ile Leu Leu Ser Arg Val Asn
65                  70                  75                  80

Asp Phe Asn Arg Ala Ser Gln Asp Thr Leu Pro Gln Leu Ile Asn Ser
                85                  90                  95

Thr Glu Ala Glu Ile Arg Asn Ile Leu Tyr Gln Gly Gln Ile Gly Lys
            100                 105                 110

Gln Asn Lys Pro Ser Val Thr Thr His Ala Lys Val Ser Asp Gln Glu
        115                 120                 125

Leu Gly Lys Gln Ser Arg Arg Ser Gln Asp Ile Ile Lys Ser Leu Gly
    130                 135                 140

Phe Leu Ser Ser Asp Gln Lys Asp Ile Leu Val Lys Ser Ile Ser Ser
145                 150                 155                 160

Ser Lys Asp Ser Gln Leu Ile Leu Lys Phe Val Thr Gln Ala Thr Gln
                165                 170                 175

Leu Asn Asn Ala Glu Ser Thr Lys Ala Lys Gln Met Ala Gln Asn Asp
            180                 185                 190

Val Ala Leu Ile Lys Asn Ile Ser Pro Glu Val Leu Glu Glu Tyr Lys
        195                 200                 205

Glu Lys Ile Gln Arg Ala Ser Thr Lys Ser Gln Val Asp Glu Phe Val
    210                 215                 220

Ala Glu Ala Lys Lys Val Val Asn Ser Asn Lys Glu Thr Leu Val Asn
225                 230                 235                 240

Gln Ala Asn Gly Lys Lys Gln Glu Ile Ala Lys Leu Glu Asn Leu Ser
                245                 250                 255

Asn Asp Glu Met Leu Arg Tyr Asn Thr Ala Ile Asp Asn Val Val Lys
            260                 265                 270

Gln Tyr Asn Glu Gly Lys Leu Asn Ile Thr Ala Ala Met Asn Ala Leu
        275                 280                 285

Asn Ser Ile Lys Gln Ala Ala Gln Glu Val Ala Gln Lys Asn Leu Gln
    290                 295                 300

Lys Gln Tyr Ala Lys Lys Ile Glu Arg Ile Ser Ser Lys Gly Leu Ala
305                 310                 315                 320

Leu Ser Lys Lys Ala Lys Glu Ile Tyr Glu Lys His Lys Ser Ile Leu
                325                 330                 335

Pro Thr Pro Gly Tyr Tyr Ala Asp Ser Val Gly Thr Tyr Leu Asn Arg
            340                 345                 350

Phe Arg Asp Lys Gln Thr Phe Gly Asn Arg Ser Val Trp Thr Gly Gln
        355                 360                 365

Ser Gly Leu Asp Glu Ala Lys Lys Met Leu Asp Glu Val Lys Lys Leu
    370                 375                 380

Leu Lys Glu Leu Gln Asp Leu Thr Arg Gly Thr Lys Glu Asp Lys Lys
385                 390                 395                 400

Pro Asp Val Lys Pro Glu Ala Lys Pro Glu Ala Lys Pro Asp Val Lys
                405                 410                 415

Pro Glu Ala Lys Pro Asp Val Lys Pro Glu Ala Lys Pro Asp Val Lys
            420                 425                 430

Pro Glu Ala Lys
        435

<210> SEQ ID NO 7
<211> LENGTH: 364
<212> TYPE: PRT
<213> ORGANISM: Group B Streptococcus

<400> SEQUENCE: 7

Thr Ser Ser Gly Ile Ser Ala Ser Ile Pro His Lys Lys Gln Val Asn
1               5                   10                  15

Leu Gly Ala Val Thr Leu Lys Asn Leu Ile Ser Lys Tyr Arg Gly Asn
            20                  25                  30

Asp Lys Ala Ile Ala Ile Leu Leu Ser Arg Val Asn Asp Phe Asn Arg
        35                  40                  45

Ala Ser Gln Asp Thr Leu Pro Gln Leu Ile Asn Ser Thr Glu Ala Glu
    50                  55                  60

Ile Arg Asn Ile Leu Tyr Gln Gly Gln Ile Gly Lys Gln Asn Lys Pro
65                  70                  75                  80

Ser Val Thr Thr His Ala Lys Val Ser Asp Gln Glu Leu Gly Lys Gln
                85                  90                  95

Ser Arg Arg Ser Gln Asp Ile Ile Lys Ser Leu Gly Phe Leu Ser Ser
            100                 105                 110

Asp Gln Lys Asp Ile Leu Val Lys Ser Ile Ser Ser Lys Asp Ser
        115                 120                 125

Gln Leu Ile Leu Lys Phe Val Thr Gln Ala Thr Gln Leu Asn Asn Ala
    130                 135                 140

Glu Ser Thr Lys Ala Lys Gln Met Ala Gln Asn Asp Val Ala Leu Ile
145                 150                 155                 160

Lys Asn Ile Ser Pro Glu Val Leu Glu Glu Tyr Lys Glu Lys Ile Gln
                165                 170                 175

Arg Ala Ser Thr Lys Ser Gln Val Asp Glu Phe Val Ala Glu Ala Lys
            180                 185                 190

Lys Val Val Asn Ser Asn Lys Glu Thr Leu Val Asn Gln Ala Asn Gly
        195                 200                 205

Lys Lys Gln Glu Ile Ala Lys Leu Glu Asn Leu Ser Asn Asp Glu Met
    210                 215                 220

Leu Arg Tyr Asn Thr Ala Ile Asp Asn Val Val Lys Gln Tyr Asn Glu
225                 230                 235                 240

Gly Lys Leu Asn Ile Thr Ala Ala Met Asn Ala Leu Asn Ser Ile Lys
                245                 250                 255

Gln Ala Ala Gln Glu Val Ala Gln Lys Asn Leu Gln Lys Gln Tyr Ala
            260                 265                 270

Lys Lys Ile Glu Arg Ile Ser Ser Lys Gly Leu Ala Leu Ser Lys Lys
        275                 280                 285

Ala Lys Glu Ile Tyr Glu Lys His Lys Ser Ile Leu Pro Thr Pro Gly
    290                 295                 300

Tyr Tyr Ala Asp Ser Val Gly Thr Tyr Leu Asn Arg Phe Arg Asp Lys
305                 310                 315                 320

Gln Thr Phe Gly Asn Arg Ser Val Trp Thr Gly Gln Ser Gly Leu Asp
            325                 330                 335

Glu Ala Lys Lys Met Leu Asp Glu Val Lys Lys Leu Leu Lys Glu Leu
            340                 345                 350

Gln Asp Leu Thr Arg Gly Thr Lys Glu Asp Lys Lys
            355                 360

<210> SEQ ID NO 8
<211> LENGTH: 595
<212> TYPE: PRT
<213> ORGANISM: Group B Streptococcus

<400> SEQUENCE: 8

Met Asn Asn Glu Lys Lys Val Lys Tyr Phe Leu Arg Lys Thr Ala
1               5                   10                  15

Tyr Gly Leu Ala Ser Met Ser Ala Ala Phe Ala Val Cys Ser Gly Ile
            20                  25                  30

Val His Ala Asp Thr Ser Ser Gly Ile Ser Ala Ser Ile Pro His Lys
            35                  40                  45

Lys Gln Val Asn Leu Gly Ala Val Thr Leu Lys Asn Leu Ile Ser Lys
        50                  55                  60

Tyr Arg Gly Asn Asp Lys Ala Ile Ala Ile Leu Leu Ser Arg Val Asn
65                  70                  75                  80

Asp Phe Asn Arg Ala Ser Gln Asp Thr Leu Pro Gln Leu Ile Asn Ser
                85                  90                  95

Thr Glu Ala Glu Ile Arg Asn Ile Leu Tyr Gln Gly Gln Ile Gly Lys
            100                 105                 110

Gln Asn Lys Pro Ser Val Thr Thr His Ala Lys Val Ser Asp Gln Glu
        115                 120                 125

Leu Gly Lys Gln Ser Arg Arg Ser Gln Asp Ile Ile Lys Ser Leu Gly
130                 135                 140

Phe Leu Ser Ser Asp Gln Lys Asp Ile Leu Val Lys Ser Ile Ser Ser
145                 150                 155                 160

Ser Lys Asp Ser Gln Leu Ile Leu Lys Phe Val Thr Gln Ala Thr Gln
                165                 170                 175

Leu Asn Asn Ala Glu Ser Thr Lys Ala Lys Gln Met Ala Gln Asn Asp
            180                 185                 190

Val Ala Leu Ile Lys Asn Ile Ser Pro Glu Val Leu Glu Glu Tyr Lys
        195                 200                 205

Glu Lys Ile Gln Arg Ala Ser Thr Lys Ser Gln Val Asp Glu Phe Val
210                 215                 220

Ala Glu Ala Lys Lys Val Val Asn Ser Asn Lys Glu Thr Leu Val Asn
225                 230                 235                 240

Gln Ala Asn Gly Lys Lys Gln Glu Ile Ala Lys Leu Glu Asn Leu Ser
                245                 250                 255

Asn Asp Glu Met Leu Arg Tyr Asn Thr Ala Ile Asp Asn Val Val Lys
            260                 265                 270

Gln Tyr Asn Glu Gly Lys Leu Asn Ile Thr Ala Ala Met Asn Ala Leu
        275                 280                 285

Asn Ser Ile Lys Gln Ala Ala Gln Glu Val Ala Gln Lys Asn Leu Gln
    290                 295                 300

Lys Gln Tyr Ala Lys Lys Ile Glu Arg Ile Ser Ser Lys Gly Leu Ala
305                 310                 315                 320

Leu Ser Lys Lys Ala Lys Glu Ile Tyr Glu Lys His Lys Ser Ile Leu
                325                 330                 335

```
Pro Thr Pro Gly Tyr Tyr Ala Asp Ser Val Gly Thr Tyr Leu Asn Arg
            340                 345                 350

Phe Arg Asp Lys Gln Thr Phe Gly Asn Arg Ser Val Trp Thr Gly Gln
        355                 360                 365

Ser Gly Leu Asp Glu Ala Lys Lys Met Leu Asp Glu Val Lys Lys Leu
    370                 375                 380

Leu Lys Glu Leu Gln Asp Leu Thr Arg Gly Thr Lys Glu Asp Lys Lys
385                 390                 395                 400

Pro Asp Val Lys Pro Glu Ala Lys Pro Glu Ala Lys Pro Asp Val Lys
                405                 410                 415

Pro Glu Ala Lys Pro Asp Val Lys Pro Glu Ala Lys Pro Asp Val Lys
            420                 425                 430

Pro Glu Ala Lys Pro Asp Val Lys Pro Glu Ala Lys Pro Asp Val Lys
        435                 440                 445

Pro Glu Ala Lys Pro Asp Val Lys Pro Lys Ala Lys Pro Asp Val Lys
    450                 455                 460

Pro Glu Ala Lys Pro Asp Val Lys Pro Asp Val Lys Pro Asp Val Lys
465                 470                 475                 480

Pro Glu Ala Lys Pro Glu Asp Lys Pro Asp Val Lys Pro Asp Val Lys
                485                 490                 495

Pro Glu Ala Lys Pro Asp Val Lys Pro Glu Ala Lys Pro Glu Ala Lys
            500                 505                 510

Pro Glu Ala Lys Pro Glu Ala Lys Pro Glu Ala Lys Pro Glu Ala Lys
        515                 520                 525

Pro Asp Val Lys Pro Glu Ala Lys Pro Asp Val Lys Pro Glu Ala Lys
    530                 535                 540

Pro Glu Ala Lys Pro Glu Ala Lys Ser Glu Ala Lys Pro Glu Ala Lys
545                 550                 555                 560

Leu Glu Ala Lys Pro Glu Ala Lys Pro Ala Thr Lys Lys Ser Val Asn
                565                 570                 575

Thr Ser Gly Asn Leu Ala Ala Lys Lys Ala Ile Glu Asn Lys Lys Tyr
            580                 585                 590

Ser Lys Lys
        595

<210> SEQ ID NO 9
<211> LENGTH: 8
<212> TYPE: PRT
<213> ORGANISM: Group B Streptococcus

<400> SEQUENCE: 9

Lys Pro Asp Val Lys Pro Glu Ala
 1               5

<210> SEQ ID NO 10
<211> LENGTH: 8
<212> TYPE: PRT
<213> ORGANISM: Group B Streptococcus

<400> SEQUENCE: 10

Lys Pro Glu Ala Lys Pro Asp Val
 1               5

<210> SEQ ID NO 11
<211> LENGTH: 8
<212> TYPE: PRT
<213> ORGANISM: Group B Streptococcus
```

-continued

```
<400> SEQUENCE: 11

Lys Pro Lys Ala Lys Pro Asp Val
1               5

<210> SEQ ID NO 12
<211> LENGTH: 8
<212> TYPE: PRT
<213> ORGANISM: Group B Streptococcus

<400> SEQUENCE: 12

Lys Pro Asp Val Lys Pro Asp Val
1               5

<210> SEQ ID NO 13
<211> LENGTH: 8
<212> TYPE: PRT
<213> ORGANISM: Group B Streptococcus

<400> SEQUENCE: 13

Lys Pro Glu Ala Lys Pro Glu Asp
1               5

<210> SEQ ID NO 14
<211> LENGTH: 8
<212> TYPE: PRT
<213> ORGANISM: Group B Streptococcus

<400> SEQUENCE: 14

Lys Pro Glu Ala Lys Pro Glu Ala
1               5

<210> SEQ ID NO 15
<211> LENGTH: 8
<212> TYPE: PRT
<213> ORGANISM: Group B Streptococcus

<400> SEQUENCE: 15

Lys Pro Asp Val Lys Pro Glu Ala
1               5

<210> SEQ ID NO 16
<211> LENGTH: 1890
<212> TYPE: DNA
<213> ORGANISM: Group B Streptococcus

<400> SEQUENCE: 16
atgaataata acgaaaaaaa agtaaaatac tttttaagaa aaacagctta tggtttggcc      60
tcaatgtcag cagcgtttgc tgtatgtagt ggtattgtac acgcggatac tagttcagga    120
atatcggctt caattcctca taagaaacaa gttaatttag gggcggttac tctgaagaat    180
ttgatttcta aatatcgtgg taatgacaaa gctattgcta cttttttaag tagagtaaat    240
gattttaata gagcatcaca ggatacactt ccacaattaa ttaatagtac tgaagcagaa    300
attagaaata tttatatcca ggacaaaatt ggtaagcaaa ataaaccaag tgtaactaca    360
catgctaaag ttagtgatca agaactaggt aagcagtcaa gacgttctca agatatcatt    420
aagtcattag gtttcctttc atcagaccaa aaagatattt tagttaaatc tattagctct    480
tcaaaagatt cgcaacttat tcttaaattt gtaactcaag ccacgcaact gaataatgct    540
gaatcaacaa agctaagca aatggctcaa aatgacgtgg ccttaataaa aaatataagc    600
cccgaagtct tagaagaata taagaaaaaa attcaaagag ctagcactaa gagtcaagtt    660
gatgagtttg tagcagaagc taaaaaagtt gttaattcca ataaagaaac gttggtaaat    720
```

```
caggccaatg gtaaaaagca agaaattgct aagttagaaa atttatctaa cgatgaaatg    780
ttgagatata atactgcaat tgataatgta gtgaaacagt ataatgaagg taagctcaat    840
attactgctg caatgaatgc tttaaatagt attaagcaag cagcacagga agttgcccag    900
aaaaacttac aaaagcagta tgctaaaaaa attgaaagaa taagttcaaa aggattagcg    960
ttatctaaaa aggctaaaga aatttatgaa aagcataaaa gtattttgcc tacacctgga   1020
tattatgcag actctgtggg aacttatttg aataggttta gagataaaca aactttcgga   1080
aataggagtg tttggactgg tcaaagtgga cttgatgaag caaaaaaaat gcttgatgaa   1140
gtcaaaaagc ttttaaaaga acttcaagac cttaccagag gtactaaaga agataaaaaa   1200
ccagacgtta agccagaagc caaaccagag gccaaaccag acgttaagcc agaggccaaa   1260
ccagacgtta agccagaagc taagccagac gttaaaccag aagctaagcc agacgttaaa   1320
ccagaagcta agccagacgt taaaccagaa gctaagccag acgttaaacc aaaggccaaa   1380
ccagacgtta agccagaagc taagccagac gttaaaccag acgttaaacc agacgttaag   1440
ccagaggcca accagagga taagccagac gttaaaccag acgttaagcc agaagctaaa   1500
ccagacgtta agccagaggc caaaccagaa gctaagccag aagctaagcc agaagctaag   1560
ccagaggcca accagaagc taagccagac gttaagccag aagctaaacc agacgttaaa   1620
ccagaggcta agccagaagc taaaccagag gctaagtcag aagctaaacc agaggctaag   1680
ctagaagcta accagaggc caaaccagca accaaaaaat cggttaatac tagcggaaac   1740
ttggcggcta aaaagctat tgaaaacaaa agtatagta aaaaattacc atcaacgggt   1800
gaagccgcaa gtccactctt agcaattgta tcactaattg ttatgttaag tgcaggtctt   1860
attacgatag ttttaaagca taaaaaaaat                                     1890

<210> SEQ ID NO 17
<211> LENGTH: 585
<212> TYPE: DNA
<213> ORGANISM: Group B Streptococcus

<400> SEQUENCE: 17
ccagacgtta agccagaagc caaaccagag gccaaaccag acgttaagcc agaggccaaa     60
ccagacgtta agccagaagc taagccagac gttaaaccag aagctaagcc agacgttaaa    120
ccagaagcta agccagacgt taaaccagaa gctaagccag acgttaaacc aaaggccaaa    180
ccagacgtta agccagaagc taagccagac gttaaaccag acgttaaacc agacgttaag    240
ccagaggcca accagagga taagccagac gttaaaccag acgttaagcc agaagctaaa    300
ccagacgtta agccagaggc caaaccagaa gctaagccag aagctaagcc agaagctaag    360
ccagaggcca accagaagc taagccagac gttaagccag aagctaaacc agacgttaaa    420
ccagaggcta agccagaagc taaaccagag gctaagtcag aagctaaacc agaggctaag    480
ctagaagcta accagaggc caaaccagca accaaaaaat cggttaatac tagcggaaac    540
ttggcggcta aaaagctat tgaaaacaaa agtatagta aaaaa                      585

<210> SEQ ID NO 18
<211> LENGTH: 1410
<212> TYPE: DNA
<213> ORGANISM: Group B Streptococcus

<400> SEQUENCE: 18
ggtattgtac acgcggatac tagttcagga atatcggctt caattcctca taagaaacaa     60
gttaatttag gggcggttac tctgaagaat ttgatttcta aatatcgtgg taatgacaaa    120
```

```
gctattgcta tacttttaag tagagtaaat gattttaata gagcatcaca ggatacactt      180
ccacaattaa ttaatagtac tgaagcagaa attagaaata ttttatatca aggacaaatt      240
ggtaagcaaa ataaaccaag tgtaactaca catgctaaag ttagtgatca agaactaggt      300
aagcagtcaa gacgttctca agatatcatt aagtcattag gtttcctttc atcagaccaa      360
aaagatattt tagttaaatc tattagctct tcaaaagatt cgcaacttat tcttaaattt      420
gtaactcaag ccacgcaact gaataatgct gaatcaacaa agctaagca aatggctcaa       480 aatgacgtgg ccttaataaa aaatataagc cccgaagtct tagaagaata taagaaaaaa      540
attcaaagag ctagcactaa gagtcaagtt gatgagtttg tagcagaagc taaaaaagtt      600
gttaattcca ataaagaaac gttggtaaat caggccaatg gtaaaaagca agaaattgct      660
aagttagaaa atttatctaa cgatgaaatg ttgagatata atactgcaat tgataatgta      720
gtgaaacagt ataatgaagg taagctcaat attactgctg caatgaatgc tttaaatagt      780
attaagcaag cagcacagga agttgcccag aaaaacttac aaaagcagta tgctaaaaaa      840
attgaaagaa taagttcaaa aggattagcg ttatctaaaa aggctaaaga aatttatgaa       900
aagcataaaa gtattttgcc tacacctgga tattatgcag actctgtggg aacttatttg      960
aataggttta gagataaaca aactttcgga aataggagtg tttggactgg tcaaagtgga     1020
cttgatgaag caaaaaaaat gcttgatgaa gtcaaaaagc ttttaaaaga acttcaagac     1080
cttaccagag gtactaaaga agataaaaaa ccagacgtta agccagaagc caaaccagag     1140
gccaaaccag acgttaagcc agaggccaaa ccagacgtta agccagaagc taagccagac     1200
gttaaaccag aagctaagcc agacgttaaa ccagaagcta agccagacgt taaaccagaa     1260
gctaagccag acgttaaacc aaaggccaaa ccagacgtta agccagaagc taagccagac     1320
gttaaaccag acgttaaacc agacgttaag ccagaggcca accagagga taagccagac     1380 gttaaaccag acgttaagcc agaagctaaa                                      1410

<210> SEQ ID NO 19
<211> LENGTH: 15
<212> TYPE: DNA
<213> ORGANISM: Group B Streptococcus

<400> SEQUENCE: 19
ttaccatcaa cgggt                                                       15

<210> SEQ ID NO 20
<211> LENGTH: 34
<212> TYPE: DNA
<213> ORGANISM: Group B Streptococcus

<400> SEQUENCE: 20
ggaattccat atgcacgcgg atactagttc agga                                  34

<210> SEQ ID NO 21
<211> LENGTH: 31
<212> TYPE: DNA
<213> ORGANISM: Group B Streptococcus

<400> SEQUENCE: 21
cccgctcgag aattgctaag agtggacttg c                                     31

<210> SEQ ID NO 22
<211> LENGTH: 1728
<212> TYPE: DNA
<213> ORGANISM: Group B Streptococcus
```

<400> SEQUENCE: 22

```
cacgcggata ctagttcagg aatatcggct tcaattcctc ataagaaaca agttaattta        60
ggggcggtta ctctgaagaa tttgatttct aaatatcgtg gtaatgacaa agctattgct       120
atacttttaa gtagagtaaa tgattttaat agagcatcac aggatacact tccacaatta       180
attaatagta ctgaagcaga aattagaaat attttatatc aaggacaaat tggtaagcaa       240
aataaaccaa gtgtaactac acatgctaaa gttagtgatc aagaactagg taagcagtca       300
agacgttctc aagatatcat taagtcatta ggtttccttt catcagacca aaaagatatt       360
ttagttaaat ctattagctc ttcaaaagat tcgcaactta ttcttaaatt tgtaactcaa       420
gccacgcaac tgaataatgc tgaatcaaca aaagctaagc aaatggctca aaatgacgtg       480
gccttaataa aaaatataag ccccgaagtc ttagaagaat ataagaaaaa aattcaaaga       540
gctagcacta agagtcaagt tgatgagttt gtagcagaag ctaaaaaagt tgttaattcc       600
aataaagaaa cgttggtaaa tcaggccaat ggtaaaaagc aagaaattgc taagttagaa       660
aatttatcta acgatgaaat gttgagatat aatactgcaa ttgataatgt agtgaaacag       720
tataatgaag gtaagctcaa tattactgct gcaatgaatg cttttaaatag tattaagcaa       780
gcagcacagg aagttgccca gaaaaactta caaaagcagt atgctaaaaa aattgaaaga       840
ataagttcaa aaggattagc gttatctaaa aaggctaaaa aatttatga aaagcataaa       900
agtattttgc ctacacctgg atattatgca gactctgtgg gaacttattt gaataggttt       960
agagataaac aaactttcgg aaataggagt gtttggactg gtcaaagtgg acttgatgaa      1020
gcaaaaaaaa tgcttgatga agtcaaaaag cttttaaaag aacttcaaga ccttaccaga      1080
ggtactaaag aagataaaaa accagacgtt aagccagaac ccaaaccaga ggccaaacca      1140
gacgttaagc cagaggccaa accagacgtt aagccagaag ctaagccaga cgttaaacca      1200
gaagctaagc cagacgttaa accagaagct aagccagacg ttaaaccaga agctaagcca      1260
gacgttaaac caaaggccaa accagacgtt aagccagaag ctaagccaga cgttaaacca      1320
gacgttaaac cagacgttaa gccagaggcc aaaccagagg ataagccaga cgttaaacca      1380
gacgttaagc cagaagctaa accagacgtt aagccagagg ccaaaccaga agctaagcca      1440
gaagctaagc cagaagctaa gccagaggcc aaaccagaag ctaagccaga cgttaagcca      1500
gaagctaaac cagacgttaa accagaggct aagccagaag ctaaaccaga ggctaagtca      1560
gaagctaaac cagaggctaa gctagaagct aaaccagagg ccaaaccagc aaccaaaaaa      1620
tcggttaata ctagcggaaa cttggcggct aaaaaagcta ttgaaaacaa aaagtatagt      1680
aaaaaattac catcaacggg tgaagccgca agtccactct tagcaatt                    1728
```

<210> SEQ ID NO 23
<211> LENGTH: 598
<212> TYPE: PRT
<213> ORGANISM: Group B Streptococcus

<400> SEQUENCE: 23

```
Met His Ala Asp Thr Ser Ser Gly Ile Ser Ala Ser Ile Pro His Lys
  1               5                  10                  15

Lys Gln Val Asn Leu Gly Ala Val Thr Leu Lys Asn Leu Ile Ser Lys
                 20                  25                  30

Tyr Arg Gly Asn Asp Lys Ala Ile Ala Ile Leu Leu Ser Arg Val Asn
             35                  40                  45

Asp Phe Asn Arg Ala Ser Gln Asp Thr Leu Pro Gln Leu Ile Asn Ser
         50                  55                  60
```

```
Thr Glu Ala Glu Ile Arg Asn Ile Leu Tyr Gln Gly Gln Ile Gly Lys
 65                  70                  75                  80

Gln Asn Lys Pro Ser Val Thr Thr His Ala Lys Val Ser Asp Gln Glu
                 85                  90                  95

Leu Gly Lys Gln Ser Arg Arg Ser Gln Asp Ile Ile Lys Ser Leu Gly
            100                 105                 110

Phe Leu Ser Ser Asp Gln Lys Asp Ile Leu Val Lys Ser Ile Ser Ser
        115                 120                 125

Ser Lys Asp Ser Gln Leu Ile Leu Lys Phe Val Thr Gln Ala Thr Gln
130                 135                 140

Leu Asn Asn Ala Glu Ser Thr Lys Ala Lys Gln Met Ala Gln Asn Asp
145                 150                 155                 160

Val Ala Leu Ile Lys Asn Ile Ser Pro Glu Val Leu Glu Glu Tyr Lys
                165                 170                 175

Glu Lys Ile Gln Arg Ala Ser Thr Lys Ser Gln Val Asp Glu Phe Val
            180                 185                 190

Ala Glu Ala Lys Lys Val Val Asn Ser Asn Lys Glu Thr Leu Val Asn
        195                 200                 205

Gln Ala Asn Gly Lys Lys Gln Glu Ile Ala Lys Leu Glu Asn Leu Ser
210                 215                 220

Asn Asp Glu Met Leu Arg Tyr Asn Thr Ala Ile Asp Asn Val Val Lys
225                 230                 235                 240

Gln Tyr Asn Glu Gly Lys Leu Asn Ile Thr Ala Ala Met Asn Ala Leu
                245                 250                 255

Asn Ser Ile Lys Gln Ala Ala Gln Glu Val Ala Gln Lys Asn Leu Gln
            260                 265                 270

Lys Gln Tyr Ala Lys Lys Ile Glu Arg Ile Ser Ser Lys Gly Leu Ala
        275                 280                 285

Leu Ser Lys Lys Ala Lys Glu Ile Tyr Glu Lys His Lys Ser Ile Leu
290                 295                 300

Pro Thr Pro Gly Tyr Tyr Ala Asp Ser Val Gly Thr Tyr Leu Asn Arg
305                 310                 315                 320

Phe Arg Asp Lys Gln Thr Phe Gly Asn Arg Ser Val Trp Thr Gly Gln
                325                 330                 335

Ser Gly Leu Asp Glu Ala Lys Lys Met Leu Asp Glu Val Lys Lys Leu
            340                 345                 350

Leu Lys Glu Leu Gln Asp Leu Thr Arg Gly Thr Lys Glu Asp Lys Lys
        355                 360                 365

Pro Asp Val Lys Pro Glu Ala Lys Pro Glu Ala Lys Pro Asp Val Lys
370                 375                 380

Pro Glu Ala Lys Pro Asp Val Lys Pro Glu Ala Lys Pro Asp Val Lys
385                 390                 395                 400

Pro Glu Ala Lys Pro Asp Val Lys Pro Glu Ala Lys Pro Asp Val Lys
                405                 410                 415

Pro Glu Ala Lys Pro Asp Val Lys Pro Lys Ala Lys Pro Asp Val Lys
            420                 425                 430

Pro Glu Ala Lys Pro Asp Val Lys Pro Asp Val Lys Pro Asp Val Lys
        435                 440                 445

Pro Glu Ala Lys Pro Glu Asp Lys Pro Asp Val Lys Pro Asp Val Lys
450                 455                 460

Pro Glu Ala Lys Pro Asp Val Lys Pro Glu Ala Lys Pro Glu Ala Lys
465                 470                 475                 480

Pro Glu Ala Lys Pro Glu Ala Lys Pro Glu Ala Lys Pro Glu Ala Lys
```

```
                485                 490                 495
Pro Asp Val Lys Pro Glu Ala Lys Pro Asp Val Lys Pro Glu Ala Lys
            500                 505                 510

Pro Glu Ala Lys Pro Glu Ala Lys Ser Glu Ala Lys Pro Glu Ala Lys
            515                 520                 525

Leu Glu Ala Lys Pro Glu Ala Lys Pro Ala Thr Lys Lys Ser Val Asn
            530                 535                 540

Thr Ser Gly Asn Leu Ala Ala Lys Lys Ala Ile Glu Asn Lys Lys Tyr
545                 550                 555                 560

Ser Lys Lys Leu Pro Ser Thr Gly Glu Ala Ala Ser Pro Leu Leu Ala
                565                 570                 575

Ile Val Ser Leu Ile Val Met Leu Ser Ala Gly Leu Ile Thr Leu Glu
            580                 585                 590

His His His His His His
        595

<210> SEQ ID NO 24
<211> LENGTH: 34
<212> TYPE: DNA
<213> ORGANISM: Group B Streptococcus

<400> SEQUENCE: 24
ggaattccat atgcacgcgg atactagttc agga                              34

<210> SEQ ID NO 25
<211> LENGTH: 30
<212> TYPE: DNA
<213> ORGANISM: Group B Streptococcus

<400> SEQUENCE: 25
cccgctcgag acctctggta aggtcttgaa                                   30

<210> SEQ ID NO 26
<211> LENGTH: 1083
<212> TYPE: DNA
<213> ORGANISM: Group B Streptococcus

<400> SEQUENCE: 26
cacgcggata ctagttcagg aatatcggct tcaattcctc ataagaaaca agttaattta    60
ggggcggtta ctctgaagaa tttgatttct aaatatcgtg gtaatgacaa agctattgct   120
atacttttaa gtagagtaaa tgattttaat agagcatcac aggatacact tccacaatta   180
attaatagta ctgaagcaga attagaaat attttatatc aaggacaaat tggtaagcaa    240
aataaaccaa gtgtaactac acatgctaaa gttagtgatc aagaactagg taagcagtca   300
agacgttctc aagatatcat taagtcatta ggtttccttt catcagacca aaagatatt    360 ttagttaaat ctattagctc ttcaaaagat tcgcaactta ttcttaaatt tgtaactcaa   420
gccacgcaac tgaataatgc tgaatcaaca aaagctaagc aaatggctca aatgacgtg    480 gccttaataa aaatataag ccccgaagtc ttagaagaat ataagaaaa aattcaaaga    540 gctagcacta gagtcaagt tgatgagttt gtagcagaag ctaaaaaagt tgttaattcc   600
aataaagaaa cgttggtaaa tcaggccaat ggtaaaaagc aagaaattgc taagttagaa   660
aatttatcta acgatgaaat gttgagatat aatactgcaa tgataatgt agtgaaacag    720 tataatgaag gtaagctcaa tattactgct gcaatgaatg ctttaaatag tattaagcaa   780
gcagcacagg aagttgccca gaaaacttta caaaagcagt atgctaaaaa aattgaagag   840
ataagttcaa aaggattagc gttatctaaa aaggctaaag aaatttatga aaagcataaa   900
```

```
agtattttgc ctacacctgg atattatgca gactctgtgg gaacttattt gaataggttt    960
agagataaac aaactttcgg aaataggagt gtttggactg gtcaaagtgg acttgatgaa   1020
gcaaaaaaaa tgcttgatga agtcaaaaag ctttttaaaag aacttcaaga ccttaccaga   1080
ggt                                                                 1083
```

<210> SEQ ID NO 27
<211> LENGTH: 370
<212> TYPE: PRT
<213> ORGANISM: Group B Streptococcus

<400> SEQUENCE: 27

```
Met His Ala Asp Thr Ser Ser Gly Ile Ser Ala Ser Ile Pro His Lys
 1               5                  10                  15

Lys Gln Val Asn Leu Gly Ala Val Thr Leu Lys Asn Leu Ile Ser Lys
            20                  25                  30

Tyr Arg Gly Asn Asp Lys Ala Ile Ala Ile Leu Leu Ser Arg Val Asn
        35                  40                  45

Asp Phe Asn Arg Ala Ser Gln Asp Thr Leu Pro Gln Leu Ile Asn Ser
 50                  55                  60

Thr Glu Ala Glu Ile Arg Asn Ile Leu Tyr Gln Gly Gln Ile Gly Lys
65                  70                  75                  80

Gln Asn Lys Pro Ser Val Thr Thr His Ala Lys Val Ser Asp Gln Glu
                85                  90                  95

Leu Gly Lys Gln Ser Arg Arg Ser Gln Asp Ile Ile Lys Ser Leu Gly
            100                 105                 110

Phe Leu Ser Ser Asp Gln Lys Asp Ile Leu Val Lys Ser Ile Ser Ser
        115                 120                 125

Ser Lys Asp Ser Gln Leu Ile Leu Lys Phe Val Thr Gln Ala Thr Gln
130                 135                 140

Leu Asn Asn Ala Glu Ser Thr Lys Ala Lys Gln Met Ala Gln Asn Asp
145                 150                 155                 160

Val Ala Leu Ile Lys Asn Ile Ser Pro Glu Val Leu Glu Glu Tyr Lys
                165                 170                 175

Glu Lys Ile Gln Arg Ala Ser Thr Lys Ser Gln Val Asp Glu Phe Val
            180                 185                 190

Ala Glu Ala Lys Lys Val Val Asn Ser Asn Lys Glu Thr Leu Val Asn
        195                 200                 205

Gln Ala Asn Gly Lys Lys Gln Glu Ile Ala Lys Leu Glu Asn Leu Ser
    210                 215                 220

Asn Asp Glu Met Leu Arg Tyr Asn Thr Ala Ile Asp Asn Val Val Lys
225                 230                 235                 240

Gln Tyr Asn Glu Gly Lys Leu Asn Ile Thr Ala Ala Met Asn Ala Leu
                245                 250                 255

Asn Ser Ile Lys Gln Ala Ala Gln Glu Val Ala Gln Lys Asn Leu Gln
            260                 265                 270

Lys Gln Tyr Ala Lys Lys Ile Glu Arg Ile Ser Ser Lys Gly Leu Ala
        275                 280                 285

Leu Ser Lys Lys Ala Lys Glu Ile Tyr Glu Lys His Lys Ser Ile Leu
    290                 295                 300

Pro Thr Pro Gly Tyr Tyr Ala Asp Ser Val Gly Thr Tyr Leu Asn Arg
305                 310                 315                 320

Phe Arg Asp Lys Gln Thr Phe Gly Asn Arg Ser Val Trp Thr Gly Gln
                325                 330                 335
```

```
Ser Gly Leu Asp Glu Ala Lys Lys Met Leu Asp Glu Val Lys Lys Leu
            340                 345                 350

Leu Lys Glu Leu Gln Asp Leu Thr Arg Gly Leu Glu His His His
        355                 360                 365

His His
    370

<210> SEQ ID NO 28
<211> LENGTH: 32
<212> TYPE: DNA
<213> ORGANISM: Group B Streptococcus

<400> SEQUENCE: 28
ggaattccat atggctgaat caacaaaagc ta                                32

<210> SEQ ID NO 29
<211> LENGTH: 30
<212> TYPE: DNA
<213> ORGANISM: Group B Streptococcus

<400> SEQUENCE: 29
cccgctcgag acctctggta aggtcttgaa                                   30

<210> SEQ ID NO 30
<211> LENGTH: 645
<212> TYPE: DNA
<213> ORGANISM: Group B Streptococcus

<400> SEQUENCE: 30
gctgaatcaa caaaagctaa gcaaatggct caaaatgacg tggccttaat aaaaaatata   60
agccccgaag tcttagaaga atataaagaa aaaattcaaa gagctagcac taagagtcaa  120
gttgatgagt ttgtagcaga agctaaaaaa gttgttaatt ccaataaaga aacgttggta  180
aatcaggcca atggtaaaaa gcaagaaatt gctaagttag aaaatttatc taacgatgaa  240
atgttgagat ataatactgc aattgataat gtagtgaaac agtataatga aggtaagctc  300
aatattactg ctgcaatgaa tgctttaaat agtattaagc aagcagcaca ggaagttgcc  360
cagaaaaact acaaaagca gtatgctaaa aaaattgaaa gaataagttc aaaaggatta  420
gcgttatcta aaaaggctaa agaaatttat gaaaagcata aagtatttt gcctacacct  480
ggatattatg cagactctgt gggaacttat ttgaataggt ttagagataa acaaactttc  540
ggaaatagga gtgtttggac tggtcaaagt ggacttgatg aagcaaaaaa aatgcttgat  600
gaagtcaaaa agcttttaaa agaacttcaa gaccttacca gaggt               645

<210> SEQ ID NO 31
<211> LENGTH: 224
<212> TYPE: PRT
<213> ORGANISM: Group B Streptococcus

<400> SEQUENCE: 31

Met Ala Glu Ser Thr Lys Ala Lys Gln Met Ala Gln Asn Asp Val Ala
  1               5                  10                  15

Leu Ile Lys Asn Ile Ser Pro Glu Val Leu Glu Glu Tyr Lys Glu Lys
             20                  25                  30

Ile Gln Arg Ala Ser Thr Lys Ser Gln Val Asp Glu Phe Val Ala Glu
         35                  40                  45

Ala Lys Lys Val Val Asn Ser Asn Lys Glu Thr Leu Val Asn Gln Ala
     50                  55                  60

Asn Gly Lys Lys Gln Glu Ile Ala Lys Leu Glu Asn Leu Ser Asn Asp
```

```
                65                  70                  75                  80
Glu Met Leu Arg Tyr Asn Thr Ala Ile Asp Asn Val Val Lys Gln Tyr
                        85                  90                  95

Asn Glu Gly Lys Leu Asn Ile Thr Ala Ala Met Asn Ala Leu Asn Ser
                100                 105                 110

Ile Lys Gln Ala Ala Gln Glu Val Ala Gln Lys Asn Leu Gln Lys Gln
                115                 120                 125

Tyr Ala Lys Lys Ile Glu Arg Ile Ser Ser Lys Gly Leu Ala Leu Ser
        130                 135                 140

Lys Lys Ala Lys Glu Ile Tyr Glu Lys His Lys Ser Ile Leu Pro Thr
145                 150                 155                 160

Pro Gly Tyr Tyr Ala Asp Ser Val Gly Thr Tyr Leu Asn Arg Phe Arg
                165                 170                 175

Asp Lys Gln Thr Phe Gly Asn Arg Ser Val Trp Thr Gly Gln Ser Gly
                180                 185                 190

Leu Asp Glu Ala Lys Lys Met Leu Asp Glu Val Lys Lys Leu Leu Lys
        195                 200                 205

Glu Leu Gln Asp Leu Thr Arg Gly Leu Glu His His His His His His
    210                 215                 220
```

<210> SEQ ID NO 32
<211> LENGTH: 31
<212> TYPE: DNA
<213> ORGANISM: Group B Streptococcus

<400> SEQUENCE: 32
ggaattccat atgccagacc ttaccagagg t                                    31

<210> SEQ ID NO 33
<211> LENGTH: 29
<212> TYPE: DNA
<213> ORGANISM: Group B Streptococcus

<400> SEQUENCE: 33
cccgctcgag cgtaataaga cctgcactt                                       29

<210> SEQ ID NO 34
<211> LENGTH: 702
<212> TYPE: DNA
<213> ORGANISM: Group B Streptococcus

<400> SEQUENCE: 34
caagacctta ccagaggtac taagaagat aaaaaaccag acgttaagcc agaagccaaa      60
ccagaggcca aaccagacgt taagccagag gccaaaccag acgttaagcc agaagctaag    120
ccagacgtta accagaagc taagccagac gttaaaccag aagctaagcc agacgttaaa    180
ccagaagcta agccagacgt taaaccaaag gccaaaccag acgttaagcc agaagctaag    240
ccagacgtta accagacgt taaccagac gttaagccag aggccaaacc agaggataag      300
ccagacgtta accagacgt taagccagaa gctaaccag acgttaagcc agaggccaaa      360
ccagaagcta agccagaagc taagccagaa gctaagccag aggccaaacc agaagctaag    420
ccagacgtta agccagaagc taaccagac gttaaccag aggctaagcc agaagctaaa      480
ccagaggcta agtcagaagc taaccagag gctaagctag aagctaaacc agaggccaaa    540
ccagcaacca aaaatcggt taatactagc ggaaacttgg cggctaaaaa agctattgaa    600
aacaaaaagt atagtaaaaa attaccatca acgggtgaag ccgcaagtcc actcttagca    660
attgtatcac taattgttat gttaagtgca ggtcttatta cg                       702

<210> SEQ ID NO 35
<211> LENGTH: 243
<212> TYPE: PRT
<213> ORGANISM: Group B Streptococcus

<400> SEQUENCE: 35

```
Met Gln Asp Leu Thr Arg Gly Thr Lys Glu Asp Lys Lys Pro Asp Val
 1               5                  10                  15
Lys Pro Glu Ala Lys Pro Glu Ala Lys Pro Asp Val Lys Pro Glu Ala
                20                  25                  30
Lys Pro Asp Val Lys Pro Glu Ala Lys Pro Asp Val Lys Pro Glu Ala
            35                  40                  45
Lys Pro Asp Val Lys Pro Glu Ala Lys Pro Asp Val Lys Pro Glu Ala
        50                  55                  60
Lys Pro Asp Val Lys Pro Lys Ala Lys Pro Asp Val Lys Pro Glu Ala
65                  70                  75                  80
Lys Pro Asp Val Lys Pro Asp Val Lys Pro Asp Val Lys Pro Glu Ala
                85                  90                  95
Lys Pro Glu Asp Lys Pro Asp Val Lys Pro Asp Val Lys Pro Glu Ala
            100                 105                 110
Lys Pro Asp Val Lys Pro Glu Ala Lys Pro Glu Ala Lys Pro Glu Ala
        115                 120                 125
Lys Pro Glu Ala Lys Pro Glu Ala Lys Pro Glu Ala Lys Pro Asp Val
    130                 135                 140
Lys Pro Glu Ala Lys Pro Asp Val Lys Pro Glu Ala Lys Pro Glu Ala
145                 150                 155                 160
Lys Pro Glu Ala Lys Ser Glu Ala Lys Pro Glu Ala Lys Leu Glu Ala
                165                 170                 175
Lys Pro Glu Ala Lys Pro Ala Thr Lys Lys Ser Val Asn Thr Ser Gly
            180                 185                 190
Asn Leu Ala Ala Lys Lys Ala Ile Glu Asn Lys Lys Tyr Ser Lys Lys
        195                 200                 205
Leu Pro Ser Thr Gly Glu Ala Ala Ser Pro Leu Leu Ala Ile Val Ser
    210                 215                 220
Leu Ile Val Met Leu Ser Ala Gly Leu Ile Thr Leu Glu His His His
225                 230                 235                 240
His His His
```

<210> SEQ ID NO 36
<211> LENGTH: 32
<212> TYPE: DNA
<213> ORGANISM: Group B Streptococcus

<400> SEQUENCE: 36
ggaattccat atggctgaat caacaaaagc ta     32

<210> SEQ ID NO 37
<211> LENGTH: 29
<212> TYPE: DNA
<213> ORGANISM: Group B Streptococcus

<400> SEQUENCE: 37
cccgctcgag cgtaataaga cctgcactt     29

<210> SEQ ID NO 38
<211> LENGTH: 1329
<212> TYPE: DNA

-continued

<213> ORGANISM: Group B Streptococcus

<400> SEQUENCE: 38

```
gctgaatcaa caaaagctaa gcaaatggct caaaatgacg tggccttaat aaaaaatata    60
agccccgaag tcttagaaga atataaagaa aaaattcaaa gagctagcac taagagtcaa   120
gttgatgagt ttgtagcaga agctaaaaaa gttgttaatt ccaataaaga aacgttggta   180
aatcaggcca atggtaaaaa gcaagaaatt gctaagttag aaaatttatc taacgatgaa   240
atgttgagat ataatactgc aattgataat gtagtgaaac agtataatga aggtaagctc   300
aatattactg ctgcaatgaa tgctttaaat agtattaagc aagcagcaca ggaagttgcc   360
cagaaaaact acaaaagca gtatgctaaa aaaattgaaa gaataagttc aaaaggatta   420
gcgttatcta aaaaggctaa agaaatttat gaaaagcata aaagtatttt gcctacacct   480
ggatattatg cagactctgt gggaacttat ttgaataggt ttagagataa acaaactttc   540
ggaaatagga gtgtttggac tggtcaaagt ggacttgatg aagcaaaaaa aatgcttgat   600
gaagtcaaaa agcttttaaa agaacttcaa gaccttacca gaggtactaa agaagataaa   660
aaaccagacg ttaagccaga agccaaacca gaggccaaac cagacgttaa gccagaggcc   720
aaaccagacg ttagccaga agctaagcca gacgttaaac cagaagctaa gccagacgtt   780
aaaccagaag ctaagccaga cgttaaacca gaagctaagc cagacgttaa ccaaaggcc   840
aaaccagacg ttaagccaga agctaagcca gacgttaaac cagacgttaa ccagacgtt   900
aagccagagg ccaaaccaga ggataagcca gacgttaaac cagacgttaa gccagaagct   960
aaaccagacg ttaagccaga ggccaaacca gaagctaagc cagaagctaa gccagaagct  1020
aagccagagg ccaaaccaga agctaagcca gacgttaagc cagaagctaa accagacgtt  1080
aaaccagagg ctaagccaga agctaaacca gaggctaagt cagaagctaa accagaggct  1140
aagctagaag ctaaaccaga ggccaaacca gcaaccaaaa aatcggttaa tactagcgga  1200
aacttggcgg ctaaaaaagc tattgaaaac aaaaagtata gtaaaaaatt accatcaacg  1260
ggtgaagccg caagtccact cttagcaatt gtatcactaa ttgttatgtt aagtgcaggt  1320
cttattacg                                                           1329
```

<210> SEQ ID NO 39
<211> LENGTH: 452
<212> TYPE: PRT
<213> ORGANISM: Group B Streptococcus

<400> SEQUENCE: 39

```
Met Ala Glu Ser Thr Lys Ala Lys Gln Met Ala Gln Asn Asp Val Ala
 1               5                  10                  15

Leu Ile Lys Asn Ile Ser Pro Glu Val Leu Glu Tyr Lys Glu Lys
             20                  25                  30

Ile Gln Arg Ala Ser Thr Lys Ser Gln Val Asp Glu Phe Val Ala Glu
         35                  40                  45

Ala Lys Lys Val Val Asn Ser Asn Lys Glu Thr Leu Val Asn Gln Ala
     50                  55                  60

Asn Gly Lys Lys Gln Glu Ile Ala Lys Leu Glu Asn Leu Ser Asn Asp
 65                  70                  75                  80

Glu Met Leu Arg Tyr Asn Thr Ala Ile Asp Asn Val Val Lys Gln Tyr
                 85                  90                  95

Asn Glu Gly Lys Leu Asn Ile Thr Ala Ala Met Asn Ala Leu Asn Ser
            100                 105                 110

Ile Lys Gln Ala Ala Gln Glu Val Ala Gln Lys Asn Leu Gln Lys Gln
```

```
                 115                 120                 125
Tyr Ala Lys Lys Ile Glu Arg Ile Ser Ser Lys Gly Leu Ala Leu Ser
130                 135                 140

Lys Lys Ala Lys Glu Ile Tyr Glu Lys His Lys Ser Ile Leu Pro Thr
145                 150                 155                 160

Pro Gly Tyr Tyr Ala Asp Ser Val Gly Thr Tyr Leu Asn Arg Phe Arg
                165                 170                 175

Asp Lys Gln Thr Phe Gly Asn Arg Ser Val Trp Thr Gly Gln Ser Gly
            180                 185                 190

Leu Asp Glu Ala Lys Lys Met Leu Asp Glu Val Lys Lys Leu Leu Lys
        195                 200                 205

Glu Leu Gln Asp Leu Thr Arg Gly Thr Lys Glu Asp Lys Lys Pro Asp
    210                 215                 220

Val Lys Pro Glu Ala Lys Pro Glu Ala Lys Pro Asp Val Lys Pro Glu
225                 230                 235                 240

Ala Lys Pro Asp Val Lys Pro Glu Ala Lys Pro Asp Val Lys Pro Glu
                245                 250                 255

Ala Lys Pro Asp Val Lys Pro Glu Ala Lys Pro Asp Val Lys Pro Glu
            260                 265                 270

Ala Lys Pro Asp Val Lys Pro Lys Ala Lys Pro Asp Val Lys Pro Glu
        275                 280                 285

Ala Lys Pro Asp Val Lys Pro Asp Val Lys Pro Asp Val Lys Pro Glu
    290                 295                 300

Ala Lys Pro Glu Asp Lys Pro Asp Val Lys Pro Asp Val Lys Pro Glu
305                 310                 315                 320

Ala Lys Pro Asp Val Lys Pro Glu Ala Lys Pro Glu Ala Lys Pro Glu
                325                 330                 335

Ala Lys Pro Glu Ala Lys Pro Glu Ala Lys Pro Glu Ala Lys Pro Asp
            340                 345                 350

Val Lys Pro Glu Ala Lys Pro Asp Val Lys Pro Glu Ala Lys Pro Glu
        355                 360                 365

Ala Lys Pro Glu Ala Lys Ser Glu Ala Lys Pro Glu Ala Lys Leu Glu
    370                 375                 380

Ala Lys Pro Glu Ala Lys Pro Ala Thr Lys Lys Ser Val Asn Thr Ser
385                 390                 395                 400

Gly Asn Leu Ala Ala Lys Lys Ala Ile Glu Asn Lys Lys Tyr Ser Lys
                405                 410                 415

Lys Leu Pro Ser Thr Gly Glu Ala Ala Ser Pro Leu Leu Ala Ile Val
            420                 425                 430

Ser Leu Ile Val Met Leu Ser Ala Gly Leu Ile Thr Leu Glu His His
        435                 440                 445

His His His His
    450

<210> SEQ ID NO 40
<211> LENGTH: 34
<212> TYPE: DNA
<213> ORGANISM: Group B Streptococcus

<400> SEQUENCE: 40
ggaattccat atgcacgcgg atactagttc agga                               34

<210> SEQ ID NO 41
<211> LENGTH: 34
<212> TYPE: DNA
<213> ORGANISM: Group B Streptococcus
```

<400> SEQUENCE: 41
cccgctcgag attattcagt tgcgtggctt gagt                                34

<210> SEQ ID NO 42
<211> LENGTH: 438
<212> TYPE: DNA
<213> ORGANISM: Group B Streptococcus

<400> SEQUENCE: 42
cacgcggata ctagttcagg aatatcggct tcaattcctc ataagaaaca agttaattta    60
ggggcggtta ctctgaagaa tttgatttct aaatatcgtg gtaatgacaa agctattgct   120
atactttaa gtagagtaaa tgattttaat agagcatcac aggatacact tccacaatta    180
attaatagta ctgaagcaga aattagaaat attttatatc aaggacaaat tggtaagcaa   240
aataaaccaa gtgtaactac acatgctaaa gttagtgatc aagaactagg taagcagtca   300
agacgttctc aagatatcat taagtcatta ggtttccttt catcagacca aaaagatatt   360
ttagttaaat ctattagctc ttcaaaagat tcgcaactta ttcttaaatt tgtaactcaa   420
gccacgcaac tgaataat                                                 438

<210> SEQ ID NO 43
<211> LENGTH: 155
<212> TYPE: PRT
<213> ORGANISM: Group B Streptococcus

<400> SEQUENCE: 43

Met His Ala Asp Thr Ser Ser Gly Ile Ser Ala Ser Ile Pro His Lys
 1               5                  10                  15

Lys Gln Val Asn Leu Gly Ala Val Thr Leu Lys Asn Leu Ile Ser Lys
            20                  25                  30

Tyr Arg Gly Asn Asp Lys Ala Ile Ala Ile Leu Leu Ser Arg Val Asn
        35                  40                  45

Asp Phe Asn Arg Ala Ser Gln Asp Thr Leu Pro Gln Leu Ile Asn Ser
    50                  55                  60

Thr Glu Ala Glu Ile Arg Asn Ile Leu Tyr Gln Gly Gln Ile Gly Lys
65                  70                  75                  80

Gln Asn Lys Pro Ser Val Thr Thr His Ala Lys Val Ser Asp Gln Glu
                85                  90                  95

Leu Gly Lys Gln Ser Arg Arg Ser Gln Asp Ile Ile Lys Ser Leu Gly
           100                 105                 110

Phe Leu Ser Ser Asp Gln Lys Asp Ile Leu Val Lys Ser Ile Ser Ser
       115                 120                 125

Ser Lys Asp Ser Gln Leu Ile Leu Lys Phe Val Thr Gln Ala Thr Gln
   130                 135                 140

Leu Asn Asn Leu Glu His His His His His
145                 150                 155

<210> SEQ ID NO 44
<211> LENGTH: 31
<212> TYPE: DNA
<213> ORGANISM: Group B Streptococcus

<400> SEQUENCE: 44
cccgctcgag actagtgaca aaccttggaa t                                  31

<210> SEQ ID NO 45
<211> LENGTH: 36

<210> SEQ ID NO 45
<211> LENGTH: 36
<212> TYPE: DNA
<213> ORGANISM: Group B Streptococcus

<400> SEQUENCE: 45
gtcagcacgg tttgccataa accgaaaggt ctatcc                               36

<210> SEQ ID NO 46
<211> LENGTH: 34
<212> TYPE: DNA
<213> ORGANISM: Group B Streptococcus

<400> SEQUENCE: 46
acctttcggt ttatggcaaa cgctgctgac attg                                 34

<210> SEQ ID NO 47
<211> LENGTH: 31
<212> TYPE: DNA
<213> ORGANISM: Group B Streptococcus

<400> SEQUENCE: 47
cccgctcgag acagataagc ctaagcgact t                                    31

<210> SEQ ID NO 48
<211> LENGTH: 32
<212> TYPE: DNA
<213> ORGANISM: Group B Streptococcus

<400> SEQUENCE: 48
ccccgccggg atccccaacc cttatcaaaa ga                                   32

<210> SEQ ID NO 49
<211> LENGTH: 34
<212> TYPE: DNA
<213> ORGANISM: Group B Streptococcus

<400> SEQUENCE: 49
ctctgcatgg tcgacataga aacaacccaa accc                                 34

<210> SEQ ID NO 50
<211> LENGTH: 34
<212> TYPE: DNA
<213> ORGANISM: Group B Streptococcus

<400> SEQUENCE: 50
ggaattccat atgcacgcgg atactagttc agga                                 34

<210> SEQ ID NO 51
<211> LENGTH: 31
<212> TYPE: DNA
<213> ORGANISM: Group B Streptococcus

<400> SEQUENCE: 51
cccgctcgag aattgctaag agtggacttg c                                    31

<210> SEQ ID NO 52
<211> LENGTH: 34
<212> TYPE: DNA
<213> ORGANISM: Group B Streptococcus

<400> SEQUENCE: 52
ggaattccat atgcacgcgg atactagttc agga                                 34

<210> SEQ ID NO 53
<211> LENGTH: 30

```
<212> TYPE: DNA
<213> ORGANISM: Group B Streptococcus

<400> SEQUENCE: 53
cccgctcgag acctctggta aggtcttgaa                                    30

<210> SEQ ID NO 54
<211> LENGTH: 31
<212> TYPE: DNA
<213> ORGANISM: Group B Streptococcus

<400> SEQUENCE: 54
ggaattccat atgccagacc ttaccagagg t                                  31

<210> SEQ ID NO 55
<211> LENGTH: 29
<212> TYPE: DNA
<213> ORGANISM: Group B Streptococcus

<400> SEQUENCE: 55
cccgctcgag cgtaataaga cctgcactt                                     29

<210> SEQ ID NO 56
<211> LENGTH: 630
<212> TYPE: PRT
<213> ORGANISM: Group B Streptococcus

<400> SEQUENCE: 56
```

| Met | Asn | Asn | Asn | Glu | Lys | Lys | Val | Lys | Tyr | Phe | Leu | Arg | Lys | Thr | Ala |
|---|---|---|---|---|---|---|---|---|---|---|---|---|---|---|---|
| 1 | | | | 5 | | | | | 10 | | | | | 15 | |

Tyr Gly Leu Ala Ser Met Ser Ala Ala Phe Ala Val Cys Ser Gly Ile
              20                  25                  30

Val His Ala Asp Thr Ser Ser Gly Ile Ser Ala Ser Ile Pro His Lys
          35                  40                  45

Lys Gln Val Asn Leu Gly Ala Val Thr Leu Lys Asn Leu Ile Ser Lys
     50                  55                  60

Tyr Arg Gly Asn Asp Lys Ala Ile Ala Ile Leu Leu Ser Arg Val Asn
65                  70                  75                  80

Asp Phe Asn Arg Ala Ser Gln Asp Thr Leu Pro Gln Leu Ile Asn Ser
                 85                  90                  95

Thr Glu Ala Glu Ile Arg Asn Ile Leu Tyr Gln Gly Gln Ile Gly Lys
            100                 105                 110

Gln Asn Lys Pro Ser Val Thr Thr His Ala Lys Val Ser Asp Gln Glu
        115                 120                 125

Leu Gly Lys Gln Ser Arg Arg Ser Gln Asp Ile Ile Lys Ser Leu Gly
    130                 135                 140

Phe Leu Ser Ser Asp Gln Lys Asp Ile Leu Val Lys Ser Ile Ser Ser
145                 150                 155                 160

Ser Lys Asp Ser Gln Leu Ile Leu Lys Phe Val Thr Gln Ala Thr Gln
                165                 170                 175

Leu Asn Asn Ala Glu Ser Thr Lys Ala Lys Gln Met Ala Gln Asn Asp
            180                 185                 190

Val Ala Leu Ile Lys Asn Ile Ser Pro Glu Val Leu Glu Glu Tyr Lys
        195                 200                 205

Glu Lys Ile Gln Arg Ala Ser Thr Lys Ser Gln Val Asp Glu Phe Val
    210                 215                 220

Ala Glu Ala Lys Lys Val Val Asn Ser Asn Lys Glu Thr Leu Val Asn
225                 230                 235                 240

-continued

```
Gln Ala Asn Gly Lys Lys Gln Glu Ile Ala Lys Leu Glu Asn Leu Ser
            245                 250                 255
Asn Asp Glu Met Leu Arg Tyr Asn Thr Ala Ile Asp Asn Val Val Lys
        260                 265                 270
Gln Tyr Asn Glu Gly Lys Leu Asn Ile Thr Ala Ala Met Asn Ala Leu
    275                 280                 285
Asn Ser Ile Lys Gln Ala Ala Gln Glu Val Ala Gln Lys Asn Leu Gln
290                 295                 300
Lys Gln Tyr Ala Lys Lys Ile Glu Arg Ile Ser Ser Lys Gly Leu Ala
305                 310                 315                 320
Leu Ser Lys Lys Ala Lys Glu Ile Tyr Glu Lys His Lys Ser Ile Leu
                325                 330                 335
Pro Thr Pro Gly Tyr Tyr Ala Asp Ser Val Gly Thr Tyr Leu Asn Arg
            340                 345                 350
Phe Arg Asp Lys Gln Thr Phe Gly Asn Arg Ser Val Trp Thr Gly Gln
        355                 360                 365
Ser Gly Leu Asp Glu Ala Lys Lys Met Leu Asp Glu Val Lys Lys Leu
    370                 375                 380
Leu Lys Glu Leu Gln Asp Leu Thr Arg Gly Thr Lys Glu Asp Lys Lys
385                 390                 395                 400
Pro Asp Val Lys Pro Glu Ala Lys Pro Glu Ala Lys Pro Asp Val Lys
                405                 410                 415
Pro Glu Ala Lys Pro Asp Val Lys Pro Glu Ala Lys Pro Asp Val Lys
            420                 425                 430
Pro Glu Ala Lys Pro Asp Val Lys Pro Glu Ala Lys Pro Asp Val Lys
        435                 440                 445
Pro Glu Ala Lys Pro Asp Val Lys Pro Lys Ala Lys Pro Asp Val Lys
    450                 455                 460
Pro Glu Ala Lys Pro Asp Val Lys Pro Asp Val Lys Pro Asp Val Lys
465                 470                 475                 480
Pro Glu Ala Lys Pro Glu Asp Lys Pro Asp Val Lys Pro Asp Val Lys
                485                 490                 495
Pro Glu Ala Lys Pro Asp Val Lys Pro Glu Ala Lys Pro Glu Ala Lys
            500                 505                 510
Pro Glu Ala Lys Pro Glu Ala Lys Pro Glu Ala Lys Pro Glu Ala Lys
        515                 520                 525
Pro Asp Val Lys Pro Glu Ala Lys Pro Asp Val Lys Pro Glu Ala Lys
    530                 535                 540
Pro Glu Ala Lys Pro Glu Ala Lys Ser Glu Ala Lys Pro Glu Ala Lys
545                 550                 555                 560
Leu Glu Ala Lys Pro Glu Ala Lys Pro Ala Thr Lys Lys Ser Val Asn
                565                 570                 575
Thr Ser Gly Asn Leu Ala Ala Lys Lys Ala Ile Glu Asn Lys Lys Tyr
            580                 585                 590
Ser Lys Lys Leu Pro Ser Thr Gly Glu Ala Ala Ser Pro Leu Leu Ala
        595                 600                 605
Ile Val Ser Leu Ile Val Met Leu Ser Ala Gly Leu Ile Thr Ile Val
    610                 615                 620
Leu Lys His Lys Lys Asn
625                 630

<210> SEQ ID NO 57
<211> LENGTH: 630
<212> TYPE: PRT
<213> ORGANISM: Group B Streptococcus
```

<400> SEQUENCE: 57

```
Met Asn Asn Asn Glu Lys Lys Val Lys Tyr Phe Leu Arg Lys Thr Ala
1               5                   10                  15
Tyr Gly Leu Ala Ser Met Ser Ala Ala Phe Ala Val Cys Ser Gly Ile
            20                  25                  30
Val His Ala Asp Thr Ser Ser Gly Ile Ser Ala Ser Ile Pro His Lys
        35                  40                  45
Lys Gln Val Asn Leu Gly Ala Val Thr Leu Lys Asn Leu Ile Ser Lys
    50                  55                  60
Tyr Arg Gly Asn Asp Lys Ala Ile Ala Ile Leu Leu Ser Arg Val Asn
65                  70                  75                  80
Asp Phe Asn Arg Ala Ser Gln Asp Thr Leu Pro Gln Leu Ile Asn Ser
                85                  90                  95
Thr Glu Ala Glu Ile Arg Asn Ile Leu Tyr Gln Gly Gln Ile Gly Lys
            100                 105                 110
Gln Asn Lys Pro Ser Val Thr Thr His Ala Lys Val Ser Asp Gln Glu
        115                 120                 125
Leu Gly Lys Gln Ser Arg Arg Ser Gln Asp Ile Ile Lys Ser Leu Gly
    130                 135                 140
Phe Leu Ser Ser Asp Gln Lys Asp Ile Leu Val Lys Ser Ile Ser Ser
145                 150                 155                 160
Ser Lys Asp Ser Gln Leu Ile Leu Lys Phe Val Thr Gln Ala Thr Gln
                165                 170                 175
Leu Asn Asn Ala Glu Ser Thr Lys Ala Lys Gln Met Ala Gln Asn Asp
            180                 185                 190
Val Ala Leu Ile Lys Asn Ile Ser Pro Glu Val Leu Glu Gly Tyr Lys
        195                 200                 205
Glu Lys Ile Gln Arg Ala Ser Thr Lys Ser Gln Val Asp Glu Phe Val
    210                 215                 220
Ala Glu Ala Lys Lys Val Val Asn Ser Asn Lys Glu Thr Leu Val Asn
225                 230                 235                 240
Gln Ala Asn Gly Lys Lys Gln Glu Ile Ala Lys Leu Glu Asn Leu Ser
                245                 250                 255
Asn Asp Glu Met Leu Arg Tyr Asn Thr Ala Ile Asp Asn Val Val Lys
            260                 265                 270
Gln Tyr Asn Glu Gly Lys Leu Asn Ile Thr Ala Ala Met Asn Ala Leu
        275                 280                 285
Asn Ser Ile Lys Gln Ala Gln Glu Val Ala Gln Lys Asn Leu Gln
    290                 295                 300
Lys Gln Tyr Ala Lys Lys Ile Glu Arg Ile Ser Ser Lys Gly Leu Ala
305                 310                 315                 320
Leu Ser Lys Lys Ala Lys Glu Ile Tyr Glu Lys His Lys Ser Ile Leu
                325                 330                 335
Pro Thr Pro Gly Tyr Tyr Ala Asp Ser Val Gly Thr Tyr Leu Asn Arg
            340                 345                 350
Phe Arg Asp Lys Gln Thr Phe Gly Asn Arg Ser Val Trp Thr Gly Gln
        355                 360                 365
Ser Gly Leu Asp Glu Ala Lys Lys Met Leu Asp Glu Val Lys Lys Leu
    370                 375                 380
Leu Lys Glu Leu Gln Asp Leu Thr Arg Gly Thr Lys Glu Asp Lys Lys
385                 390                 395                 400
Pro Asp Val Lys Pro Glu Ala Lys Pro Glu Ala Lys Pro Asp Val Lys
                405                 410                 415
```

Pro Glu Ala Lys Pro Asp Val Lys Pro Glu Ala Lys Pro Asp Val Lys
                420                 425                 430

Pro Glu Ala Lys Pro Asp Val Lys Pro Glu Ala Lys Pro Asp Val Lys
                435                 440                 445

Pro Glu Ala Lys Pro Asp Val Lys Pro Lys Ala Lys Pro Asp Val Lys
                450                 455                 460

Pro Glu Ala Lys Pro Asp Val Lys Pro Asp Val Lys Pro Asp Val Lys
465                 470                 475                 480

Pro Glu Ala Lys Pro Glu Asp Lys Pro Asp Val Lys Pro Asp Val Lys
                485                 490                 495

Pro Glu Ala Lys Pro Asp Val Lys Pro Glu Ala Lys Pro Glu Ala Lys
                500                 505                 510

Pro Glu Ala Lys Pro Glu Ala Lys Pro Glu Ala Lys Pro Glu Ala Lys
                515                 520                 525

Pro Asp Val Lys Pro Glu Ala Lys Pro Asp Val Lys Pro Glu Ala Lys
                530                 535                 540

Pro Glu Ala Lys Pro Glu Ala Lys Ser Glu Ala Lys Pro Glu Ala Lys
545                 550                 555                 560

Leu Glu Ala Lys Pro Glu Ala Lys Pro Ala Thr Lys Lys Ser Val Asn
                565                 570                 575

Thr Ser Gly Asn Leu Ala Ala Lys Ala Ile Glu Asn Lys Lys Tyr
                580                 585                 590

Ser Lys Lys Leu Pro Ser Thr Gly Glu Ala Ala Ser Pro Leu Leu Ala
                595                 600                 605

Ile Val Ser Leu Ile Val Met Leu Ser Ala Gly Leu Ile Thr Ile Val
                610                 615                 620

Leu Lys His Lys Lys Asn
625                 630

<210> SEQ ID NO 58
<211> LENGTH: 727
<212> TYPE: PRT
<213> ORGANISM: Group B Streptococcus

<400> SEQUENCE: 58

Met Asn Asn Asn Glu Lys Lys Val Lys Tyr Phe Leu Arg Lys Thr Ala
1               5                   10                  15

Tyr Gly Leu Ala Ser Met Ser Ala Ala Phe Ala Val Cys Ser Gly Ile
                20                  25                  30

Val His Ala Asp Thr Ser Ser Gly Ile Ser Ala Ser Ile Pro His Lys
                35                  40                  45

Lys Gln Val Asn Leu Gly Ala Val Thr Leu Lys Asn Leu Ile Ser Lys
                50                  55                  60

Tyr Arg Gly Asn Asp Lys Ala Ile Ala Ile Leu Leu Ser Arg Val Asn
65                  70                  75                  80

Asp Phe Asn Arg Ala Ser Gln Asp Thr Leu Pro Gln Leu Ile Asn Ser
                85                  90                  95

Thr Glu Ala Glu Ile Arg Asn Ile Leu Tyr Gln Gly Gln Ile Gly Lys
                100                 105                 110

Gln Asn Lys Pro Ser Val Thr Thr His Ala Lys Val Ser Asp Gln Glu
                115                 120                 125

Leu Gly Lys Gln Ser Arg Arg Ser Gln Asp Ile Ile Lys Ser Leu Gly
                130                 135                 140

Phe Leu Ser Ser Asp Gln Lys Asp Ile Leu Val Lys Ser Ile Ser Ser
145                 150                 155                 160

```
Ser Lys Asp Ser Gln Leu Ile Leu Lys Phe Val Thr Gln Ala Thr Gln
            165                 170                 175

Leu Asn Asn Ala Glu Ser Thr Lys Ala Lys Gln Met Ala Gln Asn Asp
            180                 185                 190

Val Ala Leu Ile Lys Asn Ile Ser Pro Glu Val Leu Glu Tyr Lys
            195                 200                 205

Glu Lys Ile Gln Arg Ala Ser Thr Lys Ser Gln Val Asp Glu Phe Val
            210                 215                 220

Ala Glu Ala Lys Lys Val Val Asn Ser Asn Lys Glu Thr Leu Val Asn
225                 230                 235                 240

Gln Ala Asn Gly Lys Gln Glu Ile Ala Lys Leu Glu Asn Leu Ser
            245                 250                 255

Asn Asp Glu Met Leu Arg Tyr Asn Thr Ala Ile Asp Asn Val Val Lys
            260                 265                 270

Gln Tyr Asn Glu Gly Lys Leu Asn Ile Thr Ala Ala Met Asn Ala Leu
            275                 280                 285

Asn Ser Ile Lys Gln Ala Ala Gln Glu Val Ala Gln Lys Asn Leu Gln
            290                 295                 300

Lys Gln Tyr Ala Lys Lys Ile Glu Arg Ile Ser Ser Lys Gly Leu Ala
305                 310                 315                 320

Leu Ser Lys Lys Ala Lys Glu Ile Tyr Glu Lys His Lys Ser Ile Leu
            325                 330                 335

Pro Thr Pro Gly Tyr Tyr Ala Asp Ser Val Gly Thr Tyr Leu Asn Arg
            340                 345                 350

Phe Arg Asp Lys Gln Thr Phe Gly Asn Arg Ser Val Trp Thr Gly Gln
            355                 360                 365

Ser Gly Leu Asp Glu Ala Lys Lys Met Leu Asp Glu Val Lys Lys Leu
            370                 375                 380

Leu Lys Glu Leu Gln Asp Leu Thr Arg Gly Thr Lys Glu Asp Lys Lys
385                 390                 395                 400

Pro Asp Val Lys Pro Glu Ala Lys Pro Glu Ala Lys Pro Asn Ile Gln
            405                 410                 415

Val Pro Lys Gln Ala Pro Thr Glu Ala Ala Lys Pro Ala Leu Ser Pro
            420                 425                 430

Glu Ala Leu Thr Arg Leu Thr Thr Trp Tyr Asn Gln Ala Lys Asp Leu
            435                 440                 445

Leu Lys Asp Asp Gln Val Lys Asp Lys Tyr Val Asp Ile Leu Ala Val
            450                 455                 460

Gln Lys Ala Val Asp Gln Ala Tyr Asp His Val Glu Glu Gly Lys Phe
465                 470                 475                 480

Ile Thr Thr Asp Gln Ala Asn Gln Leu Ala Asn Lys Leu Arg Asp Ala
            485                 490                 495

Leu Gln Ser Leu Glu Leu Lys Asp Lys Lys Val Ala Lys Pro Glu Ala
            500                 505                 510

Lys Pro Glu Ala Lys Pro Asp Val Lys Pro Glu Ala Lys Pro Asp Val
            515                 520                 525

Lys Pro Glu Ala Lys Pro Asp Val Lys Pro Glu Ala Lys Pro Asp Val
            530                 535                 540

Lys Pro Glu Ala Lys Pro Asp Val Lys Pro Glu Ala Lys Pro Asp Val
545                 550                 555                 560

Lys Pro Glu Ala Lys Pro Asp Val Lys Pro Ala Lys Pro Asp Val
            565                 570                 575

Lys Pro Glu Ala Lys Pro Asp Val Lys Pro Asp Val Lys Pro Asp Val
```

```
                580                 585                 590
Lys Pro Glu Ala Lys Pro Glu Ala Lys Pro Asp Val Lys Pro Asp Val
                595                 600                 605
Lys Pro Glu Ala Lys Pro Asp Val Lys Pro Glu Ala Lys Pro Glu Ala
            610                 615                 620
Lys Pro Asp Val Lys Pro Glu Ala Lys Pro Asp Val Lys Pro Glu Ala
625                 630                 635                 640
Lys Pro Glu Ala Lys Pro Glu Ala Lys Ser Glu Ala Lys Pro Glu Ala
                645                 650                 655
Lys Leu Glu Ala Lys Pro Glu Ala Lys Pro Ala Thr Lys Lys Ser Val
                660                 665                 670
Asn Thr Ser Gly Asn Leu Ala Ala Lys Ala Ile Glu Asn Lys Lys
                675                 680                 685
Tyr Ser Lys Lys Leu Pro Ser Thr Gly Glu Ala Ala Ser Pro Leu Leu
                690                 695                 700
Ala Ile Val Ser Leu Ile Val Met Leu Ser Ala Gly Leu Ile Thr Ile
705                 710                 715                 720
Val Leu Lys His Lys Lys Asn
                725

<210> SEQ ID NO 59
<211> LENGTH: 643
<212> TYPE: PRT
<213> ORGANISM: Group B Streptococcus

<400> SEQUENCE: 59

Met Asn Asn Asn Glu Lys Lys Val Lys Tyr Phe Leu Arg Lys Thr Ala
1               5                   10                  15
Tyr Gly Leu Ala Ser Met Ser Ala Ala Phe Ala Val Cys Ser Gly Ile
                20                  25                  30
Val His Ala Asp Thr Ser Ser Gly Ile Ser Ala Ser Ile Pro His Lys
            35                  40                  45
Lys Gln Val Asn Leu Gly Ala Val Thr Leu Lys Asn Leu Ile Ser Lys
        50                  55                  60
Tyr Arg Gly Asn Asp Lys Ala Ile Ala Ile Leu Leu Ser Arg Val Asn
65                  70                  75                  80
Asp Phe Asn Arg Ala Ser Gln Asp Thr Leu Pro Gln Leu Ile Asn Ser
                85                  90                  95
Thr Glu Ala Glu Ile Arg Asn Ile Leu Tyr Gln Gly Gln Ile Gly Lys
                100                 105                 110
Gln Asn Lys Pro Ser Val Thr Thr His Ala Lys Val Ser Asp Gln Glu
            115                 120                 125
Leu Gly Lys Gln Ser Arg Arg Ser Gln Asp Ile Ile Lys Ser Leu Gly
        130                 135                 140
Phe Leu Ser Ser Asp Gln Lys Asp Ile Leu Val Lys Ser Ile Ser Ser
145                 150                 155                 160
Ser Lys Asp Ser Gln Leu Ile Leu Lys Phe Val Thr Gln Ala Thr Gln
                165                 170                 175
Leu Asn Asn Ala Glu Ser Thr Lys Ala Lys Gln Met Ala Gln Asn Asp
                180                 185                 190
Val Ala Leu Ile Lys Asn Ile Ser Pro Glu Val Leu Glu Glu Tyr Lys
            195                 200                 205
Glu Lys Ile Gln Arg Ala Ser Thr Lys Ser Gln Val Asp Glu Phe Val
        210                 215                 220
Ala Glu Ala Lys Lys Val Val Asn Ser Asn Lys Glu Thr Leu Val Asn
```

```
            225                 230                 235                 240
Gln Ala Asn Gly Lys Lys Gln Glu Ile Ala Lys Leu Glu Asn Leu Ser
                245                 250                 255
Asn Asp Glu Met Leu Arg Tyr Asn Thr Ala Ile Asp Asn Val Val Lys
                260                 265                 270
Gln Tyr Asn Glu Gly Lys Leu Asn Ile Thr Ala Ala Met Asn Ala Leu
                275                 280                 285
Asn Ser Ile Lys Gln Ala Ala Gln Glu Val Ala Gln Lys Asn Leu Gln
                290                 295                 300
Lys Gln Tyr Ala Lys Lys Ile Glu Arg Ile Ser Ser Lys Gly Leu Ala
305                 310                 315                 320
Leu Ser Lys Lys Ala Lys Glu Ile Tyr Glu Lys His Lys Ser Ile Leu
                325                 330                 335
Pro Thr Pro Gly Tyr Tyr Ala Asp Ser Val Gly Thr Tyr Leu Asn Arg
                340                 345                 350
Phe Arg Asp Lys Gln Thr Phe Gly Asn Arg Ser Val Trp Thr Gly Gln
                355                 360                 365
Ser Gly Leu Asp Glu Ala Lys Lys Met Leu Asp Glu Val Lys Lys Leu
                370                 375                 380
Leu Lys Glu Leu Gln Asp Leu Thr Arg Gly Thr Lys Glu Asp Lys Lys
385                 390                 395                 400
Pro Asp Val Lys Pro Glu Ala Lys Pro Glu Ala Lys Pro Asn Ile Gln
                    405                 410                 415
Val Pro Lys Gln Ala Pro Thr Glu Ala Ala Lys Pro Ala Leu Ser Pro
                420                 425                 430
Glu Ala Leu Thr Arg Leu Thr Thr Trp Tyr Asn Gln Ala Lys Asp Leu
                435                 440                 445
Leu Lys Asp Asp Gln Val Lys Asp Lys Tyr Val Asp Ile Leu Ala Val
                450                 455                 460
Gln Lys Ala Val Asp Gln Ala Tyr Asp His Val Glu Glu Gly Lys Phe
465                 470                 475                 480
Ile Thr Thr Asp Gln Ala Asn Gln Leu Ala Asn Lys Leu Arg Asp Ala
                485                 490                 495
Leu Gln Ser Leu Glu Leu Lys Asp Lys Lys Val Ala Lys Pro Glu Ala
                500                 505                 510
Lys Pro Glu Ala Lys Pro Glu Ala Lys Pro Glu Ala Lys Pro Glu Ala
                515                 520                 525
Lys Pro Glu Ala Lys Pro Glu Ala Lys Pro Glu Ala Lys Pro Asp Val
530                 535                 540
Lys Pro Glu Ala Lys Pro Asp Val Lys Pro Glu Ala Lys Pro Glu Ala
545                 550                 555                 560
Lys Pro Glu Ala Lys Ser Ala Lys Pro Glu Ala Lys Leu Glu Ala
                565                 570                 575
Lys Pro Glu Ala Lys Pro Ala Thr Lys Lys Ser Val Asn Thr Ser Gly
                580                 585                 590
Asn Leu Ala Ala Lys Lys Ala Ile Glu Asn Lys Lys Tyr Ser Lys Lys
                595                 600                 605
Leu Pro Ser Thr Gly Glu Ala Ala Ser Pro Leu Leu Ala Ile Val Ser
                610                 615                 620
Leu Ile Val Met Leu Ser Ala Gly Leu Ile Thr Ile Val Leu Lys His
625                 630                 635                 640
Lys Lys Asn
```

```
<210> SEQ ID NO 60
<211> LENGTH: 800
<212> TYPE: PRT
<213> ORGANISM: Group B Streptococcus
<220> FEATURE:
<221> NAME/KEY: VARIANT
<222> LOCATION: 143
<223> OTHER INFORMATION: Xaa = Any Amino Acid
<220> FEATURE:
<221> NAME/KEY: VARIANT
<222> LOCATION: 143
<223> OTHER INFORMATION: Xaa = Any Amino Acid

<400> SEQUENCE: 60

Met Asn Asn Asn Glu Lys Lys Val Lys Tyr Phe Leu Arg Lys Thr Ala
 1               5                  10                  15

Tyr Gly Leu Ala Ser Met Ser Ala Ala Phe Ala Val Cys Ser Gly Ile
                20                  25                  30

Val His Ala Asp Thr Ser Ser Gly Ile Ser Asp Ser Ile Pro His Lys
            35                  40                  45

Lys Gln Val Asn Leu Gly Ala Val Thr Leu Lys Asn Leu Ile Ser Lys
        50                  55                  60

Tyr Arg Gly Asn Asp Lys Ala Ile Ala Ile Leu Leu Ser Arg Val Asp
65                  70                  75                  80

Asp Phe Asn Arg Ala Ser Gln Asp Thr Leu Pro Gln Leu Ile Asn Ser
                85                  90                  95

Thr Glu Ala Glu Ile Asn Asn Thr Leu Pro Gln Gly Arg Ile Ile Lys
            100                 105                 110

Gln Ser Ile Pro Val Val Arg Leu Lys Val Glu Arg Leu Gly Ser Gly
        115                 120                 125

Ala Ile Lys Ala Glu Ser Ile Asn Asn Ile Lys Ala Glu Ser Xaa Asn
130                 135                 140

Lys Ile Gln Gly Lys Ser Thr Asn Thr Ile Lys Ala Glu Ser Ile Asn
145                 150                 155                 160

Lys Ile Lys Val Glu Ser Ile Asn Thr Ile Lys Ala Glu Ser Ile Asn
                165                 170                 175

Lys Ile Gln Ala Lys Pro Ile Asn Thr Ile Lys Ala Glu Ser Ile Asn
            180                 185                 190

Thr Ile Lys Ala Glu Ser Ile His Lys Ile Lys Pro Gln Ser Ile Lys
        195                 200                 205

Ser Thr Ser Ala Thr His Val Lys Val Ser Asp Gln Glu Leu Ala Lys
210                 215                 220

Gln Ser Arg Arg Ser Gln Asp Ile Ile Lys Ser Leu Gly Phe Leu Ser
225                 230                 235                 240

Ser Asp Gln Lys Asp Ile Leu Val Lys Ser Ile Ser Ser Ser Lys Asp
                245                 250                 255

Ser Gln Leu Ile Leu Lys Phe Val Thr Gln Ala Thr Gln Leu Asn Asn
            260                 265                 270

Ala Glu Ser Thr Lys Ala Lys His Met Ala Gln Asn Asp Val Ala Ser
        275                 280                 285

Ile Lys Asn Ile Ser Leu Glu Val Leu Glu Glu Tyr Lys Glu Lys Ile
290                 295                 300

Gln Arg Ala Ser Thr Lys Ser Gln Val Asp Glu Leu Val Ala Glu Ala
305                 310                 315                 320

Lys Lys Val Val Asn Ser Asn Lys Glu Thr Leu Val Asn Gln Ala Asn
                325                 330                 335

Gly Lys Lys Gln Glu Ile Ala Lys Leu Glu Asn Leu Ser Asn Asp Glu
            340                 345                 350
```

```
Met Leu Arg Tyr Asn Thr Ala Ile Asp Asn Val Val Lys Gln Tyr Asn
            355                 360                 365

Glu Gly Lys Leu Asn Ile Thr Asp Ala Met Asn Ala Leu Asn Ser Ile
        370                 375                 380

Lys Gln Ala Ala Gln Glu Val Ala Gln Lys Asn Leu Gln Lys Gln Tyr
385                 390                 395                 400

Ala Lys Lys Ile Glu Arg Ile Ser Leu Lys Gly Leu Ala Leu Ser Lys
                405                 410                 415

Lys Ala Lys Glu Ile Tyr Glu Lys His Lys Ser Ile Leu Pro Thr Pro
                420                 425                 430

Gly Tyr Tyr Ala Asp Ser Val Gly Thr Tyr Leu Asn Arg Phe Arg Asp
            435                 440                 445

Lys Arg Thr Phe Gly Asn Arg Ser Val Trp Thr Gly Gln Ser Gly Leu
        450                 455                 460

Asp Glu Ala Lys Lys Met Leu Asp Glu Val Lys Lys Leu Leu Lys Glu
465                 470                 475                 480

Leu Gln Asp Leu Thr Arg Gly Thr Lys Glu Asp Lys Lys Pro Asp Val
                485                 490                 495

Lys Pro Glu Ala Lys Pro Glu Ala Lys Pro Asn Ile Gln Val Pro Lys
                500                 505                 510

Gln Ala Pro Thr Glu Ala Ala Lys Pro Ala Leu Ser Pro Glu Ala Leu
                515                 520                 525

Thr Arg Leu Thr Thr Trp Tyr Asn Gln Ala Lys Asp Leu Leu Lys Asp
            530                 535                 540

Asp Gln Val Lys Asp Lys Tyr Val Asp Ile Leu Ala Val Gln Lys Ala
545                 550                 555                 560

Val Asp Gln Ala Tyr Asp His Val Glu Glu Gly Lys Phe Ile Thr Thr
                565                 570                 575

Asp Gln Ala Asn Gln Leu Ala Asn Lys Leu Arg Asp Ala Leu Gln Ser
            580                 585                 590

Leu Glu Leu Lys Asp Lys Lys Val Ala Lys Pro Glu Ala Lys Pro Glu
                595                 600                 605

Val Lys Pro Glu Ala Lys Pro Glu Ala Lys Pro Glu Ala Lys Pro Glu
            610                 615                 620

Ala Lys Pro Glu Val Lys Pro Asp Val Lys Pro Glu Ala Lys Pro Asp
625                 630                 635                 640

Val Lys Pro Glu Ala Lys Pro Asp Val Lys Pro Glu Val Lys Pro Asp
                645                 650                 655

Val Lys Pro Glu Ala Lys Pro Asp Val Lys Pro Glu Ala Lys Pro Asp
                660                 665                 670

Val Lys Pro Glu Val Lys Pro Glu Ala Lys Pro Glu Ala Lys Pro Glu
            675                 680                 685

Ala Lys Pro Glu Ile Lys Pro Asp Val Lys Pro Glu Ala Arg Pro Glu
            690                 695                 700

Ala Lys Pro Glu Val Lys Pro Asp Val Lys Pro Glu Ala Lys Pro Glu
705                 710                 715                 720

Ala Lys Pro Glu Val Lys Pro Asp Val Lys Pro Glu Ala Lys Pro Glu
                725                 730                 735

Ala Lys Pro Ala Thr Lys Lys Ser Val Asn Thr Ser Gly Asn Leu Ala
            740                 745                 750

Val Lys Lys Ala Ile Glu Asn Lys Lys Tyr Ser Lys Lys Leu Pro Ser
            755                 760                 765

Thr Gly Glu Ala Ala Ser Pro Leu Leu Ala Ile Val Ser Leu Ile Val
```

```
               770                 775                 780
Met Leu Ser Ala Gly Leu Ile Thr Ile Val Leu Lys His Lys Lys Asn
785                 790                 795                 800

<210> SEQ ID NO 61
<211> LENGTH: 772
<212> TYPE: PRT
<213> ORGANISM: Group B Streptococcus

<400> SEQUENCE: 61

Met Asn Asn Asn Glu Lys Lys Val Lys Tyr Phe Leu Arg Lys Thr Ala
 1               5                  10                  15

Tyr Gly Leu Ala Ser Met Ser Ala Ala Phe Ala Val Cys Ser Gly Ile
             20                  25                  30

Val His Ala Asp Thr Ser Ser Gly Ile Ser Asp Ser Ile Pro His Lys
         35                  40                  45

Lys Gln Val Asn Leu Gly Ala Val Thr Leu Lys Asn Leu Ile Ser Lys
     50                  55                  60

Tyr Arg Gly Asn Asp Lys Ala Ile Ala Ile Leu Leu Ser Arg Val Asp
65                  70                  75                  80

Asp Phe Asn Arg Ala Ser Gln Asp Thr Leu Pro Gln Leu Ile Asn Ser
                 85                  90                  95

Thr Glu Ala Glu Ile Asn Asn Thr Leu Pro Gln Gly Arg Ile Ile Lys
            100                 105                 110

Gln Ser Ile Pro Val Val Arg Leu Lys Val Glu Arg Leu Gly Ser Gly
        115                 120                 125

Ala Ile Lys Ala Glu Ser Ile Asn Asn Ile Lys Ala Glu Ser Ile Asn
    130                 135                 140

Lys Ile Gln Gly Lys Ser Thr Asn Thr Ile Lys Ala Glu Ser Ile Asn
145                 150                 155                 160

Lys Ile Lys Val Glu Ser Ile Asn Thr Ile Lys Ala Glu Ser Ile Asn
                165                 170                 175

Lys Ile Gln Ala Lys Pro Ile Asn Thr Ile Lys Ala Glu Ser Ile Asn
            180                 185                 190

Thr Ile Lys Ala Glu Ser Ile His Lys Ile Lys Pro Gln Ser Ile Lys
        195                 200                 205

Ser Thr Ser Ala Thr His Val Lys Val Ser Asp Gln Glu Leu Ala Lys
    210                 215                 220

Gln Ser Arg Arg Ser Gln Asp Ile Ile Lys Ser Leu Gly Phe Leu Ser
225                 230                 235                 240

Ser Asp Gln Lys Asp Ile Leu Val Lys Ser Ile Ser Ser Lys Asp
                245                 250                 255

Ser Gln Leu Ile Leu Lys Phe Val Thr Gln Ala Thr Gln Leu Asn Asn
            260                 265                 270

Ala Glu Ser Thr Lys Ala Lys His Met Ala Gln Asn Asp Val Ala Ser
        275                 280                 285

Ile Lys Asn Ile Ser Leu Glu Val Leu Glu Glu Tyr Lys Glu Lys Ile
    290                 295                 300

Gln Arg Ala Ser Thr Lys Ser Gln Val Asp Glu Leu Val Ala Glu Ala
305                 310                 315                 320

Lys Lys Val Val Asn Ser Asn Lys Glu Thr Leu Val Asn Gln Ala Asn
                325                 330                 335

Gly Lys Lys Gln Glu Ile Ala Lys Leu Glu Asn Leu Ser Asn Asp Glu
            340                 345                 350

Met Leu Arg Tyr Asn Thr Ala Ile Asp Asn Val Val Lys Gln Tyr Asn
```

-continued

```
            355                 360                 365
Glu Gly Lys Leu Asn Ile Thr Asp Ala Met Asn Ala Leu Asn Ser Ile
370                 375                 380

Lys Gln Ala Ala Gln Glu Val Ala Gln Lys Asn Leu Gln Lys Gln Tyr
385                 390                 395                 400

Ala Lys Lys Ile Glu Arg Ile Ser Leu Lys Gly Leu Ala Leu Ser Lys
                405                 410                 415

Lys Ala Lys Glu Ile Tyr Glu Lys His Lys Ser Ile Leu Pro Thr Pro
                420                 425                 430

Gly Tyr Tyr Ala Asp Ser Val Gly Thr Tyr Leu Asn Arg Phe Arg Asp
            435                 440                 445

Lys Arg Thr Phe Gly Asn Arg Ser Val Trp Thr Gly Gln Ser Gly Leu
450                 455                 460

Asp Glu Ala Lys Lys Met Leu Asp Glu Val Lys Lys Leu Leu Lys Glu
465                 470                 475                 480

Leu Gln Asp Leu Thr Arg Gly Thr Lys Glu Asp Lys Lys Pro Asp Val
                485                 490                 495

Lys Pro Glu Ala Lys Pro Glu Ala Lys Pro Asn Ile Gln Val Pro Lys
                500                 505                 510

Gln Ala Pro Thr Glu Ala Ala Lys Pro Ala Leu Ser Pro Glu Ala Leu
            515                 520                 525

Thr Arg Leu Thr Thr Trp Tyr Asn Gln Ala Lys Asp Leu Leu Lys Asp
530                 535                 540

Asp Gln Val Lys Asp Lys Tyr Val Asp Ile Leu Ala Val Gln Lys Ala
545                 550                 555                 560

Val Asp Gln Ala Tyr Asp His Val Glu Glu Gly Lys Phe Ile Thr Thr
                565                 570                 575

Asp Gln Ala Asn Gln Leu Ala Asn Lys Leu Arg Asp Ala Leu Gln Ser
            580                 585                 590

Leu Glu Leu Lys Asp Lys Lys Val Ala Lys Pro Glu Ala Lys Pro Glu
            595                 600                 605

Val Lys Pro Asp Val Lys Pro Glu Ala Lys Pro Asp Val Lys Pro Glu
610                 615                 620

Ala Lys Pro Asp Val Lys Pro Glu Val Lys Pro Asp Val Lys Pro Glu
625                 630                 635                 640

Ala Lys Pro Asp Val Lys Pro Glu Ala Lys Pro Asp Val Lys Pro Glu
                645                 650                 655

Val Lys Pro Glu Ala Lys Pro Glu Val Lys Pro Asp Val Lys Pro Glu
                660                 665                 670

Ala Arg Pro Glu Ala Lys Pro Glu Val Lys Pro Asp Val Lys Pro Glu
            675                 680                 685

Ala Lys Pro Glu Ala Lys Pro Glu Val Lys Pro Asp Val Lys Pro Glu
690                 695                 700

Ala Lys Pro Glu Ala Lys Pro Ala Thr Lys Lys Ser Val Asn Thr Ser
705                 710                 715                 720

Gly Asn Leu Ala Val Lys Lys Ala Ile Glu Asn Lys Lys Tyr Ser Lys
                725                 730                 735

Lys Leu Pro Ser Thr Gly Glu Ala Ala Ser Pro Leu Leu Ala Ile Val
                740                 745                 750

Ser Leu Ile Val Met Leu Ser Ala Gly Leu Ile Thr Ile Val Leu Lys
            755                 760                 765

His Lys Lys Asn
    770
```

-continued

```
<210> SEQ ID NO 62
<211> LENGTH: 199
<212> TYPE: PRT
<213> ORGANISM: Group B Streptococcus

<400> SEQUENCE: 62

Met Asn Asn Asn Glu Lys Lys Val Lys Tyr Phe Leu Arg Lys Thr Ala
 1               5                  10                  15

Tyr Gly Leu Ala Ser Met Ser Ala Ala Phe Ala Val Cys Ser Gly Ile
             20                  25                  30

Val His Ala Asp Thr Ser Ser Gly Ile Ser Asp Ser Ile Pro His Lys
         35                  40                  45

Lys Gln Val Asn Leu Gly Ala Val Thr Leu Lys Asn Leu Ile Ser Lys
     50                  55                  60

Tyr Arg Gly Asn Asp Lys Ala Ile Ala Ile Leu Leu Ser Arg Val Asp
 65                  70                  75                  80

Asp Phe Asn Arg Ala Ser Gln Asp Thr Leu Pro Gln Leu Ile Asn Ser
                 85                  90                  95

Thr Glu Ala Glu Ile Asn Asn Thr Leu Pro Gln Gly Arg Ile Ile Lys
            100                 105                 110

Gln Ser Ile Pro Val Val Arg Leu Lys Val Glu Arg Leu Gly Ser Gly
        115                 120                 125

Ala Ile Lys Ala Glu Ser Ile Asn Asn Ile Lys Ala Glu Ser Ile Asn
    130                 135                 140

Lys Ile Gln Gly Lys Ser Thr Asn Thr Ile Lys Ala Glu Ser Ile Asn
145                 150                 155                 160

Lys Ile Lys Val Glu Ser Ile Asn Thr Ile Lys Ala Glu Ser Ile Asn
                165                 170                 175

Lys Ile Gln Ala Lys Pro Ile Asn Thr Ile Lys Ala Glu Ser Ile Asn
            180                 185                 190

Thr Ile Asp Phe Leu Arg Asn
        195

<210> SEQ ID NO 63
<211> LENGTH: 522
<212> TYPE: PRT
<213> ORGANISM: Group B Streptococcus

<400> SEQUENCE: 63

Met Asn Asn Asn Glu Lys Lys Val Lys Tyr Phe Leu Arg Lys Thr Ala
 1               5                  10                  15

Tyr Gly Leu Ala Ser Met Ser Ala Ala Phe Ile Val Cys Ser Gly Ile
             20                  25                  30

Val Asn Thr Pro Thr Val Ser Ala Asp Ser Pro Asp Thr Leu Lys Val
         35                  40                  45

Glu Lys Leu Gly Lys Leu Lys Asp Val Lys Ser Val His Glu Leu Thr
     50                  55                  60

Pro Ile Ser Ile Pro Asn Glu Leu Lys Gly Ala Lys Glu Gln Ala Leu
 65                  70                  75                  80

Ser Ser Ile Ile Ser His Pro Asn Ile Thr Asn Ser Glu Val Asp Lys
                 85                  90                  95

Leu Ala Ser Asp Tyr Ser Phe Arg Ile Asn Thr Ser Asn Asp Val Asn
            100                 105                 110

Asp Val Lys Arg Leu Leu Asn Glu Phe Tyr Asn Ala Val Ala Arg Lys
        115                 120                 125

Gln Leu Asp Thr Asn Ser Ala Asp Tyr Arg Ser Lys Ile Asp Asn Ile
```

```
                130             135             140
Ser Thr Thr Gly Leu Ala Ile Ala Leu Glu Ala Lys Glu Ile Tyr Glu
145                 150                 155                 160

Ala Asn Lys Ser Ile Leu Pro His Arg Tyr Lys Asp Ser Val Gly Thr
                165                 170                 175

Tyr Val Asn Ser Phe Glu Arg Arg Ser Pro Gly Lys Phe Asn Ile
            180                 185                 190

Trp Asn Gly Gln Glu Gly Phe Asn Ala Ala Gln Lys Leu Leu Glu Asp
            195                 200                 205

Val Lys Lys Leu Leu Glu Leu Gln Asn Leu Thr Lys Asn Asn Lys
210                 215                 220

Pro Asn Ile Gln Val Pro Lys Gln Ala Pro Thr Glu Ala Ala Lys Pro
225                 230                 235                 240

Ala Leu Ser Pro Glu Ala Leu Thr Arg Leu Thr Thr Trp Tyr Asn Gln
                245                 250                 255

Ala Lys Asp Leu Leu Lys Asp Asp Gln Val Lys Asp Lys Tyr Val Asp
            260                 265                 270

Ile Leu Ser Val Gln Lys Ala Val Asp Gln Ala Tyr Asp His Val Glu
            275                 280                 285

Glu Gly Lys Phe Ile Thr Thr Asp Gln Ala Asn Gln Leu Ala Asn Lys
            290                 295                 300

Leu Arg Asp Ala Leu Gln Ser Leu Glu Leu Lys Asp Lys Val Ala
305                 310                 315                 320

Lys Pro Val Ala Lys Gly Thr Tyr Asp Val Lys Tyr Val Asp Thr Glu
                325                 330                 335

Gly Lys Glu Val Ala Lys Ser Arg His Phe Glu Gly Glu Gly Ala
            340                 345                 350

Ala Phe Val Thr Ser Ala Lys Glu Val Ala Gly Tyr Lys Leu Val Arg
            355                 360                 365

Thr Glu Gly Ala Val Ser Asn Val Phe Thr Ala Gly Ala Gln Val Arg
            370                 375                 380

Thr Tyr Val Tyr Glu Lys Val Lys Pro Glu Val Lys Pro Asp Val Lys
385                 390                 395                 400

Pro Glu Ala Lys Pro Glu Ala Lys Pro Glu Val Lys Pro Asp Val Lys
                405                 410                 415

Pro Glu Ala Lys Pro Glu Ala Lys Pro Glu Val Lys Ser Asp Val Lys
                420                 425                 430

Pro Glu Ala Lys Pro Glu Ala Lys Pro Glu Ala Lys Pro Glu Val Lys
                435                 440                 445

Pro Asp Val Lys Pro Glu Ala Lys Pro Glu Ala Lys Pro Ala Thr Lys
            450                 455                 460

Lys Ser Val Asn Thr Ser Gly Asn Leu Val Ala Lys Ala Ile Glu
465                 470                 475                 480

Asn Lys Lys Tyr Ser Lys Lys Leu Pro Ser Thr Gly Glu Ala Ala Ser
            485                 490                 495

Pro Leu Leu Ala Ile Val Ser Leu Ile Val Met Leu Ser Ala Gly Leu
            500                 505                 510

Ile Thr Ile Val Leu Lys His Lys Lys Asn
            515                 520

<210> SEQ ID NO 64
<211> LENGTH: 7
<212> TYPE: PRT
<213> ORGANISM: Group B Streptococcus
<220> FEATURE:
```

```
<221> NAME/KEY: VARIANT
<222> LOCATION: 7
<223> OTHER INFORMATION: Xaa = Gly or Ser
<220> FEATURE:
<221> NAME/KEY: VARIANT
<222> LOCATION: 7
<223> OTHER INFORMATION: Xaa = Gly or Ser

<400> SEQUENCE: 64

Tyr Ser Ser Ile Arg Lys Xaa
 1               5

<210> SEQ ID NO 65
<211> LENGTH: 7
<212> TYPE: PRT
<213> ORGANISM: Group B Streptococcus

<400> SEQUENCE: 65

Ile Lys Ala Glu Ser Ile Asn
 1               5

<210> SEQ ID NO 66
<211> LENGTH: 8
<212> TYPE: PRT
<213> ORGANISM: Group B Streptococcus
<220> FEATURE:
<221> NAME/KEY: VARIANT
<222> LOCATION: 4, 6
<223> OTHER INFORMATION: Xaa = Any Amino Acid
<220> FEATURE:
<221> NAME/KEY: VARIANT
<222> LOCATION: 4, 6
<223> OTHER INFORMATION: Xaa = Any Amino Acid

<400> SEQUENCE: 66

Lys Ile Gln Xaa Lys Xaa Asn Thr
 1               5

<210> SEQ ID NO 67
<211> LENGTH: 3120
<212> TYPE: DNA
<213> ORGANISM: Group B Streptococcus

<400> SEQUENCE: 67
atgaataata acgaaaaaaa agtaaaatac ttttttaagaa aaacagctta tggtttggcc     60
tcaatgtcag cagcgtttgc tgtatgtagt ggtattgtac acgcggatac tagttcagga    120
atatcggatt caattcctca taagaaacaa gttaatttag gggcggttac tctgaagaat    180
ttgatttcta aatatcgtgg taatgacaaa gctattgcta tacttctaag tagagtagat    240
gattttaata gagcatcaca ggatacactt ccacaattaa ttaatagtac tgaagcagaa    300
attaacaata ctttacctca gggacgaatt attaaacaga gtataccagt cgtaagatta    360
aaagttgaga gattgggaag tggtgcaatt aaggctgagt cgattaataa tattaaagct    420
gaatcaatta ataaaattca gggtaaatca actaatacaa ttaaggctga gtccattaat    480
aaaattaaag tagagtctat taatacaatc aaagccgaat caattaataa aattcaagct    540
aagccaatta acacaatcaa agccgagtct attaatacaa tagacttcct gcgaaactaa    600
aatcctagtt cacggttgat cattccagca atcaaattca ttcgtaatcc aaaccgtttg    660
cgtcgatttc gataggttgt tgaaatatat ttaaacgttt ttactttggc aaaaatattc    720
tcaaccttga ttctctcttt ggatagcgta tggttatagg ttttatcttc aagagttagt    780
ggcttaagtt tgcttgattt cctcggagtt tgcgcttgtg aatacatctt catgatccct    840
tgataaccac tgtctgccaa gattttagca gcttgtccga tgtttctgcg actcattttg    900
```

```
aacaacttca tatcgtggca atagttcact gcaatatcca aagaaacaat tctcccttgg    960
cttgtgacaa tcgcctgagc cttcatagca tgacatttct ttttaccaga ataattcgct   1020
agttgatttt tttaggacga ttgatttta cctctgttgc atccacaatc accgtatcct   1080
cagcactaag atgagttttt gaaatcgtaa aaccactttg aataagagtt gattcaaccc   1140
attgacttcg acggattaag ttgctttcgt gaatgccaaa atcagccgca atttgttcat   1200
aagtgcggta ttctcgcatg tattgaagag tagccatgag gagatcttct aagcttaact   1260
taggggttcg gccaccttt gcgtgtttac gttgataagc tgtttttaac acagctaaca   1320
tctcttcaaa agtagtgcgc tgaacaccaa caaggcgctt aaatcgtaca tcagttaatt   1380
gtttgcttgc ttcataattc atagaactat tgtaccatat tttgtttcgc aggaagtcta   1440
attaaggctg aatcaattca taaaattaaa cctcaatcaa taaaaagtac tagtgctaca   1500
catgttaaag ttagtgatca agaactagct aagcagtcaa gacgttctca agatatcatt   1560
aaatcattag gttccttc atcagaccaa aaagatattt tagttaaatc tattagctct   1620
tcaaaagatt cgcaacttat tcttaaattt gtaacacaag ccacgcaact gaataatgct   1680
gaatcaacaa aagctaggca catggctcaa aatgacgtgg cttcaataaa aaatataagc   1740
ctcgaagtct tagaagaata taaagaaaaa attcaaagag ctagcactaa gagtcaagtt   1800
gatgagcttg tagcagaagc taaaaaagtt gttaattcca ataaagaaac attggtaaat   1860
caggccaatg gtaaaaagca agaaaattgct aagttagaaa atttatctaa cgatgaaatg   1920
ttgagatata atactgcaat tgataatgta gtgaaacagt ataatgaagg taagctcaat   1980
attactgatg caatgaatgc tttaaatagt attaagcaag cagcacagga agttgcccag   2040
aaaaacttac aaaagcagta tgctaaaaaa attgaaagaa taagtttaaa aggattagcg   2100
ttatccaaaa aggctaaaga aatttatgaa aagcataaaa gtattttgcc tacacctgga   2160
tattatgcag actctgtggg aacttatttg aataggttta gagataaacg aacttcgga   2220
aatagaagtg tttggactgg tcaaagtgga cttgatgaag caaaaaaaat gcttgatgaa   2280
gtcaaaaagc ttttaaaaga acttcaagac cttaccagag gtactaaaga agataaaaaa   2340
ccagacgtta agccagaagc caaaccagag gccaaaccaa atattcaagt acctaaacaa   2400
gcacctacag aagctgcaaa accagctttg tcaccagaag ccttgacaag attgactaca   2460
tggtataatc aagctaaaga tctgcttaaa gatgatcaag taaaggacaa atatgtagat   2520
atacttgcag ttcaaaaagc tgttgaccaa gcttatgatc atgtggaaga gggaaaattt   2580
attaccactg atcaagcaaa tcaattagct aacaagctac gtgatgcttt acaaagttta   2640
gaattaaaag ataaaaaagt agccaaacca gaagctaagc cagaagttaa accagaagcc   2700
aaaccagatg ttaagccaga cgttaagcca gacgttaagc cagaagttaa accagaggct   2760
aagccagaag ccaaaccaga ggctaaacca gaattaaaac cagacgttaa gccagaggcc   2820
agaccagagc taagccagaa gttaaaccca gacgttaagc cagaggccaa accagaggct   2880
aagccagaag ttaaaccaga cgttaagcca gaggctaaac cagaagccaa accagcaacc   2940
aaaaaatcgg ttaatactag cggaaacttg gcggttaaaaa aagctattga aaacaaaaag   3000
tatagtaaaa aattaccatc aacgggtgaa gccgcaagtc cactcttagc aattgtatca   3060
ctaattgtta tgttaagtgc aggtcttatt acgatagttt taaagcataa aaaaaattaa   3120
```

US 8,377,446 B2

SERUM RESISTANCE FACTORS OF GRAM POSITIVE BACTERIA

This application is a division of Ser. No. 11/920,274 filed on Nov. 13, 2007 as a national phase application of PCT/US2006/018411 filed May 12, 2006, which claims the benefit of and incorporates by reference provisional application Ser. No. 60/680,479 filed May 13, 2005 and Ser. No. 60/740,291 filed Nov. 29, 2005.

This application incorporates by reference the contents of a 106 kb text file created on Dec. 15, 2011 and named "PAT051803_sequencelisting.txt," which is the sequence listing for this application.

FIELD OF THE INVENTION

This invention is in the fields of immunology and vaccinology. In particular, it relates to a newly identified serum resistance factor of gram positive bacteria and its use in compositions for the treatment and prevention of bacterial infection.

BACKGROUND OF THE INVENTION

The gram positive bacteria Group B Streptococcus (GBS) is one of the most important causes of life-threatening bacterial infection in newborn infants, pregnant women, the elderly and individuals with chronic illness. Other gram positive bacteria such as Streptococcus pyogenes (GBS), Streptococcus pneumoniae (Strep pneumo), and Staphylococcus aureus (Staph) are also implicated in significant morbidity and mortality worldwide.

Various streptococci express on their surface multifunctional proteins that mediate both bacterial adhesion and acquisition of immune system components, contributing to a successful colonization of host mucosal surfaces (Jarva et al., 2003; Talay, 2005). In particular, Streptococcus agalactiae (GBS) and Streptococcus pyogenes (GAS) express a number of functionally-related proteins, characterized by their capacity to bind both human immunoglobulins (Boyle, 1998) and fluid-phase complement regulators (Jarva et al., 2004; Lindahl et al., 2005). In GBS, receptors for IgA and/or IgG belong to the M protein family (Stenberg et al., 1992); M proteins interact with the type II Fc region of immunoglobulins outside their antigen-combining site (Cunningham, 2000).

In GBS, the Bac protein (beta antigen) binds with high affinity to the Fc part of human serum IgA (Bevanger, 1983; Johnson and Ferrieri, 1984; Lindahl et al., 1990; Russell-Jones et al., 1984) and to complement regulator Factor H (FH), which avoid C3b deposition on GBS surface (Areschoug et al., 2002). The binding site for IgA has been located to the N-terminal half of the protein, while the FH-binding region is at the C-terminal half of Bac (Areschoug et al., 2002; Jarva et al., 2002). Bac is structurally related to the pneumococcal Hic protein, and they bind FH in an analogous fashion (Janulczyk et al., 2000; Jarva et al., 2004).

On the other hand, GAS acquires FH by M proteins and Fba, which contributes to the bacterium's capacity to evade phagocytosis by polymorphonuclear cells (Horstmann et al., 1988; Pandiripally et al., 2002; Pandiripally et al., 2003). M-proteins also mediate acquisition of C4 binding protein (C4bp), an important regulator of complement classical pathway component C3 convertase (C4b2a) (Berggard et al., 2001; Blom et al., 2004). M protein binding to C4b has both decay accelerating activity and cofactor activity for C4b cleavage in an analogous fashion as FH in the alternative pathway (Carlsson et al., 2005; Perez-Caballero et al., 2004; Thern et al., 1995).

GAS and GBS also secrete the C5a peptidase, a multifunctional enzyme that inactivates human C5a (Jarva et al., 2003; Wexler et al., 1985) and binds fibronectin, which promotes bacterial invasion of epithelial cells (Beckmann et al., 2002; Cheng et al., 2002).

Serum resistance factors are thought to play a role in mechanisms these gram positive bacteria use to evade the host immune response. There is, therefore, a continuing need in the art for identification of novel serum resistance factors in gram positive bacteria which can be used to develop compositions for the prevention or treatment of bacterial infection.

BRIEF DESCRIPTION OF THE FIGURES

FIGS. 3A-B. Results of experiments demonstrating that recombinant BibA protein forms dimers.
FIG. 3A, Gel-filtration of recombinant BibA;
FIG. 3B, Coomassie staining.
FIG. 4A, strains 2603, 18RS21, and H36B.
FIG. 4B, strains 515 and CJB111.
FIG. 5A, FACS analysis and Western blot (strains 2603 type V and 18RS21 type II;
FIG. 5B, FACS analysis and Western blot (strain H36B type 1b).
FIG. 10A, strain 515 type 1a;
FIG. 10B, strain CJB111 type V;
FIG. 10C, strain 2603 V/R;
FIG. 10D, strain 18RS21;
FIG. 10E, strain H36B.
FIG. 11A, dot blot of native GBS proteins and GBS M1 protein overlaid with C4BP and probed with anti-C4BP antibody;
FIG. 11B, Western blot analysis of recombinant GBS proteins overlaid with C4BP and probed with anti-C4BP antibody (left, Ponceau staining).
FIG. 13. FACS analysis of BibA fragment binding to epithelial cells.
FIGS. 14A-C. Western blots of BibA protein overlaid with purified human IgG and probed with anti-human IgG-HRP conjugated antibody.
FIG. 14A, 7.5 pMol of each protein overlaid with 5 mg/ml purified human IgG;
FIG. 14B, 7.5 pMol of each protein overlaid with 1 mg/ml purified human IgG;
FIG. 14C, 15 pMol=BibA overlaid with 5 µg/ml purified human IgG.

FIG. 15. Blots showing that purified human-IgA binds to BibA protein. Left two blots, Western blot analysis of denatured BibA overlaid with purified human IgA-HRP. Right blot, dot blot analysis of native BibA overlaid with purified human IgA-HRP.

FIGS. 17A-C. Blots demonstrating that BibA-His is specific for human and rabbit IgG. FIG. 17A, human serum goat-α-human-IgG-HRP; FIG. 17B, rabbit serum goat-α-rabbit-IgG-HRP; FIG. 17C, mouse serum rabbit-α-mouse-IgG-HRP.

FIG. 19A, flow cytometry analysis of BibA on the surface of 2603 V/R GBS strain. Bacteria were incubated with a polyclonal mouse anti-BibA antibody and stained with FITC-conjugated anti-mouse IgG antibody black line histogram. The dashed line histogram indicates bacteria treated with primary and secondary antibodies alone.

FIG. 19B, immunogold electron microscopy of BibA expression on GBS strains 2603 V/R. Bacteria were absorbed to formvar-carbon-coated nickel grids and then fixed in 2% PFA. The grids were floated on drops of primary antiserum anti-BibA protein and then on secondary antibody conjugated to 10-nm gold particles.

FIG. 19C, Western blot analysis of the presence of BibA in protein extracts from GBS strain 2603 V/R. P Peptidoglycan associated protein fraction and S Bacterial supernatant protein fraction. GBS protein fractions were separated on SDS-10% PAGE gels and transferred to nitrocellulose membrane. Proteins were overlaid with a mouse anti-BibA polyclonal antibody and stained with HRP-conjugated antibody. Positive bands were detected by ECL.

FIG. 19D, flow cytometry analysis of BibA on the surface of strain 2603ΔbibA. Bacteria were incubated with a polyclonal mouse anti-BibA antibody and stained with FITC-conjugated anti-mouse IgG antibody black line histogram. The dashed line histogram indicates bacteria treated with primary and secondary antibodies alone.

FIG. 19E, immunogold electron microscopy of BibA expression on GBS strains 2603ΔbibA. Bacteria were absorbed to formvar-carbon-coated nickel grids and then fixed in 2% PFA. The grids were floated on drops of primary antiserum anti-BibA protein and then on secondary antibody conjugated to 10-nm gold particles.

FIG. 19F, flow cytometry analysis of BibA on the surface of strain 515 Ia. Bacteria were incubated with a polyclonal mouse anti-BibA antibody and stained with FITC-conjugated anti-mouse IgG antibody black line histogram. The dashed line histogram indicates bacteria treated with primary and secondary antibodies alone.

FIG. 19G, immunogold electron microscopy of BibA expression on GBS strains 515 Ia. Bacteria were absorbed to formvar-carbon-coated nickel grids and then fixed in 2% PFA. The grids were floated on drops of primary antiserum anti-BibA protein and then on secondary antibody conjugated to 10-nm gold particles.

FIG. 19H, Western blot analysis of the presence of BibA in protein extracts from GBS strains 515 Ia and 515pAM401bibA. P Peptidoglycan associated protein fraction and S Bacterial supernatant protein fraction. GBS protein fractions were separated on SDS-10% PAGE gels and transferred to nitrocellulose membrane. Proteins were overlaid with a mouse anti-BibA polyclonal antibody and stained with HRP-conjugated antibody. Positive bands were detected by ECL.

FIG. 19I, flow cytometry analysis of BibA on the surface of strain 515pAM401bibA. Bacteria were incubated with a polyclonal mouse anti-BibA antibody and stained with FITC-conjugated anti-mouse IgG antibody black line histogram. The dashed line histogram indicates bacteria treated with primary and secondary antibodies alone.

FIG. 19L, immunogold electron microscopy of BibA expression on GBS strains 515pAM401bibA. Bacteria were absorbed to formvar-carbon-coated nickel grids and then fixed in 2% PFA. The grids were floated on drops of primary antiserum anti-BibA protein and then on secondary antibody conjugated to 10-nm gold particles.

FIG. 20A, recombinant BibA separated on SDS PAGE and blotted on nitrocellulose membrane. The membrane was then overlaid with 0.5 µg/ml human, mouse or bovine purified serum IgG and positive binding to IgG revealed by secondary antibodies versus the different IgG species. To evaluate the binding ECL detection was performed. M1 protein of GBS was used as positive control, while GBS104 was used as a non-specific binding control. FIG. 20B as in FIG. 20A apart from testing the binding to human serum or secretory IgA, overlaid at a concentration of 0.5 µg/ml. The blots are representative of experiments performed at least in triplicate. FIG. 20C and FIG. 20D Different concentrations of purified recombinant BibA in PBS were spotted on a nitrocellulose membrane and overlay assay performed as in FIG. 20A. FIG. 20C, overlay with human serum IgG. FIG. 20D, overlay with human serum IgA. FIG. 20E, overlay blotting with human IgG of SDS-PAGE separated N-terminal and C-terminal constructs of BibA. FIG. 20F, overlay blotting with human IgA of SDS-PAGE separated N-terminal and C-terminal constructs of BibA.

FIG. 21A, recombinant BibA separated on SDS PAGE and blotted on nitrocellulose membrane. The membrane was overlaid with 5 µg/ml human C4BP and binding revealed by secondary antibodies versus C4BP. M1 protein of GBS was used as positive control, while GBS201 as non-specific binding control. FIG. 21B, dot blot of different concentrations of native recombinant BibA spotted on nitrocellulose membrane and overlaid with 5 µg/ml C4BP as in FIG. 21A. FIG. 21C, Western blot of SDS-PAGE separated N-terminal and C-terminal constructs of BibA overlaid with human C4BP. Experimental blotting conditions as in FIG. 21A.

FIGS. 22A-C. Graphs demonstrating binding of recombinant BibA to epithelial cells. FIG. 22A, ME180 cells were incubated for 1 h at 4° C. with increasing concentrations of recombinant BibA range 0.01-62.5 µg/ml. Then cells were washed and incubated with mouse anti-BibA antibodies followed by FITC-conjugated secondary anti-mouse antibodies. MFI Mean fluorescence intensity. The plot is representative of three independent experiments. FIG. 22B, saturation curve of BibA binding to ME180 cells. Analysis was performed on data reported on panel A. The Kd value was calculated as the BibA concentration that determines the saturation of 50% of the receptors present on cells. FIG. 22C, representative flow cytometric profiles of the binding of 10 µg/ml BibA to A549, Caco2 and 16HBE epithelial cells. Binding experimental conditions and analysis as in FIG. 22A. Dashed-line histograms represent the MFI of control cells.

FIG. 23A, ME180 cells grown in a 24 well plate were infected with GBS strains 2603 V/R, 2603ΔbibA and 2603pAM401bibA for 3 hours. Non-adherent bacteria were gently washed off and cells lysed with saponin for association assay. The white column indicates the percentage of associated bacteria in the wild type strain, the light grey column indicates the percentage of association of the BibA isogenic mutant strain and the dark grey column the association of the wild type strain overexpressing BibA. FIG. 23B, as in FIG. 23A except that infection was carried out in A549 cells. Mean values±standard deviations of three individual experiments. Data evaluated by Student's T-test, were 95% confident.

FIG. 23C, micrographs of confocal imaging analysis of the 2603 V/R strain association to A549 lung epithelial cells in comparison to the isogenic mutant strain lacking BibA gene (FIG. 23D). A549 cells were grown on glass slides were infected with GBS for 3 h. Bacteria were then stained with mouse polyclonal antisera raised against type V capsular polysaccharide and rabbit polyclonal anti-BibA antibodies. Capsule and BibA were respectively labeled with Alexa Fluor 562 red and 488 green conjugated secondary antibody. A549 cells F-actin was labeled with Alexa Fluor 622 conjugated phalloidin blue. The results shown in the figure are typical of multiple experiments.

FIG. 23E, confocal imaging analysis of the 515 Ia wild type strain and the isogenic strain carrying a plasmid containing the 515 pAM401bibA gene (FIG. 23F) in association to A549 epithelial cells.

FIGS. 27A-B. Summary of data demonstrating that expression of BibA on 515 Ia surface increases adherence to epithelial cells.

DETAILED DESCRIPTION OF THE INVENTION

Applicants have identified a serum resistance factor in a gram positive bacteria (GBS) which interacts with host cell complement pathways and is thought to be involved in the invading bacteria's complement resistance or evasion mechanisms. This newly identified serum resistance factor is referred to herein as group B streptococcus immunoglobulin-binding adhesion (BibA) (also known as GBS 3). BibA is a widely expressed protein, present in 81% of the 31 strains of GBS analyzed (Table 3).

A BLAST search against the non-redundant GenBank database revealed a low similarity of the BibA N-terminal region with a series of gram positive immunoglobulin-binding proteins such as the M-protein family of *S. pyogenes* (22% identity), Bac of *S. agalactiae* (20% identity), PspC of *S. pneumoniae* (20% identity), and Mig of *S. dysagalactiae* (27% identity). BibA shares some similarities with resistance factors of other gram-positive bacteria, such as the Hic-like proteins of *S. pneumoniae*.

The bibA gene is located between secE and nusG genes. SecE and nusG are co-transcribed in *E. coli* (Downing et al., 1990) and are adjacent in a large panel of gram positive and gram negative bacteria (Barreiro et al., 2001; Fuller et al., 1999; Jeong et al., 1993; Katayama et al., 1996; Miyake et al., 1994; Poplawski et al., 2000; Puttikhunt et al., 1995; Sharp, 1994; Syvanen et al., 1996). This evidence suggests that the present genomic localization of BibA is likely to derive from an insertion event. Of interest, two transposases present in A909 strain are members of the IS1381 family, which has been proposed as a tool for GBS subtyping (Tamura et al., 2000) and whose presence has been correlated with the evolution of the *S. agalactiae* species analyzed by multilocus sequence typing (MLST) (Hery-Arnaud et al., 2005).

Figure 1A:
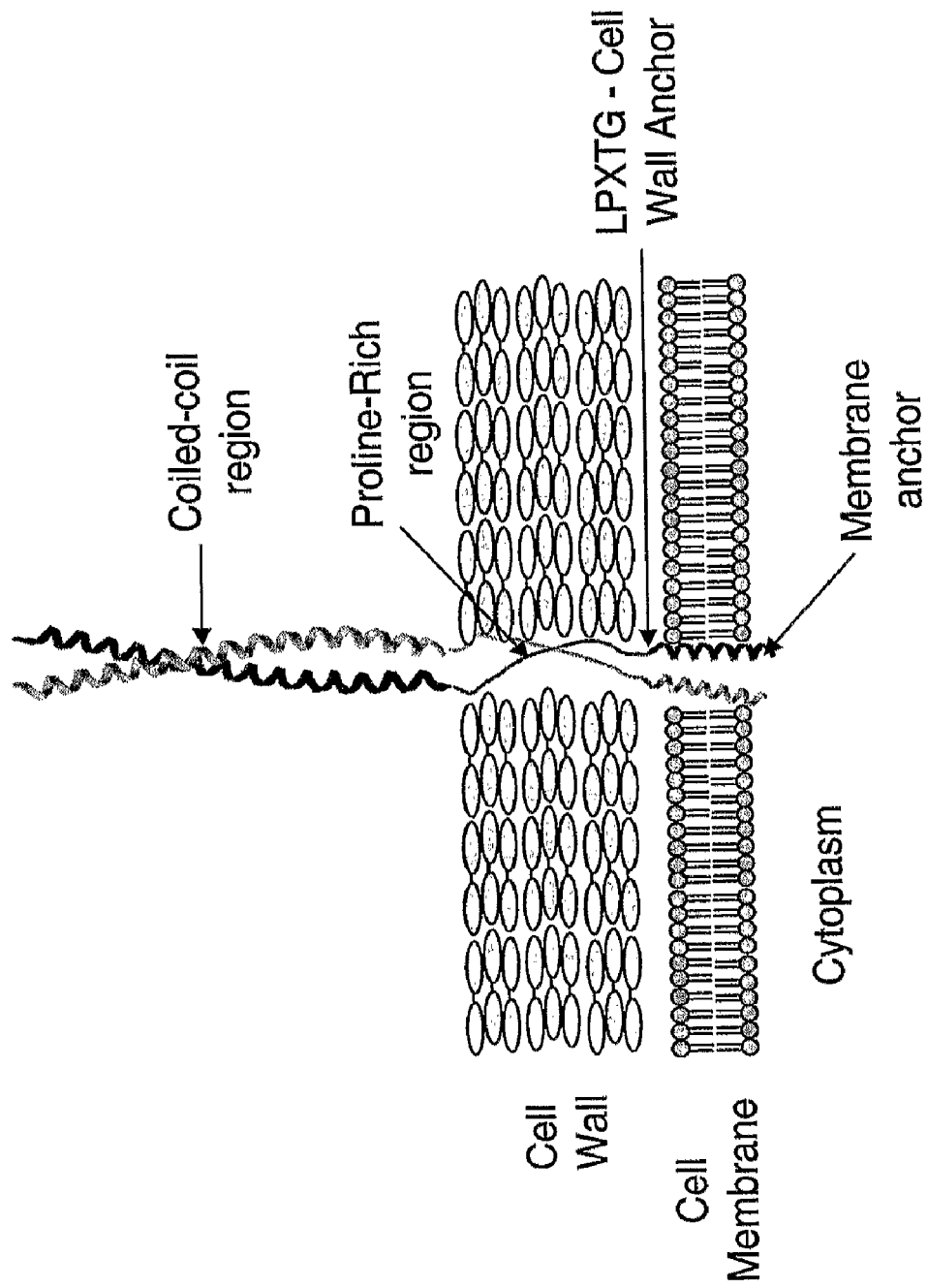
FIG. 1A. Diagram of BibA inserted in the cell membrane.
Figure 2A:
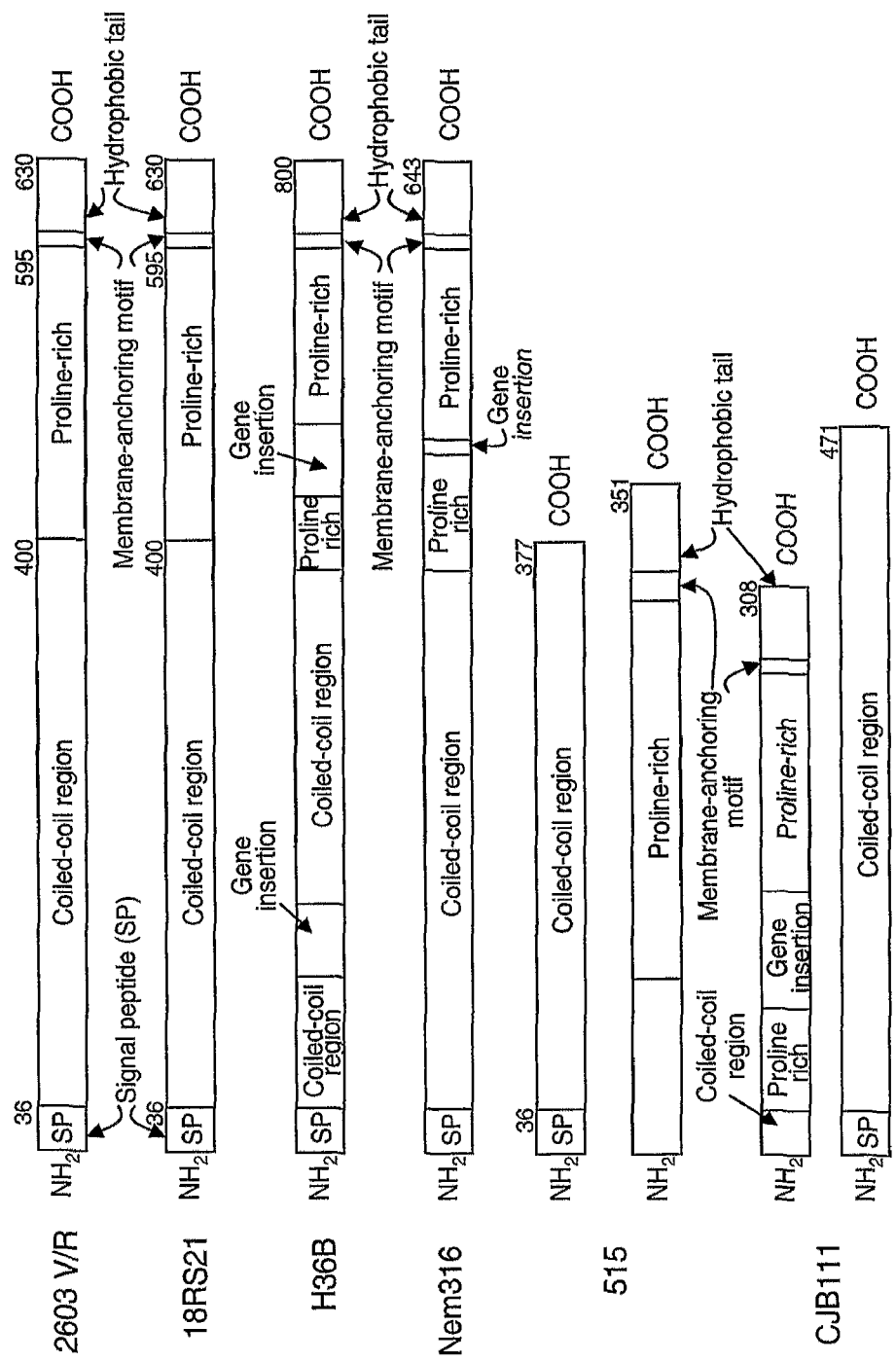
FIG. 2A. Domains of BibA proteins in different GBS strains.
Figure 2B:
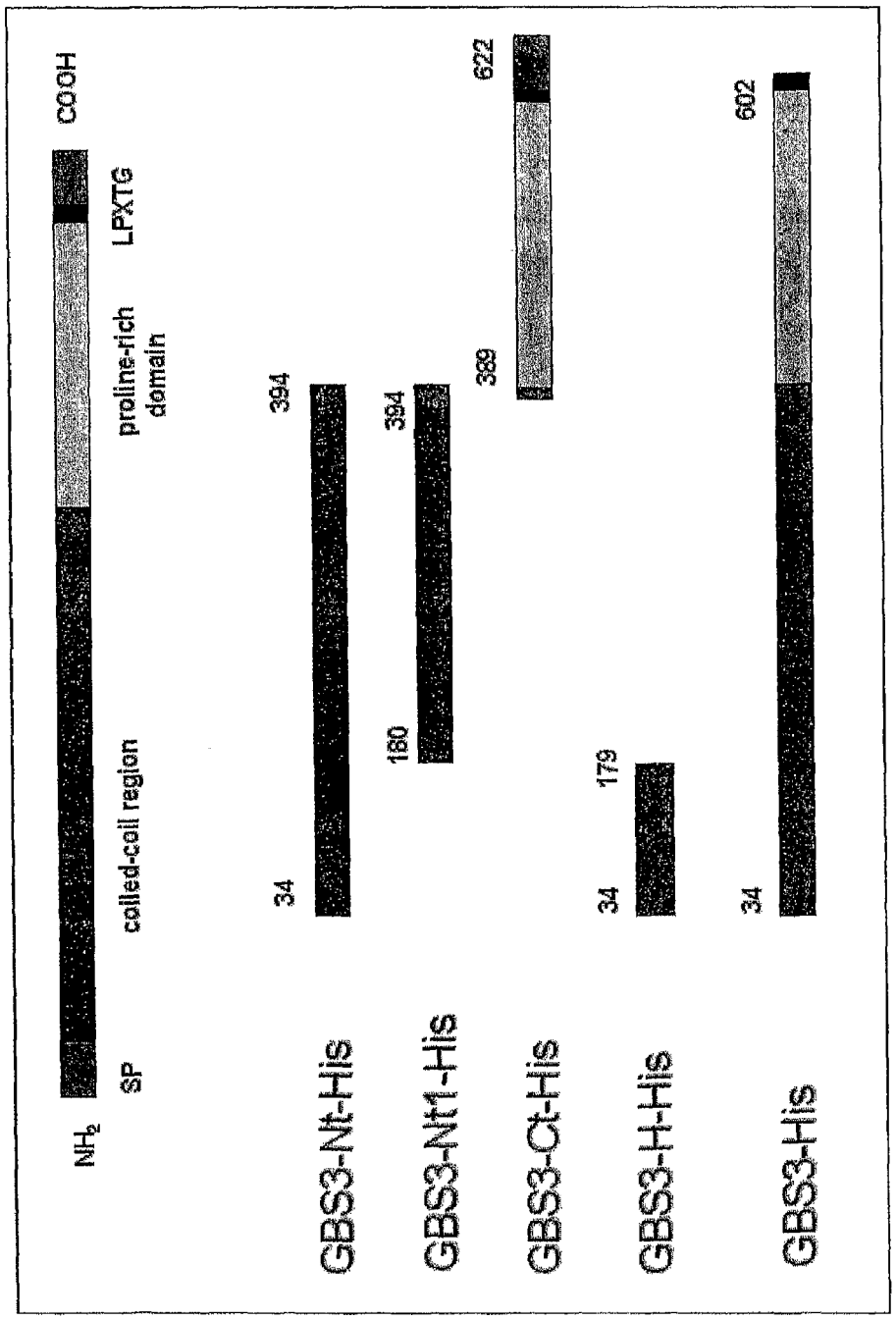
FIG. 2B. Representation of BibA cloned fragments, based on predicted functional domains.

In silico analysis of the seven GBS completed genomes revealed that BibA is a modular protein; its sequence variability is mainly due to a different number of short amino acid repeats either in N-terminal or the C-terminal domains. Full-length BibA comprises an N-terminal helix-rich region, a C-terminal proline-rich region, a LPXTG (SEQ ID NO:3) motif that anchors the protein to the cell wall peptidoglycan, and a transmembrane domain. FIGS. 1A, 2B. The coiled-coil domain of BibA is well conserved across multiple serotypes of *S. agalactiae*.

Figure 1B:
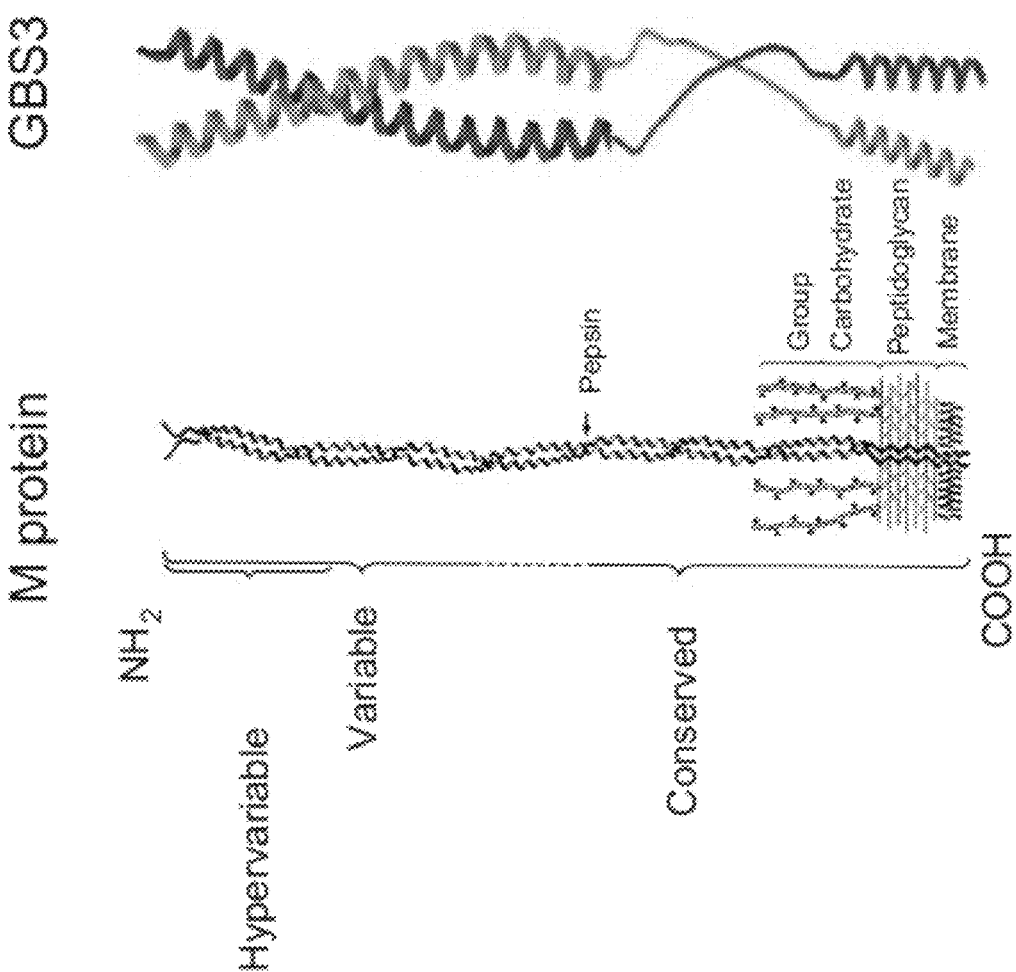
FIG. 1B, Comparison of BibA and M protein structures.

BibA is structurally related to the family of M-like proteins of *S. pyogenes* (GBS) (FIG. 1B). The secondary structure of M proteins is primarily an α-helical coiled coil structure which forms stable dimers (Phillips et al., 1981). In silico prediction of BibA secondary structure (Berger et al., 1995) reveals in the N-terminal region a helix-rich region with the propensity to form a coiled-coil arrangement (regions 283-294 and 366-400). Studies on the recombinant form of BibA suggest that, as for M proteins, BibA is able to form dimers, which are opened in non-reducing conditions. No canonical elements of secondary structure are on the contrary predicted within the proline-rich region, which suggests that this part of the molecule could adopt a poly-proline helix-like conformation.

BibA is expressed on the surface of several GBS strains, but is also recovered in GBS culture supernatants. BibA, whether expressed on the cell wall or secreted in the supernatant fractions, has an identical apparent molecular weight. This suggests that secretion of BibA might be due to either a proteolytic cleavage of the cell-wall anchoring domain or that an impaired sorting of the protein could be responsible for the secretion. Indeed, BibA has an YSSIRK-G/S-like motif (SEQ ID NO:64) in the signal peptide, which has previously been described to be present in *Staphylococcus aureus* and other gram positive pathogens (Bae and Schneewind, 2003). Such a motif is exclusively present in BibA and is conserved in all the eight GBS strains analyzed. The YSSIRK-G/S-like motif (SEQ ID NO:64) has been postulated to be involved in accelerating protein maturation (Bae and Schneewind, 2003).

Based on this evidence, we hypothesize that sortase components may be limiting for complete and efficient anchoring of BibA, which results in the incomplete processing of mature BibA and the release of the protein in the supernatant.

Functional characterization identifies BibA as a member of a group of streptococcal surface-exposed multifunctional proteins which mediate bacterial colonization and modulate host immune-response (Jarva et al., 2003; Lindahl et al., 2005). However, BibA has unique features, such as the binding both to human immunoglobulins and to complement regulator C4bp. The BibA binding site for IgA and C4bp resides in the N-terminal region of the protein. However, there is no homology to the Bac N-terminal domain specific for IgA (Lindahl et al., 1990). The lack of binding to mouse and bovine IgG suggests that BibA has a human specific functional role, as reported for other Ig-binding proteins.

Secreted BibA binds to human epithelial cells, complement (such as C4 binding protein), and specifically to human IgG and IgA. The proline-rich domain of secreted BibA is responsible for the binding interaction with human epithelial cells. Examples 8, 9. The proline-rich domain has a periodicity of 8 amino acids. Proline occupies positions b and f of the motif, which is repeated 19 times:

```
399-(aKPDVKPEAh)      (SEQ ID NO: 9)

(KPEAKPDV)6       (SEQ ID NO: 10)

KPKAKPDV         (SEQ ID NO: 11)

KPEAKPDV         (SEQ ID NO: 10)

KPDVKPDV         (SEQ ID NO: 12)

KPEAKPED         (SEQ ID NO: 13)

KPDVKPDV         (SEQ ID NO: 12)

KPEAKPDV         (SEQ ID NO: 10)

(KPEAKPEA)3       (SEQ ID NO: 14)

(KPDVKPEA)2       (SEQ ID NO: 15)

KPEAKPEA-551     (SEQ ID NO: 14)
```

The proline-rich domain, when present, is located towards the C-terminus of BibA. As illustrated in FIG. 2A, the proline-rich domain is generally located from amino acid 400 to the end of the C-terminus.

To elucidate the BibA binding region to immunoglobulins, we generated two constructs comprising the N-terminal or the C-terminal portion of the protein. BibA binding to human IgG resides predominantly in the N-terminal region of the protein, while the C-terminal region binds to a lower extent. On the other hand, the binding to human IgA was exclusively associated to the N-terminal portion of BibA. This region was also responsible for the binding of BibA to the C4bp. In addition, recombinant BibA binds to human epithelial cells of different origin, with an affinity constant of ~$10^{-8}$ M.

The coiled-coil domain is well-conserved in various GBS strains. The coiled-coil domain is responsible for the binding interaction of BibA with complement such as C4 binding protein. Example 7. The coiled-coil domain is also responsible for binding interactions with human immunoglobulins, such as IgG and IgA. Examples 10, 11, and 12. The IgA binding site appears to be in the N-terminal portion (roughly 200 amino acids) of BibA. BibA, like other coiled-coil proteins, forms dimers. Example 1.

When bacteria secrete BibA, it is believed that the proline-rich C terminus domain of the protein binds to host epithelial cells, leaving the N-terminal coiled-coil domain exposed to serum factors. The N-terminal coiled-coil domain is then thought to attract complement, such as C4 binding protein, diverting it away from the invading bacteria. Complement binding interaction with the host cell attached coiled-coil domain attracts complement activity to the host cell, further facilitating bacterial invasion.

In some strains the LPXTG (SEQ ID NO:3)/proline-rich domain is absent. FIG. 2A. When the proline-rich domain is absent or expressed separately, BibA is thought to be primarily secreted, and not surface exposed. However, even truncated or bifurcated forms of BibA are thought to divert immune system attention away from the bacterium as it approaches target host cells.

The role of BibA in GBS adhesion to cells was confirmed by the impaired ability of a BibA knock-out mutant strain to bind to both human cervical and lung epithelial cells. Complementation of the mutation restored GBS adhesive phenotype, while BibA over-expression significantly increased the binding to epithelial cells. These characteristics indicate that BibA is a novel multifunctional protein and is likely involved in GBS pathogenicity.

The soluble form of BibA protein has an apparent molecular weight on an SDS polyacrylamide gel of ~80 kDa, although its expected molecular weight is ~60 kDa. The proline-rich domain of the protein is likely to be responsible for this shift, due to the folding of BibA into a bundled-like shape. The membrane-associated form is easily degraded; a small fraction of the protein runs on a gel as an 80 kD, while the major fraction runs at a MW of ~60 kDa. This indicates that in the membrane-associated form the proline-rich motif is still associated with the cell wall components and maintains a linear structure. See Examples 2-4, 6.

Bacterial adherence to host cells is the initial step and a prerequisite for successful colonization of host mucosal surfaces. The analysis of the binding of recombinant BibA to epithelial cells revealed that the association to cells could be saturated, with an estimated affinity constant of ≈$4 \times 10^{-8}$ M. In particular, BibA binding to epithelial cell lines of lung, intestine, bronchus and cervix origin, suggests the existence of an ubiquitous receptor. BibA, like M-proteins (Courtney et al., 1994; Courtney et al., 1997; Wang and Stinson, 1994), mediates bacterial adhesion to epithelial cells. Studies of isogenic BibA-positive and BibA-negative strains indicated that the BibA-positive strain adhered to epithelial cells, while the BibA-negative strain showed greatly reduced adherence. In addition, expression of the cell-wall anchored form of BibA in a strain not exposing BibA on the surface increased its associative phenotype. Of interest, such results were confirmed in both human cervical (ME180) and lung (A549) epithelial cell lines, which are a target for GBS colonization.

These functional properties suggest that BibA is a serum resistance factor involved in GBS pathogenicity and is therefore useful as an active agent in compositions for preventing and for treating *S. agalactiae* infections.

I. BibA Polypeptides

"BibA polypeptides" of the invention comprise a portion of a BibA protein which consists of (1) a coiled-coil domain of the BibA protein; (2) a leader sequence and the coiled-coil domain of the BibA protein; (3) a proline-rich domain of the BibA protein; (4) the coiled-coil and proline-rich domains of the BibA protein; or (5) the leader sequence, the coiled-coil domain, and the proline-rich domain of the BibA protein and are free of other contiguous amino acid sequences of the BibA protein. BibA polypeptides of the invention do not comprise the amino acid sequence of a full-length BibA polypeptide.

Figure 24:
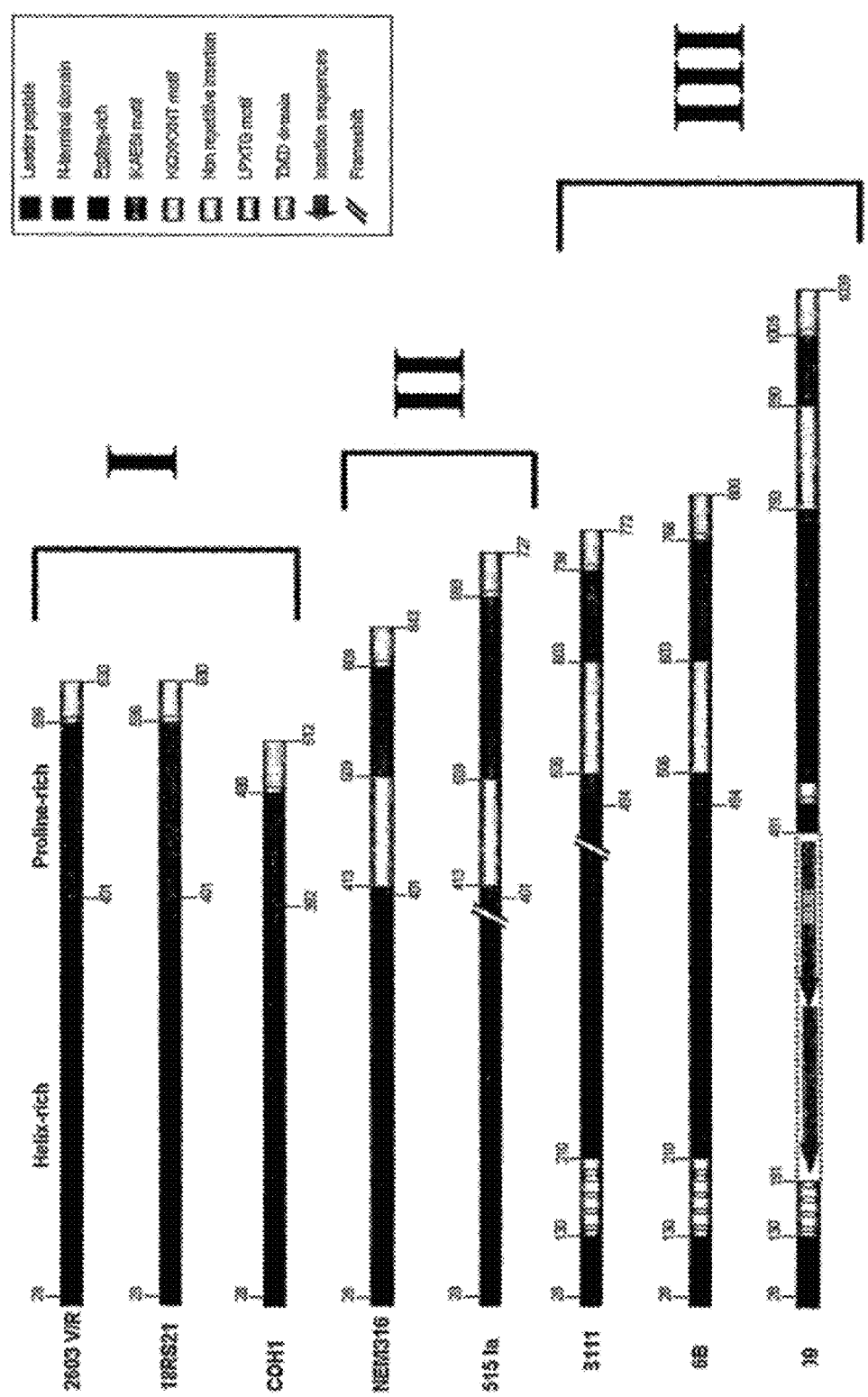
FIG. 24. Overview of sequence organization of BibA proteins. N-terminal domains are predicted to form helix-rich structures, according to prediction obtained using the Paircoil program Berger et al., 1995 at Expasy web server (domain name expasy.org). Positions of classical LPXTG (SEQ ID NO:3) cell wall anchoring motif and trans-membrane domain are also indicated.

BibA polypeptides include those polypeptides identified as "I," "II," and "III" in FIG. 24.

BibA protein from GBS serotype V isolated strain 2603 V/R has the amino acid sequence shown in SEQ ID NO:1:

MNNNEKKVKYFLRKTAYGLASMSAAFAVCSGIVHADTSSGISASIPHKKQVNLGAVTLKNLISKYRGNDKAIAILL
SRVNDFNRASQDTLPQLINSTEAEIRNILYQGQIGKQNKPSVTTHAKVSDQELGKQSRRSQDIIKSLGFLSSDQKD
ILVKSISSSKDSQLILKFVTQATQLNNAESIKAKQMAQNDVALIKNISPEVLEEYKEKIQRASTKSQVDEFVAEAK
KVVNSNKETLVNQANGKKQEIAKLENLSNDEMLRYNTAIDNVVKQYNEGKLNITAAMNALNSIKQAAQEVAQKNLQ
KQYAKKIERISSKGLALSKKAKEIYEKHKSILPTPGYYADSVGTYLNRFRDKQTFGNRSVWTGQSGLDEAKKMLDE
VKKLLKELQDLTRGTKEDKKPDVKPEAKPEAKPDVKPEAKPDVKPEAKPDVKPEAKPDVKPEAKPDVKPEAKPDVK
PKAKPDVKPEAKPDVKPDVKPDVKPEAKPEDKPDVKPDVKPEAKPDVKPEAKPEAKPEAKPEAKPEAKPDVK
PEAKPDVKPEAKPEAKPEAKSEAKPEAKLEAKPEAKPATKKSVNTSGNLAAKKAIENKKYSKK*LPSTG*EAASPLLA
IVSLIVMLSAGLITIVLKHKKN

BibA contains an N-terminal leader or signal sequence domain which is indicated by the underlined sequence at the beginning of SEQ ID NO:1 above and the C-terminal transmembrane domain which is indicated by the underlined sequence at the end of SEQ ID NO:1 above. One or more amino acids from the leader or signal sequence domain of BibA may be removed. An example of such a BibA fragment is set forth below as SEQ ID NO:2:

TSSGISASIPHKKQVNLGAVTLKNLISKYRGNDKAIAILLSRVNDFNRASQDTLPQLINSTEAEIRNILYQGQI
GKQNKPSVTTHAKVSDQELGKQSRRSQDIIKSLGFLSSDQKDILVKSISSSKDSQLILKFVTQATQLNNAESTK
AKQMAQNDVALIKNISPEVLEEYKEKIQRASTKSQVDEFVAEAKKVVNSNKETLVNQANGKKQEIAKLENLSND
EMLRYNTAIDNVVKQYNEGKLNITAAMNALNSIKQAAQEVAQKNLQKQYAKKIERISSKGLALSKKAKEIYEKH
KSILPTPGYYADSVGTYLNRFRDKQTFGNRSVWTGQSGLDEAKKMLDEVKKLLKELQDLTRGTKEDKKPDVKPE
AKPEAKPDVKPEAKPDVKPEAKPDVKPEAKPDVKPEAKPDVKPEAKPDVKPKAKPDVKPEAKPDVKPDVKPDVK
PEAKPEDKPDVKPDVKPEAKPDVKPEAKPEAKPEAKPEAKPEAKPDVKPEAKPDVKPEAKPEAKPEAKSE
AKPEAKLEAKPEAKPATKKSVNTSGNLAAKKAIENKKYSKKLPSTGEAASPLLAIVSLIVMLSAGLITIVLKHK
KN

BibA also contains an amino acid motif indicative of a cell wall anchor:

LPXTG (SEQ ID NO:3, shown in bold and italics in SEQ ID NO:1 above).

In one embodiment, the leader or signal sequence domain, the transmembrane and cytoplasmic domains, and the cell wall anchor motif are removed from the BibA sequence to leave the coiled-coil and proline-rich segments as set forth below as SEQ ID NO:4:

TSSGISASIPHKKQVNLGAVTLKNLISKYRGNDKAIAILLSRVNDFNRASQDTLPQLINSTEAEIRNILYQGQI

GKQNKPSVTTHAKVSDQELGKQSRRSQDIIKSLGFLSSDQKDILVKSISSSKDSQLILKFVTQATQLNNAESTK

AKQMAQNDVALIKNISPEVLEEYKEKIQRASTKSQVDEFVAEAKKVVNSNKETLVNQANGKKQEIAKLENLSND

EMLRYNTAIDNVVKQYNEGKLNITAAMNALNSIKQAAQEVAQKNLQKQYAKKIERISSKGLALSKKAKEIYEKH

KSILPTPGYYADSVGTYLNRFRDKQTFGNRSVWTGQSGLDEAKKMLDEVKKLLKELQDLTRGTKEDKKPDVKPE

AKPEAKPDVKPEAKPDVKPEAKPDVKPEAKPDVKPEAKPDVKPEAKPDVKPKAKPDVKPEAKPDVKPDVKPDVK

PEAKPEDKPDVKPDVKPEAKPDVKPEAKPEAKPEAKPEAKPEAKPDVKPEAKPDVKPEAKPEAKPEAKSE

AKPEAKLEAKPEAKPATKKSVNTSGNLAAKKAIENKKYSKK

The proline-rich domain of BibA is indicated below as SEQ ID NO:5.

PDVKPEAKPDVKPEAKPDVKPKAKPDVKPEAKPDVKPDVKPDVKPEAKPEDKPDVKPDVKPEAKPDVKPEAKPEAKP

EAKPEAKPEAKPEAKPDVKFEAKPDVKPEAKPEAKPEAKSEAKPEAKLEAKPEAKPATKKSVNTSGNLAAKKAIENK

KYSKK

The coiled-coil domain and signal peptide domain of BibA are set forth below as SEQ ID NO:6:

MNNNEKKVKYFLRKTAYGLASMSAAFAVCSGIVHADTSSGISASIPHKKQVNLGAVTLKNLISKYRGNDKAIAILL

SRVNDFNRASQDTLPQLINSTEAEIRNILYQGQIGKQNKPSVTTHAKVSDQELGKQSRRSQDIIKSLGFLSSDQKD

ILVKSISSSKDSQLILKFVTQATQLNNAESTKAKQMAQNDVALIKNISPEVLEEYKEKIQRASTKSQVDEFVAEAK

KVVNSNKETLVNQANGKKQEIAKLENLSNDEMLRYNTAIDNVVKQYNEGKLNITAAMNALNSIKQAAQEVAQKNLQ

KQYAKKIERISSKGLALSKKAKEIYEKHKSILPTPGYYADSVGTYLNRFRDKQTFGNRSVWTGQSGLDEAKKMLDE

VKKLLKELQDLTRGTKEDKKPDVKPEAKPEAKPDVKPEAKPDVKPEAKPDVKPEAK

The highly conserved coiled-coil domain of BibA is located towards the N-terminus of the protein and is underlined in the BibA SEQ ID NO:1 sequence below. The underlined fragment corresponding to the coiled-coil domain of BibA is set forth below as SEQ ID NO:7:

SEQ ID NO: 1
MNNNEKKVKYFLRKTAYGLASMSAAFAVCSGIVHAD<u>TSSGISASIPHKKQVNLGAVTLKNLISKYRGNDKAIAILL

SRVNDFNRASQDTLPQLINSTEAEIRNILYQGQIGKQNKPSVTTHAKVSDQELGKQSRRSQDIIKSLGFLSSDQKD

ILVKSISSSKDSQLILKFVTQATQLNNAESTKAKQMAQNDVALIKNISPEVLEEYKEKIQRASTKSQVDEFVAEAK

KVVNSNKETLVNQANGKKQEIAKLENLSNDEMLRYNTAIDNVVKQYNEGKLNITAAMNALNSIKQAAQEVAQKNLQ

KQYAKKIERISSKGLALSKKAKEIYEKHKSILPTPGYYADSVGTYLNRFRDKQTFGNRSVWTGQSGLDEAKKMLDE

VKKLLKELQDLTRGTKEDKK</u>PDVKPEAKPEAKPDVKPEAKPDVKPEAKPDVKPEAKPDVKPEAKPDVKPEAKPDVK

PKAKPDVKPEAKPDVKPDVKPDVKPEAKPEDKPDVKPDVKPEAKPDVKPEAKPEAKPEAKPEAKPEAKPEAKPDVK

PEAKPDVKPEAKPEAKPEAKSEAKPEAKLEAKPEAKPATKKSVNTSGNLAAKKAIENKKYSKKLPSTGEAASPLLA

IVSLIVMLSAGLITIVLKHKKN

SEQ ID NO: 7
TSSGISASIPHKKQVNLGAVTLKNLISKYRGNDKAIAILLSRVNDFNRASQDTLPQLINSTEAEIRNILYQGQI

GKQNKPSVTTHAKVSDQELGKQSRRSQDIIKSLGPISSDQKDILVKSISSSKDSQLILKFVTQATQLNNAESTK

AKQMAQNDVALIKNISPEVLEEYKEKIQRASTKSQVDEFVAEAKKVVNSNKETLVNQANGKKQEIAKLENLSND

EMLRYNTAIDNVVKQYNEGKLNITAAMNALNSIKQAAQEVAQKNLQKQYAKKIERISSKGLALSKKAKEIYEKH

KSILPTPGYYADSVGTYLNRFRDKQTFGNRSVWTGQSGLDEAKKMLDEVKKLLKELQDLTRGTKEDKK

The signal peptide (amino acids 1-36), coiled coil domain, and proline-rich domain of BibA are set forth below in SEQ ID NO:8:

MNNNEKKVKYFLRKTAYGLASMSAAFAVCSGIVHADTSSGISASIPHKKQVNLGAVTLKNLISKYRGNDKAIAILL

SRVNDFNRASQDTLPQLINSTEAEIRNILYQGQIGKQNKPSVTTHAKVSDQELGKQSRRSQDIIKSLGFLSSDQKD

ILVKSISSSKDSQLILKFVTQATQLNNAESTKAKQMAQNDVALIKNISPEVLEEYKEKIQRASTKSQVDEFVAEAK

KVVNSNKETLVNQANGKKQEIAKLENLSNDEMLRYNTAIDNVVKQYNEGKLNITAAMNALNSIKQAAQEVAQKNLQ

KQYAKKIERISSKGLALSKKAKEIYEKHKSILPTPGYYADSVGTYLNRFRDKQTFGNRSVWTGQSGLDEAKKMLDE

VKKLLKELQDLTRGTKEDKKPDVKPEAKPEAKPDVKPEAKPDVKPEAKPDVKPEAKPDVKPEAKPDVKPEAKPDVK

PKAKPDVKPEAKPDVKPDVKPDVKPEAKPEDKPDVKPDVKPEAKPDVKPEAKPEAKPEAKPEAKPEAKPDVKP

EAKPDVKPEAKPEAKPEAKSEAKPEAKLEAKPEAKPATKKSVNTSGNLAAKKAIENKKYSKK

II. Nucleic Acid Molecules Encoding BibA Polypeptides

The invention includes nucleic acid molecules which encode BibA polypeptides. The invention also includes nucleic acid molecules comprising nucleotide sequences having at least 50% sequence identity to such molecules. Depending on the particular sequence, the degree of sequence identity is preferably greater than 50% (e.g., 60%, 70%, 75%, 80%, 85%, 90%, 91%, 92%, 93%, 94%, 95%, 96%, 97%, 98%, 99% or more). Identity between nucleotide sequences is preferably determined by the Smith-Waterman homology search algorithm as implemented in the MPSRCH program (Oxford Molecular), using an affine gap search with parameters gap open penalty=12 and gap extension penalty=1.

The invention also provides nucleic acid molecules which can hybridize to these molecules. Hybridization reactions can be performed under conditions of different "stringency." Conditions which increase stringency of a hybridization reaction are widely known and published in the art. See, e.g., page 7.52 of Sambrook et al., Molecular Cloning: A Laboratory Manual, 1989. Examples of relevant conditions include (in order of increasing stringency): incubation temperatures of 25° C., 37° C., 50° C., 55° C., and 68° C.; buffer concentrations of 10×SSC, 6×SSC, 1×SSC, and 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art. See, e.g., Sambrook, 1989; Ausubel et al., eds., *Short Protocols in Molecular Biology*, 4th ed., 1999; U.S. Pat. No. 5,707,829; Ausubel et al., eds., *Current Protocols in Molecular Biology*, Supplement 30, 1987.

In some embodiments, nucleic acid molecules of the invention hybridize to a target under low stringency conditions; in other embodiments, nucleic acid molecules of the invention hybridize under intermediate stringency conditions; in preferred embodiments, nucleic acid molecules of the invention hybridize under high stringency conditions. An example of a low stringency hybridization condition is 50° C. and 10×SSC. An example of an intermediate stringency hybridization condition is 55° C. and 1×SSC. An example of a high stringency hybridization condition is 68° C. and 0.1×SSC.

Nucleic acid molecules comprising fragments of these sequences are also included in the invention. These comprise at least n consecutive nucleotides of these sequences and, depending on the particular sequence, n is 10 or more (e.g., 12, 14, 15, 18, 20, 25, 30, 35, 40, 50, 60, 70, 80, 90, 100, 150, 200, or more).

Nucleic acids (and polypeptides) of the invention may include sequences which:
(a) are identical (i.e., 100% identical) to the sequences disclosed in the sequence listing;
(b) share sequence identity with the sequences disclosed in the sequence listing;
(c) have 1, 2, 3, 4, 5, 6, 7, 8, 9, or 10 single nucleotide or amino acid alterations (deletions, insertions, substitutions), which may be at separate locations or may be contiguous, as compared to the sequences of (a) or (b); and,
(d) when aligned with a particular sequence from the sequence listing using a pairwise alignment algorithm, a moving window of x monomers (amino acids or nucleotides) moving from start (N-terminus or 5') to end (C-terminus or 3'), such that for an alignment that extends to p monomers (where p>x) there are p−x+1 such windows, each window has at least x·y identical aligned monomers, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [Needleman & Wunsch (1970) J. Mol. Biol. 48, 443-453], using default parameters (e.g., with Gap opening penalty=10.0, and with Gap extension penalty=0.5, using the EBLOSUM62 scoring matrix). This algorithm is conveniently implemented in the needle tool in the EMBOSS package [Rice et al. (2000) Trends Genet. 16:276-277].

The nucleic acids and polypeptides of the invention may additionally have further sequences to the N-terminus/5' and/or C-terminus/3' of these sequences (a) to (d).

Nucleic acid molecules of the invention can be single- or double-stranded and can be used, for example, to produce BibA polypeptides in vitro (i.e., a recombinant protein) or in vivo (as a DNA vaccine). The invention also provides single-stranded nucleic acid molecules which can hybridize to other nucleic acid molecules of the invention, preferably under "high stringency" conditions (e.g., 65° C. in a 0.1×SSC, 0.5% SDS solution).

Nucleic acid molecules of the invention can comprise DNA or RNA, including analogues, such as those containing modified backbones (e.g., phosphorothioates, etc.), and also peptide nucleic acids (PNA), etc. Nucleic acid molecules of the invention can comprise portions of genomic DNA, cDNA, or mRNA. Nucleic acid molecules of the invention do not encode full-length BibA proteins.

An example of a nucleic acid molecule which encodes a full-length BibA protein from which portions encoding BibA polypeptides can be derived is set forth below as SEQ ID NO:16:

```
ATGAATAATAACGAAAAAAAGTAAAATACTTTTTAAGAAAAACAGCTTATGGTTTGGCCTCAATGTCAGCAGCGT
TTGCTGTATGTAGTGGTATTGTACACGCGGATACTAGTTCAGGAATATCGGCTTCAATTCCTCATAAGAAACAAGT
TAATTTAGGGGCGGTTACTCTGAAGAATTTGATTTCTAAATATCGTGGTAATGACAAAGCTATTGCTATACTTTTA
AGTAGAGTAAATGATTTTAATAGAGCATCACAGGATACACTTCCACAATTAATTAATAGTACTGAAGCAGAAATTA
GAAATATTTTATATCAAGGACAAATTGGTAAGCAAAATAAACCAAGTGTAACTACACATGCTAAAGTTAGTGATCA
AGAACTAGGTAAGCAGTCAAGACGTTCTCAAGATATCATTAAGTCATTAGGTTTCCTTTCATCAGACCAAAAAGAT
ATTTTAGTTAAATCTATTAGCTCTTCAAAAGATTCGCAACTTATTCTTAAATTTGTAACTCAAGCCACGCAACTGA
ATAATGCTGAATCAACAAAAGCTAAGCAAATGGCTCAAAATGACGTGGCCTTAATAAAAAATATAAGCCCCGAAGT
CTTAGAAGAATATAAAGAAAAAATTCAAAGAGCTAGCACTAAGAGTCAAGTTGATGAGTTTGTAGCAGAAGCTAAA
AAAGTTGTTAATTCCAATAAAGAAACGTTGGTAAATCAGGCCAATGGTAAAAAGCAAGAAATTGCTAAGTTAGAAA
ATTTATCTAACGATGAAATGTTGAGATATAATACTGCAATTGATAATGTAGTGAAACAGTATAATGAAGGTAAGCT
CAATATTACTGCTGCAATGAATGCTTTAAATAGTATTAAGCAAGCAGCACAGGAAGTTGCCCAGAAAAACTTACAA
AAGCAGTATGCTAAAAAAATTGAAAGAATAAGTTCAAAAGGATTAGCGTTATCTAAAAAGGCTAAAGAAATTTATG
AAAAGCATAAAAGTATTTTGCCTACACCTGGATATTATGCAGACTCTGTGGGAACTTATTTGAATAGGTTTAGAGA
TAAACAAACTTTCGGAAATAGGAGTGTTTGGACTGGTCAAAGTGGACTTGATGAAGCAAAAAAAATGCTTGATGAA
GTCAAAAAGCTTTTAAAAGAACTTCAAGACCTTACCAGAGGTACTAAAGAAGATAAAAAACCAGACGTTAAGCCAG
AAGCCAAACCAGAGGCCAAACCAGACGTTAAGCCAGAGGCCAAACCAGACGTTAAGCCAGAAGCTAAGCCAGACGT
TAAACCAGAAGCTAAGCCAGACGTTAAACCAGAAGCTAAGCCAGACGTTAAACCAGAAGCTAAGCCAGACGTTAAA
CCAAAGGCCAAACCAGACGTTAAGCCAGAAGCTAAGCCAGACGTTAAACCAGACGTTAAACCAGACGTTAAGCCAG
AGGCCAAACCAGAGGATAAGCCAGACGTTAAACCAGACGTTAAGCCAGAAGCTAAACCAGACGTTAAGCCAGAGGC
CAAACCAGAAGCTAAGCCAGAAGCTAAGCCAGAAGCTAAGCCAGAGGCCAAACCAGAAGCTAAGCCAGACGTTAAG
CCAGAAGCTAAACCAGACGTTAAACCAGAGGCTAAGCCAGAAGCTAAACCAGAGGCTAAGTCAGAAGCTAAACCAG
AGGCTAAGCTAGAAGCTAAACCAGAGGCCAAACCAGCAACCAAAAAATCGGTTAATACTAGCGGAAACTTGGCGGC
TAAAAAAGCTATTGAAAACAAAAGTATAGTAAAAAATTACCATCAACGGGTGAAGCCGCAAGTCCACTCTTAGCA
ATTGTATCACTAATTGTTATGTTAAGTGCAGGTCTTATTACGATAGTTTTAAAGCATAAAAAAAAT
```

Other embodiments of the invention provide nucleic acid molecules which encode a proline-rich domain of a BibA polypeptide. An example of such a nucleic acid molecule is set forth below as SEQ ID NO:17:

```
CCAGACGTTAAGCCAGAAGCCAAACCAGAGGCCAAACCAGACGTTAAGCCAGAGGCCAAACCAGACGTTAAGCCAGA
AGCTAAGCCAGACGTTAAACCAGAAGCTAAGCCAGACGTTAAACCAGAAGCTAAGCCAGACGTTAAACCAGAAGCTA
AGCCAGACGTTAAACCAAAGGCCAAACCAGACGTTAAGCCAGAAGCTAAGCCAGACGTTAAACCAGACGTTAAACCA
GACGTTAAGCCAGAGGCCAAACCAGAGGATAAGCCAGACGTTAAACCAGACGTTAAGCCAGAAGCTAAACCAGACGT
TAAGCCAGAGGCCAAACCAGAAGCTAAGCCAGAAGCTAAGCCAGAAGCTAAGCCAGAGGCCAAACCAGAAGCTAAGC
CAGACGTTAAGCCAGAAGCTAAACCAGACGTTAAACCAGAGGCTAAGCCAGAAGCTAAACCAGAGGCTAAGTCAGAA
GCTAAACCAGAGGCTAAGCTAGAAGCTAAACCAGAGGCCAAACCAGCAACCAAAAAATCGGTTAATACTAGCGGAAA
CTTGGCGGCTAAAAAAGCTATTGAAAACAAAAGTATAGTAAAAAA
```

A nucleic acid molecule encoding a highly conserved coiled-coil domain and proline-rich domain of a BibA polypeptide is set forth below as SEQ ID NO:18:

```
GGTATTGTACACGCGGATACTAGTTCAGGAATATCGGCTTCAATTCCTCATAAGAAACAAGTTAATTTAGGGCGGT
TACTCTGAAGAATTTGATTTCTAAATATCGTGGTAATGACAAAGCTATTGCTATACTTTTAAGTAGAGTAAATGATT
TTAATAGAGCATCACAGGATACACTTCCACAATTAATTAATAGTACTGAAGCAGAAATTAGAAATATTTTATATCAA
GGACAAATTGGTAAGCAAAATAAACCAAGTGTAACTACACATGCTAAAGTTAGTGATCAAGAACTAGGTAAGCAGTC
AAGACGTTCTCAAGATATCATTAAGTCATTAGGTTTCCTTTCATCAGACCAAAAAGATATTTTAGTTAAATCTATTA
GCTCTTCAAAAGATTCGCAACTTATTCTTAAATTTGTAACTCAAGCCACGCAACTGAATAATGCTGAATCAACAAAA
GCTAAGCAAATGGCTCAAAATGACGTGGCCTTAATAAAAAATATAAGCCCCGAAGTCTTAGAAGAATATAAAGAAAA
AATTCAAAGAGCTAGCACTAAGAGTCAAGTTGATGAGTTTGTAGCAGAAGCTAAAAAAGTTGTTAATTCCAATAAAG
AAACGTTGGTAAATCAGGCCAATGGTAAAAAGCAAGAAATTGCTAAGTTAGAAAATTTATCTAACGATGAAATGTTG
AGATATAATACTGCAATTGATAATGTAGTGAAACAGTATAATGAAGGTAAGCTCAATATTACTGCTGCAATGAATGC
TTTAAATAGTATTAAGCAAGCAGCACAGGAAGTTGCCCAGAAAAACTTACAAAAGCAGTATGCTAAAAAAATTGAAA
GAATAAGTTCAAAAGGATTAGCGTTATCTAAAAAGGCTAAAGAAATTTATGAAAAGCATAAAAGTATTTTGCCTACA
CCTGGATATTATGCAGACTCTGTGGGAACTTATTTGAATAGGTTTAGAGATAAACAAACTTTCGGAAATAGGAGTGT
TTGGACTGGTCAAAGTGGACTTGATGAAGCAAAAAAAATGCTTGATGAAGTCAAAAAGCTTTTAAAAGAACTTCAAG
ACCTTACCAGAGGTACTAAAGAAGATAAAAAACCAGACGTTAAGCCAGAAGCCAAACCAGAGGCCAAACCAGACGTT
AAGCCAGAGGCCAAACCAGACGTTAAGCCAGAAGCTAAGCCAGACGTTAAACCAGAAGCTAAGCCAGACGTTAAACC
AGAAGCTAAGCCAGACGTTAAACCAGAAGCTAAGCCAGACGTTAAACCAAAGGCCAAACCAGACGTTAAGCCAGAAG
CTAAGCCAGACGTTAAACCAGACGTTAAACCAGACGTTAAGCCAGAGGCCAAACCAGAGGATAAGCCAGACGTTAAA
CCAGACGTTAAGCCAGAAGCTAAA
```

A nucleic acid molecule which encodes a cell wall anchor of BibA is set forth as SEQ ID NO:19: TTACCATCAACGGGT.

III. Preparation of Nucleic Acid Molecules

Nucleic acid molecules of the invention can be prepared in many ways, for example, by chemical synthesis, from genomic or cDNA libraries (e.g., using primer-based amplification methods, such as PCR), from the organism itself, etc.) and can take various forms (e.g. single-stranded, double-stranded, vectors, probes, etc.). They are preferably prepared in substantially pure form (i.e. substantially free from other GBS or host cell nucleic acids).

Nucleic acid molecules can be synthesized, in whole or in part, using chemical methods well known in the art. See Caruthers et al., *Nucl. Acids Res. Symp. Ser.* 215-223, 1980; Horn et al. *Nucl. Acids Res. Symp. Ser.* 225-232, 1980; Hunkapiller et al. (1984), Nature 310: 105-111; Grantham et al. (1981), Nucleic Acids Res. 9: r43-r74.

cDNA molecules can be made with standard molecular biology techniques, using mRNA as a template. cDNA molecules can thereafter be replicated using molecular biology techniques well known in the art. An amplification technique, such as PCR, can be used to obtain additional copies of polynucleotides of the invention, using either genomic DNA or cDNA as a template.

If desired, nucleotide sequences can be engineered using methods generally known in the art to alter coding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Sequence modifications, such as the addition of a purification tag sequence or codon optimization, can be used to facilitate expression. For example, the N-terminal leader sequence may be replaced with a sequence encoding for a tag protein such as polyhistidine ("HIS") or glutathione S-transferase ("GST"). Such tag proteins may be used to facilitate purification, detection, and stability of the expressed protein. Codons preferred by a particular prokaryotic or eukaryotic host can be selected to increase the rate of protein expression or to produce an RNA transcript having desirable properties, such as a half-life which is longer than that of a transcript generated from the naturally occurring sequence. These methods are well known in the art and are further described in WO05/032582.

IV. Production of BibA Polypeptides

BibA polypeptides can be produced recombinantly, for example, by culturing a host cell transformed with nucleic acid molecules of the invention under conditions which permit polypeptide expression. BibA polypeptides can be synthesized by chemical means, or can be prepared from full-length BibA protein isolated from *S. agalactiae*.

A. Recombinant Production of Polypeptides

1. Nucleic Acid Molecules

Any nucleic acid molecule which encodes a particular BibA polypeptide can be used to produce that polypeptide recombinantly. Recombinant production of BibA polypeptides can be facilitated by adding a nucleotide sequence encoding a tag protein in frame to the nucleotide sequence encoding the BibA polypeptide such that the polypeptide is expressed as a fusion protein comprising the tag protein and the GBS polypeptide. Such tag proteins can facilitate purification, detection, and stability of the expressed protein. Tag proteins suitable for use in the invention include a polyarginine tag (Arg-tag), polyhistidine tag (His-tag), FLAG-tag, Strep-tag, c-myc-tag, S-tag, calmodulin-binding peptide, cellulose-binding domain, SBP-tag, chitin-binding domain, glutathione S-transferase-tag (GST), maltose-binding protein, transcription termination anti-termination factor (NusA), *E. coli* thioredoxin (TrxA), and protein disulfide isomerase I (DsbA). Preferred tag proteins include His-tag and GST. See Terpe et al., Appl Microbiol Biotechnol (2003) 60:523-33.

After purification, a tag protein may optionally be removed from the expressed fusion protein, i.e., by specifically tailored enzymatic treatments known in the art. Commonly used proteases include enterokinase, tobacco etch virus (TEV), thrombin, and factor $X_a$.

2. Expression Constructs

A nucleic acid molecule which encodes a polypeptide can be inserted into an expression construct which contains the necessary elements for the transcription and translation of the inserted coding sequence. Methods which are well known to those skilled in the art can be used to construct expression constructs containing coding sequences and appropriate transcriptional and translational control elements. These methods include in vitro recombinant DNA techniques, synthetic techniques, and in vivo genetic recombination.

3. Host Cells

The heterologous host can be prokaryotic or eukaryotic. *E. coli* is a preferred host cell, but other suitable hosts include *Bacillus subtilis, Vibrio cholerae, Salmonella typhi, Salmonella typhimurium, Neisseria lactamica, Neisseria cinerea, Mycobacteria* (e.g., *M. tuberculosis*), yeasts, etc.

A host cell strain can be chosen for its ability to modulate the expression of the inserted sequences or to process the expressed polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities are available from the American Type Culture Collection (ATCC; 10801 University Boulevard, Manassas, Va. 20110-2209) and can be chosen to ensure the correct modification and processing of a foreign protein. See WO 01/98340.

Expression constructs can be introduced into host cells using well-established techniques which include, but are not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun" methods, and DEAE- or calcium phosphate-mediated transfection.

Host cells transformed with expression constructs can be cultured under conditions suitable for the expression and recovery of the protein from cell culture. The protein produced by a transformed cell can be secreted or contained intracellularly depending on the nucleotide sequence and/or the expression construct used. Those of skill in the art understand that expression constructs can be designed to contain signal sequences which direct secretion of soluble polypeptides through a prokaryotic or eukaryotic cell membrane.

B. Purification

BibA polypeptides of the invention can be isolated from the appropriate *Streptococcus agalactiae* bacterium or from an engineered host cell. A purified BibA polypeptide is separated from other components in the cell, such as proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified BibA polypeptide is at least 80% pure; preferably, the preparations are 90%, 95%, or 99% pure. Purity of the preparations can be assessed by any means known in the art, such as SDS-polyacrylamide gel electrophoresis. Where appropriate, polypeptides can be solubilized, for example, with urea.

C. Chemical Synthesis

BibA polypeptides of the invention can be synthesized, for example, using solid-phase techniques. See, e.g., Merrifield, *J. Am. Chem. Soc.* 85, 2149-54, 1963; Roberge et al., *Science* 269, 202-04, 1995. Synthesis can be performed using manual techniques or by automation. Automated synthesis can be achieved, for example, using Applied Biosystems 431A Peptide Synthesizer (Perkin Elmer). Optionally, fragments of a polypeptide can be separately synthesized and combined using chemical methods to produce the final molecule.

V. Antibodies

Antibodies can be generated to bind specifically to a BibA polypeptide or other antigen and can be used therapeutically and diagnostically. The term "antibody" includes intact immunoglobulin molecules, as well as fragments thereof which are capable of binding an antigen. These include hybrid (chimeric) antibody molecules (e.g., Winter et al., *Nature* 349, 293-99, 1991; U.S. Pat. No. 4,816,567); F(ab')$_2$ and F(ab) fragments and $F_v$ molecules; non-covalent heterodimers (e.g., Inbar et al., *Proc. Natl. Acad. Sci. U.S.A.* 69, 2659-62, 1972; Ehrlich et al., *Biochem* 19, 4091-96, 1980); single-chain $F_v$ molecules (sFv) (e.g., Huston et al., *Proc. Natl. Acad. Sci. U.S.A.* 85, 5897-83, 1988); dimeric and trimeric antibody fragment constructs; minibodies (e.g., Pack et al., *Biochem* 31, 1579-84, 1992; Cumber et al., *J. Immunology* 149B, 120-26, 1992); humanized antibody molecules (e.g., Riechmann et al., *Nature* 332, 323-27, 1988; Verhoeyan et al., *Science* 239, 1534-36, 1988; and U.K. Patent Publication No. GB 2,276,169, published 21 Sep. 1994); and any functional fragments obtained from such molecules, as well as antibodies obtained through non-conventional processes such as phage display. Preferably, the antibodies are monoclonal antibodies. Methods of obtaining monoclonal antibodies are well known in the art.

Preferred antibodies of the invention specifically bind to an epitope in the N-terminal domain, coiled-coil domain, or proline-rich domain of BibA. Typically, at least 6, 7, 8, 10, or 12 contiguous amino acids are required to form an epitope. However, epitopes which involve non-contiguous amino acids may require more, e.g., at least 15, 25, or 50 amino acids. Various immunoassays (e.g., Western blots, ELISAs, radioimmunoassays, immunohistochemical assays, immunoprecipitations, or other immunochemical assays known in the art) can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. A preparation of antibodies which specifically bind to a particular antigen typically provides a detection signal at least 5-, 10-, or 20-fold higher than a detection signal provided with other proteins when used in an immunochemical assay. Preferably, the antibodies do not detect other proteins in immunochemical assays and can immunoprecipitate the particular antigen from solution.

Polypeptides can be used to immunize a mammal, such as a mouse, rat, rabbit, guinea pig, monkey, or human, to produce polyclonal antibodies. If desired, an antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to an antigen can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495-497, 1985; Kozbor et al., *J. Immunol. Methods* 81, 31-42, 1985; Cote et al., *Proc. Natl. Acad. Sci.* 80, 2026-2030, 1983; Cole et al., *Mol. Cell Biol.* 62, 109-120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851-6855, 1984; Neuberger et al., *Nature* 312, 604-608, 1984; Takeda et al., *Nature* 314, 452-454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (Burton, *Proc. Natl. Acad. Sci.* 88, 11120-23, 1991).

Single-chain antibodies also can be constructed using a DNA amplification method, such as PCR, using hybridoma cDNA as a template (Thirion et al., 1996, *Eur. J. Cancer Prev.* 5, 507-11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159-63. Construction of bivalent, bispecific single-chain antibodies is taught in Mallender & Voss, 1994, *J. Biol. Chem.* 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497-501; Nicholls et al., 1993, *J. Immunol. Meth.* 165, 81-91).

Antibodies which specifically bind to a particular antigen also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833-3837, 1989; Winter et al., *Nature* 349, 293-299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

VI. Compositions Comprising One or More Active Agents

The invention provides compositions for preventing and for treating *S. agalactiae* infection. Compositions of the invention comprise at least one active agent. The active agent can be a BibA polypeptide, a nucleic acid molecule encoding a BibA polypeptide, or antibodies which specifically bind to a BibA polypeptide. Suitable BibA polypeptides include, for example, those identified in groups "I," "II," and "III" in FIG. 24. Compositions of the invention can include one or more BibA polypeptides of two or more of these groups.

Compositions of the invention can include one or more additional active agents. Such agents include, but are not limited to one or more (a) GBS antigens, (b) non-GBS antigens, (c) nucleic acid molecules encoding (a) or (b), and antibodies which specifically bind to (a) or (b).

A. GBS Antigens

GBS antigens which can be included in compositions of the invention include antigenic portions of the GBS proteins disclosed in WO 02/34771 (e.g., GBS1-GBS689), which is incorporated herein by reference in its entirety. Preferred antigens include GBS 80, GBS 104, GBS 322, GBS 67, GBS 276, and GBS 59.

B. Non-GBS Antigens

Compositions of the invention may be administered in conjunction with one or more antigens for use in therapeutic, prophylactic, or diagnostic methods of the present invention. Compositions of the invention optionally can comprise one or more additional polypeptide antigens which are not derived from *S. agalactiae* proteins. Preferred antigens include those listed below. Additionally, the compositions of the present invention may be used to treat or prevent infections caused by any of the below-listed pathogens. In addition to combination with the antigens described below, the compositions of the invention may also be combined with an adjuvant as described herein.

Antigens for use with the invention include, but are not limited to, one or more of the following antigens set forth below, or antigens derived from one or more of the pathogens set forth below:

1. Bacterial Antigens

Bacterial antigens suitable for use in the invention include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides:* Meningitides antigens may include proteins (such as those identified in References 1-7), saccharides (including a polysaccharide, oligosaccharide or lipopolysaccharide), or outer-membrane vesicles (References 8, 9, 10, 11) purified or derived from *N. meningitides* serogroup such as A, C, W135, Y, and/or B. Meningitides protein antigens may be selected from adhesions, autotransporters, toxins, Fe acquisition proteins, and membrane associated proteins (preferably integral outer membrane protein).

*Streptococcus pneumoniae:* Streptococcus pneumoniae antigens may include a saccharide (including a polysaccharide or an oligosaccharide) and/or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. Nos. 6,699,703, 6,800,744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GBS 40), fusions of fragments of GBS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis:* Moraxella antigens include antigens identified in WO 02/18595 and WO 99/58562, outer membrane protein antigens (HMW-OMP), C-antigen, and/or LPS.

*Bordetella pertussis:* Pertussis antigens include *pertussis* holotoxin (PT) and filamentous haemagglutinin (FHA) from *B. pertussis*, optionally also combination with pertactin and/or agglutinogens 2 and 3 antigen.

*Staphylococcus aureus:* Staphylococcus aureus antigens include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis:* S. epidermidis antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as CRM197. Additionally antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib antigens include a Hib saccharide antigen.

*Pseudomonas aeruginosa:* Pseudomonas antigens include endotoxin A, Wzz protein, *P. aeruginosa* LPS, more particularly LPS isolated from PAO1 (O5 serotype), and/or Outer Membrane Proteins, including Outer Membrane Proteins F (OprF) (Infect Immun. 2001 May; 69(5): 3510-3515).

*Legionella pneumophila.* Bacterial antigens may be derived from *Legionella pneumophila.*

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae:* Gonorrhoeae antigens include Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243).

*Chlamydia trachomatis:* Chlamydia trachomatis antigens include antigens derived from serotypes A, B, Ba and C (agents of trachoma, a cause of blindness), serotypes L1, L2 & L3 (associated with *Lymphogranuloma venereum*), and serotypes, D-K. *Chlamydia trachomas* antigens may also include an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): Ducreyi antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori:* H. pylori antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* antigens include LPS (Infect Immun. 2002 August; 70(8): 4414).

*E. coli:* E. coli antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which can share a common B-component known as protective antigen (PA).

*Yersinia pestis* (plague): Plague antigens include F1 capsular antigen (Infect Immun. 2003 January; 71(1)): 374-383, LPS (Infect Immun. 1999 October; 67(10): 5395), *Yersinia pestis* V antigen (Infect Immun. 1997 November; 65(11): 4476-4482).

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles (Infect Immun. 2004 October; 72(10): 6148), *Mycobacterium tuberculosis* (Mtb) isocitrate dehydrogenase associated antigens (Proc Natl Acad Sci USA. 2004 Aug. 24; 101(34): 12652), and/or MPT51 antigens (Infect Immun. 2004 July; 72(7): 3829).

*Rickettsia*: Antigens include outer membrane proteins, including the outer membrane protein A and/or B (OmpB) (Biochim Biophys Acta. 2004 Nov. 1; 1702(2):145), LPS, and surface protein antigen (SPA) (J. Autoimmun. 1989 June; 2 Suppl:81).

*Listeria monocytogenes*. Bacterial antigens may be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* 0139, antigens of IEM108 vaccine (Infect Immun. 2003 October; 71(10):5498-504), and/or Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, Infect Immun. 2001 May; 69(5): 3323-3334), VlsE Antigenic Variation Protein (J Clin Microbiol. 1999 December; 37(12): 3997).

*Porphyromonas gingivalis*: Antigens include *P. gingivalis* outer membrane protein (OMP).

*Klebsiella*: Antigens include an OMP, including OMP A, or a polysaccharide optionally conjugated to tetanus toxoid.

Further bacterial antigens of the invention may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens of the present invention may be derived from gram-negative or gram-positive bacteria. The antigens of the present invention may be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example CRM197). Such conjugation may be direct conjugation effected by reductive amination of carbonyl moieties on the saccharide to amino groups on the protein, as provided in U.S. Pat. No. 5,360,897 and Can J Biochem Cell Biol. 1984 May; 62(5):270-5. Alternatively, the saccharides can be conjugated through a linker, such as, with succinamide or other linkages provided in Bioconjugate Techniques, 1996 and CRC, Chemistry of Protein Conjugation and Cross-Linking, 1993.

2. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

*Orthomyxovirus*: Viral antigens may be derived from an *Orthomyxovirus*, such as Influenza A, B and C. *Orthomyxovirus* antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., J Gen Virol. 2004 November; 85(Pt 11):3229). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 or NSP-4. Togavirus antigens are preferably selected from E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al., Hepatology (1991) 14:381).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens may be derived from Calciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible Gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: HIVIIIb, HIVSF2, HIVLAV, HIVLAI, HIVMN, HIV-1CM235, HIV-1US4.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, μ1, μ2, σ1, σ2, or σ3, or nonstructural proteins σNS, μNS, or σ1s. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly δ-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomyavirus viruses include BK virus and JK virus. Polyomavirus antigens may be selected from VP1, VP2 or VP3.

Further provided are antigens, compositions, methods, and microbes included in Vaccines, 4th Edition (Plotkin and Orenstein ed. 2004); Medical Microbiology 4th Edition (Murray et al. ed. 2002); Virology, 3rd Edition (W. K. Joklik ed. 1988); Fundamental Virology, 2nd Edition (B. N. Fields and D. M. Knipe, eds. 1991), which are contemplated in conjunction with the compositions of the present invention.

3. Fungal Antigens

Fungal antigens for use in the invention may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

4. STD Antigens

The compositions of the invention may include one or more antigens derived from a sexually transmitted disease (STD). Such antigens may provide for prophylactis or therapy for STD's such as chlamydia, genital herpes, hepatitis (such as HCV), genital warts, gonorrhoea, syphilis and/or chancroid (See, WO00/15255). Antigens may be derived from one or more viral or bacterial STD's. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli,* and *Streptococcus agalactiae.* Examples of specific antigens derived from these pathogens are described above.

5. Respiratory Antigens

The compositions of the invention may include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific antigens derived from these pathogens are described above.

6. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens may be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of *Orthomyxovirus* (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli.* Examples of specific antigens derived from these pathogens are described above.

7. Antigens Suitable for Use in Elderly or Immunocompromised Individuals

The compositions of the invention may include one or more antigens suitable for use in elderly or immunocompromised individuals. Such individuals may need to be vaccinated more frequently, with higher doses or with adjuvanted formulations to improve their immune response to the targeted antigens. Antigens which may be targeted for use in Elderly or Immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae, Orthomyxovirus* (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

8. Antigens Suitable for Use in Adolescent Vaccines

The compositions of the invention may include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

9. Antigen Formulations

In other aspects of the invention, methods of producing microparticles having adsorbed antigens are provided. The methods comprise: (a) providing an emulsion by dispersing a mixture comprising (i) water, (ii) a detergent, (iii) an organic solvent, and (iv) a biodegradable polymer selected from the group consisting of a poly(α-hydroxy acid), a polyhydroxy butyric acid, a polycaprolactone, a polyorthoester, a polyanhydride, and a polycyanoacrylate. The polymer is typically present in the mixture at a concentration of about 1% to about 30% relative to the organic solvent, while the detergent is typically present in the mixture at a weight-to-weight detergent-to-polymer ratio of from about 0.00001:1 to about 0.1:1 (more typically about 0.0001:1 to about 0.1:1, about 0.001:1 to about 0.1:1, or about 0.005:1 to about 0.1:1); (b) removing the organic solvent from the emulsion; and (c) adsorbing an antigen on the surface of the microparticles. In certain embodiments, the biodegradable polymer is present at a concentration of about 3% to about 10% relative to the organic solvent.

Microparticles for use herein will be formed from materials that are sterilizable, non-toxic and biodegradable. Such materials include, without limitation, poly(α-hydroxy acid), polyhydroxybutyric acid, polycaprolactone, polyorthoester, polyanhydride, PACA, and polycyanoacrylate. Preferably, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

Further antigens may also include an outer membrane vesicle (OMV) preparation.

Additional formulation methods and antigens (especially tumor antigens) are provided in U.S. patent Ser. No. 09/581,772.

10. Antigen References

The following references include antigens useful in conjunction with the compositions of the present invention:

1 WO99/24578
2 WO99/36544.
3 WO99/57280.
4 WO00/22430.
5 Tettelin et al. (2000) Science 287:1809-1815.
6 WO96/29412.
7 Pizza et al. (2000) Science 287:1816-1820.
8 PCT WO 01/52885.
9 Bjune et al. (1991) Lancet 338(8775).
10 Fuskasawa et al. (1999) Vaccine 17:2951-2958.
11 Rosenqist et al. (1998) Dev. Biol. Strand 92:323-333.
12 Constantino et al. (1992) Vaccine 10:691-698.
13 Constantino et al. (1999) Vaccine 17:1251-1263.
14 Watson (2000) Pediatr Infect Dis J 19:331-332.
15 Rubin (20000) Pediatr Clin North Am 47:269-285,v.
16 Jedrzejas (2001) Microbiol Mol Biol Rev 65:187-207.
17 filed on 3 Jul. 2001 claiming priority from GB-0016363.4; WO 02/02606; PCT IB/01/00166.
18 Kalman et al. (1999) Nature Genetics 21:385-389.
19 Read et al. (2000) Nucleic Acids Res 28:1397-406.
20 Shirai et al. (2000) J. Infect. Dis 181(Suppl 3):S524-S527.
21 WO99/27105.
22 WO00/27994.
23 WO00/37494.
24 WO99/28475.
25 Bell (2000) Pediatr Infect Dis J 19:1187-1188.
26 Iwarson (1995) APMIS 103:321-326.
27 Gerlich et al. (1990) Vaccine 8 Suppl:S63-68 & 79-80.
28 Hsu et al. (1999) Clin Liver Dis 3:901-915.
29 GBStofsson et al. (1996) N. Engl. J. Med. 334:349-355.
30 Rappuoli et al. (1991) TIBTECH 9:232-238.
31 Vaccines (1988) eds. Plotkin & Mortimer. ISBN 0-7216-1946-0,
32 Del Guidice et al. (1998) Molecular Aspects of Medicine 19:1-70.
33 WO93/018150.
34 WO99/53310.
35 WO98/04702.
36 Ross et al. (2001) Vaccine 19:135-142.
37 Sutter et al. (2000) Pediatr Clin North Am 47:287-308.
38 Zimmerman & Spann (1999) Am Fan Physician 59:113-118, 125-126.
39 Dreensen (1997) Vaccine 15 Suppl" S2-6.
40 MMWR Morb Mortal Wkly rep 1998 January 16:47(1): 12, 9.
41 McMichael (2000) Vaccine 19 Suppl 1:S101-107.
42 Schuchat (1999) Lancer 353(9146):51-6.
43 GB patent applications 0026333.5, 0028727.6 & 0105640.7.
44 Dale (1999) Infect Disclin North Am 13:227-43, viii.
45 Ferretti et al. (2001) PNAS USA 98: 4658-4663.
46 Kuroda et al. (2001) Lancet 357(9264):1225-1240; see also pages 1218-1219.
47 Ramsay et al. (2001) Lancet 357(9251):195-196.
48 Lindberg (1999) Vaccine 17 Suppl 2:S28-36.
49 Buttery & Moxon (2000) J R Coil Physicians Long 34:163-168.
50 Ahmad & Chapnick (1999) Infect Dis Clin North Am 13:113-133, vii.
51 Goldblatt (1998) J. Med. Microbiol. 47:663-567.
52 European patent 0 477 508.
53 U.S. Pat. No. 5,306,492.
54 WO98/42721.
55 Conjugate Vaccines (eds. Cruse et al.) ISBN 3805549326, particularly vol. 10:48-114.
56 Hermanson (1996) Bioconjugate Techniques ISBN: 012323368 & 012342335X.
57 EP 0372501.
58 EP 0378881.
59 EP 0427347.
60 WO93/17712.
61 WO98/58668.
62 EP 0471177.
63 WO00/56360.
64 WO00/67161.

The contents of all of the above cited patents, patent applications and journal articles are incorporated by reference as if set forth fully herein.

Where a saccharide or carbohydrate antigen is used, it is preferably conjugated to a carrier protein in order to enhance immunogenicity. See Ramsay et al. (2001) Lancet 357(9251): 195-196; Lindberg (1999) Vaccine 17 Suppl 2:S28-36; Buttery & Moxon (2000) J R Coll Physicians Lond 34:163-168; Ahmad & Chapnick (1999) Infect Dis Clin North Am 13:113-133, vii; Goldblatt (1998) J. Med. Microbiol. 47:563-567; European patent 0 477 508; U.S. Pat. No. 5,306,492; WO98/42721; Conjugate Vaccines (eds. Cruse et al.) ISBN 3805549326, particularly vol. 10:48-114; Hermanson (1996) Bioconjugate Techniques ISBN: 0123423368 or 012342335X. Preferred carrier proteins are bacterial toxins or toxoids, such as diphtheria or tetanus toxoids. The CRM197 diphtheria toxoid is particularly preferred.

Other carrier polypeptides include the *N. meningitidis* outer membrane protein (EP-A-0372501), synthetic peptides (EP-A-0378881 and EP-A 0427347), heat shock proteins (WO 93/17712 and WO 94/03208), pertussis proteins (WO 98/58668 and EP A 0471177), protein D from *H. influenzae* (WO 00/56360), cytokines (WO 91/01146), lymphokines, hormones, growth factors, toxin A or B from *C. difficile* (WO 00/61761), iron-uptake proteins (WO 01/72337), etc. Where a mixture comprises capsular saccharide from both serigraphs A and C, it may be preferred that the ratio (w/w) of MenA saccharide:MenC saccharide is greater than 1 (e.g., 2:1, 3:1, 4:1, 5:1, 10:1 or higher). Different saccharides can be conjugated to the same or different type of carrier protein. Any suitable conjugation reaction can be used, with any suitable linker where necessary.

Toxic protein antigens may be detoxified where necessary e.g., detoxification of pertussis toxin by chemical and/or genetic means.

VII. Pharmaceutical Compositions

In some embodiments pharmaceutical compositions of the invention comprise a BibA polypeptide (with or without other active agents, as disclosed above). In other embodiments pharmaceutical compositions comprise a nucleic acid molecule encoding the BibA polypeptide (with or without nucleic acid molecules encoding other active agents, as described above). Nucleic acid vaccines are described, for example, in Robinson & Torres (1997) *Seminars in Immunology* 9:271-283; Donnelly et al. (1997) *Ann. Rev Immunol* 15:617-648; Scott-Taylor & Dalgleish (2000) *Expert Opin Investig Drugs* 9:471-480; Apostolopoulos & Plebanski (2000) *Curr Opin Mol Ther* 2:441-447; Ilan (1999) *Curr Opin Mol Ther* 1:116-120; Dubensky et al. (2000) *Mol Med* 6:723-732; Robinson & Pertmer (2000) *Adv Virus Res* 55:1-74; Donnelly et al. (2000) *Am J Respir Crit Care Med* 162(4 Pt 2):S190-193 Davis (1999) *Mt. Sinai J. Med.* 66:84-90. Typically the nucleic acid molecule is a DNA molecule, e.g., in the form of a plasmid. In other embodiments pharmaceutical compositions comprise antibodies which specifically bind to a BibA polypeptide Immunogenic compositions of the invention are preferably vaccine compositions. The pH of such compositions preferably is between 6 and 8, preferably about 7. The pH can be maintained by the use of a buffer. The composition can be sterile and/or pyrogen-free. The composition can be isotonic with respect to humans. Vaccines according to the invention may be used either prophylactically or therapeutically, but will typically be prophylactic and can be used to treat animals (including companion and laboratory mammals), particularly humans.

A. Pharmaceutically Acceptable Carriers

Compositions of the invention will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) *Remington: The Science and Practice of Pharmacy* 20th ed., ISBN:0683306472.

B. Immunoregulatory Agents

1. Adjuvants

Vaccines of the invention may be administered in conjunction with other immunoregulatory agents. In particular, compositions will usually include an adjuvant. Adjuvants for use with the invention include, but are not limited to, one or more of the following set forth below:

a. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of Vaccine Design . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

In one embodiment the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment the adjuvant of the invention comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (isoelectric point=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

b. Oil-Emulsions

Oil-emulsion compositions suitable for use as adjuvants in the invention include squalene-water emulsions, such as MF59 (5% Squalene, 0.5% TWEEN™ 80, and 0.5% Span 85, formulated into submicron particles using a microfluidizer). See WO90/14837. See also, Podda, Vaccine (2001) 19: 2673-2680; Frey et al., Vaccine (2003) 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN™ 80 (polyoxyethylenesorbitan monooleate), and/or 0.25-1.0% SPAN 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., in Vaccine Design The Subunit and Adjuvant Approach (Powell, M. F. and Newman, M. J. eds.) Plenum Press, New York, 1995, pp. 277-296). MF59 contains 4-5% w/v Squalene (e.g. 4.3%), 0.25-0.5% w/v TWEEN™ 80, and 0.5% w/v SPAN 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v TWEEN™ 80, and 0.75% w/v SPAN 85™ and optionally MTP-PE. Yet another submicron oil-in-water emulsion is MF75, also known as SAF, containing 10% squalene, 0.4% TWEEN™ 80, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in WO90/14837 and U.S. Pat. Nos. 6,299,884 and 6,451,325.

Complete Freund's adjuvant (CFA) and incomplete Freund's adjuvant (IFA) may also be used as adjuvants in the invention.

c. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr, et al., Advanced Drug Delivery Reviews (1998) 32:247-271. See also Sjolander, et al., Advanced Drug Delivery Reviews (1998) 32:321-338.

d. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., Virology (2002) 293:273-280; Lenz et al., Journal of Immunology (2001) 5246-5355; Pinto, et al., Journal of Infectious Diseases (2003) 188:327-338; and Gerber et al., Journal of Virology (2001) 75(10):4752-4760. Virosomes are discussed further in, for example, Gluck et al., Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) Vaccine 20 Suppl 5:B17-23} and the INFLUVAC PLUS™ product.

e. Bacterial or Microbial Derivatives

Adjuvants suitable for use in the invention include bacterial or microbial derivatives such as:

i. Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC 529. See Johnson et al. (1999) Bioorg Med Chem Lett 9:2273-2278.

ii. Lipid A Derivatives

Lipid A derivatives include derivatives of lipid A from *Escherichia coli* such as OM-174. OM-174 is described for example in Meraldi et al., Vaccine (2003) 21:2485-2491; and Pajak, et al., Vaccine (2003) 21:836-842.

f. Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., Nucleic Acids Research (2003) 31(9): 2393-2400; WO02/26757 and WO99/62923 for examples of possible analog substitutions. The adjuvant effect of CpG oligonucleotides is further discussed in Krieg, Nature Medicine (2003) 9(7): 831-835; McCluskie, et al., FEMS Immunology and Medical Microbiology (2002) 32:179-185; WO98/40100; U.S. Pat. Nos. 6,207,646; 6,239,116 and 6,429,199.

The CpG sequence may be directed to TLR9, such as the motif GTCGTT or TTCGTT. See Kandimalla, et al., Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., J. Immunol. (2003) 170(8):4061-4068; Krieg, TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., BBRC (2003) 306:948-953; Kandimalla, et al., Biochemical Society Transactions (2003) 31 (part 3):664-658; Bhagat et al., BBRC (2003) 300:853-861 and WO03/035836.

g. ADP-Ribosylating Toxins and Detoxified Derivatives Thereof

Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon, et al., Infection and Immunity (2002) 70(6):3012-3019; Pizza, et al., Vaccine (2001) 19:2534-2541; Pizza, et al., Int. J. Med. Microbiol (2000) 290(4-5):455-461; Scharton-Kersten et al., Infection and Immunity (2000) 68(9):5306-5313; Ryan et al., Infection and Immunity (1999) 67(12):6270-6280; Partidos et al., Immunol. Lett. (1999) 67(3):209-216; Peppoloni et al., Vaccines (2003) 2(2):285-293; and Pine et al., (2002) J. Control Release (2002) 85(1-3):263-270. Numerical reference for amino acid substitutions is preferably based on the alignments of the A and B subunits of ADP-ribosylating toxins set forth in Domenighini et al., Mol. Microbiol (1995) 15(6): 1165-1167.

h. Bioadhesives and Mucoadhesives

Bioadhesives and mucoadhesives may also be used as adjuvants in the invention. Suitable bioadhesives include esterified hyaluronic acid microspheres (Singh et al. (2001) J. Cont. Role. 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention. See WO99/27960.

i. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non toxic (e.g. a poly(α-hydroxy acid), a polyhydroxybutyric acid, a polyorthoester, a polyanhydride, a polycaprolactone, etc.), with poly(lactide co glycolide) are preferred, optionally treated to have a negatively-charged surface (e.g. with SDS) or a positively-charged surface (e.g. with a cationic detergent, such as CTAB).

j. Liposomes

Examples of liposome formulations suitable for use as adjuvants are described in U.S. Pat. Nos. 6,090,406, 5,916,588, and EP 0 626 169.

k. Polyoxyethylene ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

l. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

m. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyld-isoglutamine (nor-MDP), and N acetylmuramyl-1-alanyl-d-isoglutaminyl-1-alanine-2-(1'-2'-dipalmitoyl-sn-glycero-3-hydroxyphosphoryloxy)-ethylamine MTP-PE).

n. Imidazoquinoline Compounds

Examples of imidazoquinoline compounds suitable for use adjuvants in the invention include Imiquimod and its analogues, described further in Stanley, Clin Exp Dermatol (2002) 27(7):571-577; Jones, Curr Opin Investig Drugs (2003) 4(2):214-218; and U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612.

o. Thiosemicarbazone Compounds

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-$\alpha$.

p. Tryptanthrin Compounds

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-$\alpha$.

The invention may also comprise combinations of aspects of one or more of the adjuvants identified above. For example, the following adjuvant compositions may be used in the invention:

(1) a saponin and an oil-in-water emulsion (WO99/11241);
(2) a saponin (e.g., QS21)+a non-toxic LPS derivative (e.g. 3dMPL) (see WO94/00153);
(3) a saponin (e.g., QS21)+a non-toxic LPS derivative (e.g. 3dMPL)+a cholesterol;
(4) a saponin (e.g., QS21)+3dMPL+IL 12 (optionally+a sterol) (WO98/57659);
(5) combinations of 3dMPL with, for example, QS21 and/or oil-in-water emulsions (See European patent applications 0835318, 0735898 and 0761231);
(6) SAF, containing 10% Squalane, 0.4% Tween 80, 5% pluronic-block polymer L121, and thr-MDP, either microfluidized into a submicron emulsion or vortexed to generate a larger particle size emulsion.
(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and
(8) one or more mineral salts (such as an aluminum salt)+a non-toxic derivative of LPS (such as 3dPML).
(9) one or more mineral salts (such as an aluminum salt)+ an immunostimulatory oligonucleotide (such as a nucleotide sequence including a CpG motif).

q. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-$\gamma$), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

VIII. Therapeutic Methods

The invention provides methods for inducing or increasing an immune response to *S. agalactiae* using the compositions described above. The immune response is preferably protective and can include antibodies and/or cell-mediated immunity (including systemic and mucosal immunity). Immune responses include booster responses. Compositions comprising antibodies can be used to treat *S. agalactiae* infections.

Diseases caused by GBS which can be prevented or treated according to the invention include, but are not limited to, sepsis, meningitis in newborns, and newborn pneumonia. The compositions may also be effective against other streptococcal bacteria, e.g., GBS.

A. Tests to Determine the Efficacy of the Immune Response

One way of assessing efficacy of therapeutic treatment involves monitoring GBS infection after administration of the composition of the invention. One way of assessing efficacy of prophylactic treatment involves monitoring immune responses against the GBS antigens in the compositions of the invention after administration of the composition.

Another way of assessing the immunogenicity of the component proteins of the immunogenic compositions of the present invention is to express the proteins recombinantly and to screen patient sera or mucosal secretions by immunoblot. A positive reaction between the protein and the patient serum indicates that the patient has previously mounted an immune response to the protein in question; i.e., the protein is an immunogen. This method may also be used to identify immunodominant proteins and/or epitopes.

Another way of checking efficacy of therapeutic treatment involves monitoring GBS infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the GBS antigens in the compositions of the invention after administration of the composition. Typically, GBS serum specific antibody responses are determined post-immunization but pre-challenge whereas mucosal GBS-specific antibody body responses are determined post-immunization and post-challenge.

The vaccine compositions of the present invention can be evaluated in in vitro and in vivo animal models prior to host, e.g., human, administration. A particularly useful mouse model is the Active Maternal Immunization assay described in Example 21, below. This is an in vivo protection assay in which female mice are immunized with the test antigen composition. The female mice are then bred and their pups are challenged with a lethal dose of GBS. Serum titers of the female mice during the immunization schedule are measured as well as the survival time of the pups after challenge.

For example, groups of 4 CD-1 outbred female mice 6-8 weeks old (Charles River Laboratories, Calco Italy) are immunized with one or more GBS antigens (e.g., 20 µg of a BibA polypeptide suspended in 100 µl of PBS). Each group receives 3 doses at days 0, 21 and 35. Immunization is performed through intra-peritoneal injection of the protein with an equal volume of Complete Freund's Adjuvant (CFA) for the first dose and Incomplete Freund's Adjuvant (IFA) for the following two doses. In each immunization scheme negative and positive control groups are used. Immune response is monitored by using serum samples taken on day 0 and 49. The sera are analyzed as pools from each group of mice.

The immune response may be one or both of a TH1 immune response and a TH2 response. The immune response may be an improved or an enhanced or an altered immune response. The immune response may be one or both of a systemic and a mucosal immune response. Preferably the immune response is an enhanced system and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA.

Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFN$\gamma$, and TNF$\beta$), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising a BibA polypeptide of the present invention (or nucleic acid molecule encoding a BibA polypeptide) may be used either alone or in combination with other GBS antigens optionally with an immunoregulatory agent capable of eliciting a Th1 and/or Th2 response.

The invention also comprises an immunogenic composition comprising one or more immunoregulatory agent, such as a mineral salt, such as an aluminium salt and an oligonucleotide containing a CpG motif. Most preferably, the immunogenic composition includes both an aluminium salt and an oligonucleotide containing a CpG motif. Alternatively, the immunogenic composition includes an ADP ribosylating toxin, such as a detoxified ADP ribosylating toxin and an oligonucleotide containing a CpG motif. Preferably, one or more of the immunoregulatory agents include an adjuvant. The adjuvant may be selected from one or more of the group consisting of a TH1 adjuvant and TH2 adjuvant, further discussed below.

The compositions of the invention will preferably elicit both a cell mediated immune response as well as a humoral immune response in order to effectively address a GBS infection. This immune response will preferably induce long lasting (e.g., neutralizing) antibodies and a cell mediated immunity that can quickly respond upon exposure to a BibA polypeptide.

In addition to a BibA polypeptide (or nucleic acid molecule encoding a BibA polypeptide), an immunogenic composition can comprise one or more GBS antigen(s) which elicits a neutralizing antibody response and one or more GBS antigen(s) which elicit a cell mediated immune response. In this way, the neutralizing antibody response prevents or inhibits an initial GBS infection while the cell-mediated immune response capable of eliciting an enhanced Th1 cellular response prevents further spreading of the GBS infection. Preferably, the immunogenic composition comprises one or more GBS surface antigens and one or more GBS cytoplasmic antigens, such as a cytoplasmic antigen capable of eliciting a Th1 cellular response.

B. Preparation of Compositions

The compositions of the invention may be prepared in various forms. For example, a composition can be prepared as an injectable, either as a liquid solution or a suspension. Solid forms suitable for solution in, or suspension in, liquid vehicles prior to injection can also be prepared (e.g., a lyophilized composition). A composition can be prepared for oral administration, such as a tablet or capsule, as a spray, or as a syrup (optionally flavored). A composition can be prepared for pulmonary administration, e.g., as an inhaler, using a fine powder or a spray. A composition can be prepared as a suppository or pessary. A composition can be prepared for nasal, aural or ocular administration e.g., as drops. A composition can be in kit form, designed such that a combined composition is reconstituted just prior to administration to a patient. Such kits may comprise one or more GBS or other antigens in liquid form and one or more lyophilized antigens.

Immunogenic compositions used as vaccines comprise an immunologically effective amount of a BibA polypeptide (or a nucleic acid molecule encoding a BibA polypeptide) or BibA antibodies, as well as any other components, as needed, such as antibiotics. An "immunologically effective amount" is an amount which, when administered to an individual, either in a single dose or as part of a series, increases a measurable immune response or prevents or reduces a clinical symptom.

In another embodiment, the antibiotic is administered subsequent to the administration of a composition of the invention or the composition comprising the one or more surface-exposed and/or surface-associated GBS antigens of the invention. Examples of antibiotics suitable for use in the treatment of a GBS infection include but are not limited to penicillin or a derivative thereof.

C. Methods of Administration

Compositions of the invention will generally be administered directly to a patient. The compositions of the present invention may be administered, either alone or as part of a composition, via a variety of different routes. Certain routes may be favored for certain compositions, as resulting in the generation of a more effective immune response, preferably a CMI response, or as being less likely to induce side effects, or as being easier for administration.

Delivery methods include parenteral injection (e.g., subcutaneous, intraperitoneal, intravenous, intramuscular, or interstitial injection) and rectal, oral (e.g., tablet, spray), vaginal, topical, transdermal (e.g., see WO 99/27961), transcutaneous (e.g., see WO02/074244 and WO02/064162), intranasal (e.g., see WO03/028760), ocular, aural, and pulmonary or other mucosal administration.

By way of example, the compositions of the present invention may be administered via a systemic route or a mucosal route or a transdermal route or it may be administered directly into a specific tissue. As used herein, the term "systemic administration" includes but is not limited to any parenteral routes of administration. In particular, parenteral administration includes but is not limited to subcutaneous, intraperitoneal, intravenous, intraarterial, intramuscular, or intrasternal injection, intravenous, intraarterial, or kidney dialytic infusion techniques. Preferably, the systemic, parenteral administration is intramuscular injection. As used herein, the term "mucosal administration" includes but is not limited to oral, intranasal, intravaginal, intrarectal, intratracheal, intestinal and ophthalmic administration.

Teenagers and children, including toddlers and infants, can receive a vaccine for prophylactic use; therapeutic vaccines typically are administered to teenagers or adults. A vaccine intended for children may also be administered to adults e.g., to assess safety, dosage, immunogenicity, etc.

The immunogenic compositions of the present invention may be administered in combination with an antibiotic treatment regime. In one embodiment, the antibiotic is administered prior to administration of a composition of the invention.

Dosage treatment can be a single dose schedule or a multiple dose schedule. Multiple doses may be used in a primary immunization schedule and/or in a booster immunization schedule. In a multiple dose schedule the various doses may be given by the same or different routes e.g., a parenteral prime and mucosal boost, a mucosal prime and parenteral boost, etc.

The amount of active agent in a composition varies depending upon the health and physical condition of the individual to be treated, age, the taxonomic group of individual to be treated (e.g., non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range which can be determined through routine trials.

IX. Kits

The invention also provides kits comprising one or more containers of compositions of the invention or their components. Compositions can be in liquid form or can be lyophilized, as can individual components of the compositions. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other buffers, diluents, filters, needles, and syringes. The kit can also comprise a second or third container with another active agent, for example an antibiotic.

The kit can also comprise a package insert containing written instructions for methods of inducing immunity against *S. agalactiae*. The package insert can be an unapproved draft package insert or can be a package insert approved by the Food and Drug Administration (FDA) or other regulatory body.

X. Screening Methods

The invention provides assays for screening test compounds that bind to or modulate the activity of BibA. A test compound preferably (1) binds to the coiled-coil domain and blocks the interaction of BibA with complement, e.g., C4 binding protein, or the formation of BibA dimers; or (b) binds to the proline-rich domain and blocks the binding of BibA to host epithelial cells; (c) binds to the N-terminal domain of BibA and blocks the binding of BibA to IgA; or (d) binds to various portions of BibA and blocks the binding of IgG to the protein. Assays can be carried out using full-length BibA protein or BibA polypeptides of the invention.

A. Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, can be produced recombinantly, synthesized by chemical methods known in the art, or obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

B. Assays

Any method known in the art can be used to detect binding between a test compound and a domain of BibA or disruption of binding between a domain of BibA and its biological target.

In some binding assays, either the test compound or the BibA protein or polypeptide can comprise a detectable label, such as a fluorescent, radioisotopic, chemiluminescent, or enzymatic label, such as horseradish peroxidase, alkaline phosphatase, or luciferase. Methods of detecting such labels are well known in the art. Alternatively, binding can be determined without labeling either of the interactants. See, e.g., McConnell et al., *Science* 257, 1906-12, 1992. Technologies such as real-time Bimolecular Interaction Analysis (BIA) (Sjolander & Urbaniczky, *Anal. Chem.* 63, 2338-2345, 1991, and Szabo et al., *Curr. Opin. Struct. Biol.* 5, 699-705, 1995) also can be used.

In other embodiments, a BibA protein or polypeptide can be used as a "bait protein" in a two-hybrid assay or three-hybrid assay (see, e.g., U.S. Pat. No. 5,283,317; Zervos et al., *Cell* 72, 223-232, 1993; Madura et al., *J. Biol. Chem.* 268, 12046-12054, 1993; Bartel et al., *BioTechniques* 14, 920-924, 1993; Iwabuchi et al., *Oncogene* 8, 1693-1696, 1993; and Brent WO94/10300), to identify other proteins which bind to or interact with various domains of BibA.

Assays such as those described in the Examples below can be used to detect whether binding between various domains of BibA and the biological targets of those domains is disrupted or prevented by a test compound.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

BibA can Form Dimers

Figure 3A:
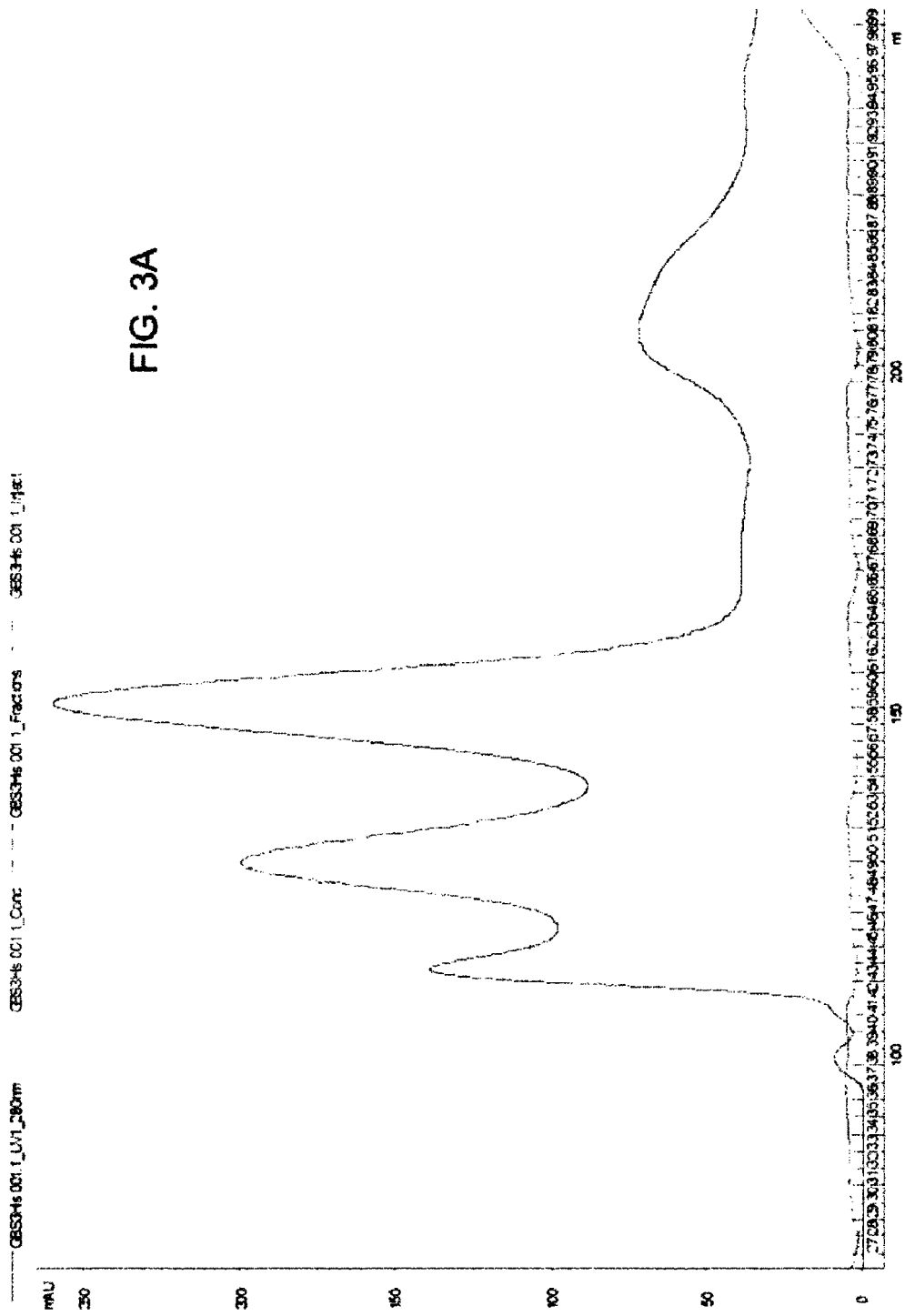

This example demonstrates that BibA can form dimers. In a high-resolution fractionation, molecules elute from the matrix pores in order of decreasing size. Smaller molecules have greater access to the pores of the matrix and hence move down the column. See FIGS. 3A and 3B.

EXAMPLE 2

BibA Protein Surface-Association

Figure 4A:
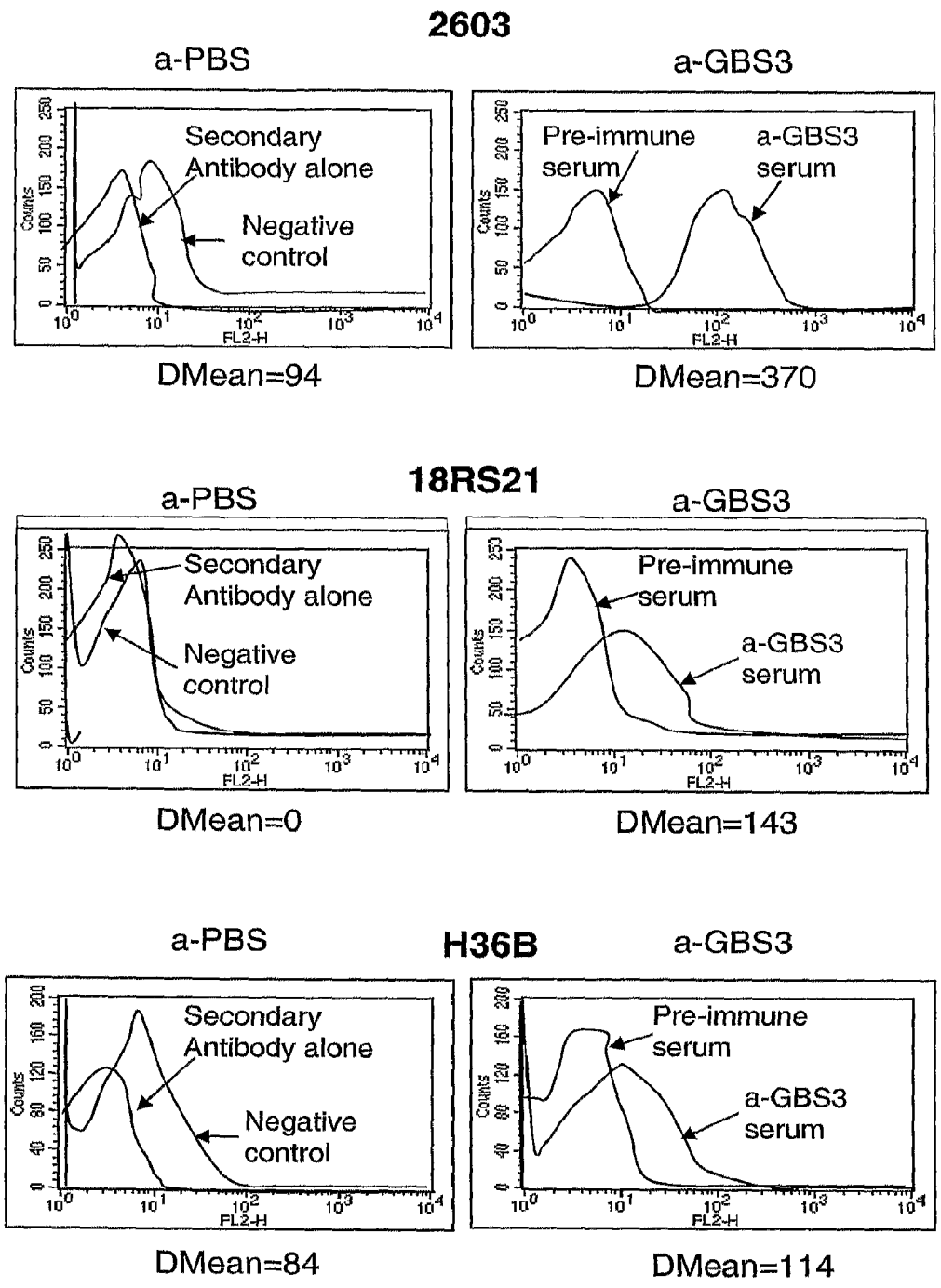
FIGS. 4A-B. BibA protein surface-association in GBS strains.
Figure 4B:
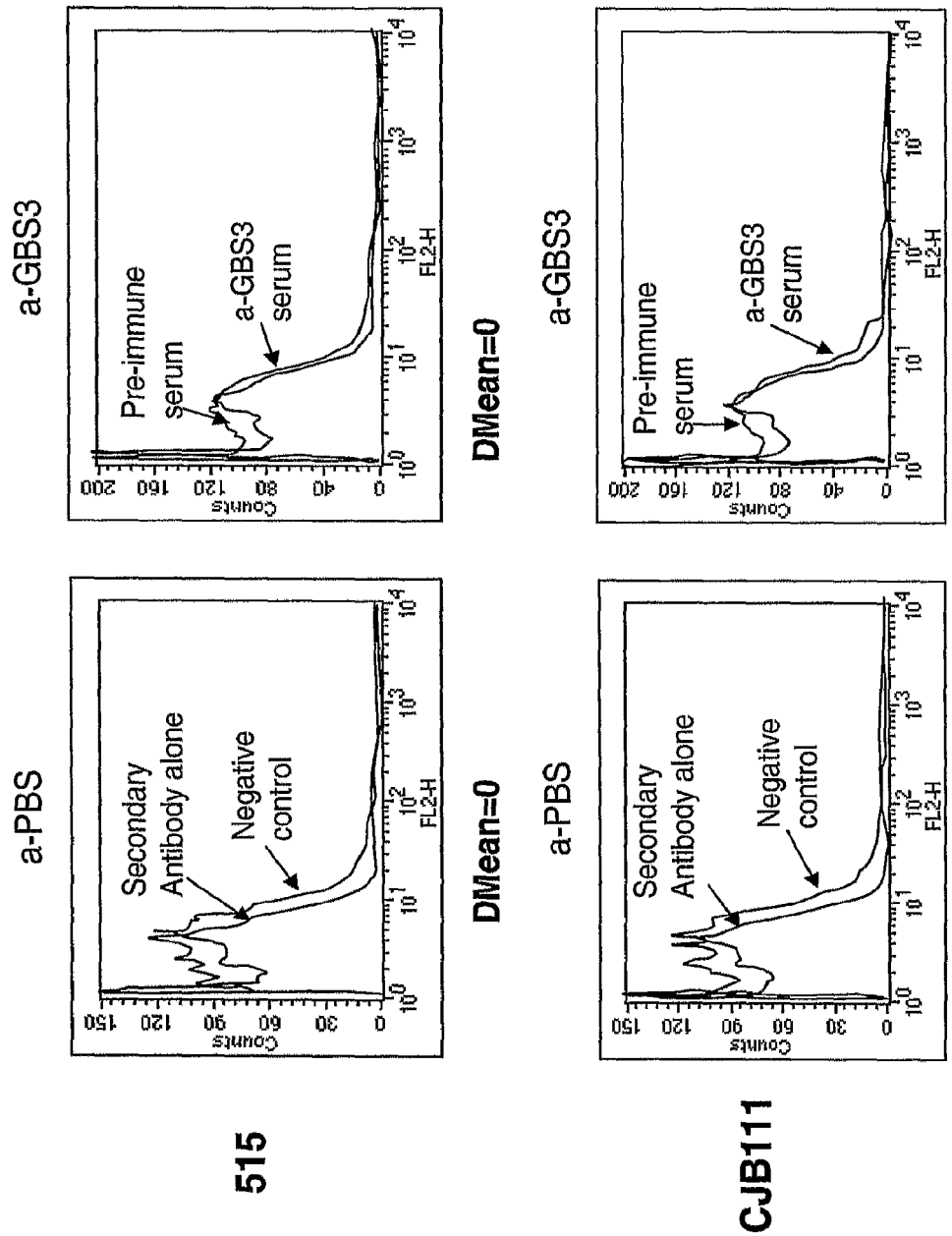

GBS bacteria were incubated with secondary FITC-conjugated α-mouse IgG antibody alone. Bacteria were also treated with mouse serum immunized with Freund adjuvant (α-PBS) as a negative control. FIGS. 4A and 4B illustrate the negative control on plots labeled "α-PBS." BibA levels are expressed as a change in mean of fluorescence between cells treated with α-BibA serum and pre-immune serum. Bacteria incubated with pre-immune serum were compared to bacteria treated with α-BibA serum to obtain a change in mean of fluorescence (Δ mean).

Figure 5A:
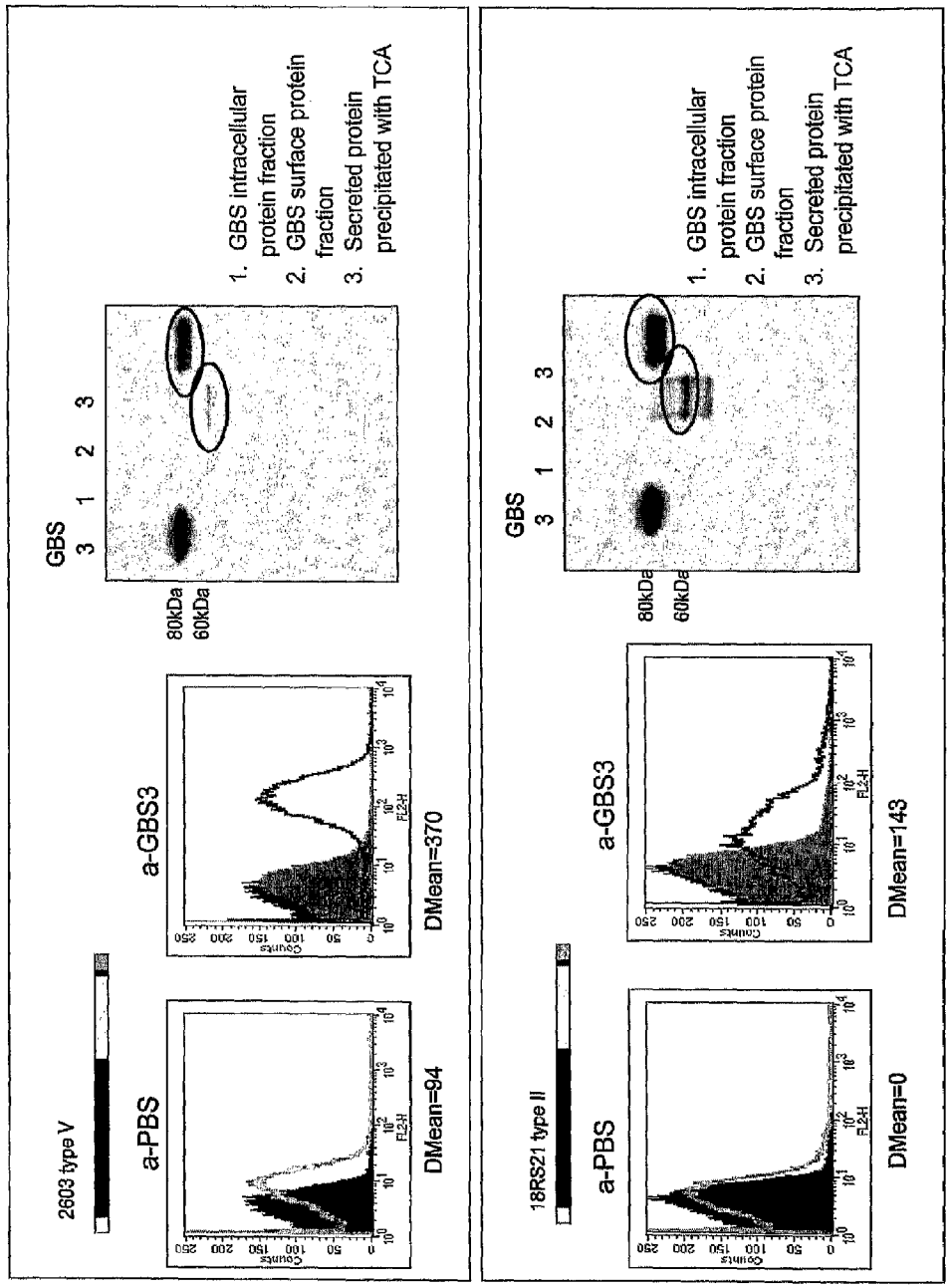
FIGS. 5A-B. Data demonstrating that BibA protein is associated with the bacterial cell membrane or in the supernatant of GBS cultures.
Figure 5B:
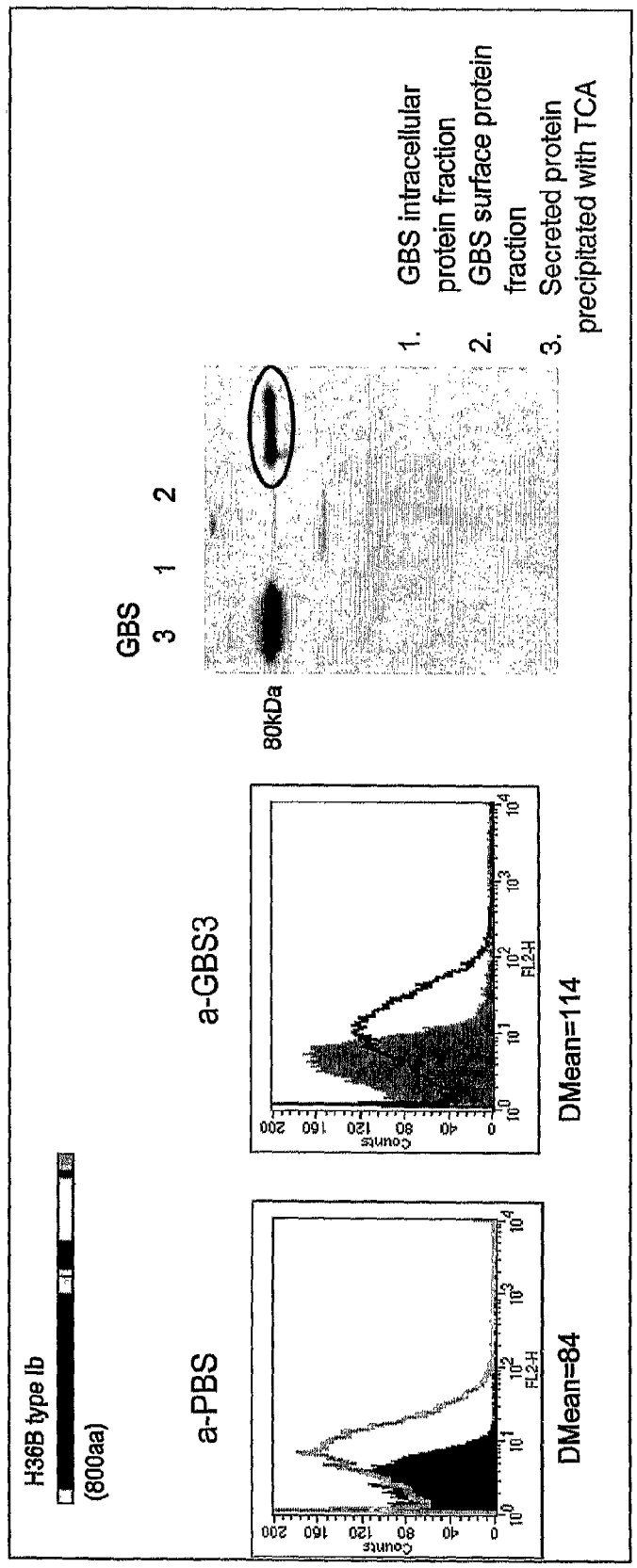

BibA protein of strains 2603, 18RS21 and H36B exhibited surface-association but strains 515 and CJB111 did not (Δmean=0). See also FIG. 5.

EXAMPLE 3

BibA Protein Clusters

GBS strain 515 (pAM401-SAG2063) was grown overnight in THB medium (10 ml). Bacterial cells from 1 ml of the overnight culture were resuspended in 5 ml of fresh THB medium and grown at 37° C. up to OD 0.5 (stationary phase). Bacteria were then centrifuged for 10 minutes at 3000 rpm at room temperature, washed, and resuspended in 1 ml of PBS. Formvar-carbon-coated nickel grids were floated on drops of GBS suspensions for 10 minutes. The grids were then fixed in 2% PFA for 15 minutes and placed in blocking solution (PBS containing 1% normal rabbit serum and 1% BSA). The grids were then floated on drops of primary antiserum against BibA (mαBibA) diluted 1:50 in blocking solution for 30 minutes at room temperature, washed with 6 drops of blocking solution, and floated on secondary antibody conjugated to 10 nm gold particles diluted 1:25 in 1% BSA for 30 minutes. The grids were then washed with 4 drops of PBS and then with 4 drops of distilled water and air dried. The grids were examined using a GEOL 1200 EX 11 transmission electron microscope.

Figure 6:
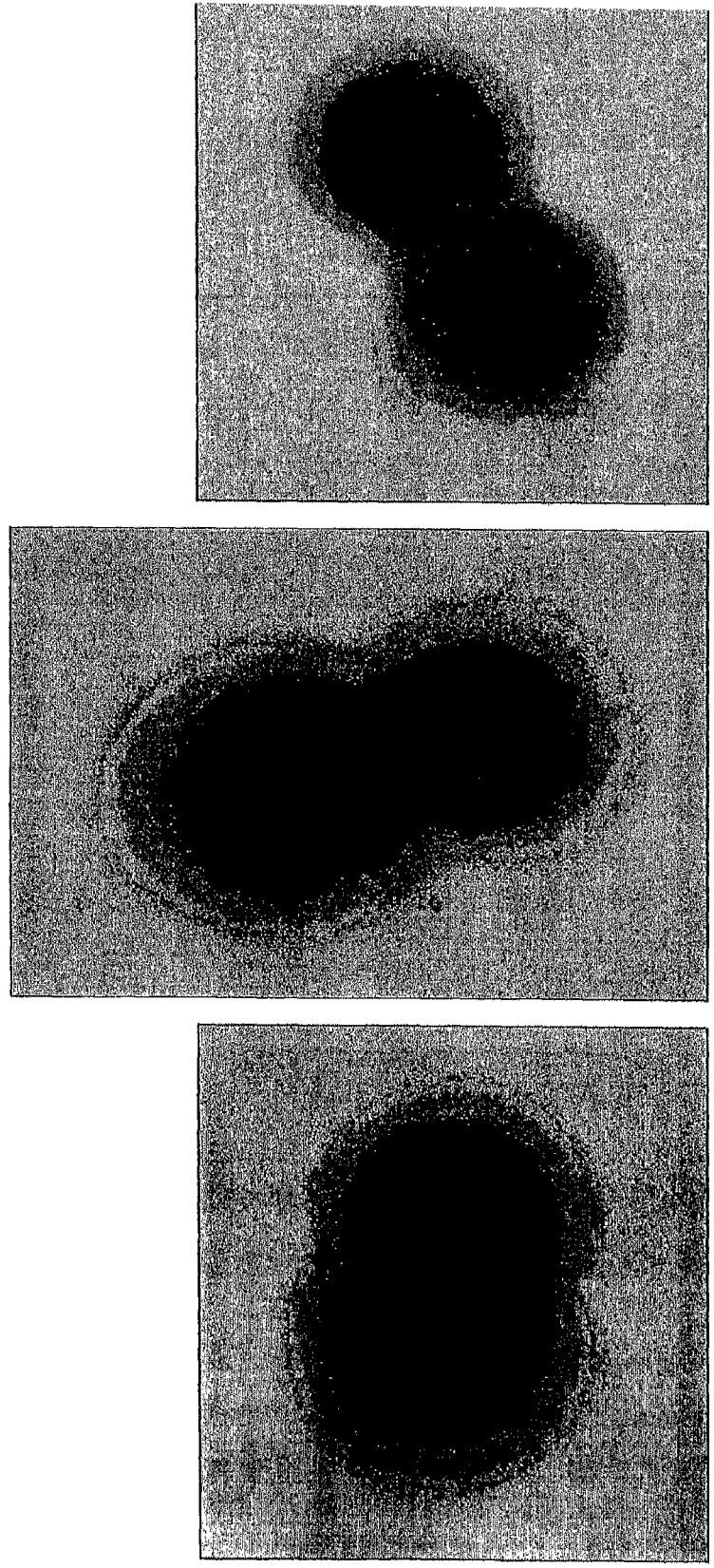
FIG. 6. Micrographs showing immunogold staining of strain 515, which expresses BibA protein of the 2603 V/R strain.

FIG. 6 shows the presence of BibA protein clusters.

EXAMPLE 4

BibA Expression on the Surface of Strain 515 pAM401

Figure 7A:
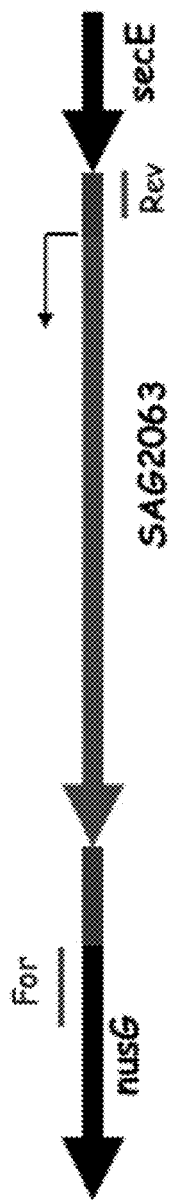
FIG. 7A. Drawing showing BibA gene from strain 2063 cloned into pAM401 vector.

BibA gene (SAG2063) including its own promoter and terminator was cloned into pAM401 vector using BamHI and SalI restriction sites as illustrated in FIG. 7A. GBS strains 2603 V/R. and 515 Ia were transformed with this construct.

Figure 7B:
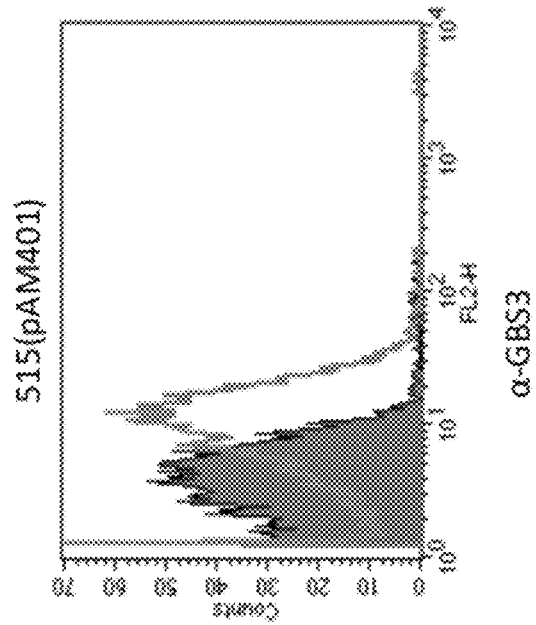
FIG. 7B. FACS analysis demonstrating that BibA is expressed on the surface of strain 515 pAM401.
Figure 7B:
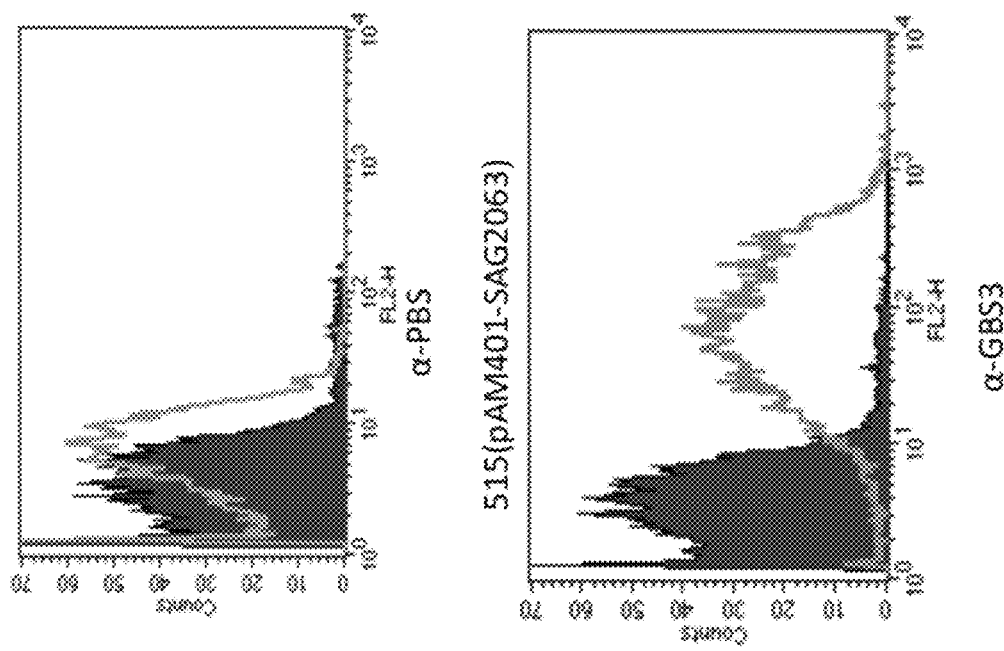

FACS analysis showed that BibA protein is exposed on the 515 (pAM401-SAG2063) surface at high levels. FIG. 7B.

EXAMPLE 5

Increased Expression of BibA on the Surface of Strain 2603

Figure 8A:
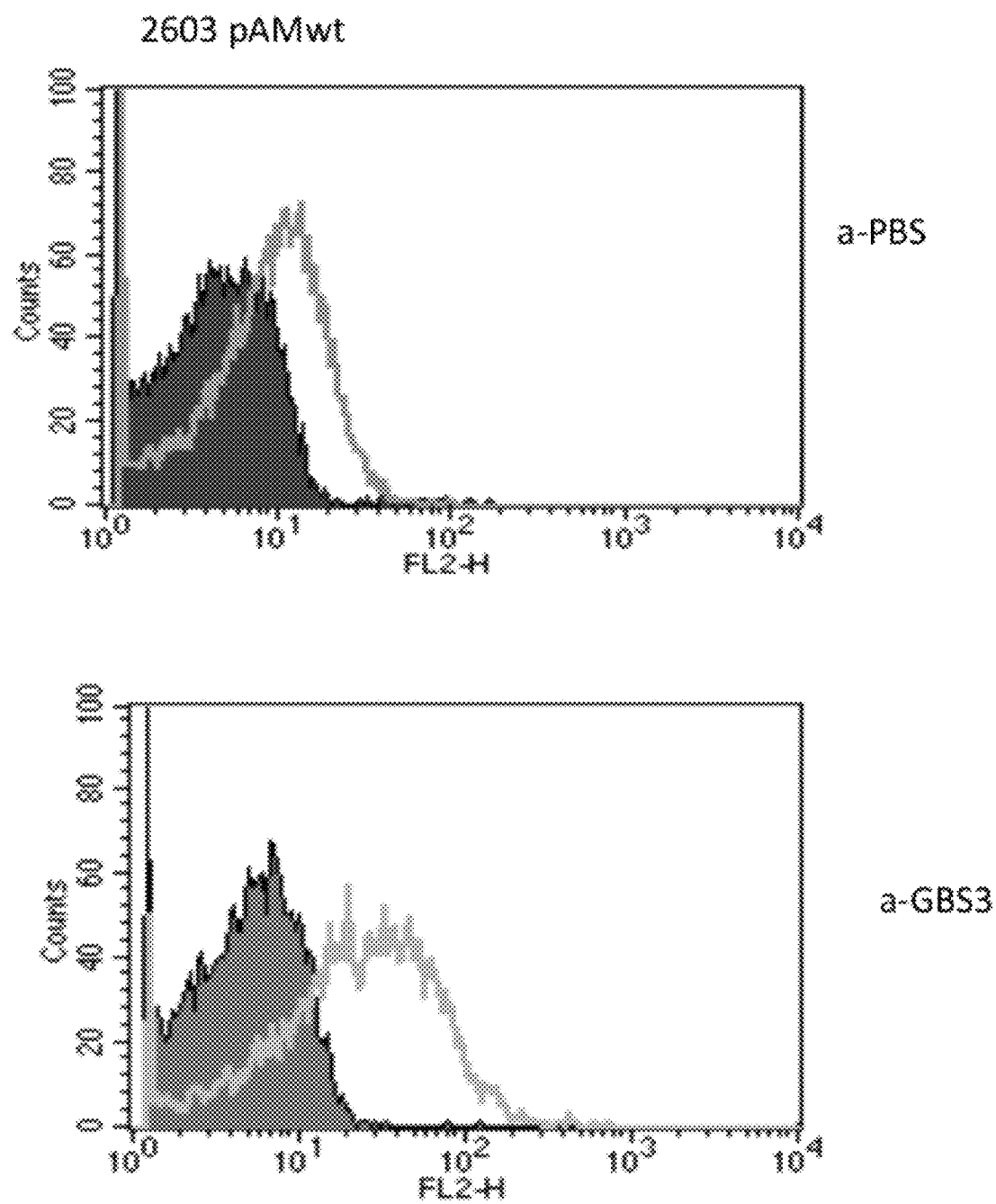
FIG. 8A. FACS analysis demonstrating increased BibA expression on the surface of strain 2603.
Figure 8B:
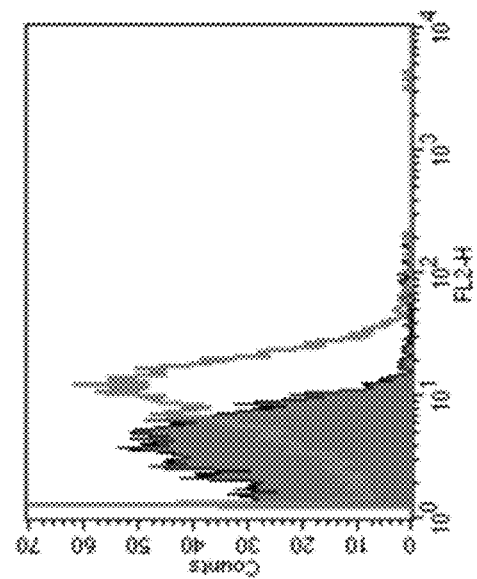
FIG. 8B, FACS analysis demonstrating BibA expression on the surface of strain 515.
Figure 8B:
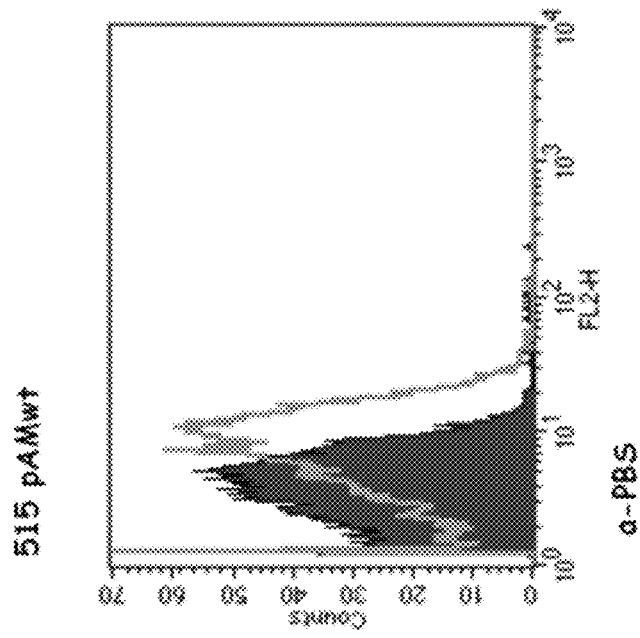

FACS analysis showed that the exposure of BibA protein on the 2603 (pAM401-SAG2063) surface is increased respect the 2603 wt strain. The results are shown in FIG. 8.

EXAMPLE 6

Secreted form of BibA

Figures 10, 10A, 10B:
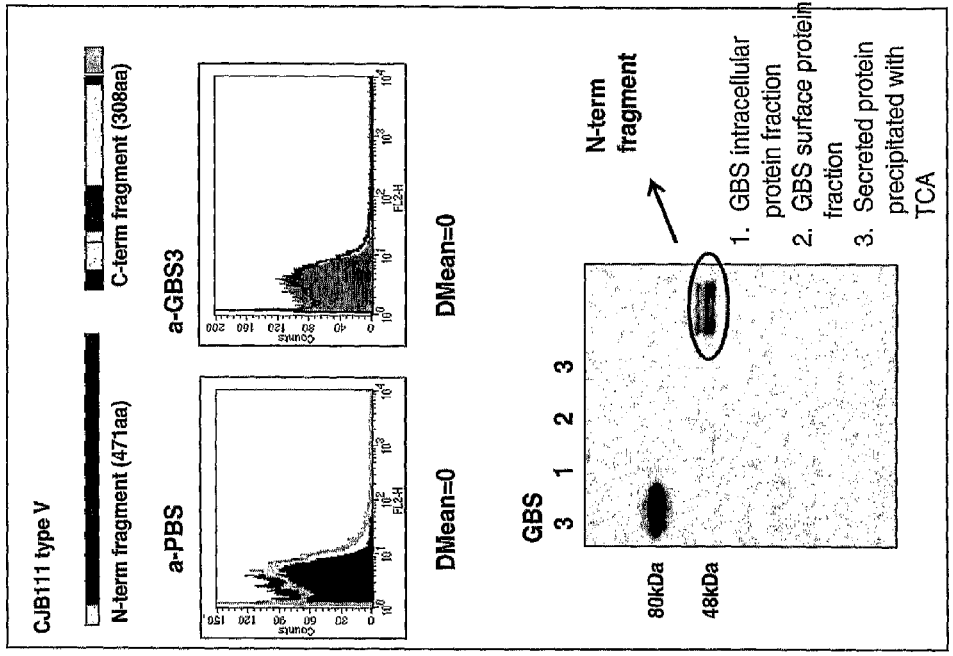
FIGS. 10A-E. Data demonstrating portions of BibA associated with the bacterial cell membrane or in the supernatant of GBS cultures.
Figure 10C:
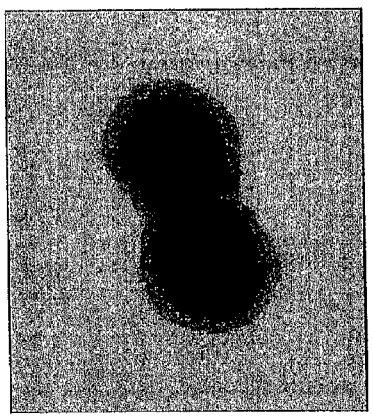
Figure 10C:
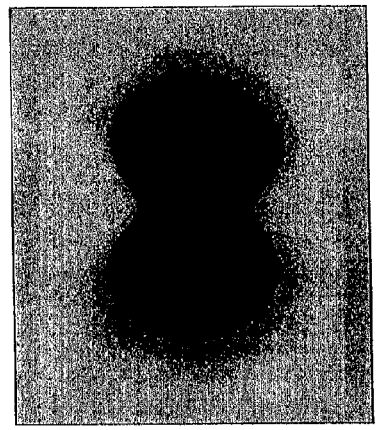
Figure 10C:
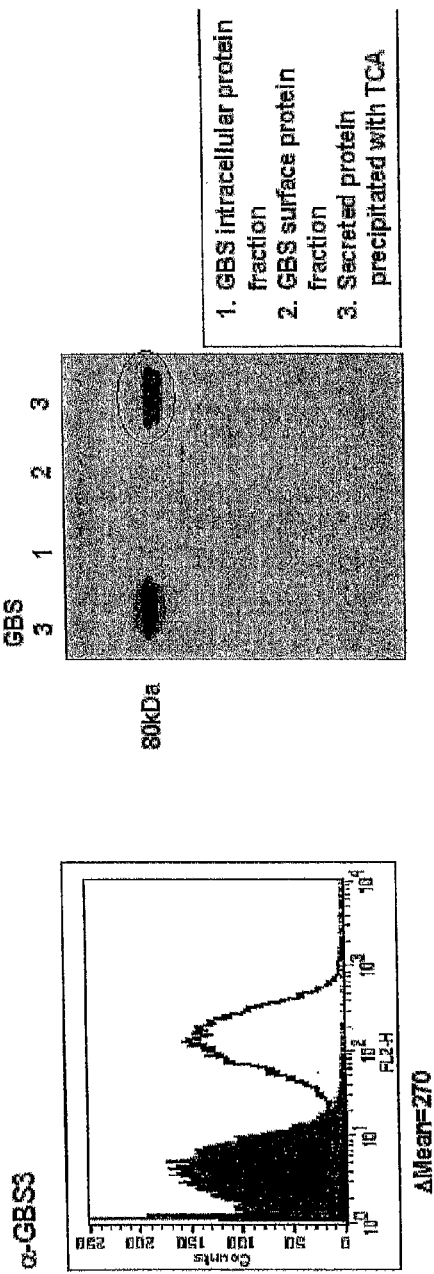
Figures 10D, 10E:
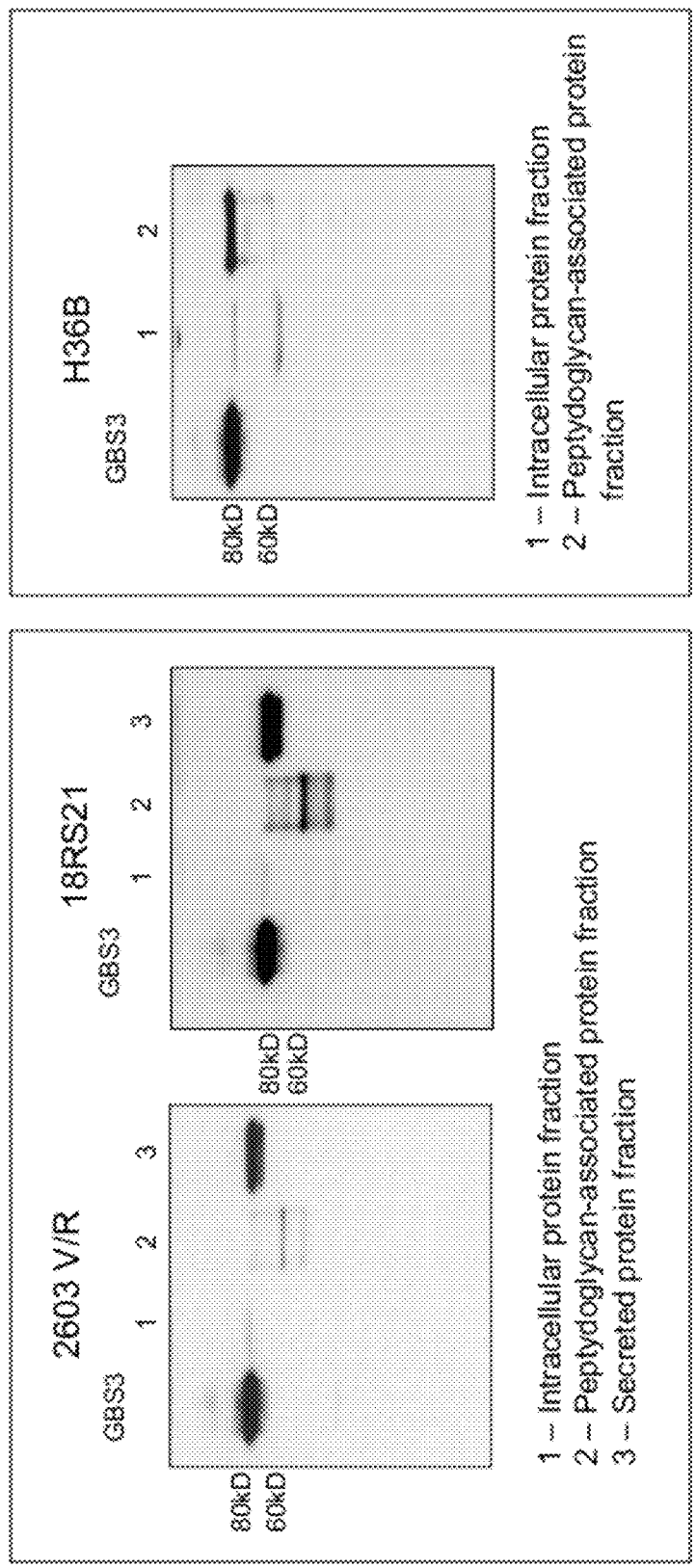

GBS protein extracts were separated via SDS-PAGE and transferred to a nitrocellulose membrane. Proteins were then overlaid with a mouse α-BibA polyclonal antibody and stained with HRP-conjugated secondary antibody. As FIG. 10 illustrates, in the separation of BibA strains 515 and CJB111, the BibA protein was found only in the culture supernatant (the secreted protein fraction). This demonstrates that the truncated form of the BibA protein in strains 515 and CJB111, which lack the proline-rich motif, is expressed in the secreted. See FIG. 10.

EXAMPLE 7

BibA Binds C4 Binding Protein (C4BP)

Figure 11A:
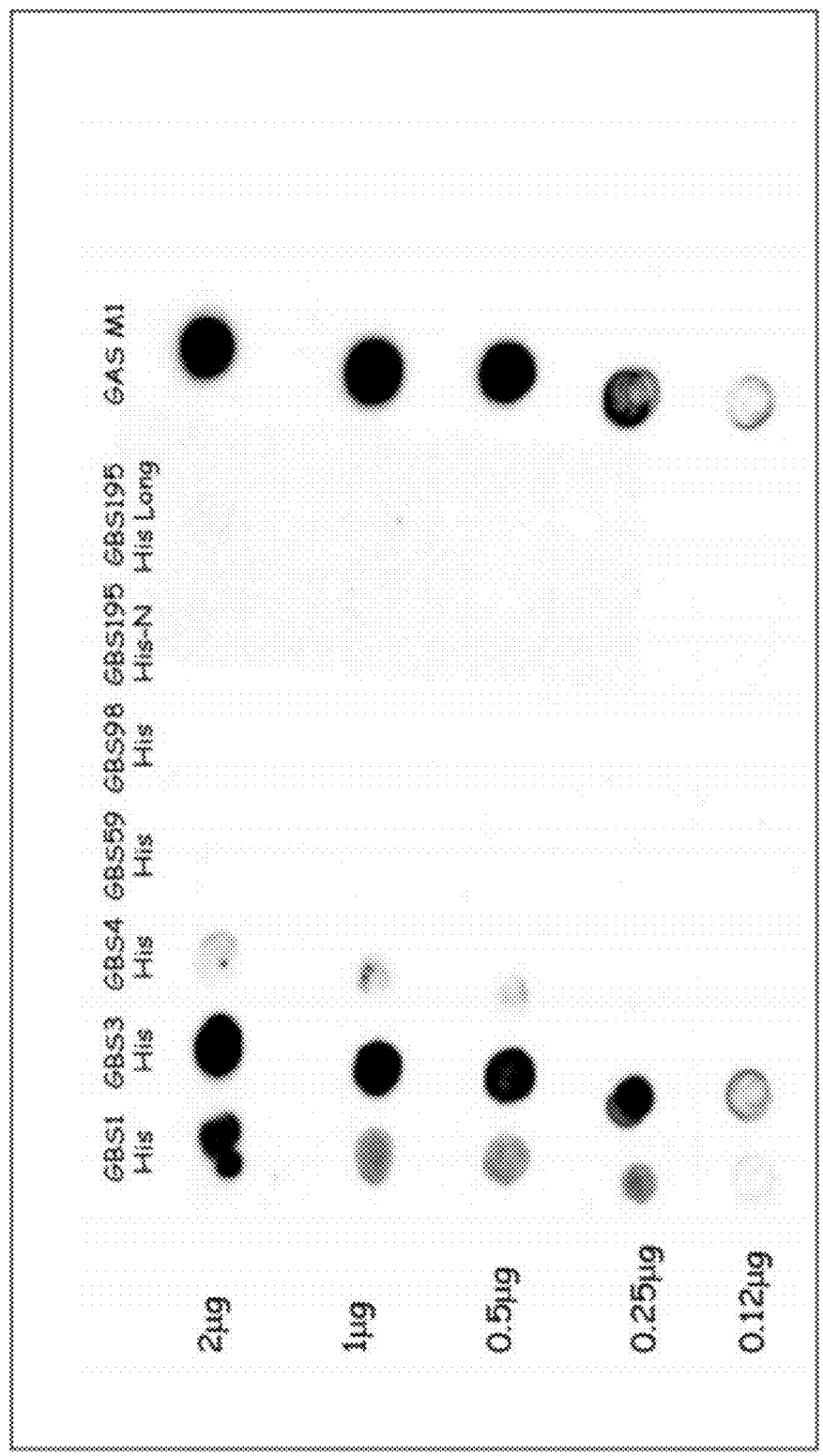
FIGS. 11A-B. Blots showing that BibA binds to C4 binding protein (C4BP).

Recombinant BibA proteins were dried onto a nitrocellulose membrane and incubated with recombinant c4-binding protein. Bound protein was then detected using a mouse a-C4BP monoclonal antibody and stained with HRP-conjugated antibody. FIG. 11A is a dot blot in which BibA protein at different concentrations is stained with the HRP-conjugated antibody, demonstrating that BibA binds C4 binding protein.

Figure 11B:
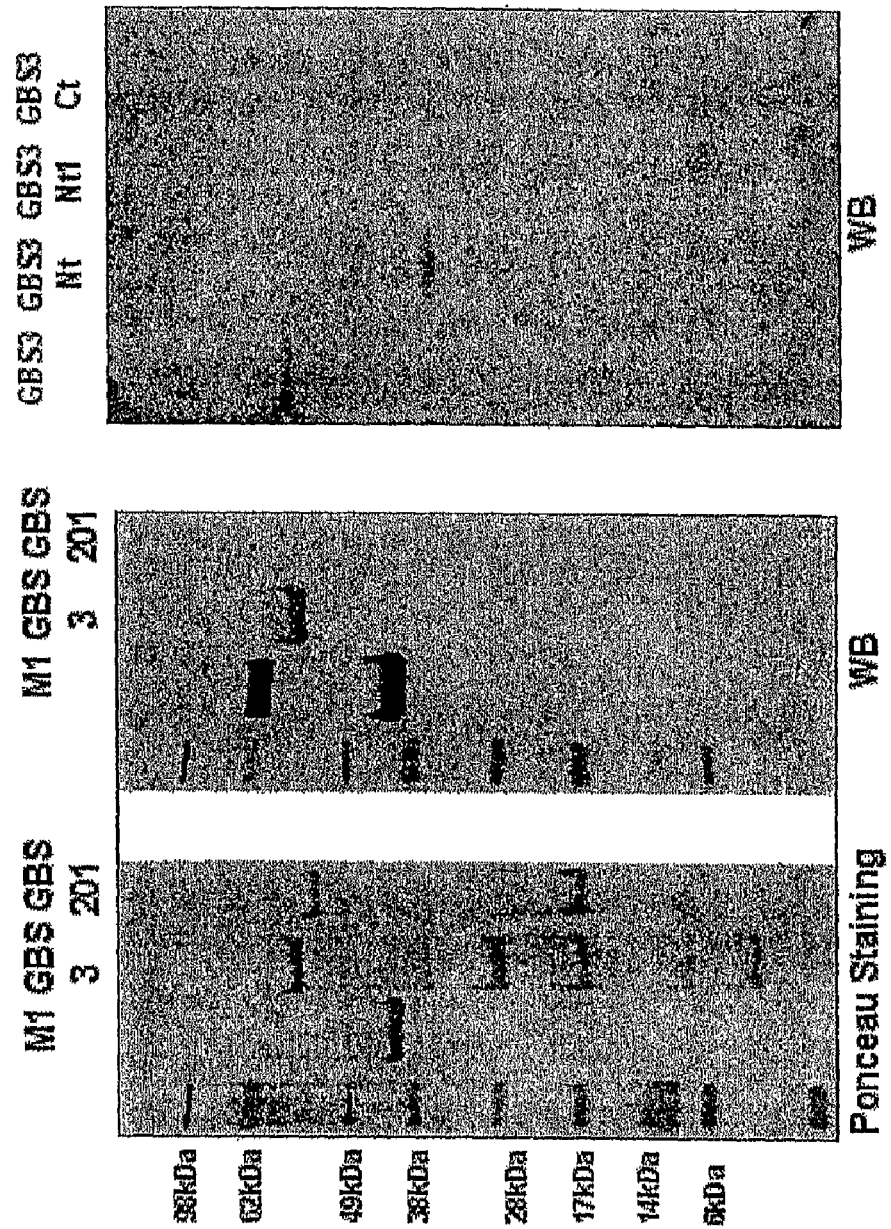

Recombinant BibA protein was separated by SDS-PAGE, blotted onto a nitrocellulose membrane and then incubated with recombinant C4-binding protein. Bound protein was then detected using a mouse a-C4BP monoclonal antibody and stained with HRP-conjugated antibody. FIG. 11B shows a Western blot that confirms that BibA binds C4 binding protein.

EXAMPLE 8

BibA Protein Binds to the Surface of Epithelial Cells

ME180 cervical cells were incubated both in the presence and in the absence of BibA protein followed by the addition of a mouse α-BibA polyclonal antibody. The ME180 cervical cells were then stained with FITC-conjugated α-mouse IgG secondary antibody. A positive control was obtained by treating the ME180 cervical cells only with the FITC-conjugated α-mouse IgG secondary antibody (i.e., in the absence of mouse α-BibA polyclonal antibody). The analysis was repeated with Caco2 intestinal cells, A549 alveolar cells, and 16HBE140 bronchial cells. As negative control we used GBS7 protein, which was cloned identically to BibA.

Figure 12A:
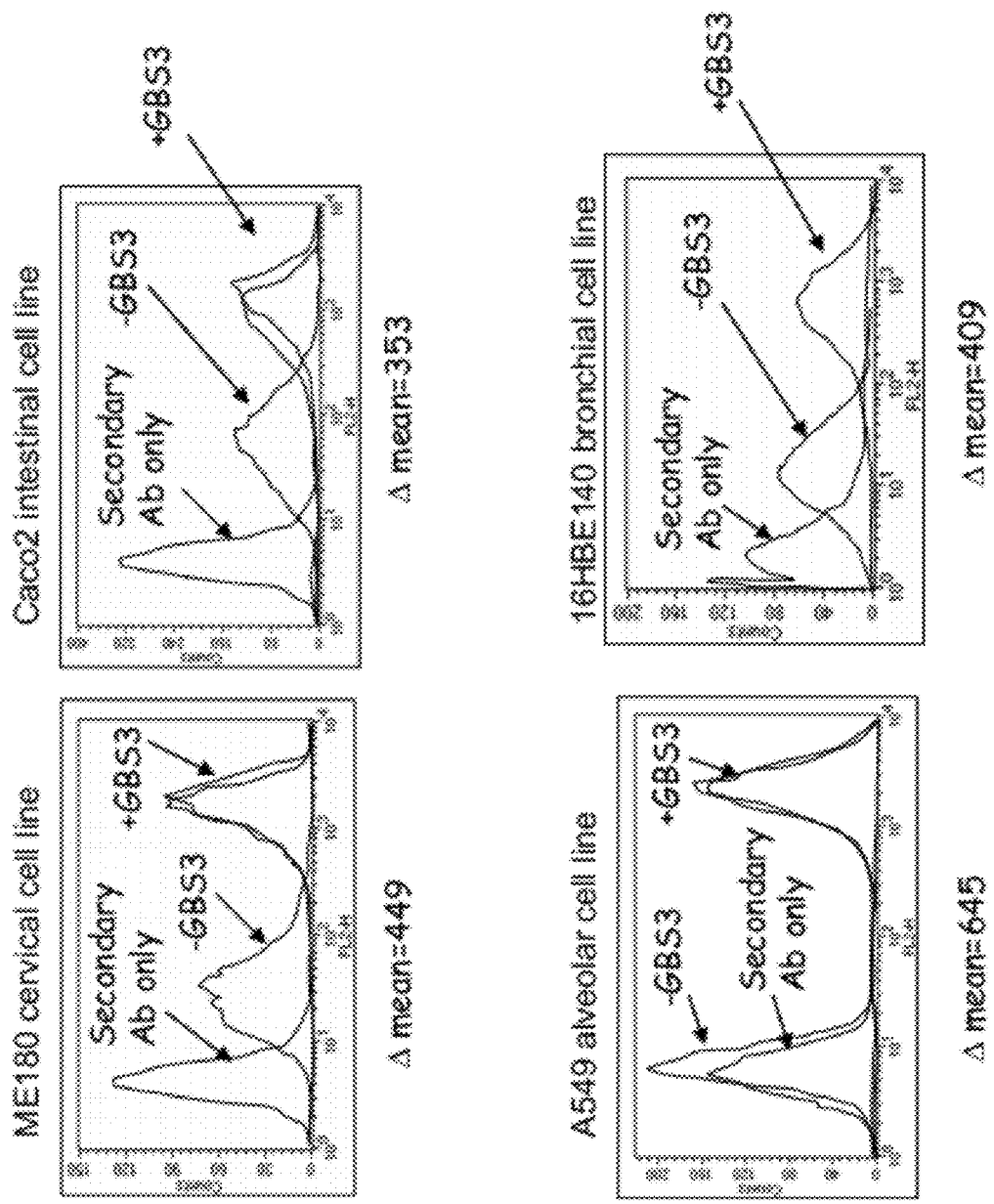
FIGS. 12A-B. FACS analysis of BibA binding to the surface of various epithelial cells.
Figure 12B:
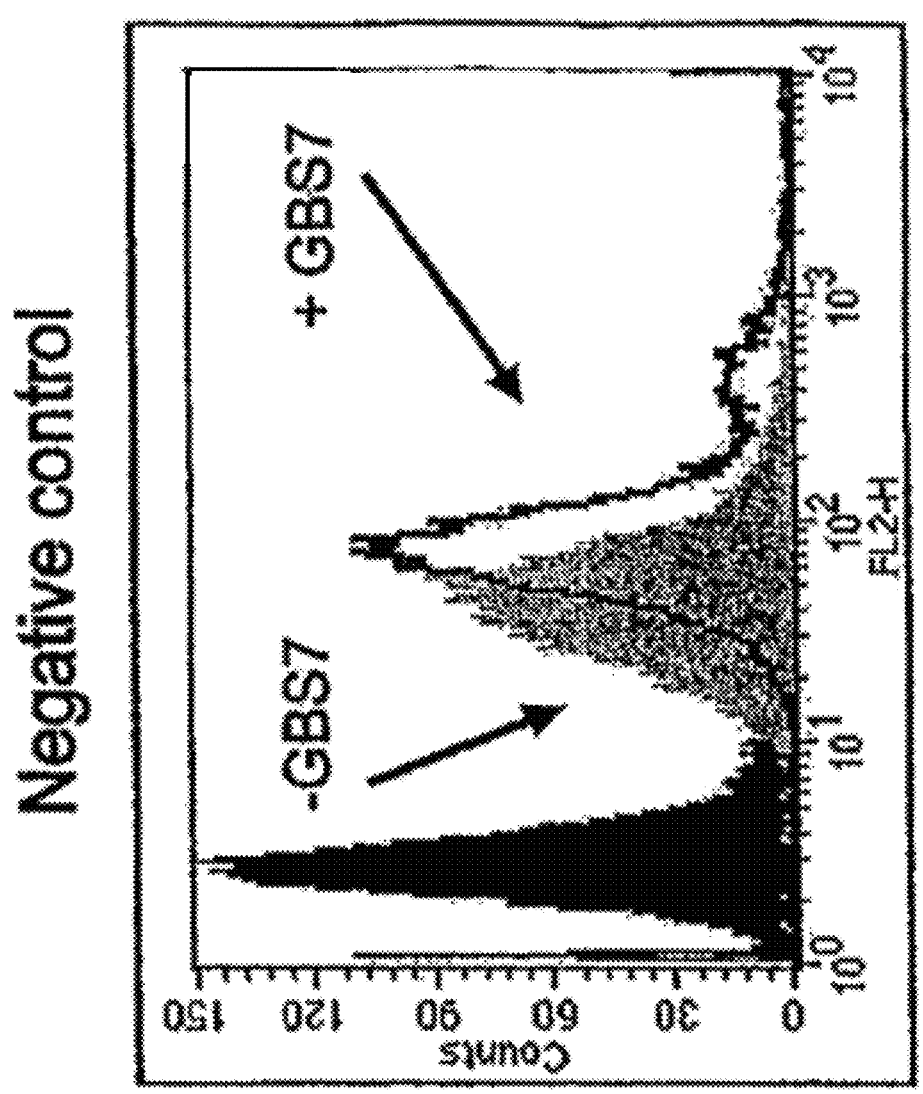

BibA binding, expressed as Dmean channel values, was measured by FACScan cytometer as difference in fluorescence intensity between cell incubated with or without BibA. Results are shown in FIG. 12. The "secondary antibody only" area indicates cells treated with FITC-conjugated antibody alone. BibA binding, expressed as Dmean channel values, was measured by FACScan cytometer as difference in fluorescence intensity between cell incubated with or without BibA. As negative control we used GBS7 protein, which was cloned identically to BibA.

EXAMPLE 9

BibA Binds to the Surface of Epithelial Cells by the Proline-Rich Motif

Epithelial cells were incubated in the presence of biotinylated BibA protein or biotinylated BibA fragments and then stained with FITC-conjugated streptavidin. The purple area indicates cells treated with FITC-conjugated streptavidin alone. BibA binding, expressed as Delta mean channel values, was measured by a FACScan cytometer as the difference in fluorescence intensity between cells incubated with or without proteins.

Figure 25:
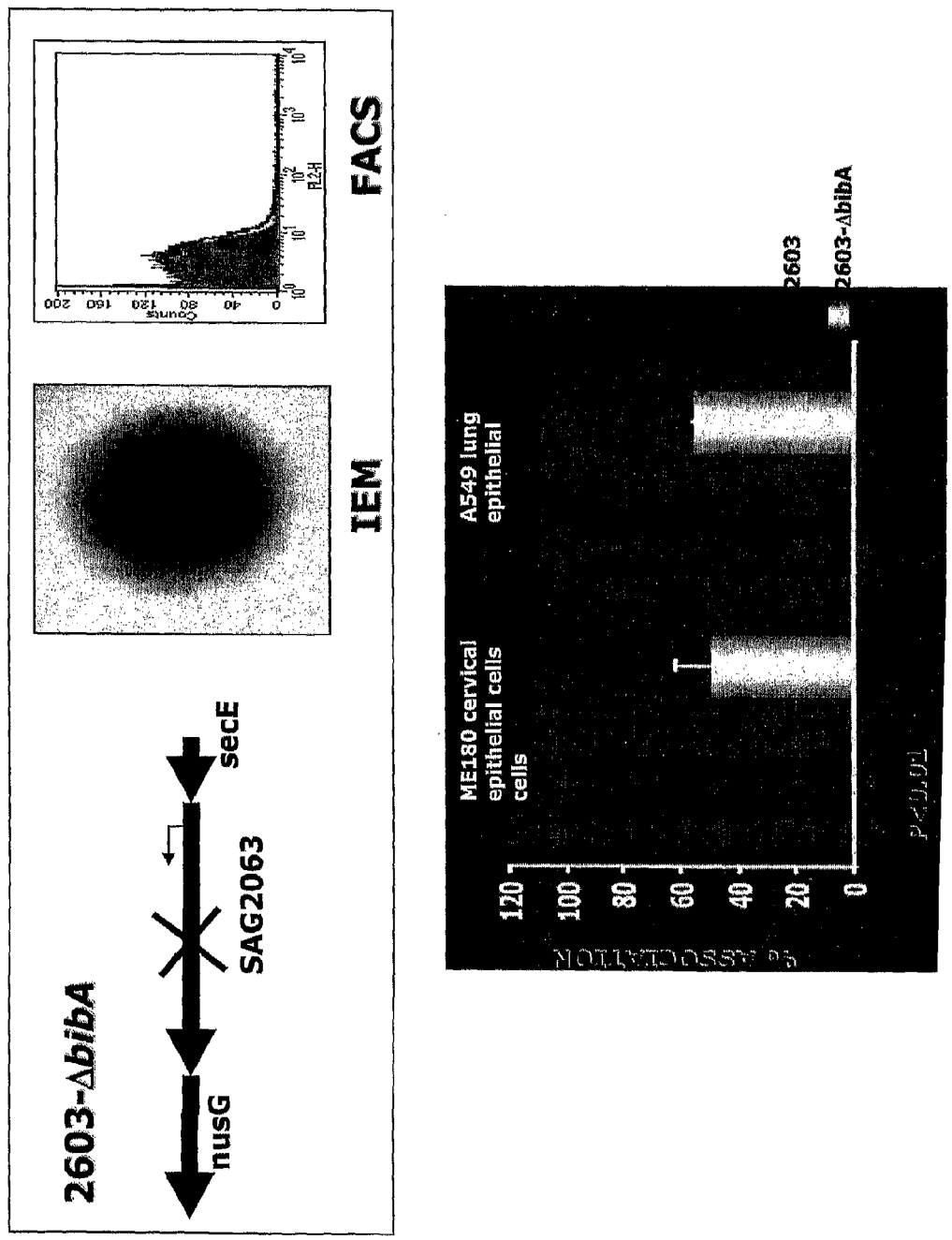
FIG. 25. Summary of data demonstrating that BibA is involved in GBS adherence to epithelial cells.
Figure 26A:
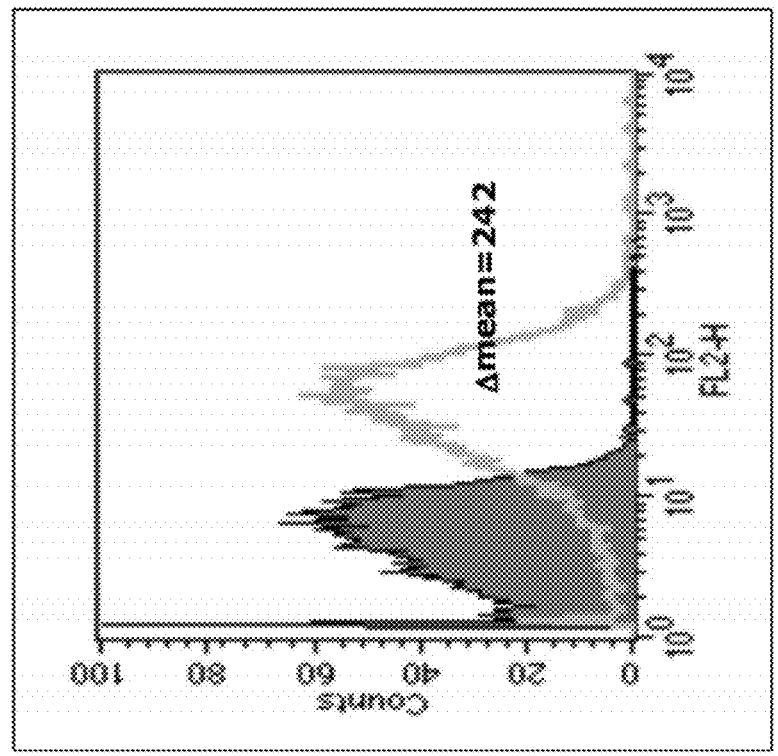
FIGS. 26A-B. Summary of data demonstrating that BibA overexpression increases GBS adherence to epithelial cells.
Figure 26A:
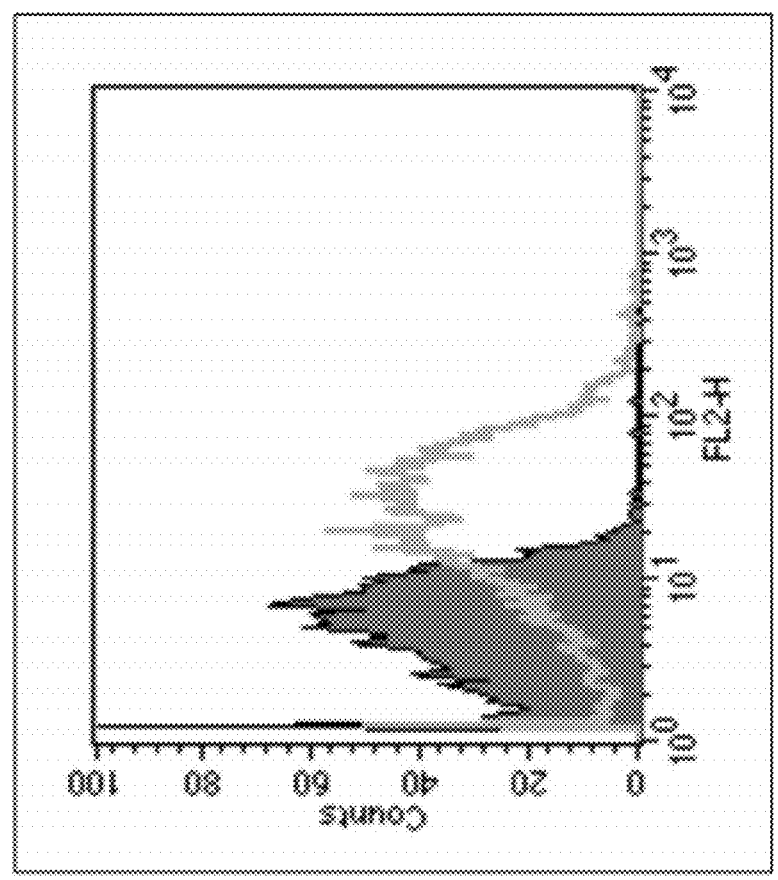
Figure 26B:
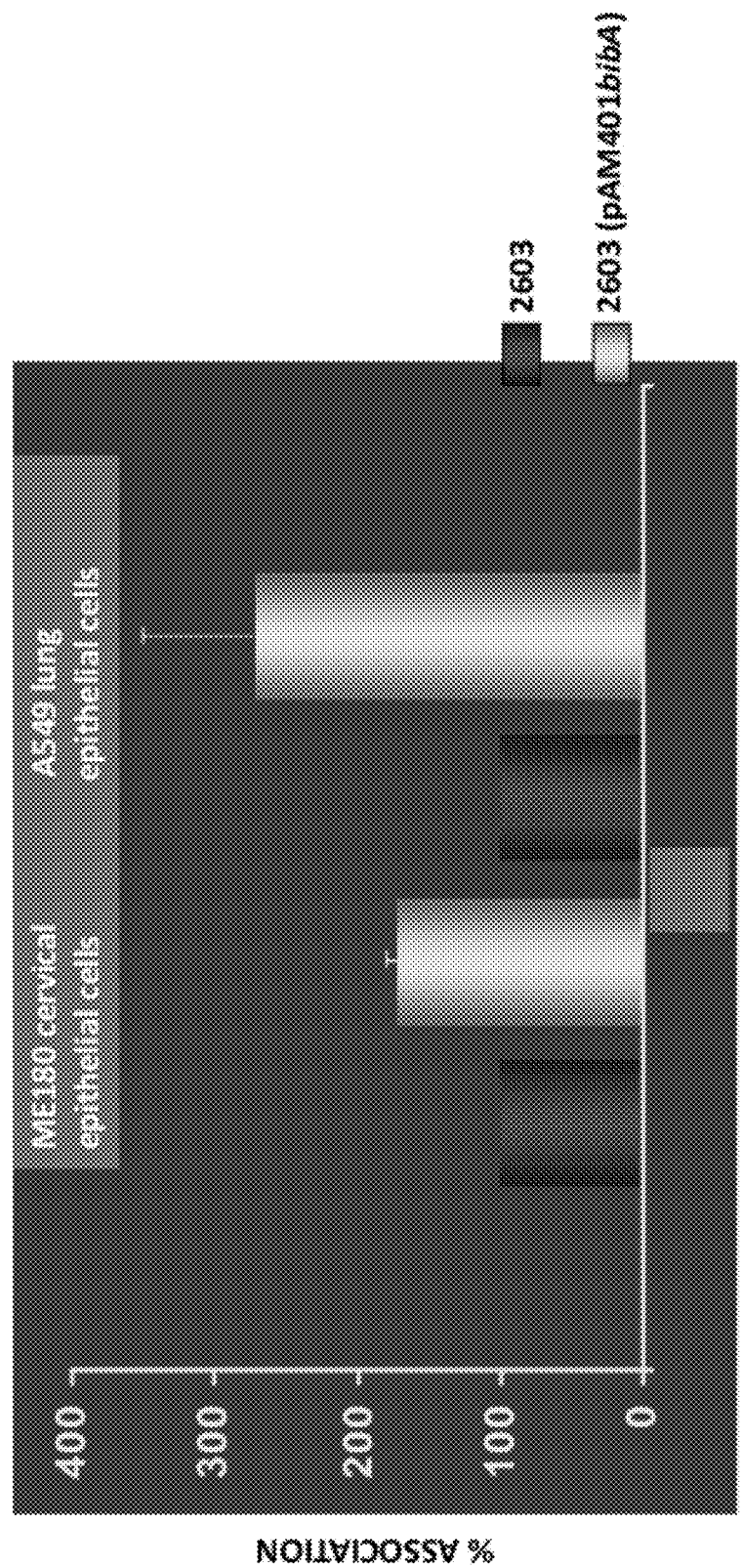
Figure 27A:
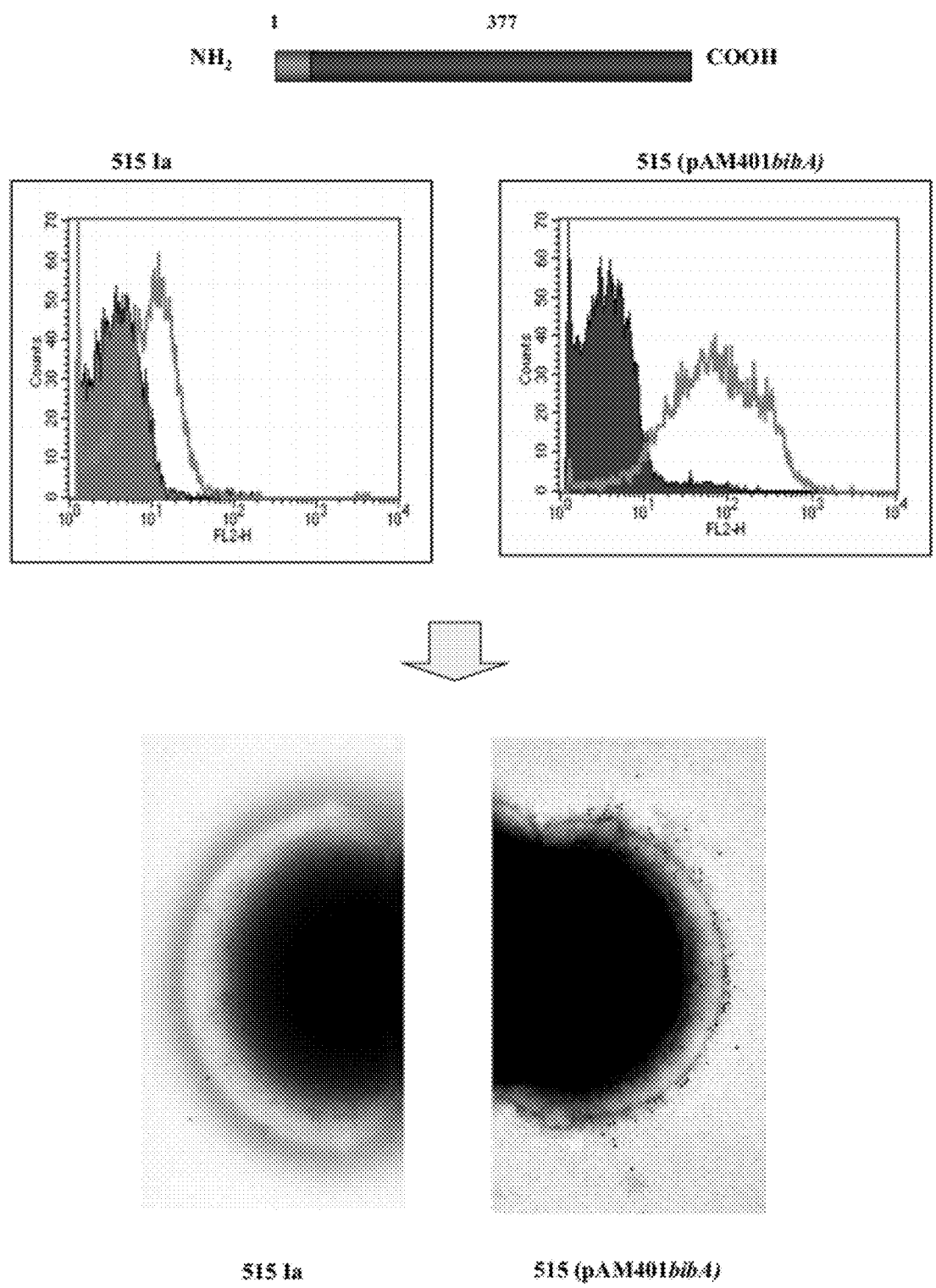
Figure 28:
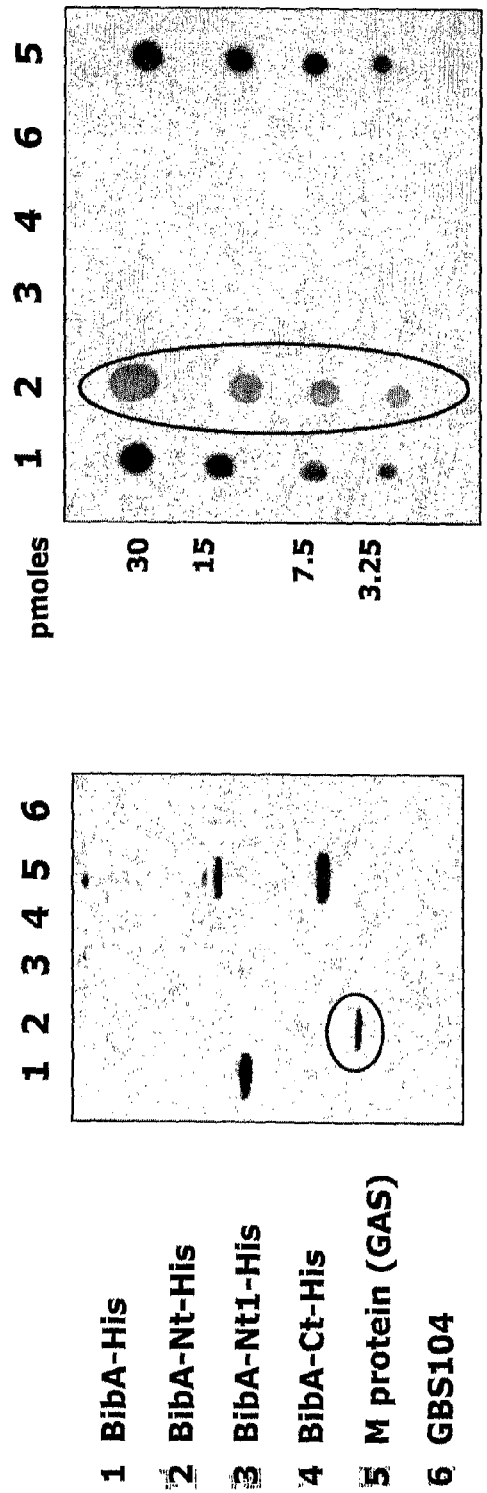
FIG. 28. Summary of data demonstrating that IgA binds to the N-terminal portion of recombinant BibA.
Figure 29:
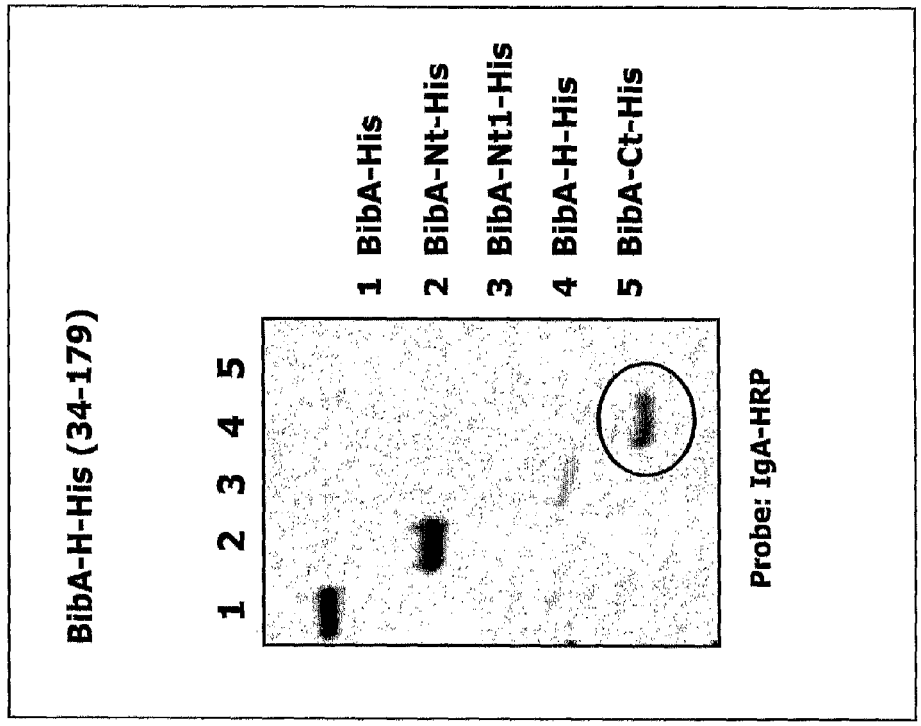
FIG. 29. Summary of data demonstrating that the IgA binding domain is contained within the first 200 amino acids of BibA.
Figure 29:
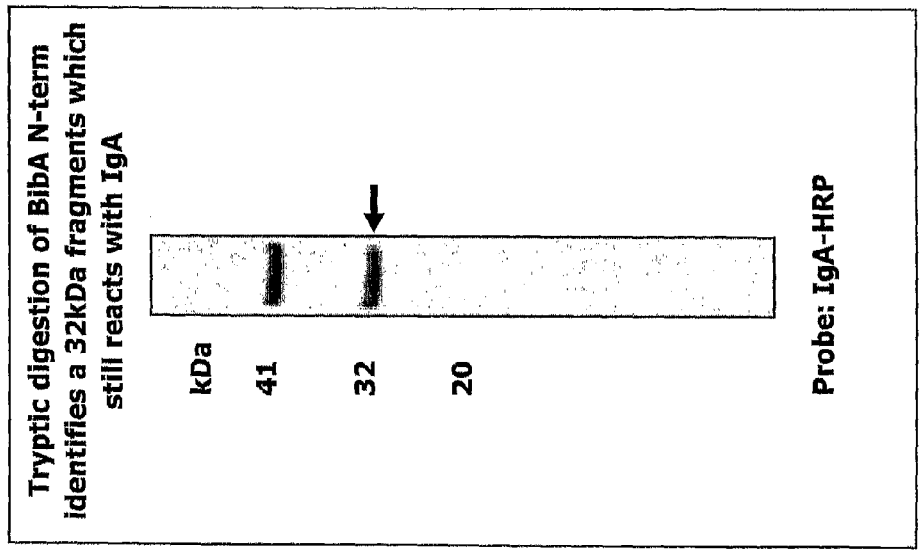

The results are shown in FIG. 13. These findings demonstrate that BibA binds to the surface of epithelial cells by the proline-rich motif. See also FIGS. 25A and 25B; FIG. 26.

EXAMPLE 10

Purified Human-IgG Binds to BibA Protein

Purified GBS3-His, GBS3-Nt-His (Nt), GBS3-Nt1-His (Nt1), GBS3-T-His (T), GBS3-Ct-His (Ct), GBS M protein (M1) (positive control) and GBS104 (negative control) were separated on SDS-4%-12% PAGE gel (200V) and transferred to nitrocellulose membrane (35V, 1 hr, 15 min). The nitrocellulose membrane was blocked for 1 hr at RT with 5% Milk-PBS-0.1% Tween20 (PBS-T) and overlaid with immunoglobulins (human-IgA or human-IgG) in PBS-T for 1 hr at RT. The membrane was washed three times with PBS-T, overlaid with secondary HRP conjugated antibodies (1:1000) in 5% Milk-PBS-0.1% Tween20, and washed three times with PBS-T. Positive binding to immunoglobulins was detected using an ECL™ substrate.

Figure 14C:
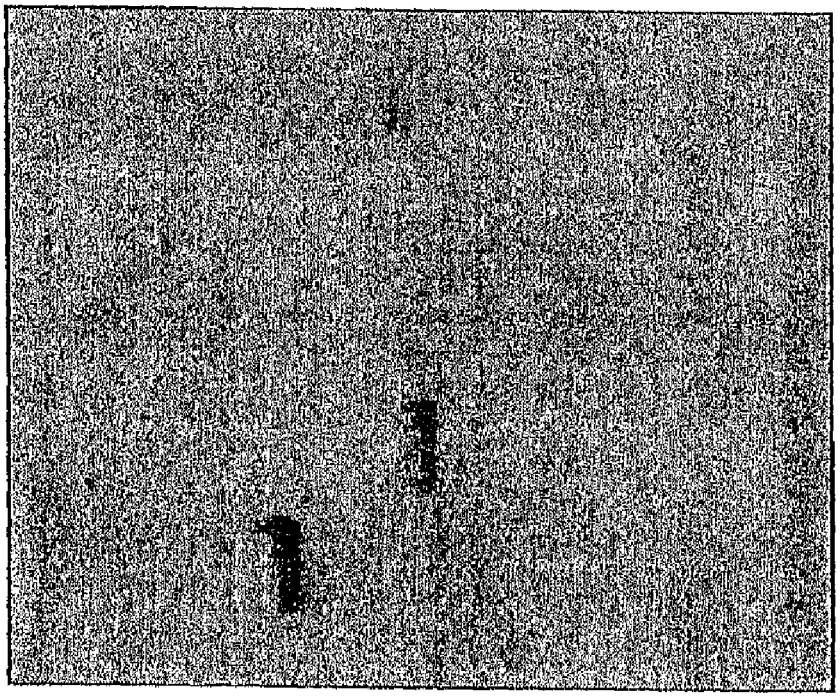

The results are shown in FIG. 14. The results demonstrate that the full-length protein and fragments of the protein bind to human IgG with different affinities.

EXAMPLE 11

BibA-His is Specific for Human and Rabbit IgG

BibA-His was separated on SDS-PAGE and then transferred to a nitrocellulose membrane. After blocking, the membranes were incubated with serum of different species and then probed with anti-IgG antibody conjugated with HRP. The proteins were revealed with a colorimetric kit.

The results are shown in FIG. 17 and Table 1. These results demonstrate that BibA-His is specific for human and rabbit IgG and does not bind mouse IgG.

EXAMPLE 12

Purified Human-IgA Binds to BibA Protein

Purified BibA-His, BibA-Nt-His (Nt), BibA-Nt1-His (Nt1), BibA-T-His (T), BibA-Ct-His (Ct), GBS M protein (M1) (positive control) and GBS104 (negative control) were separated on SDS-4%-12% PAGE gel (200V) and transferred to nitrocellulose membrane (35V, 1 hr, 15 min). The nitrocellulose membrane was blocked for 1 hr at RT with 5% Milk-PBS-0.1% Tween20 (PBS-T) and overlaid with human-IgA-HRP conjugated in PBS-T for 1 hr at RT. The membrane was washed three times with PBS-T. Positive binding to immunoglobulins was detected using an ECL™ substrate. The protein was blocked by incubating the membrane with 5% milk-PBS-T for 1 hr at RT. The membrane was incubated with human IgG-HRP (5 µg/ml) in PBS-T for 1.5 hr, then washed three times with PBS-T. Positive binding to immunoglobulins was detected using an ECL™ substrate (PIERCE kit: SuperSignal West Pico Chemiluminescent Substrate) and 4-CN kit (BIO-RAD).

Native BibA protein and portions of BibA were examined via dot blot.

Figure 15:
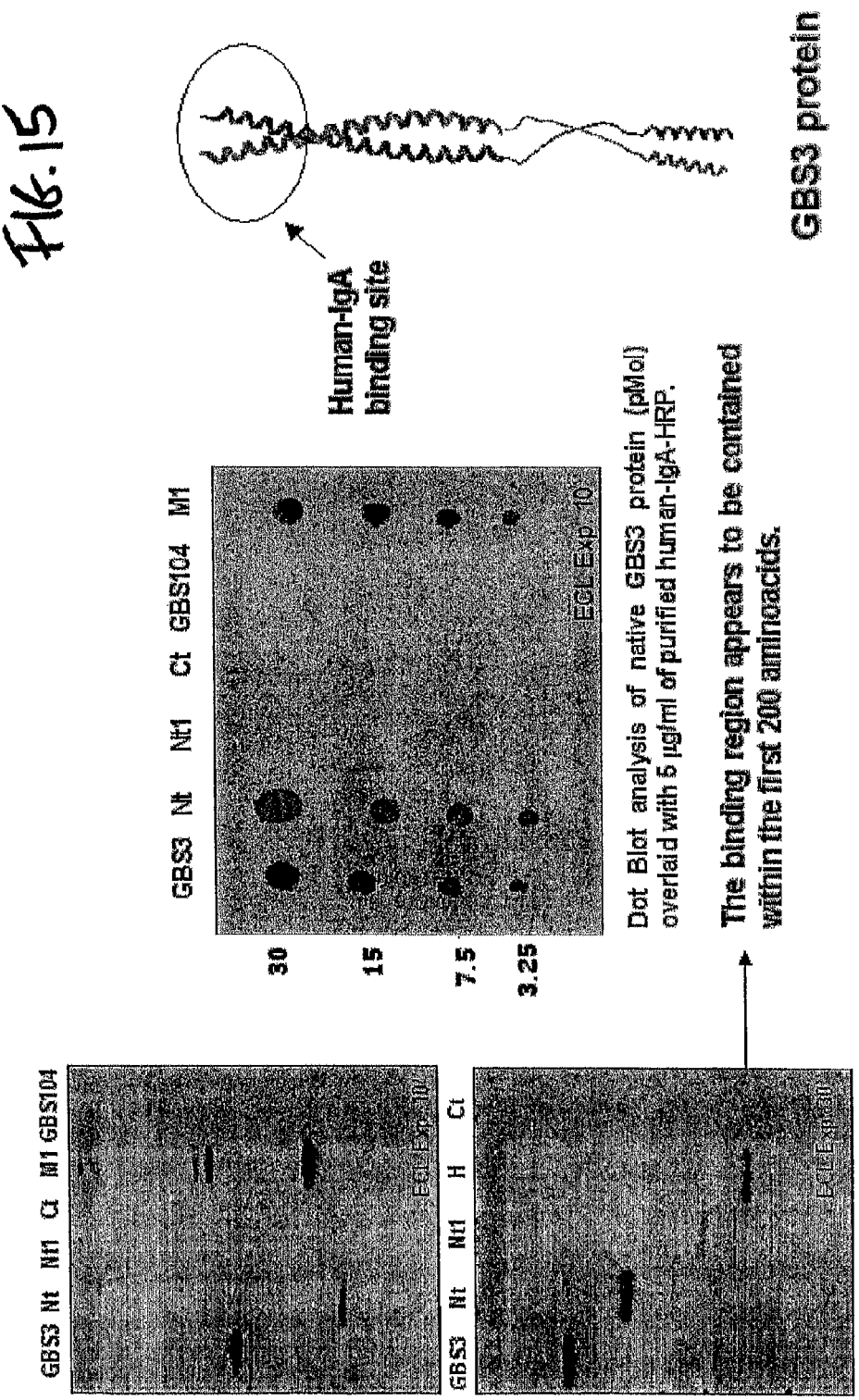

The results are shown in FIG. 15 and Table 2. These results demonstrate that the N-terminal portion of BibA binds to purified human IgA.

Figure 16:
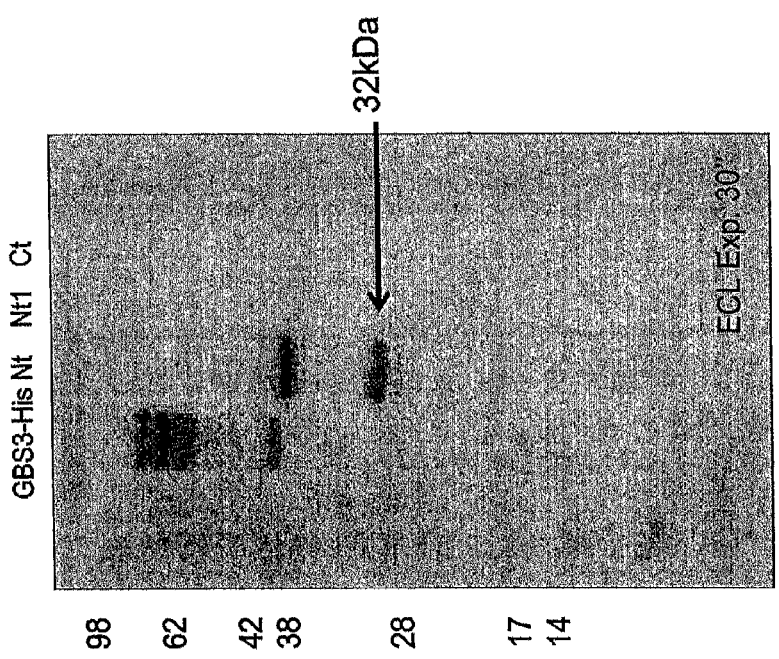
FIG. 16. Western blot showing binding of tryptic digested fragments of BibA to IgA.
Figure 18:
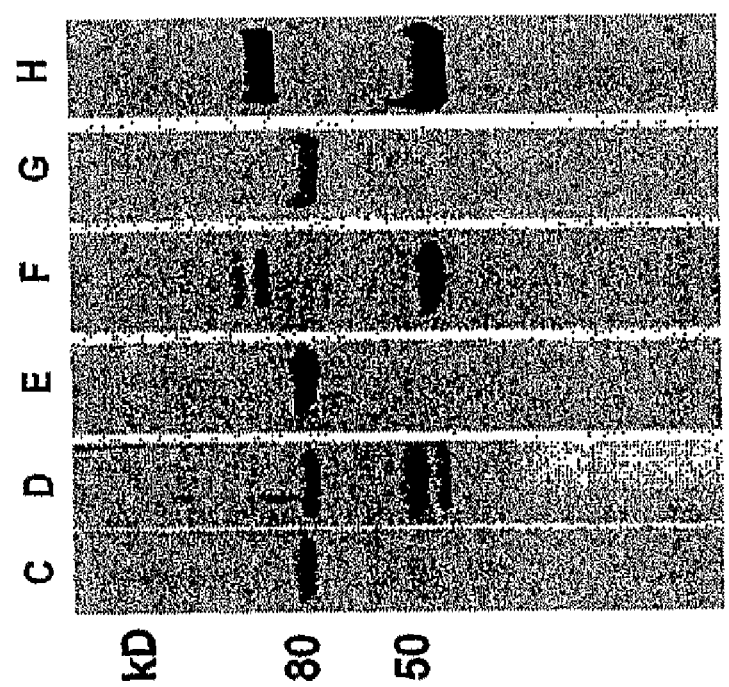
FIG. 18. Western blot showing that BibA binds to human IgG (lane C), human serum IgA (lane E) and C4BP (lane G). M protein of GBS was used as positive control (lanes D, F, H).

BibA-His and BibA fragments were digested with trypsin for 15 minutes and separated on SDS-PAGE gel. An overlay with h-IgA-HRP (1 ml/ml) was performed on the proteins transferring on nitrocellulose membrane. The results are shown in FIG. 16. Tryptic digestion produces a fragment of 32 kDa which still binds h-IgA.

Figure 9:
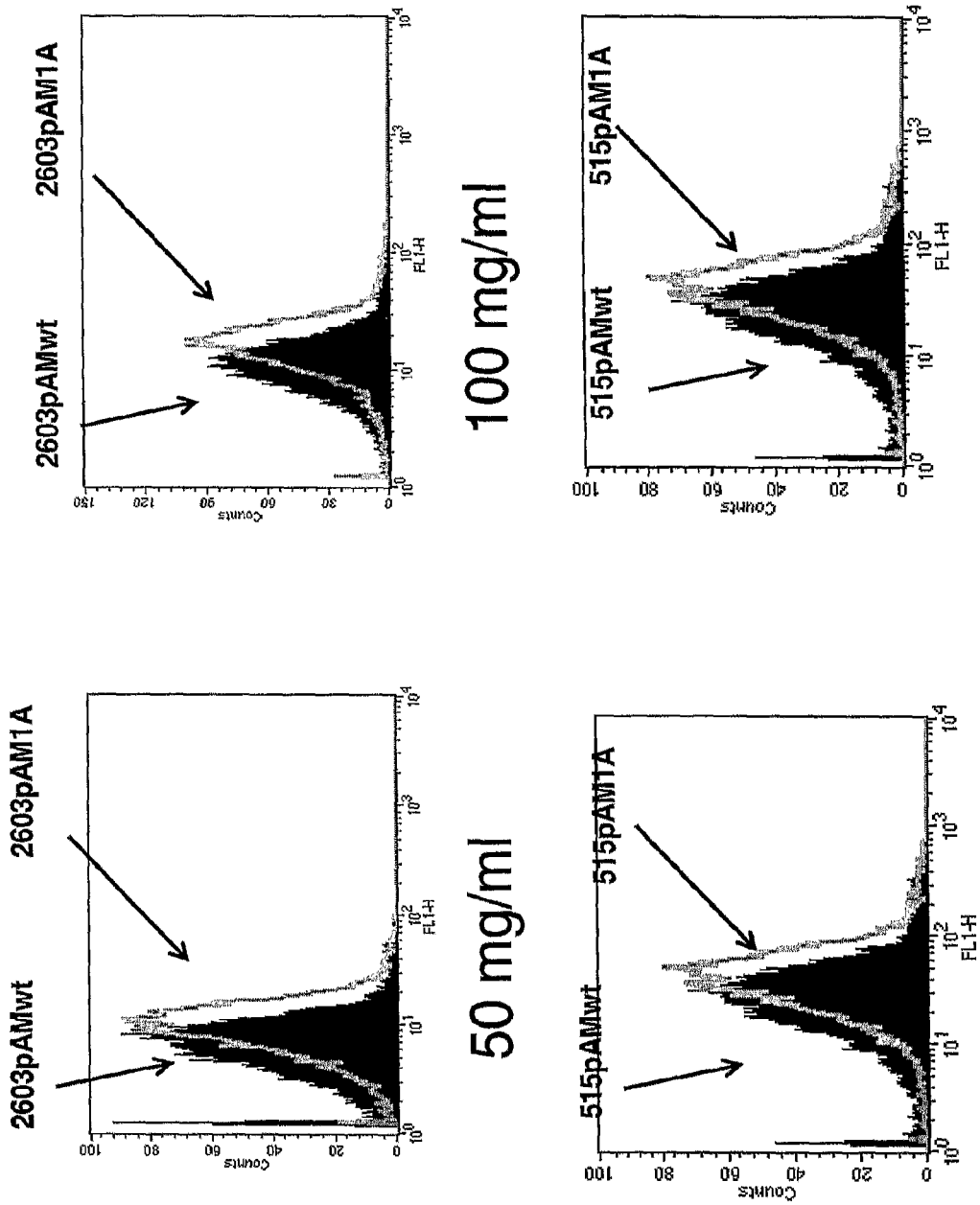
FIG. 9. FACS analysis demonstrating human-IgA-FITC binding to the surface of 2603-BibA overexpressing mutant strain.

Human-IgA-FITC binding to the surface of 2603-BibA overexpressing mutant strain is shown in FIG. 9. FACS analysis revealed an increment of IgA binding to the surface of BibA overexpressing mutants.

EXAMPLE 13

Production of Complete and Truncated Forms of BibA

Plasmids encoding complete or truncated form of BibA proteins were constructed as follows. Domains of BibA were amplified by PCR using 2603 genome as the template. The oligonucleotide primers used are listed in the Table 1. Forward primers all contained NdeI restriction sites. The reverse primers all contained XhoI restriction sites. PCR product were digested with NdeI and XhoI, gel purified and ligated with NdeI and XhoI restricted pET21b(+). All constructs were verified by DNA sequencing. The recombinant proteins were expressed His-tag proteins.

```
GBS3-His is the entire form of BibA (GBS3)

GBS3-Nt-His is the coiled-coil domain of BibA

GBS3-Nt1-His is the coiled-coil domain without the first 180 aa

GBS3-Ct-His is the proline-rich domain of BibA

GBS3-Nt3-His contained the proline-rich domain and a portion of
coiled-coil domain GBS3-T-His contained the first 180 aa GBS3-His
from 34aa to 609aa
                                                       (SEQ ID NO: 20)
Forward NdeI 5'-GGAATTCCATATGCACGCGGATACTAGTTCAGGA-3'

(SEQ ID NO: 21)
Reverse XhoI 5'-CCCGCTCGAGAATTGCTAAGAGTGGACTTGC-3'

Nucleotide sequence
                                                       (SEQ ID NO: 22)
CACGCGGATACTAGTTCAGGAATATCGGCTTCAATTCCTCATAAGAAACAAGTTAATTTAGGGG

CGGTTACTCTGAAGAATTTGATTTCTAAATATCGTGGTAATGACAAAGCTATTGCTATACTTTT

AAGTAGAGTAAATGATTTTAATAGAGCATCACAGGATACACTTCCACAATTAATTAATAGTACT

GAAGCAGAAATTAGAAATATTTTATATCAAGGACAAATTGGTAAGCAAAATAAACCAAGTGTAA

CTACACATGCTAAAGTTAGTGATCAAGAACTAGGTAAGCAGTCAAGACGTTCTCAAGATATCAT

TAAGTCATTAGGTTTCCTTTCATCAGACCAAAAAGATATTTTAGTTAAATCTATTAGCTCTTCA
```

-continued

```
AAAGATTCGCAACTTATTCTTAAATTTGTAACTCAAGCCACGCAACTGAATAATGCTGAATCAA

CAAAAGCTAAGCAAATGGCTCAAAATGACGTGGCCTTAATAAAAAATATAAGCCCCGAAGTCTT

AGAAGAATATAAAGAAAAAATTCAAAGAGCTAGCACTAAGAGTCAAGTTGATGAGTTTGTAGCA

GAAGCTAAAAAAGTTGTTAATTCCAATAAAGAAACGTTGGTAAATCAGGCCAATGGTAAAAAGC

AAGAAATTGCTAAGTTAGAAAATTTATCTAACGATGAAATGTTGAGATATAATACTGCAATTGA

TAATGTAGTGAAACAGTATAATGAAGGTAAGCTCAATATTACTGCTGCAATGAATGCTTTAAAT

AGTATTAAGCAAGCAGCACAGGAAGTTGCCCAGAAAAACTTACAAAAGCAGTATGCTAAAAAAA

TTGAAAGAATAAGTTCAAAAGGATTAGCGTTATCTAAAAAGGCTAAAGAAATTTATGAAAAGCA

TAAAAGTATTTTGCCTACACCTGGATATTATGCAGACTCTGTGGGAACTTATTTGAATAGGTTT

AGAGATAAACAAACTTTCGGAAATAGGAGTGTTTGGACTGGTCAAAGTGGACTTGATGAAGCAA

AAAAAATGCTTGATGAAGTCAAAAAGCTTTTAAAAGAACTTCAAGACCTTACCAGAGGTACTAA

AGAAGATAAAAAACCAGACGTTAAGCCAGAAGCCAAACCAGAGGCCAAACCAGACGTTAAGCCA

GAGGCCAAACCAGACGTTAAGCCAGAAGCTAAGCCAGACGTTAAACCAGAAGCTAAGCCAGACG

TTAAACCAGAAGCTAAGCCAGACGTTAAACCAGAAGCTAAGCCAGACGTTAAACCAAAGGCCAA

ACCAGACGTTAAGCCAGAAGCTAAGCCAGACGTTAAACCAGACGTTAAACCAGACGTTAAGCCA

GAGGCCAAACCAGAGGATAAGCCAGACGTTAAACCAGACGTTAAGCCAGAAGCTAAACCAGACG

TTAAGCCAGAGGCCAAACCAGAAGCTAAGCCAGAAGCTAAGCCAGAAGCTAAGCCAGAGGCCAA

ACCAGAAGCTAAGCCAGACGTTAAGCCAGAAGCTAAACCAGACGTTAAACCAGAGGCTAAGCCA

GAAGCTAAACCAGAGGCTAAGTCAGAAGCTAAACCAGAGGCTAAGCTAGAAGCTAAACCAGAGG

CCAAACCAGCAACCAAAAAATCGGTTAATACTAGCGGAAACTTGGCGGCTAAAAAAGCTATTGA

AAACAAAAGTATAGTAAAAAATTACCATCAACGGGTGAAGCC*GCAAGTCCACTCTTAGCAATT*
```

Amino acid sequence of the fragment (SEQ ID NO: 23)
```
MetHADTSSGISASIPHKKQVNLGAVTLKNLISKYRGNDKAIAILLSRVNDFNRASQDTLPQLI

NSTEAEIRNILYQGQIGKQNKPSVTTHAKVSDQELGKQSRRSQDIIKSLGFLSSDQKDILVKSI

SSSKDSQLILKFVTQATQLNNAESTKAKQMAQNDVALIKNISPEVLEEYKEKIQRASTKSQVDE

FVAEAKKVVNSNKETLVNQANGKKQEIAKLENLSNDEMLRYNTAIDNVVKQYNEGKLNITAAMN

ALNSIKQAAQEVAQKNLQKQYAKKIERISSKGLALSKKAKEIYEKHKSILPTPGYYADSVGTYL

NRFRDKQTFGNRSVWTGQSGLDEAKKMLDEVKKLLKELQDLTRGTKEDKKPDVKPEAKPEAKPD

VKPEAKPDVKPEAKPDVKPEAKPDVKPEAKPDVKPEAKPDVKPKAKPDVKPEAKPDVKPDVKPD

VKPEAKPEDKPDVKPDVKPEAKPDVKPEAKPEAKPEAKPEAKPEAKPEAKPDVKPEAKPDVKPE

AKPEAKPEAKSEAKPEAKLEAKPEAKPATKKSVNTSGNLAAKKAIENKKYSKKLPSTGEAASPL

LAIVSLIVMLSAGLITLEHHHHHH
```

GBS3-Nt-His
from 34aa to 394aa (SEQ ID NO: 24)
Forward NdeI 5'-GGAATTC<u>CATATG</u>CACGCGGATACTAGTTCAGGA-3'

(SEQ ID NO: 25)
Reverse XhoI 5'-CCCG<u>CTCGAG</u>ACCTCTGGTAAGGTCTTGAA-3'

Nucleotide sequence (SEQ ID NO: 26):
```
CACGCGGATACTAGTTCAGGAATATCGGCTTCAATTCCTCATAAGAAACAAGTTAATTTAGGGG

CGGTTACTCTGAAGAATTTGATTTCTAAATATCGTGGTAATGACAAAGCTATTGCTATACTTTT

AAGTAGAGTAAATGATTTTAATAGAGCATCACAGGATACACTTCCACAATTAATTAATAGTACT
```

-continued

```
GAAGCAGAAATTAGAAATATTTTATATCAAGGACAAATTGGTAAGCAAAATAAACCAAGTGTAA

CTACACATGCTAAAGTTAGTGATCAAGAACTAGGTAAGCAGTCAAGACGTTCTCAAGATATCAT

TAAGTCATTAGGTTTCCTTTCATCAGACCAAAAAGATATTTTAGTTAAATCTATTAGCTCTTCA

AAAGATTCGCAACTTATTCTTAAATTTGTAACTCAAGCCACGCAACTGAATAATGCTGAATCAA

CAAAAGCTAAGCAAATGGCTCAAAATGACGTGGCCTTAATAAAAAATATAAGCCCCGAAGTCTT

AGAAGAATATAAAGAAAAAATTCAAAGAGCTAGCACTAAGAGTCAAGTTGATGAGTTTGTAGCA

GAAGCTAAAAAAGTTGTTAATTCCAATAAAGAAACGTTGGTAAATCAGGCCAATGGTAAAAAGC

AAGAAATTGCTAAGTTAGAAAATTTATCTAACGATGAAATGTTGAGATATAATACTGCAATTGA

TAATGTAGTGAAACAGTATAATGAAGGTAAGCTCAATATTACTGCTGCAATGAATGCTTTAAAT

AGTATTAAGCAAGCAGCACAGGAAGTTGCCCAGAAAAACTTACAAAAGCAGTATGCTAAAAAAA

TTGAAAGAATAAGTTCAAAAGGATTAGCGTTATCTAAAAAGGCTAAAGAAATTTATGAAAAGCA

TAAAAGTATTTTGCCTACACCTGGATATTATGCAGACTCTGTGGGAACTTATTTGAATAGGTTT

AGAGATAAACAAACTTTCGGAAATAGGAGTGTTTGGACTGGTCAAAGTGGACTTGATGAAGCAA

AAAAAATGCTTGATGAAGTCAAAAAGCTTTTAAAAGAACTTCAAGACCTTACCAGAGGT
```

Amino acid sequence of the fragment (SEQ ID NO: 27)

MetHADTSSGISASIPHKKQVNLGAVTLKNLISKYRGNDKAIAILLSRVNDFNRASQDTLPQLIN

STEAEIRNILYQGQIGKQNKPSVTTHAKVSDQELGKQSRRSQDIIKSLGFLSSDQKDILVKSISS

SKDSQLILKFVTQATQLNNAESTKAKQMAQNDVALIKNISPEVLEEYKEKIQRASTKSQVDEFVA

EAKKVVNSNKETLVNQANGKKQEIAKLENLSNDEMLRYNTAIDNVVKQYNEGKLNITAAMNALNS

IKQAAQEVAQKNLQKQYAKKIERISSKGLALSKKAKEIYEKHKSILPTEGYYADSVGTYLNRFRD

KQTFGNRSVWTGQSGLDEAKKMLDEVKKLLKELQDLTRGLEHHHHHH

BibA-Nt1-His
from 180aa to 394aa (SEQ ID NO: 28)

Forward NdeI 5'-GGAATTC<u>CATATG</u>GCTGAATCAACAAAAGCTA-3'

SEQ ID NO: 29)

Reverse XhoI 5'-CCCG<u>CTCGAG</u>ACCTCTGGTAAGGTCTTGAA-3'

Nucleotide sequence (SEQ ID NO: 30):

```
GCTGAATCAACAAAAGCTAAGCAAATGGCTCAAAATGACGTGGCCTTAATAAAAAATATAAGCC

CCGAAGTCTTAGAAGAATATAAAGAAAAAATTCAAAGAGCTAGCACTAAGAGTCAAGTTGATGA

GTTTGTAGGAGAAGCTAAAAAAGTTGTTAATTCCAATAAAGAAACGTTGGTAAATCAGGCCAAT

GGTAAAAAGCAAGAAATTGCTAAGTTAGAAAATTTATCTAACGATGAAATGTTGAGATATAATA

CTGCAATTGATAATGTAGTGAAACAGTATAATGAAGGTAAGCTCAATATTACTGCTGCAATGAA

TGCTTTAAATAGTATTAAGCAAGGAGCACAGGAAGTTGCCCAGAAAAACTTACAAAAGCAGTAT

GCTAAAAAAATTGAAAGAATAAGTTCAAAAGGATTAGCGTTATCTAAAAAGGCTAAAGAAATTT

ATGAAAAGCATAAAAGTATTTTGCCTACACCTGGATATTATGCAGACTCTGTGGGAACTTATTT

GAATAGGTTTAGAGATAAACAAACTTTCGGAAATAGGAGTGTTTGGACTGGTCAAAGTGGACTT

GATGAAGCAAAAAAAATGCTTGATGAAGTCAAAAAGCTTTTAAAAGAACTTCAAGACCTTACCA

GAGGT
```

Amino acid sequence of the fragment (SEQ ID NO: 31)

MetAESTKAKQMAQNDVALIKNISPEVLEEYKEKIQRASTKSQVDEFVAEAKKVVNSNKETLVN

QANGKKQEIAKLENLSNDEMLRYNTAIDNVVKQYNEGKLNITAAMNALNSIKQAAQEVAQKNLQ

KQYAKKIERISSKGLALSKKAKEIYEKHKSILPTPGYYADSVGTYLNRFRDKQTFGNRSVWTGQ

SGLDEAKKMLDEVKKLLKELQDLTRGLEHHHHHH

GBS3-Ct-His
from 389aa to 622aa

Forward NdeI 5'-GGAATTCCATATGCCAGACCTTACCAGAGGT-3' (SEQ ID NO: 32)

Reverse XhoI 5'-CCCGCTCGAGCGTAATAAGACCTGCACTT-3' (SEQ ID NO: 33)

Nucleotide sequence (SEQ ID NO: 34):
CAAGACCTTACCAGAGGTACTAAAGAAGATAAAAAACCAGACGTTAAGCCAGAAGCCAAACCAG

AGGCCAAACCAGACGTTAAGCCAGAGGCCAAACCAGACGTTAAGCCAGAAGCTAAGCCAGACGT

TAAACCAGAAGCTAAGCCAGACGTTAAACCAGAAGCTAAGCCAGACGTTAAACCAGAAGCTAAG

CCAGACGTTAAACCAAAGGCCAAACCAGACGTTAAGCCAGAAGCTAAGCCAGACGTTAAACCAG

ACGTTAAACCAGACGTTAAGCCAGAGGCCAAACCAGAGGATAAGCCAGACGTTAAACCAGACGT

TAAGCCAGAAGCTAAACCAGACGTTAAGCCAGAGGCCAAACCAGAAGCTAAGCCAGAAGCTAAG

CCAGAAGCTAAGCCAGAGGCCAAACCAGAAGCTAAGCCAGACGTTAAGCCAGAAGCTAAACCAG

ACGTTAAACCAGAGGCTAAGCCAGAAGCTAAACCAGAGGCTAAGTCAGAAGCTAAACCAGAGGC

TAAGCTAGAAGCTAAACCAGAGGCCAAACCAGCAACCAAAAAATCGGTTAATACTAGCGGAAAC

TTGGCGGCTAAAAAGCTATTGAAAACAAAAGTATAGTAAAAAATTACCATCAACGGGTGAAG

CCGCAAGTCCACTCTTAGCAATTGTATCACTAATTGTTATGTTAAGTGCAGGTCTTATTACG

Amino acid sequence of the fragment
(SEQ ID NO: 35)
MetQDLTRGTKEDKKPDVKPEAKPEAKPDVKPEAKPDVKPEAKPDVKPEAKPDVKPEAKPDVKP

EAKPDVKPKAKPDVKPEAKPDVKPDVKPDVKPEAKPEDKPDVKPDVKPEAKPDVKPEAKPEAKP

EAKPEAKPEAKPEAKPDVKPEAKPDVKPEAKPEAKPEAKSEAKPEAKLEAKPEAKPATKKSVNT

SGNLAAKKAIENKKYSKKLPSTGEAASPLLAIVSLIVMLSAGLITLEHHHHHH

GBS3-Nt3-His
From 180aa to 622aa

Primer 7 NdeI 5'-GGAATTCCATATGGCTGAATCAACAAAAGCTA-3' (SEQ ID NO: 36)

Primer 9 XhoI 5'-CCCGCTCGAGCGTAATAAGACCTGCACTT-3' (SEQ ID NO: 37)

Nucleotide sequence (SEQ ID NO: 38):
GCTGAATCAACAAAAGCTAAGCAAATGGCTCAAAATGACGTGGCCTTAATAAAAAATATAAGCC

CCGAAGTCTTAGAAGAATATAAAGAAAAAATTCAAAGAGCTAGCACTAAGAGTCAAGTTGATGA

GTTTGTAGGAGAAGCTAAAAAAGTTGTTAATTCCAATAAAGAAACGTTGGTAAATCAGGCCAAT

GGTAAAAAGCAAGAAATTGCTAAGTTAGAAAATTTATCTAACGATGAAATGTTGAGATATAATA

CTGCAATTGATAATGTAGTGAAACAGTATAATGAAGGTAAGCTCAATATTACTGCTGCAATGAA

TGCTTTAAATAGTATTAAGCAAGCAGCACAGGAAGTTGCCCAGAAAAACTTACAAAAGCAGTAT

GCTAAAAAATTGAAAGAATAAGTTCAAAAGGATTAGCGTTATCTAAAAAGGCTAAAGAAATTT

ATGAAAAGCATAAAAGTATTTTGCCTACACCTGGATATTATGCAGACTCTGTGGGAACTTATTT

GAATAGGTTTAGAGATAAACAAACTTTCGGAAATAGGAGTGTTTGGACTGGTCAAAGTGGACTT

GATGAAGCAAAAAAAATGCTTGATGAAGTCAAAAAGCTTTTAAAAGAACTTCAAGACCTTACCA

GAGGTACTAAAGAAGATAAAAAACCAGACGTTAAGCCAGAAGCCAAACCAGAGGCCAAACCAGA

CGTTAAGCCAGAGGCCAAACCAGACGTTAAGCCAGAAGCTAAGCCAGACGTTAAACCAGAAGCT

-continued

```
AAGCCAGACGTTAAACCAGAAGCTAAGCCAGACGTTAAACCAGAAGCTAAGCCAGACGTTAAAC

CAAAGGCCAAACCAGACGTTAAGCCAGAAGCTAAGCCAGACGTTAAACCAGACGTTAAACCAGA

CGTTAAGCCAGAGGCCAAACCAGAGGATAAGCCAGACGTTAAACCAGACGTTAAGCCAGAAGCT

AAACCAGACGTTAAGCCAGAGGCCAAACCAGAAGCTAAGCCAGAAGCTAAGCCAGAAGCTAAGC

CAGAGGCCAAACCAGAAGCTAAGCCAGACGTTAAGCCAGAAGCTAAACCAGACGTTAAACCAGA

GGCTAAGCCAGAAGCTAAACCAGAGGCTAAGTCAGAAGCTAAACCAGAGGCTAAGCTAGAAGCT

AAACCAGAGGCCAAACCAGCAACCAAAAAATCGGTTAATACTAGGGGAAACTTGGCGGCTAAAA

AAGCTATTGAAAACAAAAGTATAGTAAAAAATTACCATCAACGGGTGAAGCCGCAAGTCCACT

CTTAGCAATTGTATCACTAATTGTTATGTTAAGTGCAGGTCTTATTACG
```

Amino acid sequence of the fragment (SEQ ID NO: 39):
MetAESTKAKQMAQNDVALIKNISPEVLEEYKEKIQRASTKSQVDEFVAEAKKVVNSNKETLVN

QANGKKQEIAKLENLSNDEMLRYNTAIDNVVKQYNEGKLNITAAMNALNSIKQAAQEVAQKNLQ

KQYAKKIERISSKGLALSKKAKEIYEKHKSILPTPGYYADSVGTYLNRFRDKQTFGNRSVWTGQ

SGLDEAKKMLDEVKKLLKELQDLTRGTKEDKKPDVKPEAKPEAKPDVKPEAKPDVKPEAKPDVK

PEAKPDVKPEAKPDVKPEAKPDVKPKAKPDVKPEAKPDVKPDVKPDVKPEAKPEDKPDVKPDVK

PEAKPDVKPEAKPEAKPEAKPEAKPEAKPDVKPEAKPDVKPEAKPEAKPEAKSEAKPEAK

LEAKPEAKPATKKSVNTSGNLAAKKAIENKKYSKKLPSTGEAASPLLAIVSLIVMLSAGLITLE

HHHHHH

GBS3-T-His (SEQ ID NO: 40)
Primer 1 NdeI 5'-GGAATTCCATATGCACGCGGATACTAGTTCAGGA-3'

(SEQ ID NO: 41)
GBS3-T-Rev XhoI 5'-CCCGCTCGAGATTATTCAGTTGCGTGGCTTGAGT-3'

Nucleotide sequence (SEQ ID NO: 42):
```
CACGCGGATACTAGTTCAGGAATATCGGCTTCAATTCCTCATAAGAAACAAGTTAATTTAGGGG

CGGTTACTCTGAAGAATTTGATTTCTAAATATCGTGGTAATGACAAAGCTATTGCTATACTTTT

AAGTAGAGTAAATGATTTTAATAGAGCATCACAGGATACACTTCCACAATTAATTAATAGTACT

GAAGCAGAAATTAGAAATATTTTATATCAAGGACAAATTGGTAAGCAAAATAAACCAAGTGTAA

CTACACATGCTAAAGTTAGTGATCAAGAACTAGGTAAGCAGTCAAGACGTTCTCAAGATATCAT

TAAGTCATTAGGTTTCCTTTCATCAGACCAAAAAGATATTTTAGTTAAATCTATTAGCTCTTCA

AAAGATTCGCAACTTATTCTTAAATTTGTAACTCAAGCCACGCAACTGAATAAT
```

Amino acid sequence of the fragment (SEQ ID NO: 43):
MetHADTSSGISASIPHKKQVNLGAVTLKNLISKYRGNDKAIAILLSRVNDENRASQDTLPQLIN

STEAEIRNILYQGQIGKQNKPSVTTHAKVSDQELGKQSRESQDIIKSLGFLSSDQKDILVKSISS

SKDSQLILKFVTQATQLNNLEHHHHHH

EXAMPLE 14

Experimental Procedures

Cell Culture

The human cervical epithelial cell line ME180 was purchased from the American Type Culture Collection (ATCC, Rockville, Md.). ME180 cells were maintained in RPMI 1640 medium with 10% heat-inactivated fetal bovine serum (FBS). The lung carcinoma cell line A549 (type II alveolar epithelial cells) and the colon carcinoma epithelial cell line Caco2 also were supplied by the ATCC and were grown in DMEM supplemented with 10% FBS, 4.5 g/L glucose and non-essential amino acids. The human bronchial epithelial cell line 16HBE14, which is transformed with SV40 large T antigen (Grifantini et al., 2002), was cultured in DMEM supplemented with 10% FBS, 1.5 mM glutamine, and 100 μg/ml kanamycin sulfate.

Bacterial Strains and Growth Conditions

S. agalactiae strains 2603 V/R and 515 Ia were used in this study. To determine BibA protein conservation, we analyzed a panel of S. agalactiae strains. E. coli DH5α and DH10BT1 were used for cloning purposes and E. coli BL21 (DE3) for expression of BibA fusion protein. S. agalactiae was cultivated at 37° C. in Todd-Hewitt broth (THB) up to OD600 0.4. S. agalactiae strains carrying the plasmid pAM401bibA were grown in the presence of cloramphenicol (10 μg/ml). E. coli was grown in Luria broth. *E. coli* clones carrying the plasmids pAM401bibA, pJRS233ΔbibA or pET21(b)+ derivatives were grown in the presence of chloramphenicol (20 µg/ml), erythromycin (400 µg/ml) or ampicillin (100 µg/ml), respectively.

Construction of 2603 V/R bibA Deletion Mutant

The bibA gene was deleted in *S. agalactiae* strain 2603 V/R according to the procedure described in Lauer et al., 2005. The in-frame deletion fragment was obtained by Splicing Overlap Extension (SOE) PCR using the primers 5'-CCCG *CTCGAG* ACTAGTGACAAACCTTGGAAT-3' (SEQ ID NO:44), 5'-GTCAGCACGGTTTGCCATAAACCGAAAG-GTCTATCC-3' (SEQ ID NO:45), 5'-ACCTTTCGGTT-TATGGCAAACGCTGCTGACATTG-3' (SEQ ID NO:46) and 5'-CCCG *CTCGAG* ACAGATAAGCCTAAGCGACTT-3' (SEQ ID NO:47). The XhoI restriction enzyme cleavage sites were incorporated at the 5'-end of the primer (bold and italicized) to clone the fragment into the XhoI-digested pJRS233 plasmid. After cloning the in frame deletion fragment in the pJRS233, the plasmid pJRS233ΔbibA was obtained.

The plasmid pJRS233ΔbibA was then transformed into the 2603 V/R strain by electroporation and transformants were selected after growth at 30° C. on agar plates containing 1 µg/ml erythromycin. Transformants were then grown at 37° C. with erythromycin selection as described in Maguin et al., 1996. Integrant strains were serially passaged for 5 days in liquid medium at 30° C. without erythromycin selection to facilitate the excision of plasmid pJRS233ΔbibA, resulting in the bibA deletion on the chromosome. Dilutions of the serially passaged cultures were plated onto agar plates, and single colonies were tested for erythromycin sensitivity to confirm the excision of pJRS233ΔbibA.

Plasmid-Mediated Expression of BibA in *S. agalactiae*

The bibA gene including its own promoter and terminator was amplified by PCR from chromosomal DNA of *S. agalactiae* 2603 V/R using primers 5'-CCCCGCC *GGGATCC* CCAACCCTTATCAAAAGA-3' (SEQ ID NO:48) and 5'-CTCTGCATG *GTCGA* CATAGAAACAAC-CCAAACCC-3' (SEQ ID NO:49). The restriction enzymes cleavage sites BamHI and SalI were incorporated at the 5'-ends of the primers (bold and italicized) to clone the PCR product into the BamHI/SalI digested *E. coli-Streptococcus* pAM401 expression construct. The plasmid pAM401bibA was obtained by cloning the bibA gene into pAM401. Plasmid pAM401bibA was transformed by electroporation into 2603 V/R and 515 Ia strains with subsequent chloramphenicol selection.

BibA Recombinant Protein Expression and Purification

In order to express the recombinant form of BibA, the open reading frame of the bibA gene from *S. agalactiae* 2603 was used as a template. The construct was amplified by PCR using specific primers, which introduced NdeI and XhoI restriction enzyme sites:

(SEQ ID NO: 50)
5'-GGAATTCCATATGCACGCG GATACTAGTTCAGGA-3'
and (SEQ ID NO: 51)
5'-CCCGCTCGAGAATTGCTAAGAGTGG ACTTGC-3'.

In the case of BibA N-terminal construct (aa 34-394) the following amplification primers were used:

(SEQ ID NO: 52)
5'-GGAATTCCATATGCACGCGGATACTAGTTCAGGA-3'
and (SEQ ID NO: 53)
5'-CCC GCTCGAGACCTCTGGTAAGGTCTTGAA-3'.

For BibA C-terminal construct (aa 389-622) the following primers were used:

(SEQ ID NO: 54)
5'-GGAATTCCATATGCCAGACCTTACCAGAGGT-3'
and (SEQ ID NO: 55)
5'-CCCGCTCGAGCGTAATAAGACC TGCACTT-3'.

The PCR products were cloned into the pET21(b)+ vector, which was used to transform *E. coli* BL21 (DE3) cells. BL21 (DE3) cells were grown in LB-Amp (100 µg/ml ampicillin) and induced with IPTG at final concentration of 1 mM for 3 hours. The resulting biomass was suspended in 0.3M NaCl, 50 mM Na—PO4 buffer, pH 8.0, and cells were lysed by two passages at 18,000 psi using a Basic Z Model Cell Disrupter (Constant Systems Ltd., Daventry, UK). The sample was then loaded onto a His-Trap Ni-Activated Chelating Sepharose FF column (Amersham Biosciences, Milan, Italy) at a flow rate of 5 ml/min. Bound proteins were then eluted from the column by running a gradient from 0 to 50% of 500 mM Imidazole, 0.3 M NaCl, 50 mM Na phosphate buffer, pH 8.0 in 12 CV. The IMAC (Immobilized Metal Affinity Column) eluted material was collected in 2.5-ml fractions, and the fractions containing the BibA-His protein were pooled. The collected pools were then loaded onto a HiLoad 26/60 Superdex 200 gel filtration column (Amersham Biosciences, Milan, Italy). The protein was eluted isocratically at 2.5 ml/min flow rate collecting 2.5-ml fractions.

Bacterial Extracts

GBS protein extracts were prepared by growing bacteria up to $OD_{600}$ 0.4. The resulting pellet washed in PBS and incubated for 1 hr at 37° C. in 500 µl of Tris-HCl 50 mM (pH6.8) containing protease inhibitors and 400 U/ml of mutanolysin (SIGMA, MO, USA). The bacterial suspension was then pelleted and supernatants containing peptidoglycan-associated proteins were used for Western blotting analysis of BibA. In order to prepare GBS extracts containing the secreted protein fraction, supernatant of bacteria cultures grown to $OD_{600}$ 0.4 were collected and directly used in PAGE.

Fluorescence-Activated Cell Sorter Analysis

In order to quantify the exposure of BibA on bacterial surface, GBS was grown up to OD600 0.4 and incubated with rabbit anti-BibA serum or rabbit anti-PBS serum (negative control) in 0.1% BSA plus 20% of normal calf serum (NCS) for 1 hr at 4° C. Bacteria were then washed in PBS containing 0.1% BSA and incubated with phicoerytrin (PE)-conjugated secondary antibodies (Jackson Immuno Research Inc., PA, USA) for 45 min at 4° C. After washing, bacteria were fixed with 2% PFA for 20 min at RT, resuspended in 200 µl of PBS, and analyzed by a FACSscan flow cytometer (Becton Dickinson) using the Cell Quest software program from Becton Dickinson.

In the binding assay, ME180 or A549 cells were mixed with different concentrations of BibA and incubated for 1 hr at 4° C. Cells were subsequently incubated for 45 min. at 4° C. with rabbit anti-BibA serum in 5% FCS. Cells were then washed twice in PBS and incubated for 45 min. at 4° C. with the PE-conjugated secondary antibodies. Cell-bound fluorescence was analyzed with a FACS using the Cell Quest program. MFI values of cells incubated with or without protein were compared.

Association Assay

ME180 and A549 epithelial cells were infected with approximately 10 bacteria/cell in infection medium (basal medium without antibiotics) supplemented with 2% FBS in 200 µl volumes. At the end of a 3-hour incubation at 37□C. in 5% CO2 (v/v), total colony-forming units (c.f.u.) were estimated after addition of 1% saponin to the wells contents. Adhesiveness was quantified by determining the ratio of cell-associated c.f.u. versus total c.f.u. present in the assay.

Immunogold Labeling and Electron Microscopy

GBS strains 2603 V/R, 2603ΔbibA, 515 Ia and 515pAM401bibA were grown overnight in THB medium (10 ml). Bacterial cells from 1 ml of the overnight culture were resuspended in 5 ml of fresh THB medium and grown at 37° C. up to OD 0.3 (exponential phase). Bacteria were then centrifuged for 10 min at 3000 rpm (RT), washed and resuspended in 1 ml of PBS. Formvar-carbon-coated nickel grids were floated on drops of GBS suspensions for 5 min. The grids were then fixed in 2% PFA for 5 min, and placed in blocking solution (PBS containing 1% normal rabbit serum and 1% BSA) for 30 min. The grids were then floated on drops of primary antiserum against the BibA protein diluted 1:20 in blocking solution for 30 min at RT, washed with six drops of blocking solution, and floated on secondary antibody conjugated to 10-nm gold particles diluted 1:10 in 1% BSA for 30 min. The grids were examined by using a TEM GEOL 1200EX II transmission electron microscope.

Confocal Immunofluorescence Microscopy

A549 cells were grown to confluence in a Lab-TekII Chamber Slide System (Nalgene) in 1 ml of DMEM supplemented with 10% FBS, 4.5 g/L glucose and non-essential amino acids. Cells were then infected with bacteria at a MOI 10:1 and incubated at 37° C. for 2 hr. Cells were then fixed in 2% paraformaldehyde for 30 min at room temperature (RT) or at 4° C. overnight. After fixing, the monolayers were blocked with 3% BSA and incubated for 1 hr at RT with a mix of mouse anti-capsule and rabbit anti-BibA polyclonal antibodies diluted in 1% BSA. Bacteria were then stained, for 1 hr at RT, with goat anti-mouse and anti-rabbit Alexa fluor (Molecular Probes) conjugated antibodies (excitation at 568 nm and 488 nm, respectively). F-actin was stained with Alexa Fluor 622 conjugated phalloidin. The chamber walls were then removed from the glass slide. A Slow Fade reagent kit (Molecular Probes) used to mount cover slips. The slides were viewed with a Bio-Rad confocal scanning microscope.

Dot Blot and Western Blot Analyses

In dot blot analysis, purified recombinant BibA protein (range ~2 µg-0.01 µg) was absorbed to a nitrocellulose membrane by using a BIORAD dot blot system. After saturation with 5% milk, the membrane was incubated with 0.5 µg/ml of serum purified human-IgA (Pierce) or human IgG (SIGMA). After washing, the membrane was incubated with HRP-conjugated rabbit anti-human IgA (Dako) or HRP-conjugated goat anti-human IgG (BD) and positive binding detected by ECL.

The same protocol was used to test the binding of BibA to C4BP. Purified C4BP derived from citrated human plasma was purchased from Kordia Life Science, (Leiden, N. Dak.). Mouse monoclonal anti-C4BP antibodies (BIOTREND Chemikalien GmbH, Köln) were used to reveal C4BP binding to BibA.

Western blot analysis of BibA binding to Ig or C4BP was performed by transferring SDS-PAGE separated proteins to nitrocellulose membranes (Portran). Membranes were then blocked in 5% milk and overlaid for 1 hr with 5 µg/ml of (a) purified IgG from normal human serum (SIGMA); (b) purified IgG from normal mouse serum (SIGMA); c) purified IgG from bovine serum (SIGMA); d) purified IgA from human serum (Pierce); (e) purified IgA from human colostrums (SIGMA); or (f) human plasma C4BP (Kordia Life Science, ND). After washing, membranes were incubated with the respective HRP-conjugated secondary antibodies, and detection was performed by ECL.

Sequence Analysis

The alignment of 2603 V/R (GenBank Accession Number NP_689049; SEQ ID NO:56), 18RS21 (AAJO00000000; SEQ ID NO:57), 515 Ia (AAJP00000000; SEQ ID NO:58), NEM316 (NP_736451; SEQ ID NO:59), H36B (AAJS00000000; SEQ ID NO:60), CJB111 (AAJQ00000000; SEQ ID NO:61), A909 (YP_330593; SEQ ID NO:62; see also SEQ ID NO:67) and COH1 (AAJR00000000; SEQ ID NO:63) strains was performed using ClustalW (Thompson et al., 1994).

EXAMPLE 15

Additional Evidence that BibA is Exposed on GBS Surface

As shown in FIG. 19A, FACS analysis of 2603 V/R strain grown at exponential phase ($OD_{600}$=0.35) revealed a shift in bacterial fluorescence after staining with anti-BibA antibody. This indicated that BibA is exposed on GBS surface. This finding was further confirmed by transmission immuno-electron microscopy (IEM) showing positive immunogold labeling of BibA on 2603 V/R surface (FIG. 19B). Western blot analysis of 2603 V/R bacterial extracts showed the presence of a single band recognized by anti-BibA antibodies in both peptidoglycan-associated protein fraction and bacteria supernatants (FIG. 19C). The band identified as BibA has an apparent MW of ≈80 kD (FIG. 19C), compared to the expected MW of 66 kD. We believe that the presence of a prolin-rich motif in the C-terminal region of BibA is responsible for such a discrepancy. Indeed, it is known that prolin-rich regions may retard protein electrophoretic migration (Hollingshead et al., 1986). Comparative analysis of bacteria grown at exponential or stationary phases revealed no differences in the expression of BibA as surface exposed or secreted protein (data not shown). As expected, BibA knockout mutant strain showed nor BibA FACS positive fluorescence neither immunogold surface labeling (FIGS. 19D and 19E).

In order to demonstrate that the anchoring of BibA to the cell wall was due to the presence of the LPXTG (SEQ ID NO:3) motif, we investigated BibA surface exposure in the strain 515 Ia, in which, due to a frameshift, the protein is lacking the LPXTG (SEQ ID NO:3) motif and therefore is predicted to be expressed in a truncated form (Tettelin et al., 2005). Both FACS analysis and IEM confirmed that in such a strain BibA was not surface exposed (FIGS. 19E and 19F). Moreover, Western blot analysis showed that BibA was found in 515 Ia bacterial supernatant, but not in the peptidoglycan associated fraction (FIG. 19G). The apparent molecular weight of 38 kD is in agreement with the predicted truncated form. When we introduced in the strain 515 Ia a plasmid carrying the 2603 V/R region containing the bibA gene and its regulatory elements (pAM401bibA), BibA was translocated and anchored on the bacterial surface, as demonstrated by Western blotting, FACS and IEM analysis (FIGS. 19H, 19I and 19L).

EXAMPLE 16

BibA Specifically Binds to Human Immunoglobulins

Figure 20A:
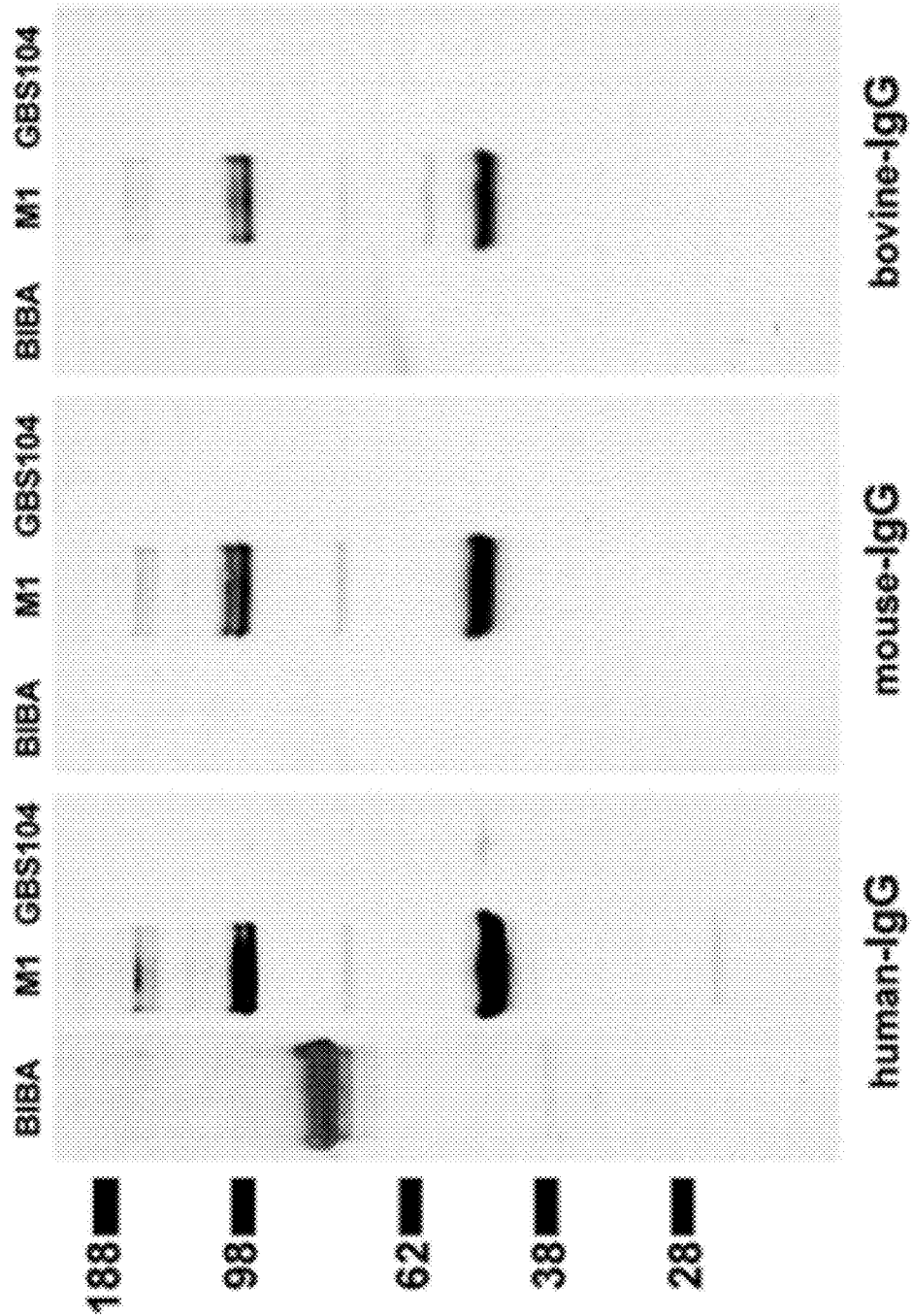
FIGS. 20A-F. Western blots demonstrating that BibA binds to human immunoglobulins.

Because sequence analysis of BibA indicated some similarity with streptococcal immunoglobulin-binding proteins, we performed Western blotting analysis of recombinant BibA overlaid with purified serum-derived immunoglobulins (Ig). Experimental positive control was the M1 protein of GBS, which is an IgG and IgA binding protein (Cunningham, 2000). The recently reported GBS pilus component protein GBS104 (Lauer et al., 2005) was used as unrelated negative control. As shown in FIG. 20A, BibA specifically bound to purified human serum IgG, but not to mouse or bovine IgG. On the other hand, M1 protein reacted with human, mouse and bovine IgG isoforms at similar levels.

Figure 20B:
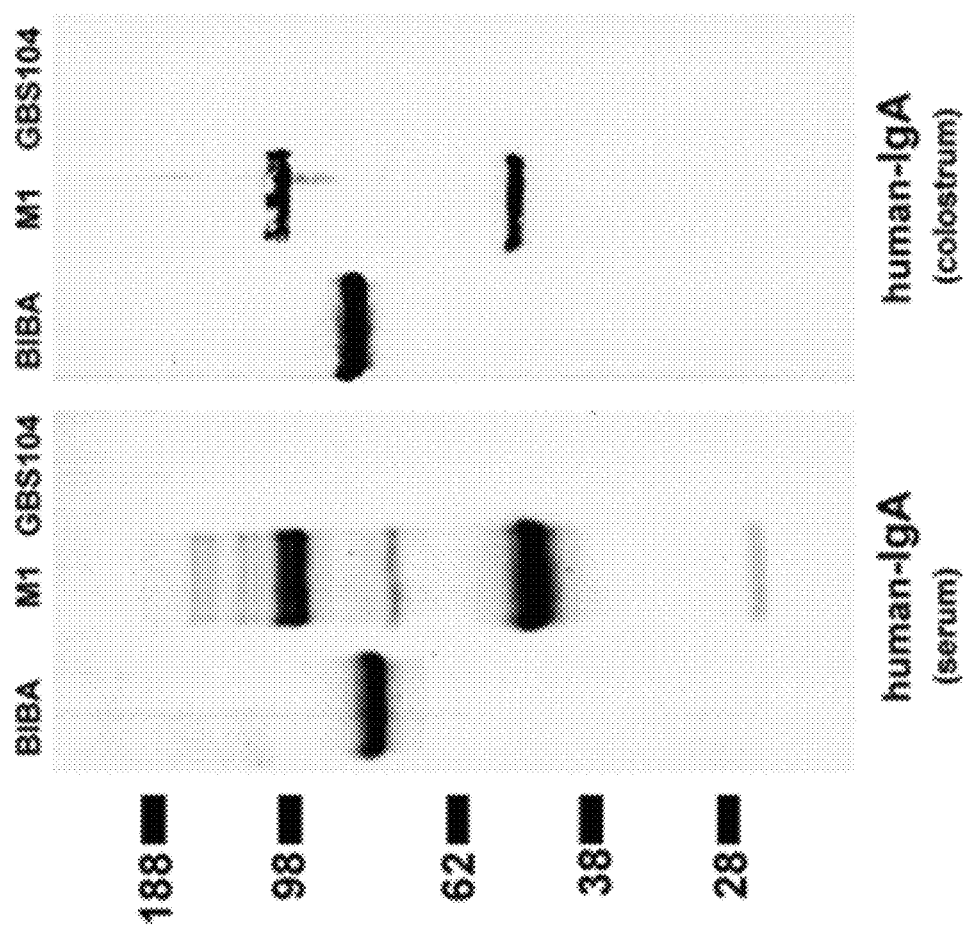
Figure 20D:
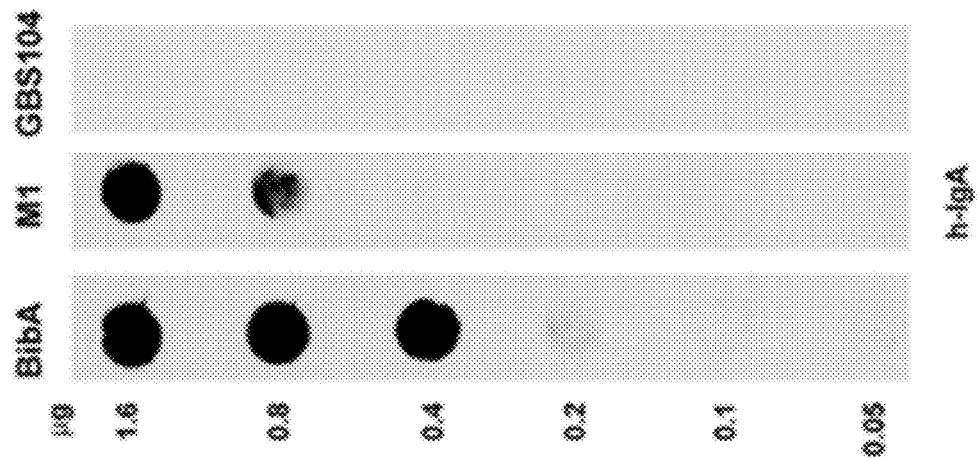
Figure 20C:
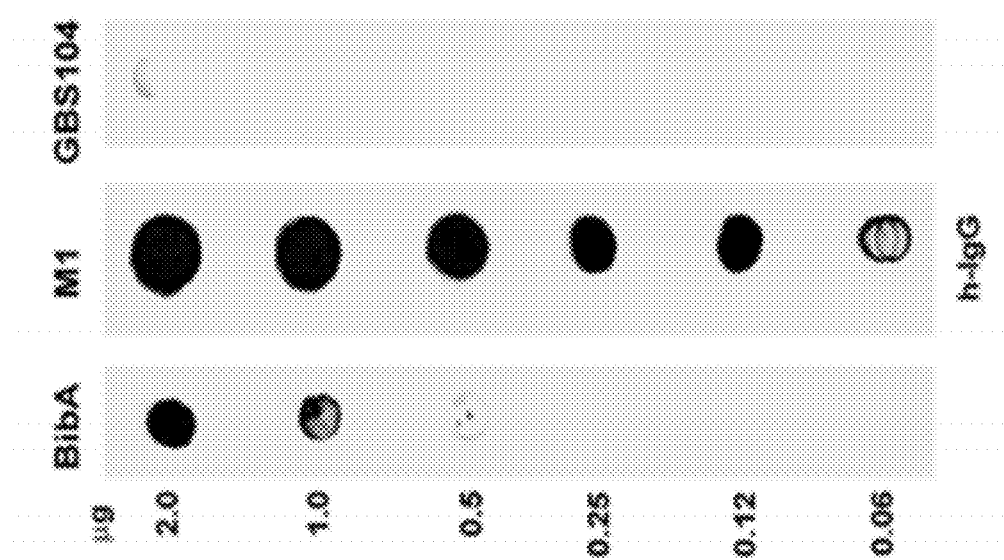

BibA binding to purified human serum- or secretory colostrums-derived IgA was also tested. As for the M1 protein, BibA positively recognizes both serum-derived and secretory IgA (FIG. 20B). In order to demonstrate that the binding properties were not due to the gel denaturing conditions, we performed native dot-blot experiments. Recombinant BibA protein was serially diluted on nitrocellulose membrane and probed with 0.5 μg/ml purified human serum IgG and IgA. As shown in FIGS. 20C and 20D, probing of native BibA with Ig confirmed the binding to human IgG and IgA. The reactivity of BibA for human IgA appeared to be stronger than that for human IgG. Indeed, a positive binding to IgA was already observed at a concentration of BibA of 0.4 μg, while for IgG the concentration of BibA necessary to the binding was of 1.0 μg (FIG. 20D). On the contrary, a strong binding to IgG was detected only up BibA (FIG. 20C).

Figure 20F:
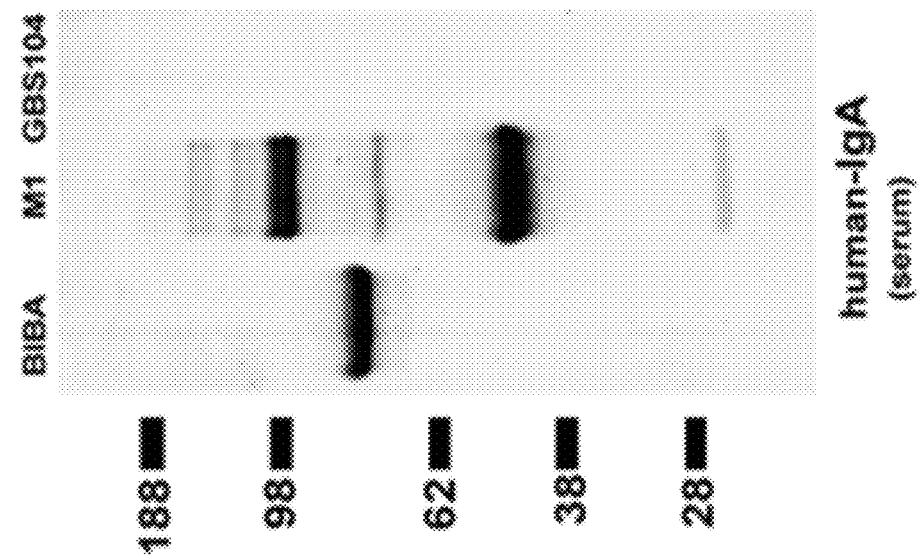
Figure 20E:
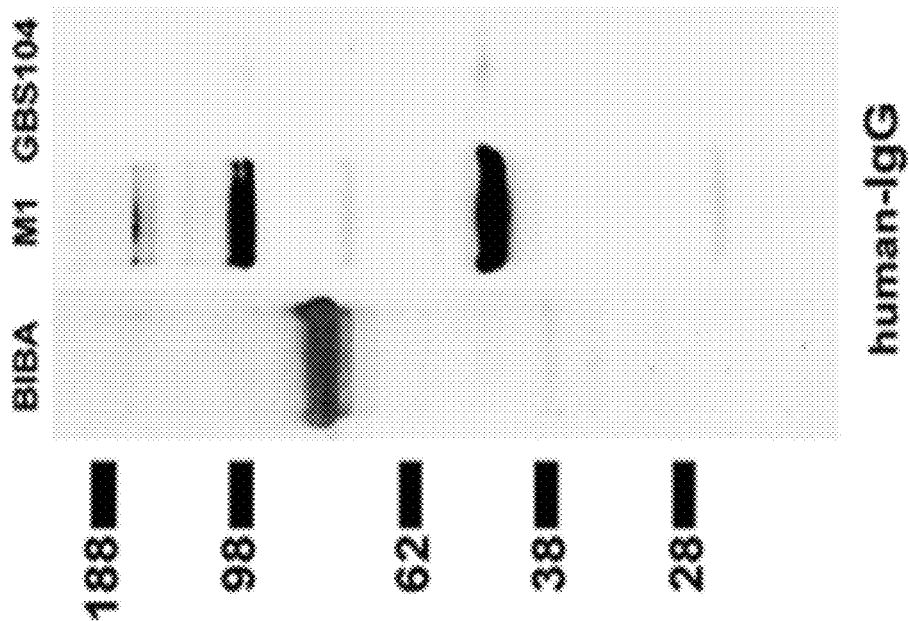

In order to elucidate the BibA binding region to Ig, we generated two constructs comprising the N-terminal portion of BibA (aa 34-394) or the C-terminal (aa 400-600). These two BibA constructs have been tested for binding to human IgG and IgA in overlay immunoblotting assays. As shown in FIG. 20E, BibA binding to human IgG resided prevalently in the N-terminal region of the protein, although some binding was observed also associated to the C-terminal portion. On the other hand, the binding to human IgA was exclusively associated to the N-terminal portion of BibA (FIG. 20F).

EXAMPLE 17

BibA Binds to Human Complement Regulator C4bp

Figure 21:
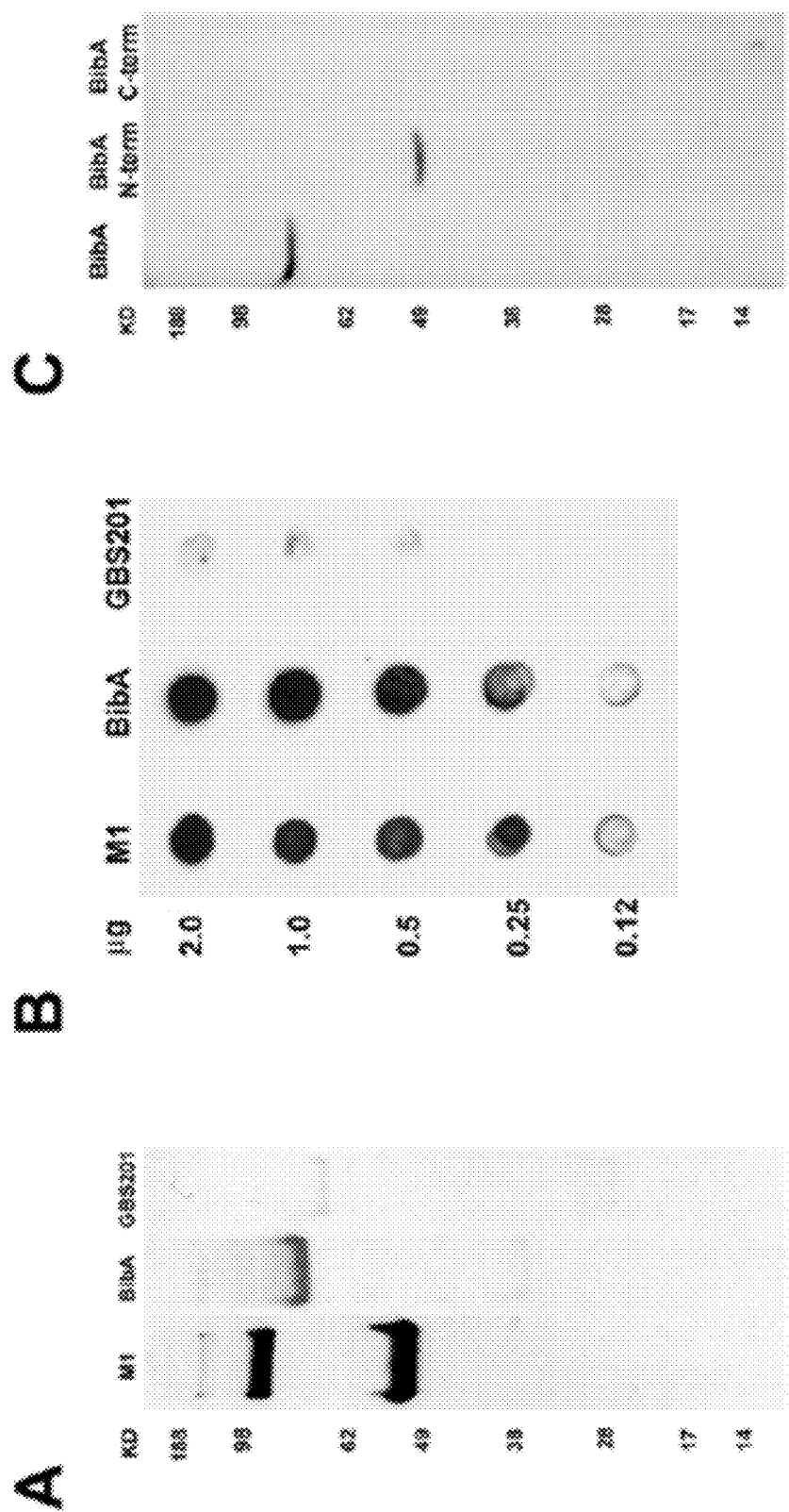
FIGS. 21A-C. Data demonstrating that BibA binds to human C4BP.

Because both BibA and M proteins bind to human IgA, we asked if the previously described (Carlsson et al, 2003) ability of M proteins to bind C4b-binding protein (C4bp) was also carried by BibA. We tested BibA binding activity by C4bp overlay blots in both denaturing and non-denaturing conditions. As shown in FIG. 21, recombinant BibA separated in SDS-gel electrophoresis (FIG. 21A) or spotted in the native form on nitrocellulose membrane (FIG. 21B) highly reacts with C4bp overlaid at 5 μg/ml. M1 similarly bound to C4bp in both conditions, while a negative control protein (GBS201), randomly chosen from the 2603 V/R genome, did not bind. Of interest, BibA did not show any binding for the alternative complement pathway regulator Factor H. BibA N-terminal and C-terminal constructs were also tested for C4bp binding. As shown in FIG. 21C, overlay blots of SDS-PAGE separated BibA showed that the N-terminal region of the protein was sufficient to specifically bind to C4bp. No binding was observed by the C-terminal portion.

EXAMPLE 18

BibA Recombinant Protein Binds to Epithelial Cells

In silico prediction of BibA propensity to form coiled-coil regions suggested an adhesive phenotype. We initially tested the capacity of the recombinant BibA, as expressed in the 2603 V/R strain, to bind to ME180 cervical epithelial cells. BibA binding was performed by incubating cells with different concentrations of the recombinant protein for 1 h at 4° C. A rabbit polyclonal serum raised against recombinant BibA was used as primary antibody and the binding detected by R-Phycoerythrin-conjugated secondary antibody. To determine antibody unspecific binding, cells were incubated with primary polyclonal antibodies in the absence of the protein. After incubation of ME180 cells with increased concentrations of BibA, we found that the binding of BibA reached a plateau at a concentration of ≈5 μg/ml.

Figure 22C:
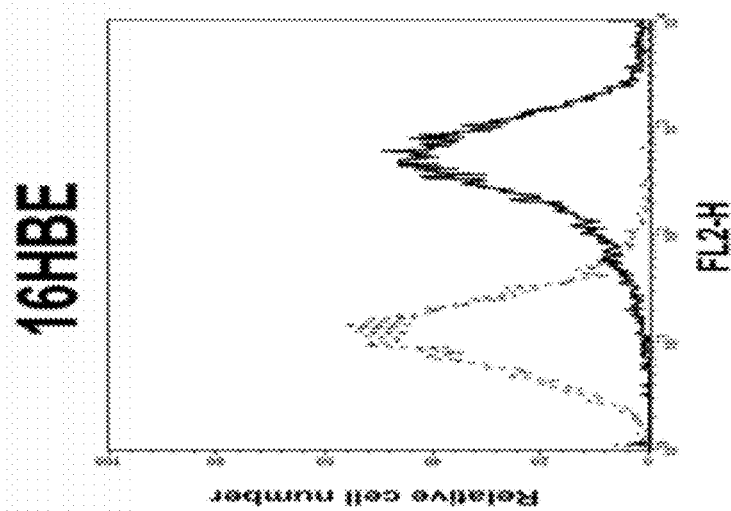
Figure 22C:
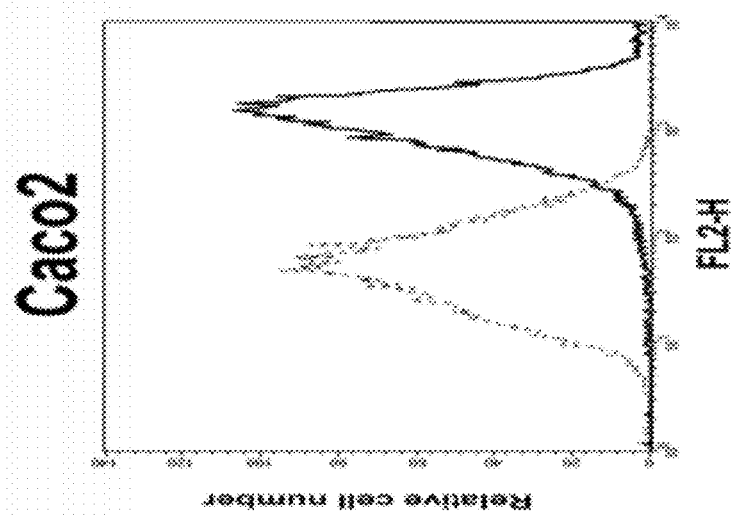
Figure 22C:
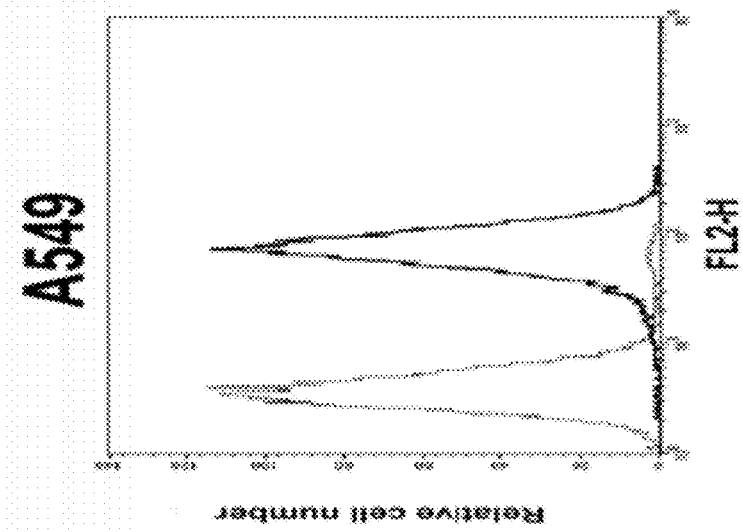

As shown in FIG. 22A, because the binding of BibA to ME180 cells could be saturated, the affinity of recombinant BibA for its putative receptor was estimated by plotting the mean of fluorescence intensity of the BibA-receptor complex versus the free BibA concentration (FIG. 22B). The Kd value was then calculated as the BibA concentration that determines the saturation of 50% of the putative receptors present on cells and evaluated to be in the order of $\approx 4 \times 10^{-8}$ M. We also tested binding of recombinant BibA to intestinal (Caco2), pulmonary (A549) and bronchial (16HBE) epithelial cell lines. Incubation of these cells with 10 μg/ml of recombinant BibA significantly increased the mean of fluorescence of the BibA-receptor complex (FIG. 22C), even if the intensity of the shift varied among the different cell types.

EXAMPLE 19

BibA is Involved in GBS Adhesion to Epithelial Cells

Figure 23B:
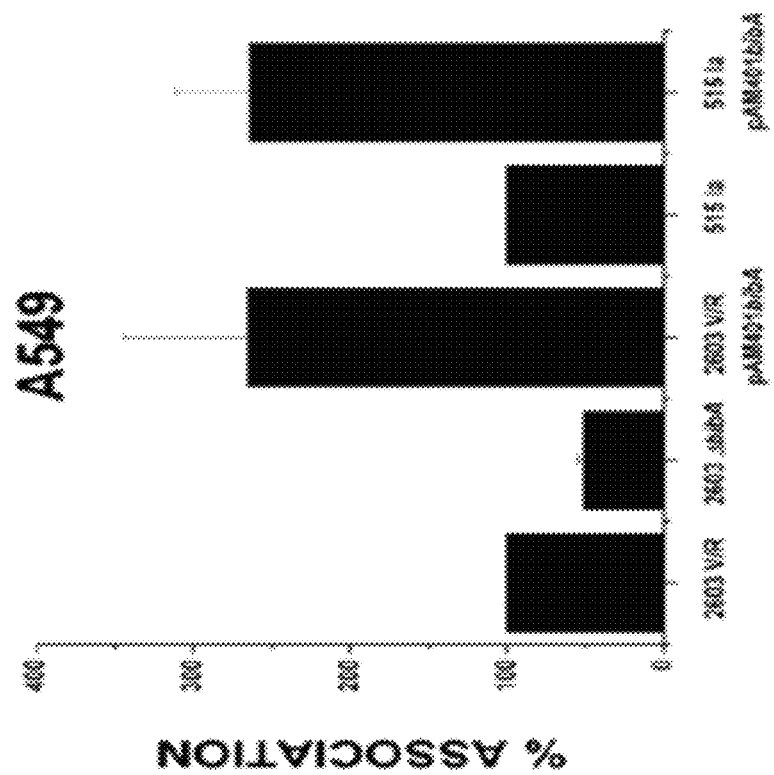
FIGS. 23A-F. Data demonstrating that BibA expression modulates GBS capacity to adhere to epithelial cells.
Figure 23A:
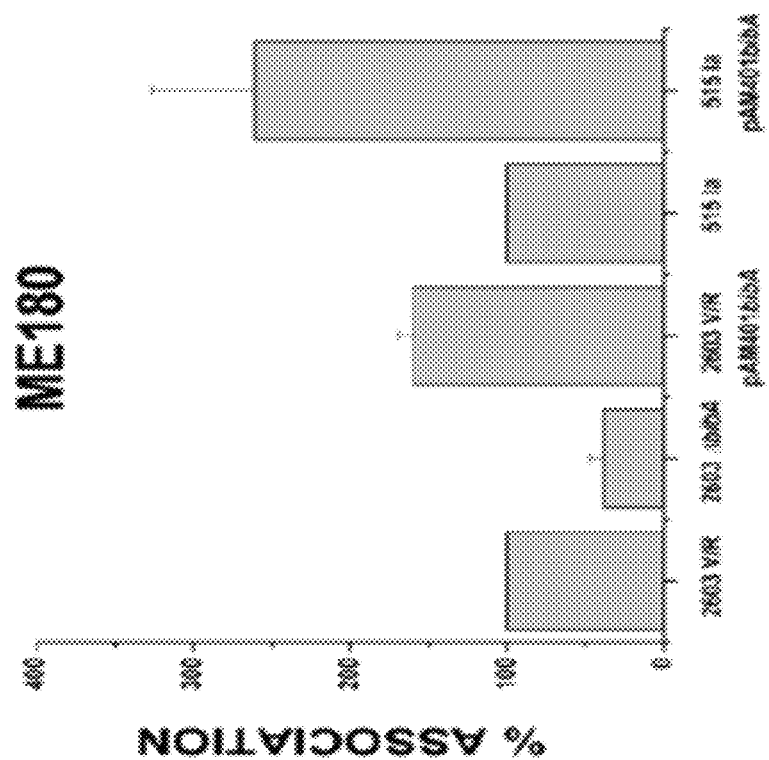

In order to confirm that recombinant BibA adhesive properties were associated to a functional role during interaction with epithelial cells, we performed association assays comparing the 2603 V/R wild type strain to the isogenic BibA knockout mutant strain, which does not express the protein on the bacterial surface (FIG. 19D). As shown in FIGS. 23A and B, the absence of BibA on the surface of 2603 V/R strain significantly reduced GBS capacity to associate to both ME180 and A549 cells (p<0.05). Complementation of the mutation by inserting the pAM401bibA plasmid restored the adhesive phenotype (data not shown). The impaired capacity of the 2603ΔbibA strain to adhere to epithelial cells was also evident in confocal imaging experiments. 2603 V/R wild type strain and the isogenic BibA knockout mutant strain were stained with rabbit anti-BibA and mouse anti-serotype V polyclonal antibodies.

Figure 23D:
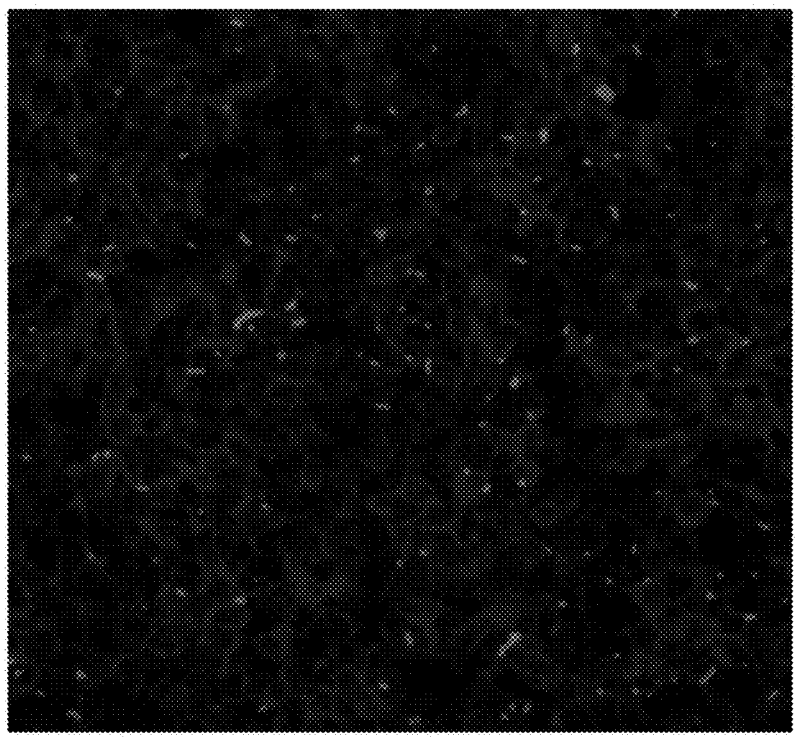
Figure 23C:
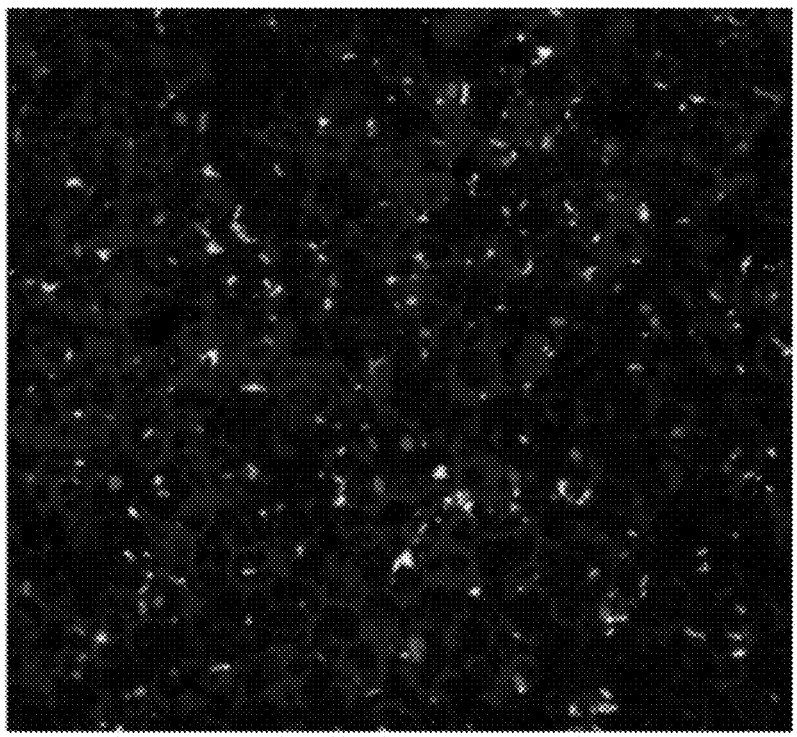

As shown in FIGS. 23C and 23D, the number of bacteria associated to epithelial cells found in a microscopy field (magnification 20×) was reduced in the BibA mutant strain. These results were in total agreement with those obtained by association assay. Transformation of the 2603 V/R wild type strain with the pAM401bibA plasmid was used as a tool to increase, BibA exposure on bacterial surface. FACS experiments confirmed that the 2603 pAM401bibA strain showed a 30% increase in the number of fluorescence intensity channels compared to the wild type strain. Association assays demonstrated that BibA overexpression was functionally related to the capacity of GBS to adhere to epithelial cells. Indeed, compared to wild type strain 2603 pAM401bibA strain showed an increased adherence to both ME180 and A549 cells (FIGS. 23A and 23B).

Figure 19:
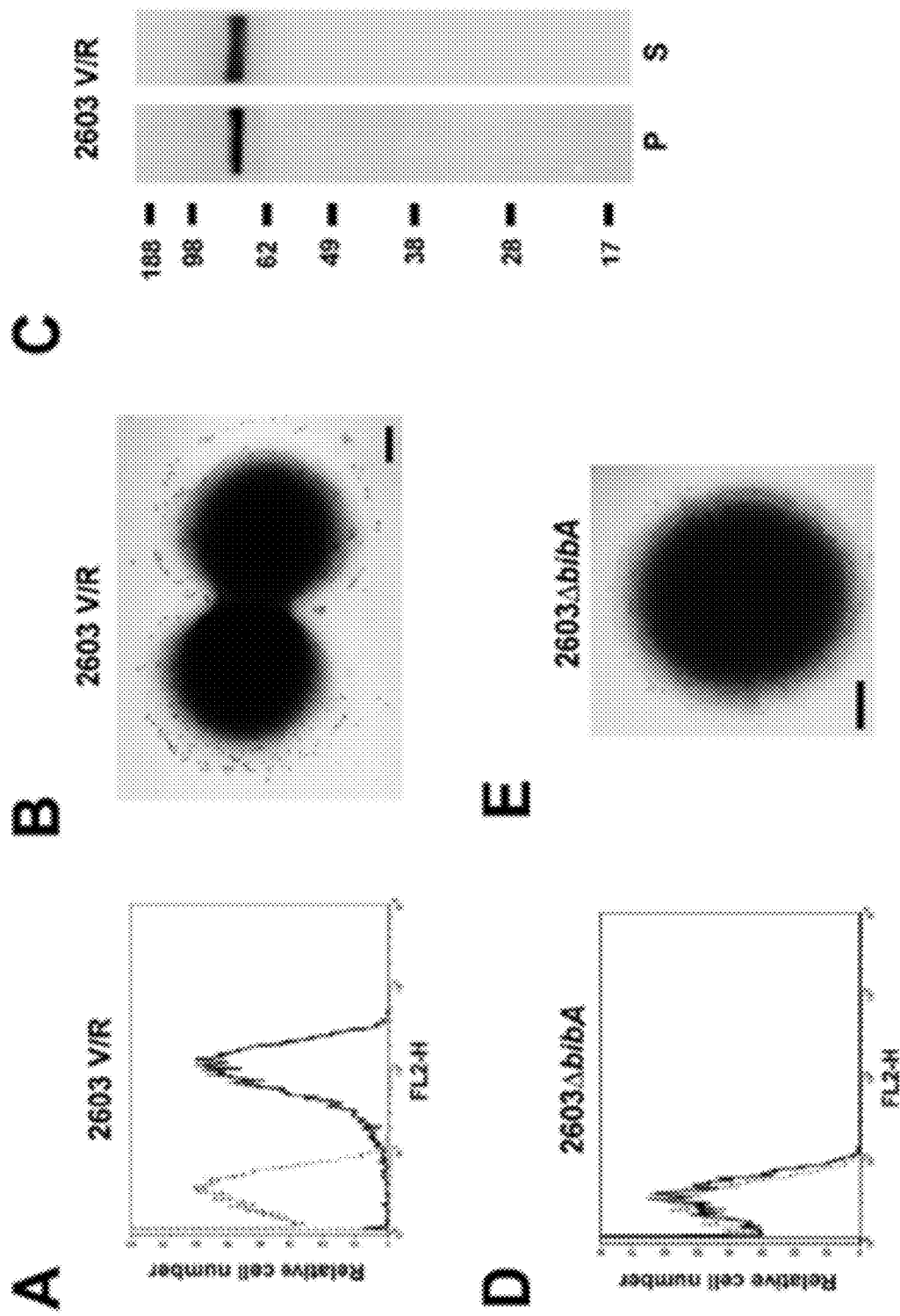
FIGS. 19A-L. Data demonstrating that BibA is expressed as surface exposed and secreted in GBS strain 2603 V/R.
Figure 23F:
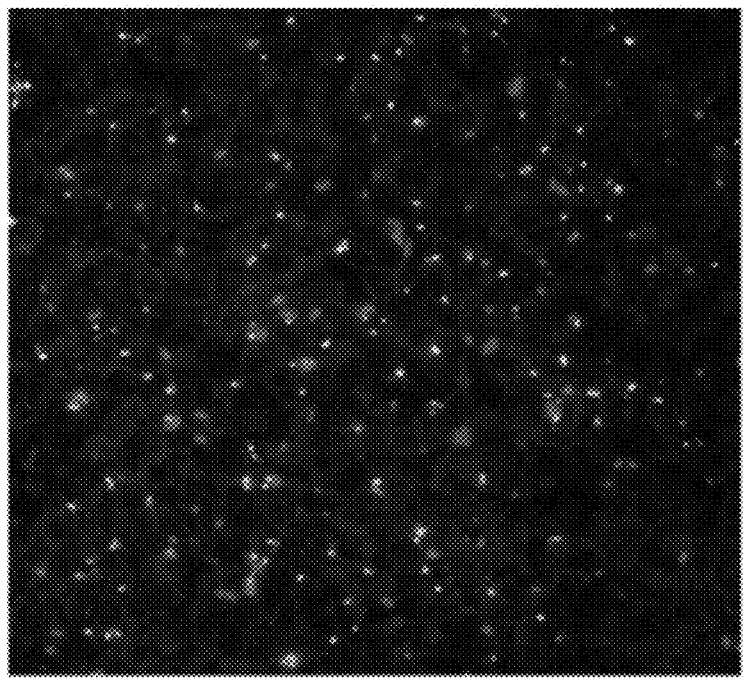
Figure 23E:

As previously shown in FIG. 19, we were able to express in the 515 Ia strain, which does not expose BibA on the surface, the 2603 V/R form of BibA (515 pAM401bibA). In order to demonstrate that such expression was associated to a functional adhesive phenotype as for 2603 V/R wild type strain, we compared association levels to epithelial cells between 515 Ia wild type strain and 515 pAM401bibA. We observed that BibA exposure on 515 Ia surface resulted in a significant increase in the percentage of associated bacteria to both ME180 and A549 cells (FIGS. 23A and 23B). This phenotype was also evident by confocal microscopy imaging (FIGS. 23E and 23F).

EXAMPLE 20

BibA Genomic Characterization

Genomic analysis on the recently sequenced genomes of 2603 V/R (Tettelin et al., 2002), NEM316 type III (Glaser et al., 2002), COH1 type III, CJB111 type V, 515 type Ia, 18RS21 type II and A909 type Ia (Tettelin et al., 2005) strains shows that bibA is present in all these strains, although interrupted by the insertion of two putative transposases on the opposite strand in A909. This insertion causes the interruption of the reading frame at nucleotide 580. The bibA gene present on 515 Ia strain shows a frame-shift, which results in a truncated form of the protein (FIG. 19G), consisting of the N-terminal 376 amino acids and lacking the proline-rich and cell wall anchoring regions. A similar frame-shift occurs in CJB111 strain, resulting in the translation of the N-terminal 469 amino acids. Such a protein fragment was found in CJB111 supernatants. Western blot analysis of GBS supernatants from 31 strains representing the most common serotypes, revealed that BibA was present in 81% of the strains (Table 4).

On the other hand, FACS analysis showed that BibA was expressed on the surface of 58% of the strains, while in 19% of them BibA was exclusively recovered in bacterial supernatants. However, BibA exposure on bacterial surface totally correlated with the presence in the supernatant.

In general, two different types of sequence variability can be observed among the different BibA proteins. The first is the presence of a variable number of brief amino acid modules, which can be observed either within the N-terminal domain, or within the proline-rich tract. In particular, the presence of a region of 97 amino acids, holding the repeats IKAESIN (SEQ ID NO:65) and KIQXKXNT (SEQ ID NO:66) is observed within the N-terminal domain in A909, CJB11 and H36B, while the number of copies of the PEAK/PDVK modules varies between 17 and 42 (see Table 3). This suggests the insertion/excision of transposable elements.

The second source of sequence variation consists of a non-repetitive tract of 97 residues within proline-reach region, which characterizes 515, NEM316, H36B, CJB111 and A909 strains. Collectively, the sequence analysis reveals that the protein exists in three different variants, one formed by strains 2603, 18RS21, and COH1, the other by NEM316 and 515, and the last one originated by CJB111, H36B and A909 (FIG. 24). However, the multiple alignment of the BibA amino acid sequences, shows that the protein is generally well conserved (amino acid identity ranges between 63.3 and 100% among N-terminal domains of different strains), with the exception of COH1, whose N-terminal region shows on average about 25% of amino acid identity to the other alleles.

EXAMPLE 21

Active Maternal Immunization Assay

A maternal immunization/neonatal pup challenge model of GBS infection is used to verify the protective efficacy of the antigens in mice. See Rodewald et al., *J. Infect. Diseases* 166, 635, 1992. CD-1 female mice (6-8 weeks old) are immunized before breeding. The mice receive 20 μg of protein per dose when immunized with a single antigen and 60 μg of protein per dose (15 μg of each antigen) when immunized with the combination of antigens. Mice are bred 2-7 days after the last immunization. Within 48 h of birth, pups are injected intraperitoneally with 50 μl of GBS culture. Challenge inocula are prepared starting from frozen cultures diluted to the appropriate concentration with THB before use. In preliminary experiments, the challenge doses per pup for each strain tested is determined to cause 90% lethality. Survival of pups is monitored for 2 days after challenge. Protection is calculated as (percentage deadControl minus percentage deadVaccine) divided by percentage deadControl multiplied by 100. Data are evaluated for statistical significance by Fisher's exact test.

EXAMPLE 22

BibA Knock-Out Mutant Strain is Cleared More Easily in Human Blood

The importance of BibA expression in bacterial survival in vivo was assessed in freshly drawn blood from human donors. GBS was grown up to $OD_{600}$ 0.4, washed, and resuspended in PBS. Inocula of $10^4$ CFU in 100 μl were mixed with 300 μl of freshly drawn human blood using heparin as anticoagulant. The tubes were incubated for 3 hours with agitation at 37° C., and dilutions were plated for determination of CFU.

As shown in Table 5, 2603 V/R wild-type strain and the isogenic 2603ΔbibA knock-out mutant strain were compared for the capacity to replicate in whole human blood. The bacterial survival index was calculated as the ratio between the number of bacteria recovered at the end of the assay versus bacteria at time 0. We tested five individual donors and found that 2603 V/R wild-type strain proliferated in human blood 5 times more efficiently than the 2603ΔbibA mutant strain. However, survival indexes varied among the different donors. In three donors, where the wild-type strain replicated slowly in blood (from 5 to 14 times), the bibA knock-out mutant strain was almost cleared. By contrast, in two donors where the wild-type strain replicated highly in blood (77 and 41 times), the bibA mutant strain still proliferated, although less efficiently (37 and 5 times, respectively). These findings suggest that in donors with a reduced anti-bactericidal activity, the contribution of BibA to GBS survival in blood is less pronounced.

EXAMPLE 23

Complement-Mediated GBS Killing by Polymorphonuclear Leukocytes (PMNs) is Affected by BibA Expression Phagocytic clearance of GBS by human blood is mainly mediated by PMNs which kill opsonized bacteria in the presence of complement. The killing by human PMNs of the 2603 V/R wild-type strain and the bibA mutant strains were compared. PMNs were obtained from heparin-anticoagulated venous blood of normal, healthy volunteers by dextran sedimentation, Ficoll-Hypaque density gradient centrifugation, and hypotonic lysis of residual erythrocytes, as described in Maione et al., *Science* 309, 148-50.

To prepare bacteria for killing experiments, 2603 V/R and 2603ΔbibA grown in THB medium were collected in mid-log pase of growth ($OD_{600}$ 0.4), washed in HBSS (Gibco-BRL), and adjusted to a density of $10^7$ CFU/ml. GBS ($10^6$ CFU) were opsonized for 15 minutes at 37° C. with 5% human serum containing anti-GBS antibodies. The bacteria were incubated for 3 h with PMNs and the number of surviving bacteria was determined by quantitative plating on TSA plates.

Figure 30:
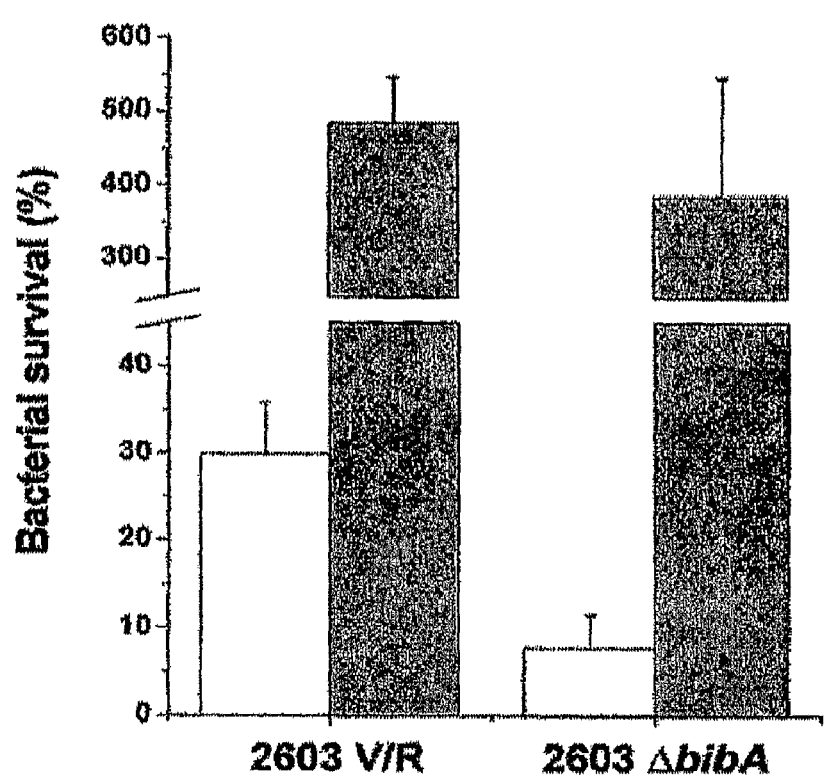
FIG. 30. BibA promotes GBS survival of PMN killing. Human neutrophils were incubated for 3 hours with GBS 2603 V/R and 2603ΔbibA mutant strains (MOI 1:1) in the presence of human serum (white bars) or complement inactivated human serum (grey bars). Percentage of viable bacteria after incubation with neutrophils is reported. A typical experiment performed in triplicate is shown. The experiment was repeated at least three times with similar results.

Incubation of GBS with human serum alone resulted in no killing. As shown in FIG. 30, at the end of the 3 h incubation, the bibA mutant strain was killed more efficiently than the wild-type strain. Indeed, only 7% of the mutant bacteria survived phagocytosis by PMNs, compared to 30% for the wild-type strain. Heat inactivation of complement resulted in survival of both wild-type and bibA mutant strains, which replicated 5- to 6-fold during the time span of the experiment (FIG. 30).

TABLE 1

|  | Total h-IgG | h-IgG1 (λ) | h-IgG2 (κ) | hIgG3 (κ) | Bovine IgG | Human serum IgG | Mouse serum IgG | Rabbit serum IgG |
|---|---|---|---|---|---|---|---|---|
| BibA-His | +++ | – | – | – | – | +++ | – | + |
| BibA-Nt-His | ++ | – | – | – | – | ++ | – | – |
| BibA-Ct-His | + | – | – | – | – | – | – | – |

TABLE 2

|  | Human serum IgA | Human colostrum-IgA |
|---|---|---|
| BibA-His | +++ | +++ |
| BibA-Nt-His | ++ | + |
| BibA-Ct-His | – | ++ |

TABLE 3

| GBS strain | Serotype | Surface* | Supernatant° | MW (kDa) |
|---|---|---|---|---|
| A909 | Ia | – | – | — |
| 515 | Ia | – | + | 38 |
| DK1 | Ia | +++ | + | 90 |
| 2177 | Ib/c | – | + | 90 |
| 5551 | Ib/c | +++ | + | 80 |
| H36B | Ib | ++ | + | 90 |
| 2129 | Ib | + | + | 80 |
| 7357b | Ib | ++ | + | 80 |
| 5518 | Ib | – | – | — |
| 18RS21 | II | ++ | + | 80 |
| 3050 | II | +++ | + | 80 |
| 5401 | II | – | + | 70 |
| 2141 | II | ++ | + | 80 |
| M732 | III | – | – | — |
| M781 | III | – | + | 60 |
| COH1 | III | – | – | — |
| 5435 | III/R | – | + | 60 |
| 5376 | III/R | – | – | — |
| 1998 | III/R | +++ | + | 80 |
| 2274 | IV | – | + | 40 |
| 1999 | IV | + | + | 90 |
| 2210 | IV | + | + | 80 |
| 2603 | V | +++ | + | 80 |
| CJB111 | V | – | + | 48 |
| 5364 | V | ++ | + | 80 |
| 2110 | V/c | ++ | + | 80 |
| 2189 | VIII | – | – | — |
| JM9130013 | VIII | ++ | + | 98 |
| JMU071 | VIII | ++ | + | 98 |
| CJB110 | NT | + | + | 60 |
| 1169 | NT | ++ | + | 60 |

*(–) MFI 0-50 (+) MFI 50-100 (++) MFI 100-200 (+++) MFI 200-300

°(–) WB negative (+) WB positive

TABLE 4

| GBS strain | PEAK/PDVK modules |
|---|---|
| COH1 | 17 |
| NEM316 | 21 |
| A909 | 25 |
| CJB111 | 29 |
| H36B | 38 |
| 2603 | 42 |
| 515 | 42 |
| 18R821 | 42 |

TABLE 5

| Survival Index (% survival) | Donor A | Donor B | Donor C | Donor D | Donor E | % survival (mean ± SD) |
|---|---|---|---|---|---|---|
| 2603 V/R | 5.2 (100) | 77.5 (100) | 5.4 (100) | 14.7 (100) | 41.3 (100) | 100 |
| 2603ΔbibA | 0.7 (12.9) | 37.6 (48.5) | 0.76 (14.1) | 1.3 (8.8) | 5.4 (13.1) | 19.5 ± 14.6 |

REFERENCES

Areschoug et al., A proline-rich region with a highly periodic sequence in Streptococcal beta protein adopts the polyproline II structure and is exposed on the bacterial surface. *J Bacteriol* 184: 6376-6383 (2002).

Bae, T., and Schneewind, O. (2003) The YSIRK-G/S motif of staphylococcal protein A and its role in efficiency of signal peptide processing. *J Bacteriol* 185: 2910-2919.

Barreiro, C., Gonzalez-Lavado, E., and Martin, J. F. (2001) Organization and transcriptional analysis of a six-gene cluster around the rplK-rplA operon of *Corynebacterium glutamicum* encoding the ribosomal proteins L11 and L1. *Appl Environ Microbiol* 67: 2183-2190.

Beckmann, C., Waggoner, J. D., Harris, T. O., Tamura, G. S., and Rubens, C. E. (2002) Identification of novel adhesins from Group B streptococci by use of phage display reveals that C5a peptidase mediates fibronectin binding. *Infect Immun* 70: 2869-2876.

Berger, B., Wilson, D. B., Wolf, E., Tonchev, T., Milla, M., and Kim, P. S. (1995) Predicting coiled coils by use of pairwise residue correlations. *Proc Natl Acad Sci USA* 92: 8259-8263.

Berggard, K., Johnsson, E., Morfeldt, E., Persson, J Stalhammar-Carlemalm, M., and Lindahl, G. (2001) Binding of human C4BP to the hypervariable region of M protein: a molecular mechanism of phagocytosis resistance in *Streptococcus pyogenes*. *Mol Microbial* 42: 539-551.

Bevanger, L. (1983) Ibc proteins as serotype markers of group B streptococci. *Acta Pathol Microbiol Immunol Scand [B]* 91: 231-234.

Blom, A. M., Villoutreix, B. O., and Dahlback, B. (2004) Complement inhibitor C4b-binding protein-friend or foe in the innate immune system? *Mol Immunol* 40: 1333-1346.

Boyle, M. D. P. (1998) Bacterial immunoglobulin-binding proteins. In *Encyclopedia of immunology*. New York: Academic Press, Inc., pp. 323-327.

Carlsson, F., Berggard, K., Stalhammar-Carlemalm, M., and Lindahl, G. (2003) Evasion of phagocytosis through cooperation between two ligand-binding regions in *Streptococcus pyogenes* M protein. *J Exp Med* 198: 1057-1068.

Carlsson, F., Sandin, C., and Lindahl, G. (2005) Human fibrinogen bound to *Streptococcus pyogenes* M protein inhibits complement deposition via the classical pathway. *Mol Microbiol* 56: 28-39.

Cheng, Q., Stafslien, D., Purushothaman, S. S., and Cleary, P. (2002) The group B streptococcal C5a peptidase is both a specific protease and an invasin. *Infect Immun* 70: 2408-2413.

Courtney, H. S., Bronze, M. S., Dale, J. B., and Hasty, D. L. (1994) Analysis of the role of M24 protein in group A streptococcal adhesion and colonization by use of omega-interposon mutagenesis. *Infect Immun* 62: 4868-4873.

Courtney, H. S., Ofek, I., and Hasty, D. L. (1997) M protein mediated adhesion of M type 24 *Streptococcus pyogenes* stimulates release of interleukin-6 by HEp-2 tissue culture cells. *FEMS Microbiol Lett* 151: 65-70.

Cunningham, M. W. (2000) Pathogenesis of group A streptococcal infections. *Clin Microbiol Rev* 13: 470-511.

Dave, S., Carmicle, S., Hammerschmidt, S., Pangburn, M. K., and McDaniel, L. S. (2004) Dual roles of PspC, a surface protein of *Streptococcus pneumoniae*, in binding human secretory IgA and factor H. *J Immunol* 173: 471-477.

Downing, W. L., Sullivan, S. L., Gottesman, M. E., and Dennis, P. P. (1990) Sequence and transcriptional pattern of the essential *Escherichia coli* secE-nusG operon. *J Bacteriol* 172: 1621-1627.

Fagan, P. K., Reinscheid, D., Gottschalk, B., and Chhatwal, G. S. (2001) Identification and characterization of a novel secreted immunoglobulin binding protein from group A streptococcus. *Infect Immun* 69: 4851-4857.

Fuller, T. E., Shea, R. J., Thacker, B. J., and Mulks, M. H. (1999) Identification of in vivo induced genes in *Actinobacillus* pleuropneumoniae. *Microb Pathog* 27: 311-327.

Glaser, P., Rusniok, C., Buchrieser, C., Chevalier, F., Frangeul, L., Msadek, T., Zouine, M., Couve, E., Lalioui, L., Poyart, C., Trieu-Cuot, P., and Kunst, F. (2002) Genome sequence of *Streptococcus agalactiae*, a pathogen causing invasive neonatal disease. *Mol Microbiol* 45: 1499-1513.

Grifantini, R., Bartolini, E., Muzzi, A., Draghi, M., Frigimelica, E., Berger, J., Ratti, G., Petracca, R., Galli, G., Agnusdei, M., Giuliani, M. M., Santini, L., Brunelli, B., Tettelin, H., Rappuoli, R., Randazzo, F., and Grandi, G. (2002) Previously unrecognized vaccine candidates against group B meningococcus identified by DNA microarrays. *Nat Biotechnol* 20: 914-921.

Hery-Arnaud, G., Bruant, G., Lanotte, P., Brun, S., Rosenau, A., van der Mee-Marquet, N., Quentin, R., and Mereghetti, L. (2005) Acquisition of insertion sequences and the GBSil intron by *Streptococcus agalactiae* isolates correlates with the evolution of the species. *J Bacteriol* 187: 6248-6252.

Hollingshead, S. K., Fischetti, V. A., and Scott, J. R. (1986) Complete nucleotide sequence of type 6 M protein of the group A *Streptococcus*. Repetitive structure and membrane anchor. *J Biol Chem* 261: 1677-1686.

Horstmann, R. D., Sievertsen, H. J., Knobloch, J., and Fischetti, V. A. (1988) Antiphagocytic activity of streptococcal M protein: selective binding of complement control protein factor H. *Proc Natl Acad Sci USA* 85: 1657-1661.

Janulczyk, R., Iannelli, F., Sjoholm, A. G., Pozzi, G., and Bjorck, L. (2000) Hic, a novel surface protein of *Streptococcus pneumoniae* that interferes with complement function. *J Biol Chem* 275: 37257-37263.

Jarva, H., Janulczyk, R., Hellwage, J., Zipfel, P. F., Bjorck, L., and Meri, S. (2002) *Streptococcus pneumoniae* evades complement attack and opsonophagocytosis by expressing the pspC locus-encoded Hic protein that binds to short consensus repeats 8-11 of factor H. *J Immunol* 168: 1886-1894.

Jarva, H., Jokiranta, T. S., Wurzner, R., and Meri, S. (2003) Complement resistance mechanisms of streptococci. *Mol Immunol* 40: 95-107.

Jarva, H., Hellwage, J., Jokiranta, T. S., Lehtinen, M. J., Zipfel, P. F., and Meri, S. (2004) The group B streptococcal beta and pneumococcal Hic proteins are structurally related immune evasion molecules that bind the complement inhibitor factor H in an analogous fashion. *J Immunol* 172: 3111-3118.

Jeong, S. M., Yoshikawa, H., and Takahashi, H. (1993) Isolation and characterization of the secE homologue gene of *Bacillus subtilis*. *Mol Microbiol* 10: 133-142.

Jerlstrom, P. G., Chhatwal, G. S., and Timmis, K. N. (1991) The IgA-binding beta antigen of the c protein complex of Group B streptococci: sequence determination of its gene and detection of two binding regions. *Mol Microbiol* 5: 843-849.

Johnson, D. R., and Ferrieri, P. (1984) Group B streptococcal Ibc protein antigen: distribution of two determinants in wild-type strains of common serotypes. *J Clin Microbiol* 19: 506-510.

Katayama, M., Sakai, Y., Okamoto, S., Ihara, F., Nihira, T., and Yamada, Y. (1996) Gene organization in the ada-rplL region of *Streptomyces virginiae*. *Gene* 171: 135-136.

Lauer, P., Rinaudo, C. D., Soriani, M., Margarit, I., Maione, D., Rosini, R., Taddei, A. R., Mora, M., Rappuoli, R., Grandi, G., and Telford, J. L. (2005) Genome analysis reveals pili in Group B *Streptococcus*. *Science* 309: 105.

Lindahl, G., Akerstrom, B., Vaerman, J. P., and Stenberg, L. (1990) Characterization of an IgA receptor from group B streptococci: specificity for serum IgA. *Eur J Immunol* 20: 2241-2247.

Lindahl, G., Stalhammar-Carlemalm, M., and Areschoug, T. (2005) Surface proteins of *Streptococcus agalactiae* and related proteins in other bacterial pathogens. *Clin Microbiol Rev* 18: 102-127.

Maguin, E., Prevost, H., Ehrlich, S. D., and Gruss, A. (1996) Efficient insertional mutagenesis in lactococci and other gram-positive bacteria. *J Bacterial* 178: 931-935.

Miyake, K., Onaka, H., Horinouchi, S., and Beppu, T. (1994) Organization and nucleotide sequence of the secE-nusG region of *Streptomyces griseus*. *Biochim Biophys Acta* 1217: 97-100.

Pandiripally, V., Gregory, E., and Cue, D. (2002) Acquisition of regulators of complement activation by *Streptococcus pyogenes* serotype M1. *Infect Immun* 70: 6206-6214.

Pandiripally, V., Wei, L., Skerka, C., Zipfel, P. F., and Cue, D. (2003) Recruitment of complement factor H-like protein 1 promotes intracellular invasion by group A streptococci. *Infect Immun* 71: 7119-7128.

Perez-Caballero, D., Garcia-Laorden, I., Cortes, G., Wessels, M. R., de Cordoba, S. R., and Alberti, S. (2004) Interaction between complement regulators and *Streptococcus pyogenes*: binding of C4b-binding protein and factor H/factor H-like protein 1 to M18 strains involves two different cell surface molecules. *J Immunol* 173: 6899-6904.

Phillips, G. N., Jr., Flicker, P. F., Cohen, C., Manjula, B. N., and Fischetti, V. A. (1981) Streptococcal M protein: alpha-helical coiled-coil structure and arrangement on the cell surface. *Proc Natl Acad Sci USA* 78: 4689-4693.

Podbielski, A., Hawlitzky, J., Pack, T. D., Flosdorff, A., and Boyle, M. D. (1994) A group A streptococcal Enn protein potentially resulting from intergenomic recombination exhibits atypical immunoglobulin-binding characteristics. *Mol Microbiol* 12: 725-736.

Poplawski, A., Gullbrand, B., and Bernander, R. (2000) The ftsZ gene of Haloferax mediterranei: sequence, conserved gene order, and visualization of the FtsZ ring. *Gene* 242: 357-367.

Puttikhunt, C., Nihira, T., and Yamada, Y. (1995) Cloning, nucleotide sequence, and transcriptional analysis of the nusG gene of *Streptomyces coelicolor* A3(2), which encodes a putative transcriptional antiterminator. *Mol Gen Genet* 247: 118-122.

Rost, B., and Sander, C. (1993) Prediction of protein secondary structure at better than 70% accuracy. *J Mol Biol* 232: 584-599.

Russell-Jones, G. J., Gotschlich, E. C., and Blake, M. S. (1984) A surface receptor specific for human IgA on group B streptococci possessing the Ibc protein antigen. *J Exp Med* 160: 1467-1475.

Sharp, P. M. (1994) Identification of genes encoding ribosomal protein L33 from *Bacillus licheniformis, Thermus thermophilus* and *Thermotoga maritima*. *Gene* 139: 135-136.

Song, X. M., Perez-Casal, J., Fontaine, M. C., and Potter, A. A. (2002) Bovine immunoglobulin A (IgA)-binding activities of the surface-expressed Mig protein of *Streptococcus dysgalactiae*. *Microbiology* 148: 2055-2064.

Stenberg, L., O'Toole, P., and Lindahl, G. (1992) Many group A streptococcal strains express two different immunoglobulin-binding proteins, encoded by closely linked genes: characterization of the proteins expressed by four strains of different M-type. *Mol Microbiol* 6: 1185-1194.

Syvanen, A. C., Amiri, H., Jamal, A., Andersson, S. G., and Kurland, C. G. (1996) A chimeric disposition of the elongation factor genes in *Rickettsia prowazekii*. *J Bacteriol* 178: 6192-6199.

Talay, S. R. (2005) Gram-positive adhesins. *Contrib Microbiol* 12: 90-113.

Tamura, G. S., Herndon, M., Przekwas, J., Rubens, C. E., Ferrieri, P., and Hillier, S. L. (2000) Analysis of restriction fragment length polymorphisms of the insertion sequence IS1381 in group B Streptococci. *J Infect Dis* 181: 364-368.

Tettelin et al., Complete genome sequence and comparative genomic analysis of an emerging human pathogen, serotype V *Streptococcus agalactiae*. *Proc Natl Acad Sci USA* 99: 12391-12396, 2002.

Tettelin et al., Genome analysis of multiple pathogenic isolates of *Streptococcus agalactiae*: Implications for the microbial "pan-genome". *Proc Natl Acad Sci USA* 102: 13950-13955, 2005.

Thern, A., Stenberg, L., Dahlback, B., and Lindahl, G. (1995) Ig-binding surface proteins of *Streptococcus pyogenes* also bind human C4b-binding protein (C4BP), a regulatory component of the complement system. *J Immunol* 154: 375-386.

Thompson, J. D., Higgins, D. G., and Gibson, T. J. (1994) CLUSTAL W: improving the sensitivity of progressive multiple sequence alignment through sequence weighting, position-specific gap penalties and weight matrix choice. *Nucleic Acids Res* 22: 4673-4680.

Wang, J. R., and Stinson, M. W. (1994) M protein mediates streptococcal adhesion to HEp-2 cells. *Infect Immun* 62: 442-448.

Wexler, D. E., Chenoweth, D. E., and Cleary, P. P. (1985) Mechanism of action of the group A streptococcal C5a inactivator. *Proc Natl Acad Sci USA* 82: 8144-8148.

---

The invention claimed is:

1. A purified preparation of antibodies which specifically bind to a portion of a polypeptide, wherein the portion of the polypeptide to which the antibodies specifically bind consists of
   (1) a "coiled-coil domain" which is at least 95% identical to amino acids 34-394 of SEQ ID NO:1 (BibA);
   (2) a "proline-rich domain" which is at least 95% identical to amino acids 389-622 of SEQ ID NO:1; or
   (3) the coiled-coil domain of (1) and the proline-rich domain of (2);
wherein the portion is free of other contiguous amino acid sequences of a protein with the amino acid sequence SEQ ID NO:1.

2. The purified preparation of antibodies of claim 1, wherein the portion consists of the proline-rich domain and wherein the amino acid sequence of the proline-rich domain is amino acids 389-622 of SEQ ID NO:1.

3. The purified preparation of antibodies of claim 1, wherein the portion consists of the coiled-coil domain and wherein the amino acid sequence of the coiled-coil domain is amino acids 34-394 of SEQ ID NO:1.

4. The purified preparation of antibodies of claim 1, wherein the portion consists of the coiled-coil domain.

5. The purified preparation of antibodies of claim 1, wherein the portion consists of the proline-rich domain.

6. The purified preparation of antibodies of claim 1, wherein the portion consists of the coiled-coil domain and the proline-rich domain.

7. The purified preparation of antibodies of claim 6, wherein the portion consists of the coiled-coil domain and wherein the proline-rich domain and wherein the amino acid sequence of the portion is at least 95% identical to SEQ ID NO:4.

8. The purified preparation of antibodies of claim 7, wherein the amino acid sequence of the portion is SEQ ID NO:4.

9. The purified preparation of antibodies of claim 1, wherein the antibodies are polyclonal.

10. The purified preparation of antibodies of claim 1, wherein the antibodies are monoclonal.

11. The purified preparation of antibodies of claim 1, wherein the antibodies are selected from the group consisting of F(ab')$_2$ fragments, F(ab) fragments, F$_v$ molecules, non-covalent heterodimers, single-chain F$_v$ molecules, dimeric antibody fragment constructs, trimeric antibody fragment constructs, minibodies, diabodies, and chimeric antibodies.

12. The purified preparation of antibodies of claim 1, wherein the antibodies are humanized.

13. The purified preparation of antibodies of claim 1, wherein the antibodies are human antibodies.

14. A composition comprising:
    the purified preparation of antibodies of claim 1; and
    a pharmaceutically acceptable carrier.

15. The composition of claim 14, further comprising an antibody which specifically binds to a polypeptide antigen which is useful in a pediatric vaccine.

16. The composition of claim 15, wherein the polypeptide antigen selected from the group consisting of *N. meningitidis, S. pneumoniae, Bordetella pertussis, Moraxella catarrhalis, Clostridium tetani, Chorinebacterim diphteriae*, respiratory syncytial virus, polio virus, measles virus, mumps virus, rubella virus, and rotavirus polypeptide antigens.

17. The composition of claim 14, further comprising an antibody which specifically binds to a polypeptide antigen which is useful in a vaccine for elderly or immunocompromised individuals.

18. The composition of claim 17, wherein the polypeptide antigen selected from the group consisting of *Enterococcus faecalis, Staphylococcus aureus, Staphylococcus epidermis, Pseudomonas aeruginosa, Legionella pneumophila, Listeria monocytogenes*, influenza virus, and parainfluenza virus polypeptide antigens.

19. A method of treating an *S. agalactiae* infection comprising administering to an individual in need thereof the composition of claim 14.

\* \* \* \* \*